US012364659B2

(12) United States Patent
Herrlein et al.

(10) Patent No.: US 12,364,659 B2
(45) Date of Patent: Jul. 22, 2025

(54) MULTICOMPONENT IN SITU COLORATION COMPOSITION

(71) Applicants: HFC PRESTIGE INTERNATIONAL HOLDING SWITZERLAND S.A.R.L, Petit-Lancy (CH); Mathias Kurt Herrlein, Kronberg am Taunus (DE); Graham Neil McKelvey, Glastutten-Hesse (DE); Simon Paul Godfrey, Oberursel (DE); Matija Crne, Wiesbaden (DE); Andrej Gross, Darmstradt (DE); Malte Bernd Hermann Afflerbach, Darmstadt (DE); Corinne Mohr, Lorsch (DE)

(72) Inventors: Mathias Kurt Herrlein, Kronberg am Taunus (DE); Graham Neil McKelvey, Glastutten-Hesse (DE); Simon Paul Godfrey, Oberursel (DE); Matija Crne, Wiesbaden (DE); Andrej Gross, Darmstradt (DE); Malte Bernd Hermann Afflerbach, Darmstadt (DE); Corinne Mohr, Lorsch (DE)

(73) Assignee: WELLA INTERNATIONAL OPERATIONS SWITZERLAND SÀRL, Petit-Lancy (CH)

( * ) Notice: Subject to any disclaimer, the term of this patent is extended or adjusted under 35 U.S.C. 154(b) by 1019 days.

(21) Appl. No.: 17/299,697

(22) PCT Filed: Oct. 1, 2019

(86) PCT No.: PCT/EP2019/076647
§ 371 (c)(1),
(2) Date: Jun. 3, 2021

(87) PCT Pub. No.: WO2020/114647
PCT Pub. Date: Jun. 11, 2020

(65) Prior Publication Data
US 2022/0054392 A1 Feb. 24, 2022

Related U.S. Application Data

(60) Provisional application No. 62/774,627, filed on Dec. 3, 2018.

(51) Int. Cl.
*A61K 8/84* (2006.01)
*A61K 8/58* (2006.01)
*A61Q 5/10* (2006.01)

(52) U.S. Cl.
CPC .............. *A61K 8/84* (2013.01); *A61K 8/585* (2013.01); *A61Q 5/10* (2013.01); *A61K 2800/43* (2013.01); *A61K 2800/95* (2013.01)

(58) Field of Classification Search
CPC ......... A61K 8/84; A61K 2800/95; A61Q 5/10
See application file for complete search history.

(56) References Cited

U.S. PATENT DOCUMENTS

| 4,559,057 | A | 12/1985 | Bogaty et al. |
| 5,258,481 | A | 11/1993 | Hesselmans et al. |
| 5,567,428 | A | 10/1996 | Hugehes |
| 5,990,479 | A | 11/1999 | Weiss et al. |
| 6,225,198 | B1 | 5/2001 | Alivisatos et al. |
| 6,451,747 | B1 | 9/2002 | Decoster |
| 6,492,484 | B2 | 12/2002 | Misumi et al. |
| 9,546,301 | B2 | 1/2017 | Derksen et al. |
| 10,011,677 | B2 | 7/2018 | Yamashita et al. |
| 10,959,919 | B2 | 3/2021 | Dahne et al. |
| 10,973,754 | B2 | 4/2021 | Herrlein et al. |
| 11,324,688 | B2 | 5/2022 | Herrlein et al. |
| 11,478,415 | B2 | 10/2022 | Herrlein et al. |
| 2003/0203978 | A1 | 10/2003 | O'Brien et al. |
| 2004/0010863 | A1 | 1/2004 | Gawtrey et al. |
| 2005/0226838 | A1 | 10/2005 | Krause et al. |
| 2006/0041026 | A1 | 2/2006 | Mahr et al. |
| 2007/0134180 | A1 | 6/2007 | Simard et al. |
| 2008/0108740 | A1 | 5/2008 | Evers |
| 2008/0184496 | A1 | 8/2008 | Brun et al. |
| 2009/0233062 | A1 | 9/2009 | Nakamura et al. |

(Continued)

FOREIGN PATENT DOCUMENTS

| CN | 111432887 A | 7/2020 |
| CN | 111432888 A | 7/2020 |

(Continued)

OTHER PUBLICATIONS

International Search Report issued in connection with PCT Application No. PCT/EP2019/057811 dated Sep. 4, 2019.
International Search Report and Written Opinion received for PCT Patent Application No. PCT/EP2019/057814, mailed on Sep. 16, 2019.
International Application Serial No. PCT/EP2019/057814, Invitation to Pay Additional Fees mailed Jul. 26, 2019.
International Search Report and Written Opinion received for PCT Patent Application No. PCT/EP2019/068186, mailed on Feb. 2, 2020.
International Search Report and Written Opinion received for PCT Patent Application No. PCT/EP2019/068187, mailed on Dec. 4, 2019.
International Search Report and written opinion received in PCT Patent Application No. PCT/EP2021/067928, mailed on Dec. 22, 2021.

(Continued)

*Primary Examiner* — Andrew S Rosenthal
(74) *Attorney, Agent, or Firm* — Dennemeyer & Associates LLC

(57) ABSTRACT

A multicomponent composition for coloration of materials such as keratin fibers, keratin material, keratin textiles including but not limited to hair, eyebrows, eyelashes, skin, nails and animal fiber textiles is disclosed. The multicomponent composition comprises a first component of a CDI link compound having inert or reactive termini and having at least two groups capable of in situ combination with carbodiimide which preferably are acid groups, a second component of a polycarbodiimide terminated by inert or reactive groups, a third component of a polyamine. Optional additional components are also disclosed.

17 Claims, 3 Drawing Sheets

(56) References Cited

U.S. PATENT DOCUMENTS

| | | |
|---|---|---|
| 2010/0083446 A1 | 4/2010 | Brun et al. |
| 2010/0088036 A1 | 4/2010 | Goddard-Clark et al. |
| 2011/0061179 A1 | 3/2011 | Cremer et al. |
| 2011/0083284 A1 | 4/2011 | Suddaby et al. |
| 2014/0242281 A1 | 8/2014 | Swarup et al. |
| 2014/0336093 A1 | 11/2014 | Koellnberger |
| 2015/0174051 A1 | 6/2015 | Teboul |
| 2016/0120284 A1 | 5/2016 | Crne et al. |
| 2016/0120285 A1 | 5/2016 | Crne et al. |
| 2016/0175212 A1 | 6/2016 | Zhou et al. |
| 2016/0235655 A1 | 8/2016 | Herrlein et al. |
| 2016/0271049 A1 | 9/2016 | Schulze et al. |
| 2017/0001045 A1 | 1/2017 | Aubert et al. |
| 2017/0158888 A1 | 6/2017 | Kang et al. |
| 2017/0189312 A1 | 7/2017 | Van Nguyen et al. |
| 2017/0189314 A1 | 7/2017 | Elsen-Wahrer et al. |
| 2018/0105718 A1 | 4/2018 | Swarup et al. |
| 2018/0263353 A1 | 9/2018 | Crne et al. |
| 2018/0263354 A1 | 9/2018 | Crne et al. |
| 2021/0220251 A1* | 7/2021 | Speckbacher ........ A61K 8/8152 |
| 2021/0401713 A1 | 12/2021 | Herrlein et al. |
| 2022/0054392 A1 | 2/2022 | Herrlein et al. |

FOREIGN PATENT DOCUMENTS

| | | |
|---|---|---|
| DE | 19913625 A1 | 9/2000 |
| DE | 102006011271 A1 | 9/2007 |
| EP | 132960 A2 | 2/1985 |
| EP | 1184426 A2 | 3/2002 |
| EP | 1600148 A1 | 11/2005 |
| EP | 1600149 A1 | 11/2005 |
| EP | 1825883 A1 | 8/2007 |
| EP | 3015134 A1 | 5/2016 |
| EP | 3015135 A1 | 5/2016 |
| EP | 3058934 A1 | 8/2016 |
| EP | 3058989 A1 | 8/2016 |
| EP | 3397346 A1 | 11/2018 |
| FR | 2899795 A1 | 10/2007 |
| FR | 2992559 A1 | 1/2014 |
| JP | S 50-034400 A | 4/1975 |
| JP | S 60-105608 A | 6/1985 |
| JP | 2005-350460 A | 12/2005 |
| JP | 2007-084510 A | 4/2007 |
| JP | 2008-502613 A | 1/2008 |
| JP | 2009-520002 A | 5/2009 |
| JP | 2010-530842 A | 9/2010 |
| JP | 2012-515219 A | 7/2012 |
| JP | 2012-530841 A | 12/2012 |
| JP | 2015-521646 A | 7/2015 |
| JP | 2017-533224 A | 11/2017 |
| KR | 101603845 B1 | 3/2016 |
| KR | 20190028636 A | 3/2019 |
| WO | 2005065632 A1 | 7/2005 |
| WO | 2007071706 A1 | 6/2007 |
| WO | 2009073759 A1 | 6/2009 |
| WO | 2011128255 A1 | 10/2011 |
| WO | 2015097308 A1 | 7/2015 |
| WO | 2016066747 A1 | 5/2016 |
| WO | 2017108599 A1 | 6/2017 |
| WO | 2017117543 A1 | 7/2017 |
| WO | WO-2017117522 A1 * | 7/2017 ............... A45D 7/04 |
| WO | 2017189585 A1 | 11/2017 |
| WO | 2017220781 A1 | 12/2017 |
| WO | 2018039314 A1 | 3/2018 |
| WO | 2018130912 A1 | 7/2018 |
| WO | 2018185345 A1 | 10/2018 |
| WO | 2018234530 A1 | 12/2018 |
| WO | 2019071204 A1 | 4/2019 |
| WO | 2019071207 A1 | 4/2019 |
| WO | 2019211050 A1 | 11/2019 |
| WO | 2020007511 A1 | 1/2020 |
| WO | 2020008073 A2 | 1/2020 |
| WO | 2020008074 A1 | 1/2020 |
| WO | 2020035362 A1 | 2/2020 |
| WO | 2020114647 A1 | 6/2020 |
| WO | 2021032837 A1 | 2/2021 |
| WO | 2021032873 A1 | 2/2021 |

OTHER PUBLICATIONS

European Search Report received for EP Patent Application No. 17195273.2, Extended European Search Report mailed Jan. 11, 2018.

International Search Report and Written Opinion received for PCT Patent Application No. PCT/US2018/054717, Mailed on Dec. 20, 2018.

International Search Report and Written Opinion received for PCT Patent Application No. PCT/US2018/054724, mailed on Feb. 26, 2019.

International Search Report and Written Opinion received for PCT Patent Application No. PCT/US2019/057812, mailed on Jan. 7, 2019.

International Search Report and Written Opinion received for PCT Patent Application No. PCT/EP2019/057811, mailed on Sep. 4, 2019.

International Search Report and written opinion received in PCT Patent Application No. PCT/EP2021/067927, mailed on Dec. 6, 2021.

International Search Report and written opinion received in PCT Patent Application No. PCT/EP2021/067926, mailed on Dec. 7, 2021.

Cansu et al, "Atmospheric Pressure Plasma Jet Treatment of Human Hair Fibers", Journal of Bio-and Tribo-Corrosion, vol. 1:7, No. 1, Feb. 4, 2015.

Zheng et al, "Adhesion of aqueous polyurethane adhesive to human hair", International Journal of Adhesion and Adhesives, Elsevier, Amsterdam, NL, vol. 48, Sep. 30, 2013, pp. 14-19.

Shima et al, "The effect of nitrogen plasma on the skin and hair follicles : a possible promising future for the treatment of alopecia", Archives of Dermatological Research, Springer Berlin Heidelberg, Berlin/ Heidelberg, vol. 312, No. 5, Dec. 6, 2019 , pp. 361-371.

Shao et al.: "Surface Treatment of Wool to Achieve Hydrophilic Fibre and the Effect on Subsequent Dyeing and Protease Treatment", Advanced Materials Research; ISSN 1662-8985; Eco-Dyeing, Finishing and Green Chemistry : Selected, Peer Reviewed Papers From The 2011 International Conference on Eco-Dyeing, Finishing and Green Chemistry (EDFGC 2011), Jun. 8-12, 2011, Hangzhou, China, vol. 441, Jan. 1, 2012 (Jan. 1, 2012), pp. 249-254.

International Search Report and written opinion received in PCT Patent Application No. PCT/EP2021/067925, mailed on Nov. 22, 2021.

International Search Report and Written Opinion received for PCT Patent Application No. PCT/EP2019/057813, mailed on Jul. 11, 2019.

International Search Report and written opinion received in PCT Patent Application No. PCT/EP2021/067924, mailed on Nov. 26, 2021.

Campiglio Chiara Emma et al., "Coss-Linking Strategies for Electrospun Gelatin Scaffolds", Materials, vol. 1, No. 15, Aug. 4, 2019.

International Search Report and written opinion received in PCT Patent Application No. PCT/EP2021/057812, mailed on Jan. 7, 2019.

International Search Report issued in connection with PCT/EP2019/076647 dated Sep. 1, 2020.

* cited by examiner

MULTICOMPONENT IN SITU COLORATION COMPOSITION

CROSS-REFERENCE TO RELATED APPLICATIONS

This is a 35 U.S.C. 371 National Stage Patent Application of International Application No. PCT/EP2019/076647, filed Oct. 1, 2019, which claims priority to U.S. provisional application 62/774,627, filed Dec. 3, 2018, each of which is hereby incorporated by reference in its entirety.

BACKGROUND

Treatments to mammalian or synthetic keratin fibers, and their surfaces (integument/nonwoven/textile), are well known in the art. Of particular note are treatments that alter the color appearance of the hair or provide other colored or reflective properties through surface treatment of the hair; dissolution (absorption) of dye molecules into the keratin fiber or attachment to the fiber surface (so called direct dyes); and/or dissolution of dye precursors into the keratin fiber, followed by reaction of these dye precursors within the hair to form dye species (so called oxidative dyeing). Surface coloration treatments and many soluble dyes can be later washed out. Alternatively, pigments can be adhered to the hair surface to alter the perceived color.

One disadvantage of the known oxidation based technologies in this area is that the methods for applying dye based coloring materials involves compositions that may in some cases cause temporary irritation to the scalp. This prevents the hair coloration experience from being pleasant or a so called wellness experience. Such coloring compositions also alter the hair structure itself, leading to oxidation of the hair surface, and partial degradation to the keratinous proteins from which the hair structure is constructed. With repeated coloring, these changes in hair structure become more pronounced. The color obtained when coloring with such composition is hard to predict, and even highly experienced users can still be surprised with the results that are obtained. Yet another drawback to known technologies is that, once the color is on the hair, the dye based coloring material is difficult to remove and/or cannot be completely removed.

Another disadvantage for the dye based approach is that the application of hair coloration materials can yields uneven results as adherence to the surface and/or penetration of hair coloration materials into the hair can vary with hair type for example for a consumer differing color results may be visible between hair roots and hair tips. This can lead to an unnatural looking result. Some desired differences may still be visible due to the non-uniformity in coloration of the underlying hair, for example subtle difference in strand to strand levels of pheomelanin and eumelanin in a consumer may yield slightly different color results, even when the same color pigments or dyes are applied to a consumer. While some strand to strand variation is needed to provide natural looking hair, too much or too little can again lead to an unnatural looking color result. Due to the number of factors that determine the final hair color result for example, the length of application time, the underlying hair color, the hair changes from root to tip, it is difficult even for experienced users to accurately predict the final color result and look.

A disadvantage of pigment based coloring approaches is the low adherent fastness of the pigment or colored material to the keratin fibers. While the low adherent fastness or remanence has been attributed to the use of film formers that are water soluble, substituting film formers that are classed as water insoluble does not deliver much better remanence. Irrespective of the film former applied, the result is effective removal of the color on the hair after only a few washings with shampoo. Especially for persons who shampoo daily, the rapid color loss creates an undesirable situation.

Another disadvantage for both dye and pigment based approaches is that the application of hair coloration materials often yields uneven results as (1) adherence and or penetration of hair coloration materials to the hair surface or within the hair can vary with hair type for example due to changes in porosity, changes in surface composition due to proximity to scalp and/or age of the user; and (2) even when material is adhered or penetrated into the hair, differences in coloration of the underlying hair, including presence of pheomelanin and eumelanin, may yield different color results, even when the same color pigments or dyes are applied across hair types/colors having different native characteristics.

There is therefore a need for an improved composition and method that not only make the hair coloring experience more pleasant, but also is user friendly, provides appropriate color and luster, and leaves the hair manageable, free flowing and capable of moving naturally and does not result in harm to hair protein.

SUMMARY

According to aspects of the invention, embodiments of the multicomponent composition for coloring treatable material, methods for its production and application, coated treatable material resulting from the multicomponent composition and methods for removal of the coating provide a surface coloration of keratin material and textiles, especially hair, that may be substantially uniform to significantly varied, may give such material an appearance of a lower or higher chroma, shiny or reflective nature. [Hereinafter the combination of keratin materials such as scalp hair, eyebrows, eyelashes, nails and skin as well as textiles will be designated as treatable material.] These aspects provide color remanence during a series of washes with shampoo or soap yet with appropriate formulations can be readily removed to leave the natural state of the treatable material and especially the natural state and/or shade of the keratin material such as hair when hair is the kind of treatable material used. These aspects significantly lessen and/or avoid treatment of treatable material that may cause breakage of keratin protein intermolecular bonds and interruption of mechanical and/or chemical linkages of textiles.

It has been discovered that application of embodiments of the multicomponent composition comprising first, second and third components to treatable material delivers significantly increased remanence. The first and second components with constituents including respectively an CDI link compound and an in situ linking material combine in situ to provide remanence, flexibility, softness and similar properties to the resulting coating. These properties are especially heightened when pretreatment with the third component of a base compound is combined with the first and second components. The combination of the third component pretreatment followed by application of the first and second components achieves a coating on the treatable material with unexpected, remarkable remanence.

One aspect of the invention concerns a multicomponent composition. Embodiments of the multicomponent composition comprise a first component comprising compound having groups capable of undergoing covalent linkage with carbodiimide groups (hereinafter CDI link groups and CDI link compound), a second component comprising an in situ linking material having carbodiimide groups, and a third component comprising a base compound having amine groups. The CDI link and carbodiimide groups are capable of forming covalent linkages in situ with each other. In addition, the in situ linking material and CDI link compound optionally are capable of chain extension by themselves through combination of reactive groups at the termini, or with combination of terminal reactive groups and a fourth component which is a nucleophilic difunctional chain extender. The reactive groups at the termini are other than carbodiimide groups. Furthermore, the first, second and third components typically comprise polymers which in addition to linking through the covalent in situ linkages are also capable of forming entanglement, dipolar, ionic or electrostatic linkages or any combination thereof among themselves and also with the treatable material.

The multicomponent composition also comprises a medium with one or more of the first, second and third components and pigment microparticles incorporated into one or more of the first, second and third components. The medium comprises a liquid organic compound capable of forming a solution with a minor amount of water such as up to about 10 percent by water (hereinafter a liquid organic compound partially miscible with water). The liquid organic compound typically is known as a volatile organic solvent. Exemplary embodiments include an alcoholic medium that may be free of intentionally added water or may have intentionally added water up to about 10 percent by weight relative to the total weight of the medium.

The first, second and third components are typically maintained separately. The first and second components of the multicomponent composition may be mixed together before application to the treatable material, may be applied separately and simultaneously to the treatable material, or may be applied sequentially to the treatable material. In some embodiments, a mixture of first, second and third components can be maintained in a slightly basic medium to minimize or temporarily and substantially to essentially prevent their reaction. Removal of the basic medium in such embodiments promotes the combination of the first, second and third components. The CDI link compound and the in situ linking material interact through their respective functional groups to form a wash resistant coating with pigment microparticles on the treatable material. Prior to sequential, simultaneous or mixed application of the first and second components to the treatable material, the third component may be applied as a pretreatment of the treatable material. Appropriate selection of the third functional groups of the base compound is believed to enable covalent, electrostatic, coordinate, hydrogen bond and/or lipophilic entanglement linking among the CDI link compound, the in situ linking material, the base compound and the treatable material. This interaction is believed to link all substances together to make them resistant to removal by ordinary means. Indeed, this combination with the pretreatment melds the components together as a highly remnant coating on treatable material.

The embodiments of the first component include a CDI link compound which may be an organic small molecule having at least two CDI link groups or an organic oligomer or polymer with at least two CDI link groups or a silicone polymer with at least two CDI link groups or an organosilicone block polymer with at least CDI link groups or any combination of the small molecule, the organic oligomer or polymer, the silicone polymer and the organosilicone block polymer. The CDI link group may be an acid group including a carboxylic acid, a sulfonic acid, a phosphoric acid or any combination thereof, or may be an amine group or may be a thiol group or may be any combination of an acid group, an amine group or a thiol group. Preferably, the CDI link group is a carboxylic acid or an amine group. More preferably, the CDI link group is a carboxylic acid. The CDI link groups are designed to interact with the carbodiimide groups of the in situ linking material (the second component) and under certain compatible circumstances, the amine groups of the third component (the base compound). The CDI link organic or silicone polymer may be any linear, branched, cyclic, dendritic, star or fullerene configuration. The organic polymer is based on various combinations of CDI link group monomeric units, olefinic monomers, polyol monomers, ester monomers, amide monomers, carbonate monomers, natural occurring monomers and polymers having repeating monomeric residues based on carbon or carbon in combination with other atoms such as oxygen and/or nitrogen and/or sulfur, and any combination thereof. The silicone polymer is based upon MDTQ alkylsiloxane units having pendant organic groups terminated by CDI link groups and/or having organic oligomeric blocks in the polymer back bone chain which have pendant CDI link groups.

The CDI link groups of the organic and silicone polymers may be arranged on the polymer backbone as pendant groups, arranged as terminal groups or may be a combination thereof. The CDI link groups number at least 2 per compound molecule and preferably may range in number from 2 to 1000 per molecule.

Embodiments of the organic and/or silicone polymers may also have terminal reactive groups that either are self-reactive or are reactive with the fourth component described below. The optional terminal reactive groups of the organic and/or silicone polymers are other than carbodiimide groups. When present, these terminal reactive groups chain extend the organic and/or silicone polymers. The terminal reactive groups of the organic and/or silicone polymers may be of the same configuration class as class of groups constituting the reactive termini of the in situ linking material. However, the reactive termini of the organic and/or silicone polymers and the reactive termini of the in situ linking material may be chosen independently.

The embodiments of the second component include an in situ linking material with multiple carbodiimide groups that are designed to interact with the CDI groups of the first component. The in situ linking material also has termini that are a) inert or b) reactive. Preferably the in situ linking material has reactive termini that are capable of and are adapted to self-react or are capable of and are adapted to react with a compatible difunctional nucleophilic compound. The difunctional nucleophilic compound is the fourth component. The in situ linking material is composed of a linear and/or branched repeating units of carbodiimide groups linked together by saturated aliphatic divalent radicals, divalent aromatic radicals or divalent alkaromatic radicals. The carbodiimide groups may be distributed throughout the core backbone or may be branch chains and/or a combination thereof. The carbodiimide groups number at least 2 per molecule and preferably may range in number from 2 to 1000 per molecule.

The embodiments of the third component include a base compound with third functional groups which are amine groups. The third functional groups are capable of forming linkages with the CDI link compound, with the in situ linking material, the treatable material, or any combination thereof. The base compound is composed of a small molecule or an oligomeric or polymeric organic or silicone core to which is covalently bonded pendant or terminal or pendant and terminal amine groups. The third component is typically and usually adapted to be combined with the treatable material as a pretreatment prior to sequential, simultaneous or mixed application of the first and second components. The third component is typically maintained in a separate container relative to the first and second components.

Embodiments of the multicomponent composition further comprise a fourth component comprising a nucleophilic or electrophilic difunctional compound serving as a chain extending agent for the second component having reactive termini that are not self-reactive. The difunctional compound may be a diamine, a diol, a dithiol, an aminoalcohol, an aminothioalcohol, a thiol-alcohol or any combination thereof. Typically, the fourth component also comprises a medium.

The molar ratio of in situ linking material to CDI link compound and to the base compound will depend upon the kinds and numbers of CDI links, carbodiimide groups, the reactive termini of the first and/or second components, the degree of covalent linking desired or needed and the size of the polymeric chains. These features combine to achieve the desired properties of the coating of the composition. The in situ linking and the optional reactive termini chain extension improve resistance of the coating toward removal with dilute soap or shampoo aqueous solutions while preserving free hair flow properties and avoid stickiness and clumping.

Embodiments of the pigment microparticles used on the multicomponent composition described herein may comprise organic pigment microparticles, which imparts color to the hair, and colored reflective microparticles, for providing light scattering properties to the colored hair. Embodiments may also include microparticle metal flakes for light reflection to add shine to the desired color or to make the hair appear to be lighter than the starting hair color.

An aspect of the invention concerning the method for combining the multicomponent composition with treatable material comprises applying the third component as a pretreatment to the treatable material and preferably at least partially drying to form pretreatable treatable material. Next, the first and second components may be sequentially or simultaneously applied or premixed and applied to the pretreatable treatable material. The pretreatable treatable material coated with the first and second components may be dried with optional heat to cause formation of a colored coating on the treatable material. The fourth component may be combined with the first and second components during their application as part of the premix or as a simultaneous addition, or prior to their application, or following their application under appropriate circumstances wherein the second component has reactive termini that are not self-reactive. The embedded pigment microparticles are somewhat to substantially uniformly distributed in and throughout the coating.

In addition to the CDI link compound, in situ linking material, base compound, difunctional nucleophile and pigment microparticles of the first, second, third and fourth components, the multicomponent composition may optionally contain additional ingredients helpful and beneficial to the treatable material and/or its coloration. These additional ingredients include but not limited to one or more of dispersants, surface treatment agents for the pigment microparticles, plasticizers, conditioners, suspending agents, thickening agents, adjuvants, moisturizers, surfactants, fatty substances, hair feel modification agents, waxes, fatty amides and soluble organic dyes of colors different from those of the pigment microparticles.

An aspect of the invention concerning the remanence of the coating on the treatable material, and especially on hair strands, comprises the ability of the coating to somewhat to substantially resist dissolution by ordinary cleaning of the treatable material such as hair. Ordinary cleaning may involve washing with soap and water, washing with an aqueous dilution of shampoo and washing with water.

An aspect of the invention concerning removal of the coating on the treatable material, such as on hair strands, comprises application of a trigger formulation designed to remove the coating. The trigger formulation embodiments of the invention may comprise a medium with an organic acid, a lipophilic organic solvent, a solubilizing organic base and water. Embodiments of the trigger formulation enable coating removal at a substantially complete level compared with the level provided by a dilute aqueous mixture of soap or a shampoo containing an anionic surfactant.

An additional aspect of the invention concerns the application of the multicomponent composition to treatable material such as brows, lashes, nails and skin as well as to hair on the scalp. Additionally, the multicomponent composition may be applied to textiles made of plant material, animal hair or fur or synthetic material. The multicomponent composition may be applied to these kinds of treatable materials and to textiles with appropriate adjustments of the composition parameters within the parameters described for hair on the scalp. Typically, the eyebrow hair may be treatable with the multicomponent composition using parameters similar to or the same as those of the multicomponent composition for hair on the scalp. The hair of eyelashes typically can be similarly treatable with the multicomponent composition for eyebrows and the viscosity adjusted to provide a somewhat more viscous composition for application to the eye lashes. For nails and skin, the parameters of the multicomponent composition may have a higher solids content and higher number of first, second and third functional groups for in in situ linking than the parameters for the hair and viscosity may be adjusted to provide embodiments that will not readily drip or otherwise flow off the nail or skin surface to which the multicomponent composition is applied. The multicomponent composition for nails and textiles will preferably have higher in situ linking to provide a durable coating or covering on the keratin nail and textiles.

DEFINITIONS

Figure 1:
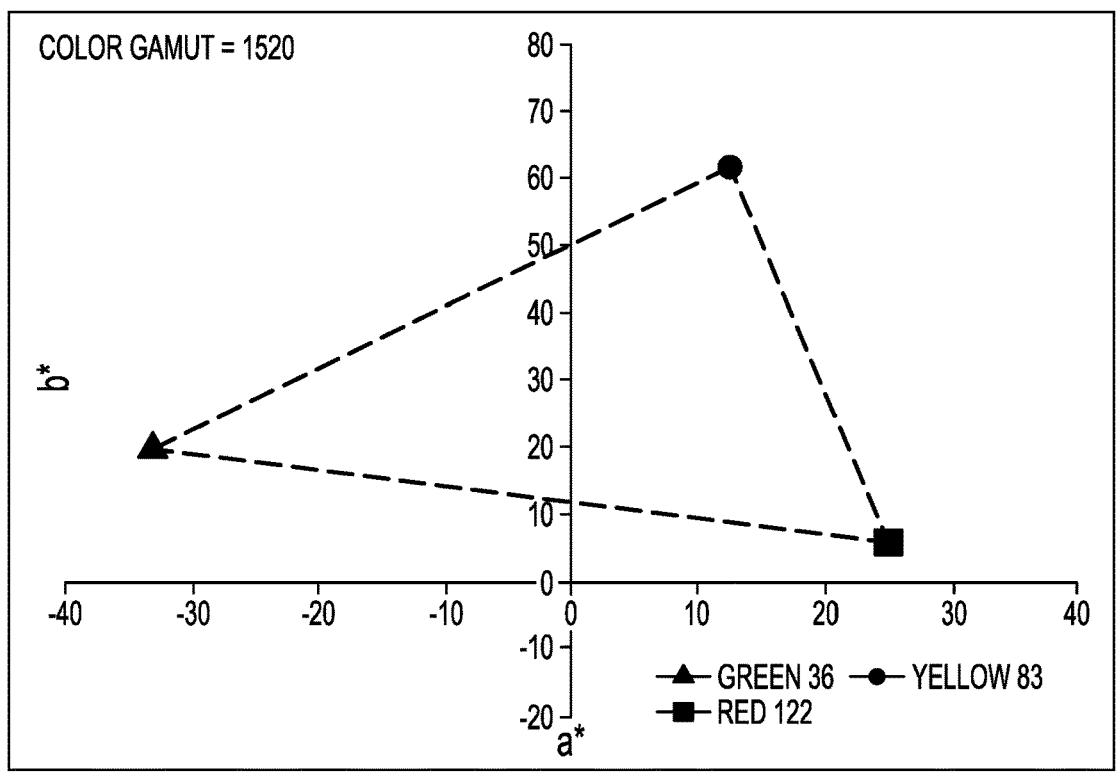
FIG. 1 depicts a Gamut plot of green, yellow and red pigments.

Unless defined otherwise, all technical and scientific terms used herein have the same meaning as commonly understood by a person of ordinary skill in the art.

As used in the specification and the appended claims, the singular forms "a," "an" and "the" include plural referents unless the context clearly dictates otherwise.

The term "may" in the context of this application means "is permitted to" or "is able to" and is a synonym for the term "can." The term "may" as used herein does not mean possibility or chance.

The term and/or in the context of this application means one or the other or both. For example, an aqueous solution of A and/or B means an aqueous solution of A alone, an aqueous solution of B alone and an aqueous solution of a combination of A and B.

The terms (meth)acrylic acid and (meth)acrylate mean herein both of the acrylic acid and methacrylic acid and both of the acrylate methacrylate esters. The parenthesis surrounding the prefix "meth" means that the term (meth) acrylic encompasses both of the methacrylic acid and acrylic acid monomers. This term has the same meaning when used with polymers. Without a parenthesis, the term "methacryl" means only the methacrylic acid and esters and does not include acrylic acid and esters. The suffix "ate" means that the term (meth)acrylate is an ester formed by combination of a monoalcohol or diol with methacrylic acid or acrylic acid.

Acid value is determined by the usual and customary method described in chemical literature.

The molecular weight of a polymer or oligomer used according to the invention may be measured by a weight average molecular weight, and the distribution of molecules of different molecular weights of a polymer or oligomer used according to the invention is determined by its polydispersity index. Molecular weight is expressed as Daltons (Da), kilo Daltons (KDa) and mega Daltons, which is million Daltons or (MDa). The acronym WMW stands for weight average molecular weight and Mn is the number average molecular weight of a given polymer. Polydispersity is a unit-less number and indicates the breadth of the distribution of the polymer molecular weights and is defined as the WMW/Mn.

The term "about" is understood to mean±10 percent of the recited number, numbers or range of numbers.

The term "about 0 wt. %" is understood to mean that no substance, compound or material to which zero (0) refers is present, up to a negligible but detectable amount is present, assuming that the detectability can be determined on a parts per million basis.

The term "hydrogen bonding" is understood to mean a compound or group that contain a hydroxyl group or a hydrogen that is part of a polar group, such as but not limited to an amine, a carboxylic acid, a urethane group, a urea group and other similar groups and that can form molecule to molecule interaction through electrostatic or ionic interaction between positive and negative dipolar or ionic groups.

As used herein, the terms "covalent, coordinate, electrostatic, ionic, dipolar and entanglement or entwining interactions" mean a chemical relationship between two atoms or two groups of atoms. The interaction includes a covalent bond between the atoms such as the covalent bond between the two carbons of ethane. The interaction includes a coordinate bond between two or more atoms such as the coordinate bond between oxygen and sulfur of the sulfate anion ($SO_4^{-2}$) or a complex of zinc and EDTA. The interaction includes an electrostatic or ionic interaction between two charged atoms or particles such as the interaction between sodium and chloride of salt or between ammonium and acetate of ammonium acetate. Dipolar interaction includes hydrogen bonding such as the interaction between water and the hydroxyl of methyl alcohol. The interaction includes entanglement or entwining which is lipophilic interaction or mechanical/physical twisting together such as is present in the molecules of polyethylene.

Where features or aspects of the invention are described in terms of Markush groups, those skilled in the art will recognize that the invention is also thereby described in terms of any individual member or subgroup of members of the Markush group. For example, if X is described as selected from the group consisting of methyl, ethyl or propyl, claims for X being methyl and claims for X being ethyl and propyl are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

If a value of a variable that is necessarily an integer, e.g., the number of carbon atoms in an alkyl group or the number of substituents on a ring, is described as a range, e.g., 0-4, what is meant is that the value can be any integer between 0 and 4 inclusive, i.e., 0, 1, 2, 3, or 4. Similarly, values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range.

Hair and hair strands mean natural or synthetic keratin fibers. Hair, hair strands and keratin fibers are used interchangeably in this document. Natural keratin fibers include those from mammals and/or on mammals including human, primate, ruminant, camelid, equine, rodent and neovison including but not limited to cow, sheep, deer, goat, buffalo, *lama*, alpaca, camel, guanaco, vicuna, horse, antelope, moose, elk, rat, mouse, beaver, rabbit, mink, monkey, ape and similar species. Natural keratin fibers may include hair, fur or nails. Synthetic fibers include polyamides, polyacrylic and polyester fibers, especially polyamide fibers which are used for artificial hair implantation.

Oligomer and polymeric compounds mean repeating units of carbon-carbon backbones with side chains of various classes of groups. The oligomeric and polymer compounds may have side chains of aliphatic groups such as alkyl and/or alkenyl groups, aromatic groups such as phenyl and/or naphthyl groups, heteroaromatic groups such as pyridinyl, quinolinyl, quinazolinyl groups, carboxyl ester groups, carbamide groups, sulfamide groups, alkoxy groups, monomeric, oligomeric and/or polymeric ether groups, monomeric, oligomeric and/or polymeric imino groups, and under some circumstances where reactive interaction with carbodiimide groups would be minimized or not competitive with carboxylic acid groups the oligomer and polymer compounds may include side chains and pendant groups containing hydroxyl groups, amine groups and/or mercapto groups. The oligomeric and polymeric compounds may be composed of a single monomeric unit structure such as polyacrylic acid or may have several different monomeric unit structures such as poly (styrene-acrylic acid-methyl acrylate). The multiple monomeric unit structures may include side chains of esters, amides and side chains such as alkyl groups or aromatic groups or similar groups which not derived from carboxylic acid groups.

As used herein, the term "transfer resistance" generally refers to the quality exhibited by compositions that are not readily removed by contact with another material, such as, for example, an item of clothing or the skin. Transfer resistance can be evaluated by any method known in the art for evaluating such. For example, transfer resistance of a composition can be evaluated by the amount of product transferred from a wearer to any other substrate after the expiration of a certain amount of time following application of the composition to the hair. The amount of composition transferred to the substrate can then be evaluated and compared. For example, a composition can be transfer resistant if a majority of the product is left on the wearer's hair. Preferably little or no composition is transferred to the substrate from the hair.

As used herein, the term "minimally alters the keratin material or fibers, upon application" generally means that after removal of the composition coating on the keratin fibers such as hair, the keratin fibers are returned to a substantially unaltered state. The state of the keratin fibers such as hair can be assessed for example using ATR FT-IR for oxidative damage as described later or through tensile testing methods known to those skilled in the art for assessing fiber strength for example using equipment such as those designed and sold by Dia-Stron™.

As used herein, the term "setting" means converting the multicomponent composition to a solid coating through the application of means designed to remove or otherwise separate the medium from the other constituents of the multicomponent composition so as to leave a solid coating of the organic polymer, in situ linking material and base compound and other optional ingredients of the composition.

The terms "in situ linking" and "in situ linkable" and "cross linkable" mean the potential at a future time to form covalent bonds and coordinate linkages between molecules to provide interactions and/or connections between molecules. The terms "in situ linked" and "cross linked" mean that in the present state, covalent bonds and coordinate linkages have already occurred. Additionally, ionic, electrostatic, entanglement, hydrogen bonding and similar non-covalent bonding interactions may also be present when there is in situ linking. The covalent nature of in situ linking enables a molecular proximity that also promotes other intermolecular interactions such as but not limited to the foregoing non-covalent bonding interactions.

"in situ" is a Latin phase meaning in its original place. In the context of this invention, it means an activity such a linking reaction or arrangement by covalent, coordinate, entanglement, ionic, hydrogen bonding, polar coupling or electrostatic activity between two or more molecules that occurs in place on the treatable material such as hair.

"Aliphatic substituent, group or component" refers to any organic group that is non-aromatic. Included are acyclic and cyclic organic compounds composed of carbon, hydrogen and optionally of oxygen, nitrogen, sulfur and other heteroatoms. This term encompasses all of the following organic groups except the following defined aromatic and heteroaromatic groups. Examples of such groups include but are not limited to alkyl, alkenyl, alkynyl, corresponding groups with heteroatoms, cyclic analogs, heterocyclic analogs, branched and linear versions and such groups optionally substituted with functional groups, as these groups and others meeting this definition of "aliphatic" are defined below.

"Aromatic substituent, group or component" refers to any and all aromatic groups including but not limited to aryl, aralkyl, alkaromatic, heteroalkylaryl, heteroalkylheteroaryl and heteroaryl groups. The term "aromatic" is general in that it encompasses all compounds containing aryl groups optionally substituted with functional groups (all carbon aromatic groups) and all compounds containing heteroaryl groups optionally substituted with functional groups (carbon-heteroatom aromatic groups), as these groups and others meeting this definition of "aromatic" are defined below. The terms under this definition of "aromatic" that include alkyl such as but not limited to aralkyl, alkaromatic and heteroalkylaryl mean that an alkyl group is covalently bound to the aromatic group especially but not limited to an arrangement in which the alkyl group is a linking group with other substituents or with another moiety or between aromatic groups, such as but not limited to 2,2-bisphenylmethylene as in 4,4'-methylene diphenyl diisocyanate.

As used herein, the term "optionally" means that the corresponding substituent or thing may or may not be present. It includes both possibilities.

"Alkyl" refers to a straight or branched hydrocarbon chain radical consisting solely of carbon and hydrogen atoms, unless otherwise specifically described as having additional heteroatoms or heterogroups. The alkyl group contains no unsaturation, having from one to twenty-two carbon atoms (e.g., C1-C24 alkyl). Whenever it appears herein, a numerical range such as "1 to 24 refers to each integer in the given range; e.g., "1 to 24 carbon atoms" means that the alkyl group may consist of 1 carbon atom, 2 carbon atoms, 3 carbon atoms, etc., up to and including 24 carbon atoms, although the present definition also covers the occurrence of the term "alkyl" where no numerical range is designated. In some embodiments, it is a C1-C4 alkyl group. Typical alkyl groups include, but are in no way limited to, methyl, ethyl, propyl, isopropyl, n-butyl, iso-butyl, sec-butyl isobutyl, tertiary butyl, pentyl, isopentyl, neopentyl, hexyl, septyl, octyl, nonyl, decyl, and the like. The alkyl is attached to the rest of the molecule by a single bond, for example, methyl (Me), ethyl (Et), n-propyl, 1-methylethyl (iso-propyl), n-butyl, n-pentyl, 1,1-dimethylethyl (t-butyl), 3-methylhexyl, 2-methylhexyl, and the like.

"Alkylenyl" refers to a straight or branched divalent hydrocarbon chain consisting solely of carbon and hydrogen atoms, unless otherwise specifically described as having additional heteroatoms or heterogroups. The alkylenyl group contains no unsaturation has a valence bond at either end of the chain and has a numerical range of carbon atoms of 1 to 24, which numerical range includes each integer in the range. An example of a divalent hydrocarbon chain designated as an alkylenyl group is —CH2-CH2-CH2-C2H2- which is butylenyl.

"Cycloalkyl" refers to a monocyclic or polycyclic radical that contains only carbon and hydrogen, and may be saturated, or partially unsaturated. Cycloalkyl groups include groups having from 3 to 24 ring atoms (i.e., C2-C10 cycloalkyl). Whenever it appears herein, a numerical range such as "3 to 24" refers to each integer in the given range; e.g., "3 to 24 carbon atoms" means that the cycloalkyl group may consist of 3 carbon atoms, etc., up to and including 10 carbon atoms. In some embodiments, it is a C3-C8 cycloalkyl radical. In some embodiments, it is a C3-C5 cycloalkyl radical. Illustrative examples of cycloalkyl groups include, but are not limited to the following moieties: cyclopropyl, cyclobutyl, cyclopentyl, cyclopentenyl, cyclohexyl, cyclohexenyl, cycloseptyl, cyclooctyl, cyclononyl, cyclodecyl, norbornyl, and the like.

"Alkoxy" refers to the group —O-alkyl, including from 1 to 24 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. "Lower alkoxy" refers to alkoxy groups containing one to six carbons. In some embodiments, C1-C4 alkyl is an alkyl group which encompasses both straight and branched chain alkyls of from 1 to 4 carbon atoms.

"Amino" or "amine" refers to an —N(Ra)2 radical group, where each Ra is independently hydrogen or linear, branched or cyclic alkyl of 1 to 6 carbons. When an —N(Ra)2 group has two Ra other than hydrogen they can be combined with the nitrogen atom to form a 4-, 5-, 6-, or 7-membered ring.

"Aryl" refers to a conjugated pi radical with six or ten ring atoms which has at least one ring having a conjugated pi electron system which is carbocyclic (e.g., phenyl, fluorenyl, and naphthyl). Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. The term includes monocyclic or monocyclic-ring polycyclic (i.e., rings which share adjacent pairs of ring atoms) groups.

"Heteroalkyl" "heteroalkenyl" and "heteroalkynyl" include optionally substituted alkyl, alkenyl and alkynyl radicals and which have one or more skeletal chain atoms selected from an atom other than carbon, e.g., oxygen, nitrogen, sulfur, phosphorus or combinations thereof. A numerical range may be given, e.g. C1-C4 heteroalkyl which refers to the chain length in total, which in this example is 24 atoms long. For example, a —CH2OCH2CH3 radical is referred to as a "C4" heteroalkyl, which includes the heteroatom center in the atom chain length description. Connection to the rest of the molecule may be through either a heteroatom or a carbon in the heteroalkyl chain.

"Heteroaryl" or heteroaromatic refers to a 5, 6 or 10-membered aromatic radical (e.g., C5-C13 heteroaryl) that includes one or more ring heteroatoms selected from nitrogen, oxygen and sulfur, and which may be a monocyclic, bicyclic, tricyclic or tetracyclic ring system. Whenever it appears herein, a numerical range refers to each integer in the given range. An N-containing "heteroaromatic" or "heteroaryl" moiety refers to an aromatic group in which at least one of the skeletal atoms of the ring is a nitrogen atom. The polycyclic heteroaryl group may be monocyclic or non-monocyclic. The heteroatom(s) in the heteroaryl radical is optionally oxidized. One or more nitrogen atoms, if present, are optionally quaternized. The heteroaryl is attached to the rest of the molecule through any atom of the ring(s). Examples of heteroaryls include, but are not limited to adeninyl, azabenzimidazolyl, azaindolyl, azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzoxazolyl, benzopyranyl, benzopyranonyl, benzofuranyl, benzofuranonyl, benzofurazanyl, benzothiazolyl, benzothienyl (benzothiophenyl), benzothieno[3,2-d]pyrimidinyl, benzotriazolyl, benzo[4,6]imidazo[1,2-a]pyridinyl, carbazolyl, cinnolinyl, cyclopenta[d]pyrimidinyl, 6,7-dihydro-5H-cyclopenta[4,5]thieno[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furazanyl, furanonyl, furo[3,2-c]pyridinyl, 5,6,7,8,9,10-hexahydrocycloocta[d]pyrimidinyl, 5,6,7,8,9,10-hexahydrocycloocta[d]pyridazinyl, 5,6,7,8,9,10-hexahydrocycloocta[d]pyridinyl, isothiazolyl, imidazolyl, imidazopyridinyl, isoxazolopyridinyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyranyl, pyrrolyl, pyrazolyl, pyrazolo[3,4-d]pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]pyrimidinyl, 6,7,8,9-tetrahydro-5H-cyclohepta[4,5]thieno[2,3-d]pyrimidinyl, 5,6,7,8-tetrahydropyrido[4,5-c]pyridazinyl, thiazolyl, thiadiazolyl, thianaphthalenyl, thiapyranyl, triazolyl, tetrazolyl, triazinyl, thieno[2,3-d]pyrimidinyl, thieno[3,2-d]pyrimidinyl, thieno[2,3-c]pyridinyl, and thiophenyl (i.e., thienyl), xanthinyl, guaninyl, quinoxalinyl, and quinazolinyl groups.

"Heterocyclic" refers to any monocyclic or polycyclic moiety comprising at least one heteroatom selected from nitrogen, oxygen and sulfur. As used herein, heterocyclyl moieties can be aromatic or nonaromatic. The moieties heteroaryl and heterocyclyl alkyl are members of the heterocyclic group.

Zeta potential relating to pigment microparticles means the electrokinetic potential of extremely small particles suspended in colloidal dispersions. It is caused by the net electrical charge at the particle interface with the suspending fluid. It is an indicator of the stability of a colloidal dispersion. The magnitude indicates the degree of electrostatic repulsion between adjacent similar charged particles in a dispersion. At zero or minimal + or − potential, rapid coagulation can occur. At a + or − zeta potential above about 40, good colloidal stability is maintained. Zeta potential can be measured using approaches known to those skilled in the art. For example a Zetasizer Nano Z from Malvern Panalytical may be used to assess the zeta potential of the components.

The term "textile" as used herein has its ordinary and customary meaning and includes cloth, fabric or other material made out of natural plant fibers, synthetic fibers, metal fibers, carbon fibers, animal fibers such as may be derived from feathers, sinew, ligament, muscle and/or bone. The fibers are combined by weaving, felting, gluing, tacking, spinning, extruding, blow melting or other-wise formed into at least a somewhat coherent mass typically considered to be cloth, fabric, sponge rubber, foam, woven or nonwoven material. Rugs, bedsheets, clothing, coats, hats, underwear, socks, seat covers, seat cushions, pillows, and similar materials are textiles. Included also is paper made of plant or synthetic material such as typing paper, writing paper, foil, parchment papers, wax paper, aluminum foil and similar flat, thin materials.

DETAILED DESCRIPTION

Aspects of the present invention generally relate to disadvantages of known technologies for coloration of treatable material, especially keratin material such as but not limited to hair by limiting damage to keratin proteins within the material, particularly after repeated dying events; facilitating the quantitative or substantially quantitative on demand removal of the color; limiting quick or inconsistent wash-out of the coloring means; limiting the potential for temporary irritation of the scalp upon applying known compositions (e.g., containing hydrogen peroxide at and an elevated pH); and shortening at least one of the treatment process and post-treatment processes, including drying time. In sum, the present invention is directed to compositions for coloration of treatable material that provide effective color to treatable material and will remain on the treatable material until it is desired to remove the color. This makes the treatment process more pleasurable for the user and or stylist. It is also desired that the results are predictable, enabling the users to achieve their target hair color result.

The composition, method and coating aspects of the invention are directed to embodiments of a multicomponent composition that are adapted to provide colored coating embodiments on the surfaces of treatable material such as but not limited to hair strands. The colored coating embodiments have "color fastness" or remanence that enables them to remain in somewhat to substantial to essential original composition on the treatable material through at least a series of washings with aqueous media containing soap and/or shampoo. Yet by manipulation of the triggering formulation according to the invention, the coating embodiments can be removed from the treatable material to leave it in its substantially to essentially natural state before application of the multicomponent composition to the treatable material. The multicomponent composition embodiments minimally alter treatable material upon their application thereon and the embodiments of the method of application may be accomplished in short times.

The embodiments of the multicomponent composition according to the invention comprise first, second, third and fourth components formulated to provide the desired coloration of treatable material, to provide the desired remanence and to provide the ability for removal without damage to the treatable material. Sequential, simultaneous or premixed application of the first and second components will provide the desired benefits. Pretreatment of the treatable material with the third component followed by sequential, simultaneous or premix application of the first and second components delivers the exceptional results for remanence and appropriate quality parameters especially for the treatable material. The combination of the three components of the multicomponent composition in the aspect of use and application to treatable material provides an unexpected synergy in delivering outstanding properties of remanence and tactile quality for the colored coating on treatable material.

A. The Multicomponent Composition

The First Component: CDI Link Compound

The first component of the multicomponent composition comprises an CDI link compound in a compatible medium. The CDI link compound comprises homopolymers, copolymers, terpolymers, multiple monomeric unit polymer embodiments and/or small molecules having at least two pendant CDI link groups. The CDI link groups may comprise acid groups including carboxylic acid groups, sulfonic acid groups and phosphoric acid groups. The CDI link groups may also comprise amine groups or thiol groups. The amine and/or thiol groups may be present alone in the CDI link compound or may be present in combination with the acid groups; however, the preferable arrangement is a CDI link compound with amine or thiol groups alone when a compound with amine or thiol groups is to be employed. Overall, carboxylic acid groups are preferred for all versions of the compound, including organic polymers, silicone polymers, organosilicone polymers and small molecules. Most preferably the CDI link compound is a carboxylic acid compound with optional reactive termini. As an organic, silicone or organosilicone polymer, the CDI link compound and especially the acid bearing compound may be configured to have a linear, branched, cyclic, dendritic, star, graft, block, or fullerene structural arrangement or any combination thereof. The polymer may be an organic polymer, a silicone polymer or an organosilicone polymer of a block configuration.

CDI Link Organic Polymers

Embodiments of the CDI link compound of the first component comprise embodiments of one or more organic polymers bearing two or more CDI groups, preferably acid groups and more preferably carboxylic acid groups. The CDI link polymer may comprise minimal to substantial water solubility or dispersibility because of the presence of the acid and or amine groups. The solubility may be enhanced by variation of pH. For example, Carbopol is an example of an organic polymer bearing carboxylic acid groups and is substantially insoluble in aqueous medium at acidic pH but can be rendered soluble is in aqueous medium at basic pH.

The CDI groups may be arranged on the organic polymer as pendant groups, arranged as terminal groups or may be a combination thereof. The CDI groups may be distributed along the organic polymer backbone, along polymer branches or any combination thereof. The CDI groups may be singly or multiply arranged at a single location of the polymer and in either arrangement may be distributed throughout the backbone and branches. The number of CDI groups per molecule of organic polymer and especially the number of carboxylic acid groups per molecule of organic polymer is least two and preferably is at least three and more preferably at least four and most preferably at least five. Not all organic polymer molecules may bear the same number of CDI groups. For the foregoing arrangements and preferences, the preferred CDI group is carboxylic acid.

Embodiments of the CDI link organic polymer comprises oligomers and polymers of appropriate monomeric units combined with CDI link monomeric units such as but not limited to olefinic carboxylic acid, olefinic sulfonic acid, olefinic phosphoric acid, olefinic amine, olefinic thiol and any compatible combination thereof, preferably olefinic carboxylic acid monomeric units. The appropriate monomeric units include but are not limited to one or more olefin monomers, ester units of diacids/diol monomers, ester units of hydroxy acid monomers, ether monomeric units, thioether monomeric units, polyol monomeric units, alkylene oxide monomeric units, alkylene imine monomeric units, urethane monomeric units urea monomeric units, amide units of diacid/diamine monomers, amide units of amino acid monomeric units, amino acid units providing peptides, gelatin or biopolymers; carbohydrate monomeric units providing alginates, cellulosic derivatives, polysaccharides; hydroxylated polyester, acrylate functionalized polyester, polyester polyurethane acrylic copolymer, polyurethane-polyglycol copolymer, polymer may be selected polycarbonate diols, styrene-allyl alcohol copolymer, ketone resins; as well as other repeating residues based on carbon or carbon in combination with other atoms such as oxygen and/or nitrogen, and any combination thereof.

The CDI link organic polymer may have non-polar, non-protic pendant moieties such as but not limited to linear, branched or cyclic alkyl groups optionally including oxygen, nitrogen, ester, oxycarbonyl, amide, thioether, ether, sulfonyl within or along the alkyl groups. These pendant moieties also include aromatic groups, heteroaromatic groups, small to oligomeric repeating carbon units, all with the same optional heteroatoms and heteroatom groups described for the alkyl chains and/or moieties. These pendant moieties may also be oligomeric or polymeric silicone moieties constructed of organosiloxane units.

The CDI link groups, preferably carboxylic acid groups, may be covalently linked to the polymer chain through any manner of linear and/or branched carbon connection arrangements or units. The connection units may covalently bear one or a multiple number of CDI link groups, preferably carboxylic acid groups. These carbon connection arrangements may be but are not limited to a carbon connection unit comprising a linear, branched or cyclic C1-C24 alkylenyl, oxyalkyenyl, alkylenyloxy or oxyalkylenyloxy unit, a C2-C24 alkanoyl or oxyalkanoyl unit, a C6-C24 aromatic or oxyaromatic unit, a C5-C24 heteroaromatic or oxyheteroaromatic unit having one or two heteroatoms selected from nitrogen, oxygen and sulfur, a (Cz-O-Cz)n polyether unit wherein z is an integer of 1 to 6 and n is an integer of 2 to 6, a (Cy-NH-Cy)m polyimino unit wherein y is an integer of 1 to 6 and m is an integer of 2 to 6. The recitation of "oxy" before or after an organic group means that the organic group such as alkylenyl is connected to the polymer chain through an oxygen. For example, an alkylenyl group is connected to the polymer chain by a carbon-carbon bond while an oxyalkylenyl group is connected to the polymer chain by a carbon-oxygen bond.

The kinds of CDI link groups of the CDI link organic polymer embodiments of the first component according to the invention have a hierarchy of reaction with the carbodiimide group. The acid group reaction rate with the carbodiimide group is fast so that the acid group competes effectively with amine and thiol groups for reaction with the carbodiimide group. For the acid groups, the carboxylic acid group provides a stable N-acyl urea configuration from the acid carbodiimide reaction. The corresponding N-sulfonyl urea and N-phosphoryl urea configurations may not have the same stability as the N-acyl urea. For this reason among others such as the availability of sulfonic acid and phosphoric acid polymers, the carboxylic acid polymers are preferred as the organic polymer version of the first component. For embodiments of the first component bearing acid and one or both of the amine and thiol groups, the stoichiometry dictates whether noticeable reaction between carbodiimide groups and the amine and/or thiol groups is present. With a sufficient stoichiometry of the carboxylic acid and carbodiimide groups, the carboxylic acid groups will out compete the amine and/or thiol groups for reaction with the carbodiimide. Also, when acid and amine groups are both present at the same time, readily available sterically unhindered amine groups may at least in part undergo reaction with the O-acyl urea intermediate formed between the acid and the carbodiimide to form an amide from the amine and acid groups of the organic polymer. To avoid or minimize this situation, the number of amine groups preferably are significantly lower than the number of acid groups in an arrangement in which the organic polymer has both. Further, the organic polymer with amine groups may be added subsequent to combination of in situ linking material and the organic polymer with acid groups. In this fashion, the stable N-acyl urea group will be formed which does not react with amine groups. The organic polymer with the preferred carboxylic acid group is adapted to combine reactively with the carbodiimide group of the second component. Consequently, if an organic polymer is to be an amine or thiol compound, the preference is to have the organic polymer be exclusively substituted by amine or thiol groups.

This substitution pattern of the acid/amine/thiol organic polymer provides a realization of the breadth of the kind of organic polymers that can function as the organic polymer through incorporation of the CDI link group. The incorporation can be accomplished as an intrinsic feature of monomeric units of the polymer such as an olefinic acid, e.g., (meth)acrylic acid) or vinyl amine or vinyl thiol by modification of a pendant group such as an amine, hydroxyl, vinyl, epoxy or other bonding group by its reaction with a small molecule carrying an acid group or amine group or thiol group to provide the pendant CDI group. The text that follows presents an understanding of the many embodiments of organic polymers having carboxylic acid groups. By simple replacement of the carboxylic acid groups of these polymers with sulfonic acid, phosphoric acid, amine or thiol groups, the corresponding organic polymers with any of the alternative CDI groups are disclosed. Preferred are the organic polymers bearing carboxylic acid groups.

Organic polymers containing acid groups may be developed from any monomeric unit containing acid groups such as carboxylic acid. The acidic units may be combined with non-acidic units which are hydrophilic or hydrophobic to provide appropriate organic polymers. Acidic units may also be grafted or bonded to pendant groups through appropriate organic coupling such as but not limited to anhydride addition to pendant amines or hydroxyl groups, free radical addition of vinyl acid monomers to pendant olefin groups, ether formation by addition of a protected hydroxy acid monomer to a pendant epoxide, silicon-oxygen coupling of pendant alkoxysilyl groups and alkoxysilylalkyl protected carboxyl monomers and similar formation of pendant acid groups. In each embodiment of the pendant acid arrangement, the resulting pendant group is a carboxylic acid group.

The organic polymers may be transformed to an acid bearing organic polymer by incorporation of one or more polymerization compatible monomeric units bearing carboxylic acid groups. Typically, a copolymerization with appropriate monomeric units some of which will bear the carboxylic acid group accomplishes the incorporation and development of the organic polymer of the first component. Incorporation of monomeric carboxylic acid compounds into organic polymers which are olefinic polymers is straightforward as the olefinic carboxylic acid will copolymerize with the other olefinic units of such polymers. For condensation polymers, incorporation can be accomplished through use of a starting monomeric unit containing a carboxylic acid group which optionally may be protected. For naturally derived polymers, conversion and/or derivatization of a pendant group such as a hydroxyl group or amine group to an acid group can be accomplished through known organic chemistry transformations. These conversions are described in the scientific literature such as in J. March, "Advanced Organic Chemistry", 4th Ed. John Wiley & Sons, New York, 1992.

Embodiments of the acid bearing organic polymer may be developed by polymerization of combinations of hydrophilic monomers and hydrophobic monomers. The hydrophilic monomers include exemplary carboxylic acid monomeric embodiments such as (meth)acrylic acid, crotonic acid, pentadienoic acid (butadienyl carboxylic acid). The organic polymer may include units of olefinic carboxylic acid monomers including (meth)acrylic acid, maleic acid, fumaric acid, itaconic acid, crotonic acid, pentenoic acid pentadienoic acid, isoprenoic acid, partially hydrolyzed polyacrylonitile and optional olefinic acid monomer derivatives that are homologs of these olefinic carboxylic acid monomers. The organic polymer may include units of the foregoing olefinic carboxylic acid monomers and in addition may include one or more monomeric units of esters of olefinic carboxylic acid monomers wherein the esterifying alcohol is a linear, branched or cyclic alkyl monoalcohol or diol of 1 to 12 carbons for the linear alkyl group (2 to 12 carbons for the diol), 3 to 12 carbons for the branched alkyl group and 3 to 12 carbons for the cyclic alkyl group, amides of said olefinic carboxylic acid monomers. N-alkyl amides of the olefinic carboxylic acid monomers wherein the alkyl group is a linear, branched or cyclic alkyl group as described for the monoalcohol, N-aminoalkyl amides of the olefinic carboxylic acid monomers wherein the amidating amine is a linear, branched or cyclic alkyl diamine with 2 to 12 carbons in the linear alkyl group, 3 to 12 carbons in the branched alkyl group and 3 to 12 carbons in the cyclic alkyl group. Neutral olefinic monomers including those of the formula: HR1C=CHR2 or HR1C=CH—CR3=CHR4 wherein R1, R2, R3 and R4 are each independently selected from hydrogen, linear alkyl of 1 to 6 carbons, branched alkyl of 3 to 6 carbons, cyclic alkyl of 3 to 10 carbons, phenyl, phenyl substituted by methyl, ethyl, OH, CONH2, COOH, —(CH2)nCOOH, NO2, CN, SO3H, SONH2, pyridyl, O2CR' wherein R' is alkyl of 1 to 3 carbons, vinyl and alkyl vinyl having 1 to 3 carbons in the alkyl group.

Preferred embodiments of the acid monomer of the organic polymer include olefinic dicarboxylic acids selected from one or more of (meth)acrylic acid, crotonic acid, pentenoic acid, hexenoic acid, maleic acid, fumaric acid, glutaconic acid, itaconic acid, citraconic acid, mesaconic acid or any combination thereof. More preferred olefinic carboxylic acids include (meth)acrylic acid, crotonic acid, maleic acid, fumaric acid and itaconic acid. Most preferred olefinic carboxylic acids include (meth)acrylic acid, crotonic acid, maleic acid and itaconic acid. Especially preferred olefinic carboxylic acids include (meth)acrylic acid and crotonic acid.

Preferred embodiments of the hydrophilic monomer of the organic polymer alone or in combination with preferred olefinic carboxylic acids include the preferred hydroxyalkyl esters of the foregoing preferred acids esterified with a C2-C6 diol including ethylene diol, propylene diol, butylene diol, pentylene diol or cyclohexane diol aminoethanol, aminopropanol and aminobutanol. Especially preferred hydroxyalkyl esters include the more preferred olefinic carboxylic acids esterified with any of these C2-C6 diols. More preferred hydroxyalkyl esters include the most preferred olefinic carboxylic acids with ethylene diol, propylene diol or butylene diol.

Additional preferred embodiments of the hydrophilic monomer of the organic polymer alone or in combination with the preferred olefinic carboxylic acids or in combination with the preferred hydroxyalkyl esters or in combination with the preferred carboxylic acids and the preferred hydroxyalkyl esters includes the aminoalkyl esters of the preferred olefinic carboxylic and sulfonic acids esterified with a C2 C4 amino alcohol including amino ethanol, amino propanol and aminobutanol. More preferred aminoalkyl esters include the more preferred olefinic carboxylic acids esterified with amino ethanol or amino propanol.

Additional preferred embodiments of the hydrophilic monomer of the organic polymer alone or in combination with preferred olefinic carboxylic acids, or in combination with the preferred hydroxyalkyl esters or in combination with the preferred amino alkyl esters and with any combination thereof include the mercapto alkyl esters of the preferred olefinic carboxylic and sulfonic acids. The preferred mercapto alcohols for these esters include mercaptoethanol, mercaptopropanol and mercaptobutanol. More preferred mercaptoalkyl esters include the more preferred olefinic carboxylic acids esterified with mercaptoethanol.

Additional preferred embodiments of the hydrophilic monomer of the organic polymer alone or in combination with preferred olefinic carboxylic acids, or in combination with the preferred hydroxyalkyl esters or in combination with the preferred amino alkyl esters, or in combination with the preferred mercaptoalkyl esters and with any combination thereof include polar olefinic monomers selected from p-hydroxystyrene, styrene-p-carboxylic acid, o,p-dihydroxystyrene, styrene-p-sulfonic acid and any combination thereof.

Additional embodiments of the hydrophilic olefinic monomer of this embodiment of the acid bearing organic polymer may be selected from:
(i) a hydroxyl ester of an olefinic carboxylic acid and a linear or branched alkyl diol of 2 to 24 carbons or a cyclic alkyl diol of 5 to 24 carbons;
(ii) an aminoalkyl ester of an olefinic carboxylic acid and a linear or branched C2-C24 aminoalkyl alcohol or a cyclic C5-C24 aminoalkyl alcohol; (ii) a mercaptoalkyl ester of an olefinic carboxylic acid, and a linear or branched C2-C23 mercaptoalkyl alcohol or a cyclic C5-C24 mercaptoalkyl alcohol;
(iii) an olefinic acid;
(iv) vinyl alcohol;
(v) vinyl alcohol ester of an olefinic carboxylic acid wherein the vinyl alcohol ester may be incorporated into an organic polymer through polymerization of a protected vinyl alcohol monomer such as vinyl acetate and exchange of the protecting group with the olefinic carboxylic acid, and within the organic polymer, the olefinic carboxylic acid is a pendant olefinoyloxy group such as but not limited to acrylyloxy or crotonyloxy;
(vi) a polar olefinic compound of the formula H$_2$C=CHC$_6$H4R wherein R is selected from selected from hydroxy, sulfonic acid, sulfinic acid, carboxylic acid, a vinyl group or a polyester polyol group having terminal and/or pendant hydroxyl groups;
(vii) an alkenylalkylalkoxysilane monomeric residue of the formula IV

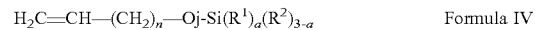

H$_2$C=CH—(CH$_2$)$_n$—Oj-Si(R$^1$)$_a$(R$^2$)$_{3-a}$        Formula IV wherein n is an integer of 2 to 6, j is zero or 1, R$^1$ is alkoxy of 1 to 6 carbons, hydroxyl, OAc, O—N=CHR or —C=CH$_2$, R$^2$ is alkyl of 1 to 3 carbons and a is an integer 1, 2 or 3;
or,
(viii) any combination of two or more of the hydroxyl ester, the aminoalkyl ester, the mercaptoalkyl ester, the olefinic acid, the vinyl alcohol, the vinyl alcohol ester, the polar olefinic compound or the functional silanyl residue.

Embodiments of the hydrophobic monomer for the acid bearing organic polymer may be selected from one or more of an olefinic carboxylate ester monomer or an olefinic carboxamide monomer, an olefinic sulfonamide monomer or any combination thereof. The olefinic carboxylate ester comprises an ester of an olefinic carboxylic acid and at least one saturated linear or branched C1 to C24 primary or secondary alcohol or a C4 to C24 cyclic or alkylcyclic alcohol. The olefinic carboxamide monomer comprises an amide of an olefinic carboxylic acid and ammonia or at least one linear or branched C1 to C24 primary amine. The olefinic sulfonamide monomer comprises an amide of an olefinic sulfonic acid and ammonia or at least one linear or branched C1 to C24 primary amine or a cyclic or alkylcyclic C4 to C24 alcohol.

Preferred embodiments of the hydrophobic monomer of the organic polymer include the alkyl esters wherein the preferred olefinic carboxylic acids are esterified with a C1 to C8 alcohol including methanol, ethanol, propanol, isopropanol, butanol, isobutanol, pentanol, isopentanol, hexanol, isohexanol, ethylhexanol, cyclohexyl alcohol. More preferred alkyl esters include the more preferred olefinic carboxylic acids esterified with ethanol, propanol, butanol, ethylhexanol or cyclohexyl alcohol. Most preferred alkyl esters include the most preferred olefinic carboxylic acids esterified with ethanol, butanol, ethylhexanol or cyclohexyl alcohol.

Additional preferred embodiments of the hydrophobic monomer of the organic polymer include non-polar olefin monomers selected from styrene, methylstyrene, ethylstyrene, propylstyrene, butadiene, 1-phenylbutadiene, isoprene or any combination thereof.

Yet additional preferred embodiments of an aromatic monomer that may be a hydrophobic monomer or a hydrophilic monomer include styrene, butadiene, phenyl butadiene, isoprene, 4-vinylbenzenecarboxamide, 4-vinyl benzoic acid, ethyl 4-vinyl benzoate, vinyl phenol, 4-vinyl-1-hydroxymethyl benzene, butene, pentene, hexene, divinyl benzene or any combination thereof.

Exemplary Embodiments of Acid Bearing Polymers

The embodiments of acid bearing compounds according to the invention include amphoteric polymers which may be selected from the following polymers: copolymers having acidic vinyl units and basic vinyl units, such as those resulting from the copolymerization of a monomer derived from a vinyl compound bearing a carboxylic group such as, more particularly, acrylic acid, methacrylic acid, maleic acid, alpha-chloroacrylic acid, and a basic monomer derived from a substituted vinyl compound containing at least one basic atom, such as, more particularly, dialkylaminoalkyl methacrylate and acrylate, dialkylaminoalkylmethacrylamides and acrylamides. Such compounds are described in U.S. Pat. No. 3,836,537.

The carboxylic acid compounds include polymers comprising units derived from: at least one monomer selected from acrylamides and methacrylamides substituted on the nitrogen atom with an alkyl group, at least one acidic comonomer containing one or more reactive carboxylic groups, selected more particularly from acrylic, methacrylic, crotonic, itaconic, maleic and fumaric acid and alkyl monoesters, having 1 to 4 carbon atoms, of maleic or fumaric acid or anhydride, and at least one basic comonomer such as esters with primary, secondary, tertiary or quaternary amine substituents of acrylic and methacrylic acids and the product of quaternization of dimethylaminoethyl methacrylate with dimethyl or diethyl sulfate. The N-substituted acrylamides or methacrylamides that are more particularly preferred according to the invention are compounds in which the alkyl groups contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides. The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer, such as the products sold as AMPHOMER LV 71, Acrylates/octylacrylamide copolymer sold as AMPHOMER 28-4961 or LOVOCRYL 47 by National Starch, are particularly used.

Additional organic polymers include but are not limited to homopolymers and copolymers of olefins; cycloolefins; butadiene; isoprene; styrene; vinyl ethers, esters, or amides; (meth)acrylic acid esters or amides containing a linear, branched, or cyclic C1-C24 alkyl group, a C6-C24 aryl group or a C2-C24 hydroxyalkyl group which all incorporate an unsaturated carboxylic acid or unsaturated di or tri acid such as (meth)acrylic acid, crotonic acid, itaconic acid, maleic acid, fumaric acid and similar unsaturated acid monomers. These polymers bearing at least two carboxylic acid groups may be obtained from monomers such as isooctyl(meth)acrylate, isononyl(meth)acrylate, 2-ethylhexyl(meth)acrylate, lauryl(meth)acrylate, isopentyl(meth)acrylate, n-butyl(meth)acrylate, isobutyl(meth)acrylate, ethyl(meth)acrylate, methyl(meth)acrylate, tert-butyl(meth)acrylate, tridecyl(meth)acrylate, stearyl(meth)acrylate, hydroxyethyl(meth)acrylate, 2-hydroxypropyl(meth)acrylate, benzyl acrylate, phenyl acrylate, and mixtures thereof. Amides monomers include but are not limited to (meth)acrylamides, such as N-alkyl(meth)acrylamides, for example of a C2-C12 alkyl, such as N-ethylacrylamide, N-t-butylacrylamide, and N-octylacrylamide; N-di(C1-C4) alkyl (meth)acrylamides and perfluoroalkyl(meth)acrylates.

Organic polymers may also include embodiments based upon a combination of olefinic carboxylic acids and a vinyl group attached to a diverse number of compounds. Included are copolymers of vinyl ester (the vinyl group being directly connected to the oxygen atom of the ester group and the vinyl ester having a saturated, linear or branched hydrocarbon-based radical of 1 to 19 carbon atoms bonded to the carbonyl of the ester group), olefinic carboxylic acid and of at least one other monomer chosen from vinyl esters (other than the vinyl ester already present), α-olefins (containing from 8 to 28 carbon atoms), alkyl vinyl ethers (in which the alkyl group contains from 2 to 18 carbon atoms), or allylic or methallylic esters (containing a linear or branched saturated hydrocarbon-based radical of 1 to 19 carbon atoms, bonded to the carbonyl of the ester group). Further non-limiting examples of the CDI link organic polymers include the following vinyl copolymers combined with olefinic carboxylic acid: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethylpropionate/vinyl stearate, allyl dimethylpropionate/vinyl stearate, vinyl propionate/vinyl stearate, vinyl dimethylpropionate/vinyl laurate, vinyl acetate/octadecyl vinyl ether, vinyl acetate/allyl stearate, vinyl acetate/1-octadecene and allyl propionate/allyl stearate. Polymerization delivers the polyvinyl compound (e.g., a version of polyolefins) with a large variation of substituent identity, all including at least two carboxylic acid groups derived from olefinic acids. Examples of vinyl monomers for such polymerization include but are not limited to vinyl alkanoate such as vinyl acetate, N-vinylpyrrolidone, vinylcaprolactam, vinyl N—(C1-C6)alkylpyrroles, vinyloxazoles, vinylthiazoles, vinylpyrimidines, vinyl pyridine, vinyl thiophene, and vinylimidazoles, olefins such as ethylene, propylene, butenes, isoprene, and butadienes.

Organic polymers as block copolymers are also included, examples of which include but are not limited to a block copolymer with at least two carboxylic acid groups derived from olefinic carboxylic acids comprising at least one block comprising styrene units or styrene derivatives (for example methylstyrene, chlorostyrene, or chloromethylstyrene). The copolymer comprising at least one styrene block may also comprise, for example, an alkylstyrene (AS) block, an ethylene/butylene (EB) block, an ethylene/propylene (EP) block, a butadiene (B) block, an isoprene (I) block, an acrylate (A) block, or a methacrylate (MA) block, or a combination of these blocks. The copolymer comprising at least one block of styrene units or styrene derivatives may be a diblock or triblock copolymer, for example of the polystyrene/polyisoprene or polystyrene/polybutadiene type, those of the polystyrene/copoly(ethylene-propylene) type or alternatively of the polystyrene/copoly(ethylene/butylene) type as well as styrene-methacrylate copolymers.

Additional acid bearing organic polymers include combinations of olefinic carboxylic acid monomers with polyalkenes and copolymers of C2-C20 alkenes, for example polybutene or butadiene.

Organic polymers also include but are not limited to polycondensates bearing carboxylic acid groups which include but are not limited to polyurethanes, polyurethane-acrylics, polyurethane-polyvinylpyrrolidones, polyester-polyurethanes, polyether-polyurethanes, polyureas, polyurea-polyurethanes, and mixtures thereof. The organic polyurethanes may be, for example, a copolymer of aliphatic, cycloaliphatic, or aromatic polyurethane, or of polyurea-polyurethane. The carboxylic acid groups may be incorporated through use of derivatized diamines or through use of olefinic carboxylic acids, eg. O-carboxy styrene, or triacids having one protected acid group. For example, incorporation of carboxylic acid groups can be accomplished by combination of the diisocyanate with a portion of a diol or diamine reaction partner having a protected pendant carboxyl or sulfonic group. Deprotection provides the pendant carboxylic acid group.

The acid bearing compounds include copolymers of C4-C8 monounsaturated carboxylic acids selected from: copolymers comprising (i) one or more maleic, fumaric, itaconic, allyloxyacetic, methallyloxyacetic, 3-allyloxypropionic, allylthioacetic, allylaminoacetic, vinylacetic, vinyloxyacetic, crotyloxyacetic, 3-butenoic, 4-pentenoic, 10-undecenoic, allylmalonic, maleamic, itaconamic, N-monohydroxyalkyl- or N-dihydroxy-alkyl-maleamic acids and (ii) at least one monomer selected from vinyl esters, vinyl ethers, vinyl halides, phenylvinyl derivatives, acrylic acid and its esters, the anhydride functions of these copolymers optionally being monoesterified or monoamidated. The polycarboxylic CDI link compounds include copolymers comprising (i) one or more maleic, citraconic or itaconic anhydride units and (ii) one or more monomers selected from allyl or methallyl esters optionally comprising one or more acrylamide, methacrylamide, [alpha]-olefin, acrylic or methacrylic ester, acrylic or methacrylic acid or vinylpyrrolidone groups in their chain, the anhydride functions of these copolymers optionally being monoesterified or monoamidated. The polycarboxylic acid compounds include polyacrylamides comprising carboxylate groups.

Additional Embodiments of the Organic Polymers with Carboxylic Acid Groups

Organic polymers may include copolymers of (meth) acrylic acid and of at least one linear, branched or cyclic (cycloaliphatic or aromatic) (meth)acrylic acid ester monomer and/or of at least one linear, branched or cyclic (cycloaliphatic or aromatic) mono- or disubstituted (meth)acrylic acid amide monomer.

Included are organic copolymers such as acrylic acid/ ethyl acrylate/N-tert-butylacrylamide terpolymers such as the product sold under the name Ultrahold 8 and that sold under the name Ultrahold Strong by the company BASF; (meth)acrylic acid/tert-butyl (meth)acrylate and/or isobutyl (meth)acrylate/C1-C4 alkyl (meth)acrylate copolymers such as the acrylic acid/tert-butyl acrylate/ethyl acrylate terpolymer sold by the company BASF under the name Luvimer 100P; (meth)acrylic acid/ethyl acrylate/methyl methacrylate terpolymers and tetrapolymers such as the ethyl acrylate/ methyl methacrylate/acrylic acid/methacrylic acid copolymer such as the product sold under the name Amerhold DR-25 by the company Amerchol; methyl methacrylate/ butyl or ethyl acrylate/hydroxyethyl or 2-hydroxypropyl acrylate or methacrylate/(meth)acrylic acid tetrapolymers such as the methyl methacrylate/butyl acrylate/hydroxyethyl methacrylate/methacrylic acid tetrapolymers sold by the company Rohm & Haas under the name Acudyne 255.

Additional examples of organic polymers include copolymers of acrylic acid and of C1-C4 alkyl methacrylate and terpolymers of vinylpyrrolidone, of acrylic acid and of C1-C20 alkyl, for example lauryl, methacrylate, such as that sold by the company ISP under the name Acrylidone M and the copolymer of methacrylic acid and of ethyl acrylate sold under the name Luvimer MAEX by the company BASF.

Yet other examples of organic polymers include amphoteric copolymers such as N-octylacrylamide/methyl methacrylate/hydroxypropyl methacrylate/acrylic acid/tert-butylaminoethyl methacrylate copolymers, in particular that sold under the name Amphomer by the company National Starch, or the copolymer Lovocryl L47 sold by the same company.

Additional examples of organic polymer include copolymers of (meth)acrylic acid and of (meth)acrylic acid esters or amides furthermore containing linear, branched or cyclic (cycloaliphatic or aromatic, which may or may not be substituted) vinyl esters, such as vinyl acetate; vinyl propionate; vinyl esters of branched acid such as vinyl versatate; vinyl esters of substituted or unsubstituted benzoic acid; these copolymers may furthermore also contain groups resulting from the copolymerization with styrene, alpha-methylstyrene or a substituted styrene. Other examples include copolymers of (meth)acrylic acid and of at least one olefinic monomer chosen from vinyl esters such as those mentioned above and containing no (meth)acrylic acid acrylamide or ester monomer. These copolymers may also contain olefinic groups resulting from the copolymerization with styrene, a-methylstyrene, a substituted styrene and optionally monoethylenic monomers such as ethylene.

Still other examples include copolymers of vinyl monoacid such as crotonic acid and vinylbenzoic acid and/or of allylic monoacid such as allyloxyacetic acid.

Organic polymers include copolymers of crotonic acid containing vinyl acetate or propionate units in their chain and optionally of other monomers such as allylic or methallylic esters, vinyl ethers or vinyl esters of a saturated, linear or branched carboxylic acid containing a long hydrocarbon chain, such as those containing at least 5 carbon atoms, it being possible for these polymers optionally to be grafted and crosslinked, or alternatively a vinyl, allylic or methallylic ester of an alpha- or beta-cyclic carboxylic acid. These copolymers may also contain olefinic groups resulting from the copolymerization with styrene, a-methylstyrene, a substituted styrene and optionally monoethylenic monomers such as ethylene.

Organic polymers include vinyl polymers such as vinyl acetate/crotonic acid/polyethylene glycol copolymers such as that sold by the company Hoechst under the name "Aristoflex A"; vinyl acetate/crotonic acid copolymers such as that sold by the company BASF Additional examples of organic polymers include the polyolefins, polyvinyls, polyesters, polyurethanes, polyethers, polycondensates and natural polymers.

The polycarboxylic acid compounds may also include those anionic polymers as sold under the FIXATE series as commercially available from Lubrizol, such as a branched block anionic polymer sold as FIXATE G-100, a branched anionic acrylate copolymer Polyacrylate-2 Crosspolymer (FIXATE SUPERHOLD polymer), Acrylates Crosspolymer-3 (FIXATE FREESTYLE Polymer), Polyacrylate-14 (FIXATE PLUS Polymer), those sold under the CARBOPOL series as commercially available from Lubrizol such as Acrylates Crosspolymer-4 (CARBOPOL AQUA SF-2), Acrylates Crosspolymer-4 (CARBOPOL AQUA CC), and those sold under the SYNTRAN series as commercially available from Interpolymer such as Acrylates Copolymer (SYNTRAN 5190), Styrene/Acrylates/Ammonium Methacrylate Copolymer (SYNTRAN 5760), and Ammonium Acrylates Copolymer (SYNTRAN KL-219C).

The polycarboxylic acid compounds of the present disclosure also includes anionic latex polymers such as acrylic copolymer and (meth)acrylate copolymers dispersions.

The polycarboxylic acid compounds include copolymers of acrylic acid or of acrylic esters, such as Acrylates/t-Butylacrylamide copolymer sold as ULTRAHOLD 8, acrylic acid/ethyl acrylate/N-tert-butylacrylamide terpolymers sold especially as ULTRAHOLD STRONG by BASF, copolymers derived from crotonic acid, such as vinyl acetate/vinyl tert-butylbenzoate/crotonic acid terpolymers and the crotonic acid/vinyl acetate/vinyl neododecanoate terpolymers sold especially as RESYN 28-29-30 by Azko Nobel, polymers derived from maleic, fumaric or itaconic acids or anhydrides with vinyl esters, vinyl ethers, vinyl halides, phenylvinyl derivatives and acrylic acid and esters thereof, such as the methyl vinyl ether/monoesterified maleic anhydride copolymers sold, for example, as GANTREZ AN or ES by ISP, the copolymers of methacrylic acid and methyl methacrylate sold as EUDRAGIT L by Rohm Pharma, the copolymers of methacrylic acid and ethyl acrylate sold as LUVIMER MAEX or MAE by BASF, the vinyl acetate/crotonic acid copolymers sold as LUVISET CA 66 by BASF, the vinyl acetate/crotonic acid copolymers grafted with polyethylene glycol sold as ARISTOFLEX A by BASF, the polymer sold as FIXATE G-100 by Noveon, and an alpha olefin hydrocarbon-maleic anhydride copolymer wax commercially available from Clariant under the tradename LICOCARE CM 401 LP 3345 (or "Clariant CM 401").

Cationic Acrylate Polymers useful as organic polymers include, for example; ttopol KX-10; Ottopol KX-99; Ottopol KX-101 from Gellner Industrial; RayCat® 65124 Specialty Polymers; FlOWLEN DOPA-15B; FlOWLEN DOPA-15 BHFS; FlOWLEN DOPA-17 HF; FlOWLEN DOPA-22; FlOWLEN DOPA-35 from Kyoeisha Chemical; MyCroFence AM 215 from Croda; WorleeCryl® 8721 from Worlee.

Acrylate polymers useful as acid bearing organic polymers and precursor organic polymers to which can be added at least two carboxylic acid groups include:
Acrylates/Beheneth-25 Methacrylate Copolymer
Acrylates/Beheneth-25 Methacrylate/Steareth-30 Methacrylate Copolymer
Acrylates/C5-8 Alkyl Acrylate Copolymer
Acrylates/C10-30 Alkyl Methacrylate Copolymer
Acrylates/C12-22 Alkyl Methacrylate Copolymer
Acrylates/Ceteth-20 Methacrylate Copolymer
Acrylates/C26-28 Olefin Copolymer
Acrylates/Ethylhexyl Acrylate Copolymer
Acrylates/Hydroxyethyl Acrylate/Lauryl Acrylate Copolymer
Acrylates/Hydroxyethyl Acrylate/Methoxyethyl Acrylate Copolymer
Acrylates/Laureth-25 Methacrylate Copolymer
Acrylates/Lauryl Methacrylate Copolymer
Acrylates/Methoxy PEG-4 Methacrylate Copolymer
Acrylates/Methoxy PEG-15 MethacrylateCopolymer
Acrylates/Methoxy PEG-23 Methacrylate Copolymer
Acrylates/Palmeth-25 Acrylate Copolymer
Acrylates/Steareth-30 Methacrylate Copolymer
Acrylates/Stearyl Methacrylate Copolymer
Acrylic Acid/C12-22 Alkyl Acrylate Copolymer
Acrylic Acid/Stearyl Acrylate Copolymer
Ammonium Acrylates/Ethylhexyl Acrylate Copolymer
Ammonium Acrylates/Methyl Styrene/Styrene Copolymer
Ammonium Styrene/Acrylates/EthylhexylAcrylate/Lauryl Acrylate Copolymer
Behenyl Methacrylate/t-Butyl Methacrylate Copolymer
Butyl Acrylate/Cyclohexyl Methacrylate Copolymer a copolymer of butyl
acrylate and cyclohexyl methacrylate film formers NR
Butyl Acrylate/Ethylhexyl Methacrylate Copolymer a copolymer of butyl
acrylate and 2-ethylhexyl methacrylate monomers film formers;
Butyl Acrylate/Hydroxyethyl Methacrylate Copolymer
Butyl Methacrylate/Acryoyloxy PG Methacrylate Copolymer
C12-22 Alkyl Acrylate/Hydroxyethylacrylate Copolymer
Cyclohexyl Methacrylate/Ethylhexyl Methacrylate Copolymer
Ethylhexyl Acrylate/Methoxy PEG-23 Methacrylate/Vinyl Acetate Copolymer
Ethylhexyl Acrylate/Methyl Methacrylate Copolymer
Glyceryl Acrylate/Acrylic Acid Copolymer
Hydroxyethyl Acrylate/Methoxyethyl Acrylate Copolymer
Methoxy PEG-23 Methacrylate/Glyceryl Diisostearate Methacrylate Copolymer
Poly C10-30 Alkyl Acrylate
Potassium Acrylates Copolymer
Potassium Acrylates/Ethylhexyl Acrylate Copolymer
Sodium Acrylates/Ethylhexyl Acrylate Copolymer
Sodium Acrylate/Vinyl Alcohol Copolymer
Acrylates/Ceteareth-20 Methacrylate Crosspolymer
Acrylates/Ceteareth-20 Methacrylate Crosspolymer-2
Acrylates Crosspolymer-3
Acrylates Crosspolymer-4
Acrylates Crosspolymer-5
Acrylates/Lauryl Methacrylate/Tridecyl Methacrylate Crosspolymer
Acrylates/Methoxy PEG-90 Methacrylate Crosspolymer
Acrylates/VA Crosspolymer Lauryl Acrylate Crosspolymer
Lauryl Acrylate/VA Crosspolymer
Methyl Methacrylate/PEG/PPG-4/3 Methacrylate Crosspolymer
Polyacrylate-1 Crosspolymer
Potassium Acrylate Crosspolymer
Sodium Acrylates/Beheneth-25 Methacrylate Crosspolymer
Poly(Methoxy PEG-9 Methacrylate)
Polybutyl Acrylate
Polybutyl Methacrylate
Polyethylacrylate
Polyhydroxyethylmethacrylate
Polyisobutyl Methacrylate
Polymethyl Acrylate
Polypropyl Methacrylate
Polystearyl Methacrylate
Sodium Polymethacrylate
Acrylates/C10-30Alkyl Acrylate Crosspolymer
Acrylates/C12-13 Alkyl Methacrylates/Methoxyethyl Acrylate Crosspolymer
Acrylates Crosspolymer
Acrylates/Ethylhexyl Acrylate Crosspolymer
Acrylates/Ethylhexyl Acrylate/Glycidyl Methacrylate Crosspolymer
Acrylates/PEG-4 Dimethacrylate Crosspolymer
Acrylates/Steareth-20 Methacrylate Crosspolymer
Acrylates/Vinyl Isodecanoate Crosspolymer
Acrylates/Vinyl Neodecanoate Crosspolymer
Allyl Methacrylate/Glycol Dimethacrylate Crosspolymer
Allyl Methacrylates Crosspolymer
Butyl Acrylate/Glycol Dimethacrylate Crosspolymer
C8-22 Alkyl Acrylates/Methacrylic Acid Crosspolymer
Glycol Dimethacrylate/Vinyl Alcohol Crosspolymer
Lauryl Methacrylate/Glycol Dimethacrylate Crosspolymer
Lauryl Methacrylate/Sodium Methacrylate Crosspolymer
Methacrylic Acid/PEG-6 Methacrylate/PEG-6 Dimethacrylate Crosspolymer
PEG/PPG-5/2 Methacrylate/Methacrylic Acid Crosspolymer
Potassium Acrylates/C10-30 Alkyl Acrylate Crosspolymer
Sodium Acrylates Crosspolymer-2
Sodium Acrylates/C10-30 Alkyl Acrylate Crosspolymer
Sodium Acrylates/Vinyl Isodecanoate Crosspolymer
Stearyl/Lauryl Methacrylate Crosspolymer Carboxylated styrene-butadiene polymers serving as organic polymers include Good-rite SB 1168, Good-rite SB 0738, Good-rite SB 1177 Lubrizol; Rovene 4011, Rovene 4019, Rovene 6140, Rovene 4049, Rovene 4310, Rovene 4306, Rovene 4457, Rovene 4041, Rovene 4150, Rovene 4151, Rovene 4176, BarrierPro 4551, Rovene 6140, Rovene 4305, Rovene 5550, Rovene 4487, Rovene 4817, Rovene 4470, Rovene 4475, Rovene 4180, Rovene 4310, Rovene 4402 from Mallard Creek Polymers; Hydro Pliolite 070 from Omnova Solutions; Lipaton SB 5521 from Synthomer The acid bearing organic polymer embodiments generally may have a modest to significant acid value ranging up to about 700, preferably about 250 to about 600, more preferably 100 to 400, most preferably 50-300 with typical acid numbers ranging approximately 75-300. The CDI link organic polymer and especially the acid bearing organic polymer may have a weight average molecular weight in the range of about 2 KDa to about 5 MDa, preferably about 2 KDa to about 100 KDa, more preferably about 2 KDa to about 25 KDa while CDI link small molecules and especially the acid bearing small molecules have molecular weights specific for their elemental compositions. The organic polymer may have a glass transition temperature of from about −125° C. to about 90° C.

The preferred arrangement of the carboxylic acid groups in the organic polymer provides that each member of the carboxylic acid group list individually and separately is present at a minimum number of two or three per majority of organic polymer molecules and may be distributed throughout the polymer backbone and/or along the branch chains. In addition, multiple carboxylic acid groups may be present at a single position on the backbone and especially on branch chains. An example of such a multiplicity would be a branch chain ending with a t-butyl group, the three termini of which have carboxylic acid groups. The number of carboxylic acid groups present in a molecule can be assessed by calculating the number average polymer molecular weight divided by the carboxylic acid group equivalent weight. Where the equivalent weight refers to the normal definition of mass of polymer which has one equivalent reactive group, in this case the carboxylic acid group. If this gives a value of 2, this shows that the average polymer has two carboxylic acid groups. Not all organic polymer molecules may have the same number of carboxylic acid groups; however, a majority to substantially greater than a majority of the organic polymer molecules such as from 95 mole percent to 98 mole percent will statistically have the same number of acid groups.

The organic polymer may be constructed with random distribution of the different monomer units along the polymer backbone and/or branches or may be block copolymers which has blocks of single monomer units or may be a graft copolymer which has one monomer unit forming the polymer backbone and a different monomer unit forming polymeric side chains. The different constructions of polymer provide differing polymer to polymer binding properties and different macromolecular characteristics. The block copolymer can provide regions of hard and soft polymer characteristics. A block copolymer can display crystalline regions and amorphous regions that can enable development of water soluble and water resistant regions. Blocks of differing electronic and lipophilic character can impart an open repulsive character to the polymer so that tightly fit inter-structures are minimized. A graft polymer or segmented polymer is capable of intertwined conformation and compact molecular dimension so as to enable tightly fitted inter-structures.

CDI Link Small Molecules

The CDI link small molecules include aliphatic and/or aromatic and/or heteroaromatic polycarboxylic acids, polysulfonic acids, polyphosphoric acids, polyamines and/or polythiols having 4 to 100 carbon atoms with optional nitrogen, oxygen and/or sulfur atoms and at least two carboxylic acid groups sulfonic acid groups, phosphoric acid groups, amine groups or thiol groups. Preferably, these small molecules include alkane polycarboxylic acids of 2 to 30 carbons, alkene polycarboxylic acids of 4 to 30 carbons and at least one unsaturation, aromatic polycarboxylic acids and heteroaromatic polycarboxylic acids. Exemplary embodiments include but are not limited to oxalic acid, malonic acid, succinic acid, glutaric acid, adipic acid, pimelic acid, 2,2,4-trimethyladipic acid and 2,4,4-trimethyladipic acid, phthalic acid, terephthalic acid, phenyldiacetic acid, phenyldipropanoic acid, phenylnaphthalenedicarboxylic acid, pyridinedicarboxylic acid, pyrimidinedicarboxylic acid, pyrroledicarboxylic acid, thiophenedicarboxylic acid, acids containing an ethylenic double bond such as, for example, acrylic acid, di-methacrylic acid, fumaric acid, maleic acid, and itaconic acid, crotonic acid and in instances in which the small molecule contains one carboxylic acid group, the amount of the small molecule combined is doubled. The unsaturation site may be polymerized post addition though use of appropriate actinic radiation (UV light). The CDI link small molecules with at least two carboxylic acid groups can combine with the polycarbodiimide and act as cross-linking moieties between the much larger carbodiimide molecules.

CDI Link Silicone Polymers

The aspect of the invention concerning the CDI link silicone is comprised of a MDTQ silicone polymer having at least two pendant organic groups bearing carboxylic acid groups, sulfonic acid groups, phosphoric acid groups, amine groups or thiol groups, preferably carboxylic acid groups. In the following discussion reference will be made to carboxylic acid groups as the CDI link groups with the understanding that the other CDI groups can serve as substitutes for the carboxylic acid groups. The silicone polymer includes a non-functional (non-acid bearing) portion and an acid bearing portion. An acid bearing silicone polymer including the non-functional portion and the carboxylic acid portion is one having carboxylic acid functional groups (hereinafter an acid bearing silicone polymer). For the acid bearing silicone polymer, the molar ratio of M type and/or D type siloxane monomeric units providing the at least two pendant organic carboxylic acid groups (hereinafter SiA units) to M type and/D type siloxane monomeric units having silicon bonded to a substituent (R) selected from the group consisting of alkyl (C1 to C6), amidoalkyl (C1 to C6), alkylamide (C1 to C6), sulfonamidoalkyl (C1 to C6) and alkylsulfonamide (C1 to C6) and any combination thereof. The siloxane units bonded to R substituents are hereinafter termed SiC units and most R substituents preferably may be methyl and/or ether. The ratio of SiA units to SiC units of the silicone polymer is in the range of from about 1:1000 to 1:10, preferably 1:1000 to 1:25, more preferably 1:600 to 1:50, most preferably 1:400 to 1:75 or 1:300 to 1:200. An SiC moiety may contain any number of other pendant groups as long as a carboxylic acid group is not present. The acid bearing silicone polymer polymer may have a weight average molecular weight ranged from about 1 kDa to about 150 kDa, preferably about 1 kDa to about 100 kDa, more preferably about 2 kDa to about 20 kDa.

The carboxylic acid functional groups may be pendant and internal to the silicone chain or branch and will terminate the end of the organic group. The pendant organic carboxylic acid group is bonded to the silicone backbone by a carbon to silicon bond between the organic group and a siloxane monomeric unit as —O—Si(R')2-O— wherein each R' is independently selected from either a pendant organic carboxylic acid group or an alkyl group of 1 to 6 carbons and at least one R' group is a pendant organic carboxylic acid group. The organic carboxylic acid group includes an organic connecting group which is further defined below in the following section titled "Formulative Structures of the Silicone Polymers." Each embodiment of the organic connecting group is terminated by the carboxylic acid group. Typical pendant carboxylic acid groups include but are not limited to such arrangements as:

—(CH$_2$)$_3$—COOH,    —CH$_2$—CH(CH$_3$)—O—CH$_2$—COOH
—(CH$_2$)$_3$—CONH—(CH$_2$)$_3$COOH,    —(CH$_2$)$_3$—NHCO—(CH$_2$)$_3$COOH and
single carboxylic acid groups such as —(CH$_2$)$_n$—COOH wherein n is 2 to 6, preferably 3 or 4 or branched chain versions thereof such as —CH$_2$—CH(CH$_3$)—CH$_2$—COOH.

The carboxylic acid functional group or groups may be pendant to the silicone chain at uniform or random locations along and within the silicone chain. The carboxylic acid functional group may also terminate the ends of the silicone chain but an acid bearing silicone polymer having terminal carboxylic acid groups preferably will also have pendant carboxylic acid groups along the silicone chain. If the acid bearing silicone polymer contains only terminal carboxylic acid groups, its weight average molecular weight preferably will be low so that its SiA:SiC ratio will conform to the foregoing values.

The acid bearing silicone polymer embodiments generally may have a modest to significant acid value ranging up to about 700, preferably about 250 to about 600, more preferably 100 to 400, most preferably 50-300 with typical acid numbers ranging approximately 75-300. The acid bearing silicone polymer may have a weight average molecular weight in the range of about 2 KDa to about 5 MDa, preferably about 2 KDa to about 100 KDa, more preferably about 2 KDa to about 50-80 KDa. The acid bearing silicone polymer may have a glass transition temperature of from about −125° C. to about 90° C.

The silicone chain of the acid bearing silicone polymer may be linear or branched and may generally be of the MDTQ configuration. In addition to the SiA moieties shown below as formula E, the chain is constructed of SiC moieties of the formulas A, B, C and D wherein R is defined as given above as the substituent (R) of the SiC moieties:

A) —O(R)$_2$Si—O— (known as a D siloxane unit)
B) —O(R)SI(—O—)$_2$  or  —O—Si(—O—)$_2$—O— (known as T siloxane unit and Q sesquisilicate unit respectively)
C) (R)$_3$SI—O— (known as M siloxane unit)
D) X—Si(R)$_2$—O with X as —OH or —OR
E) —O—SI(R')$_2$—O— with each R' independently being alkyl group or an organic carboxylic acid group and at least one R' being an organic carboxylic acid group.

For this embodiment of the acid bearing silicone polymer of the first component of the hair coloring composition, the A), B), C) and D) groups constitute together the SiC moieties defined above. The A) group provides a linear silicone chain link, the B) group provides a branched or crosslinked silicone chain link as described below, the C and D groups provide a silicone chain termination. The E group constitutes the SiA moiety defined above. The D category unit may provide a terminus site for cross linking. The R groups of the SiC moieties may be any organic group except a carboxylic acid group as defined above. Preferably the R groups are alkyl groups of 1 to 6 carbons, preferably methyl or ethyl, more preferably methyl. The distribution of the SiA moiety and the A), B), C), and D) groups of the SiC moiety follows ordered or random arrangement and the SiA to SiC ratios and weight average molecular weight ranges given above.

The silicone chain of the acid bearing silicone polymer embodiment of the first component may also include an additional unit or units to form an organosilicone block copolymer. This organo block unit is an organic oligomer chain formed from oligomerization of an polyolefinic group, a polyester group, a polyhydroxy acid ester group, a polyether group, a polyamide group, a polyurethane group or a polyurea group. The blocks are formed by linkage of the terminal group of the organic block to the terminal silicone of a silicone block through carbon-silicon bonds.

Formulative Structures of the Silicone Polymers

The acid bearing silicone polymer which may be incorporated into embodiments of the hair color composition according to the invention includes an organomodified silicone of the pendant or graft type as Formula I wherein the carboxylic acid groups are incorporated within or onto a pendant, grafted organic moiety. The organic moieties may be aliphatic linear or branched chains of 2 to 100 carbons and may include heteroatoms in the chains and/or may be aromatic or alkylaromatic groups of 6 to 36 carbons and may include heteroatoms in the aromatic groups. In addition, the organic moieties may be one or more of the organo block units described above. Heteroatoms in these instances include nitrogen, oxygen and sulfur. Additionally, as described above, the silicone includes any of the organic group C, such as but not limited to alkyl and other non-functional substituents. The polymer may contain in any order and in any number the Siloxane Unit Designations (SUD) II, III and VI. SUD I terminates the silicone polymer. The dangling valences of SUD's I, II, III and VI are the bonds to the next siloxane unit. Multiples of the SUD's bonded together form the silicone polymer. With this arrangement, the acid bearing siloxane units SUD III may appear anywhere within the polymer and may be interspaced with SUD II which contains only methyl substituents and other nonreactive groups that would not interfere with the carboxyl-carbodiimide coupling. Each instance of SUD III may be interspersed with other SUD units along the silicone chain. Each instance of SUD III may be the same or may be different from any other instance of SUD III so that the silicone polymer with acid bearing organic moieties may have SUD III units of multiple specific identities, of a few different identities or of the same identity may appear throughout the silicone chain. The substituent C is an organic group of an SiC group defined below. The variable $B_1$ is an SiC organic group, is described in detail below, and preferably is methyl or a linear or branched alkyl of 2 to 6 carbons, or a branched or cyclic alkyl group of 3 to 6 carbons. The SUD III units constitute SiA functional units. Together, SUD I, II and VI constitute SiC non-functional units.

Formula I

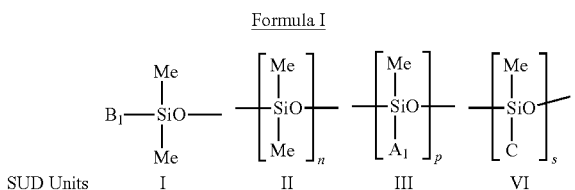

SUD Units    I      II      III      VI

The SUD's of Formula I are present according to certain number ranges. The number range n for SUD II is about 50 to 4000. The number p for SUD III is about 2 to 100. The number range s for SUD VI is about 20 to 2000. The ratio of SiA:SiC for Formula I is as given above in the general description of the Acid bearing silicone polymer.

Also included are the organo-silicones of the block copolymer type as shown in Formula II wherein the carboxylic acid groups are incorporated within or onto organic oligomer moieties. The SUD'S I, II and VI are as defined above and are repeated multiple times form the silicone portion of the block copolymer while the Organic Unit Designation (OUD) VII forms one or more organic polymer block units. The OUD's are blocks so that OUD VII may be present alone one or multiple times in the block copolymer. Multiples of the SUD units II and VI may be present as unitary blocks or as mixed units in a block and form the silicone blocks of the copolymer. The copolymer is terminated by SUD I. The organic block of OUD VII may be large or short oligomeric units of polyolefin, polyester, polyamide, polyurethane, polyol (i.e. polyether), polyurea and similar organic polymeric groups. The organic oligomeric units are substituted by organic groups A1 which bears the carboxylic acid groups as defined below. B1 is an alkyl, hydroxy or an alkoxy group as described above for Formula I.

Formula II

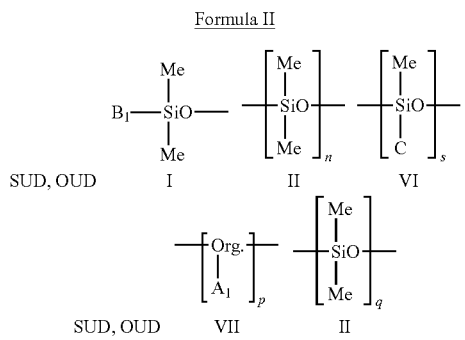

SUD, OUD    I      II      VI

SUD, OUD    VII      II

The designators n and s are the same as given above. Designator q for SUD IIq indicates a number range of about 20 to 2000. The OUD designator p indicates a number range of about 2 to 100 and is a measure of the number of A1 carboxylic acid groups present in the organic block or blocks. Number of organic blocks present may run from 1 to 100 and the size of the polymer or oligomer of the block may vary in weight average mw from 200 to 5000.

The OUD VII is analogous to an SiA unit for Formula I. SUD units I, II, VI and II (second instance) constitute SiC units. The number ratio of OUD VII units to SiC units is from about 1:1000 to about 1:10, preferably 1:1000 to 1:25, more preferably 1:600 to 1:50, most preferably 1:400 to 1:75 or 1:300 to 1:200.

Organic group A1 (OUD VII) is terminated by a carboxylic acid group may be straight, branched or mono- or polycyclic aliphatic, mono or polyunsaturated alkyl, aryl, heteroalkyl, heteroaliphatic or heteroolefinic moieties or any combination thereof comprising 3 to 150 carbon atoms together with up to 50 heteroatoms and/or heteroatom groups that establish functional polarity of the organic groups. Especially, the heteroatoms and heteroatom groups may include but are not limited to oxygen, nitrogen, sulfur, carboxamido, sulfonamido, and any combination thereof. The organic group C (OUD VI) may be the same organic group as mentioned for A1 except that C will not have a carboxylic acid group. Preferably, the organic group A1 is a linear, branched or cyclic aliphatic, heteroaliphatic, aromatic, heteroaromatic moiety or any combination thereof comprising 1 to 26 carbons (3 carbons minimum for branched and cyclic moieties) together with the foregoing heteroatoms and heteroatom groups and any combination thereof and includes the carboxylic acid group. Organic group C preferably is the same but without the carboxylic acid group. More preferably the organic group A1 is an aliphatic or heteroaliphatic moiety of 1 to 14 carbons with heteroatoms and heteroatom groups and any combination thereof (for branched or cyclic aliphatic and heteroaliphatic moieties, the minimum carbon number is 3) and includes the carboxylic acid group. More preferably organic group C is the same but without the carboxylic acid group. Especially more preferably, the organic group A1 is a linear alkyl moiety of 1 to 10 carbons or branched or cyclic alkyl moieties of 3 to 10 carbons with heteroatoms and heteroatom groups, and any combination thereof and includes the carboxylic acid group. Especially more preferably, organic group C is the same but without the carboxylic acid group. The organic groups, the preferred organic groups and more preferred organic group designated as A1 may have within the carbon chain, one or more ether groups, one or more thioether groups, one or more secondary or tertiary amino groups, one or more carboxamido groups, one or more sulfonamido groups or any combination thereof.

The preferred B1 group for Formula I and Formula II is alkyl of 1 to 6 carbons, hydroxyl or alkoxy of 1 to 6 carbons. With B1 as methyl, the terminus of the acid bearing silicone polymer is non-reactive. With B1 as hydroxyl or alkoxy, the terminus of the acid bearing silicone polymer is reactive so that multiple silicone polymer molecules can couple to form longer chains. This coupling will form macropolymers of the acid bearing silicone polymer especially as the acid groups of the acid bearing silicone polymer interacts with carbodiimide groups and with the third component, and optionally as the termini of the acid bearing silicone polymer interacts with polycarbodiimides having self-reactive termini. Although it is not a limitation of the invention, it is believed that the interaction upon macropolymer formation during application of the composition of the invention with at least a portion of this embodiment of the acid bearing silicone polymer to hair entwines the macropolymer with the hair strand thus increasing the adherence of the composition to the hair.

The foregoing acid bearing silicones or acid bearing organo silicone block polymers include siloxanes designated as a D group, Me2SiO2/1, i.e, —O—Si(Me)2-O— which are designated above as SUD II units as well as monofunctional units known as M groups, Me3SiO1/2, i.e., Me3Si—O—, and designated above as SUD I units where B1 is methyl. These acid bearing silicones or acid bearing organo silicones can also incorporate MeSiO3/2, known as silsesquioxane or T groups, and SiO4/2, known as Q groups described above as formula B). Together these silicone resin moieties are known as MDTQ with the M group being a terminal group, the D group being a linear chain group, the T group being a single cross linking group and the Q group being a multiple cross linking group. The organic T groups of two silicone chains can combine as described below to form a silicone chain cross link such as is depicted by Formula III

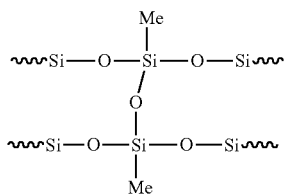

Formula III

The Q group organics can combine with T or Q groups to form silicone chain cross links such as is depicted by Formula IV.

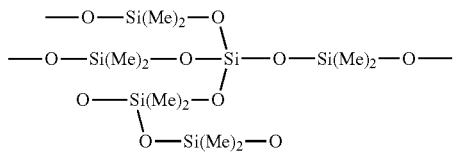

Formula IV

The acid bearing silicone polymer embodiments of the first component accordingly may include these T and Q group intersilicone and inter organo silicone chain cross links.

The weight average molecular weight range of Formulas I and II generally follows the ranges described above. Preferably for Formulas I and II, the weight average molecular weight range is from about 2 kDa to about 150 kDa, more preferably about 2 kDa to about 100 kDa, most preferably about 2 kDa to about 50 –80 kDa. Almost all of the acid bearing silicone polymer embodiments of Formulas I and II are liquid at ambient temperature and pressure so that for practical purposes they have no glass transition temperature (Tg). For some higher weight average molecular weight acid bearing silicone polymer embodiments of Formulas I and II, the glass transition temperature range for Formulas I and II is low, in the neighborhood of –40° C. to 10° C., preferably –30° C. to 0° C.

Examples and Specific Embodiments of the Acid Bearing Silicone Polymers

Examples of acid bearing silicone polymer of Formula I where SUD's I and VI are absent, SUD III forms both termini and the remainder of the polymer is SUD II include: dual-end carboxy silicones X-22-162C from Shin Etsu and Silform INX (INCI name: Bis-Carboxydecyl Dimethicone) from Momentive. Other exemplary embodiments of Formula I include those in which SUD VI is absent, SUD III forms one terminus and at least one internal group, SUD I forms the other terminus with B1 as a linear alkyl group of 1 to 20 carbons and SUD II forms the remainder of the silicone polymer. An example of this compound is a single-end carboxy silicone X-22-3710 from Shin Etsu. Other exemplary embodiments of Formula I have SUD I with B1 as methyl at both termini, SUD III forms the internal portion of the silicone polymer and SUD II and VI are absent. These exemplary embodiments have weight average molecular weights ranging from 400 Da to 5 KDa and are highly acidic. An example of this acid bearing silicone is a side-chain carboxy silicone X-22-3701E from Shin Etsu. Additional examples of similar acid bearing silicone polymers that include SUD II as well as SUD I and III include Grandsil PCA such as in Grandsil SiW-PCA-10 (INCI name: Dimethicone (and) PCA Dimethicone (and) Butylene Glycol (and) Decyl Glucoside from Grant Industries.

Among the silicones of Formula I are those that contain polyvinyl acid/ester units as the SUD VI units in which the organic moiety C is a divalent oligomer or polymer that is also bonded to an SUD VI unit of another silicone molecule. Exemplary embodiments are acid bearing copolymers comprised of organic polymer cross linking moieties and silicone backbone chains, resulting in an organically cross linked polymer structure. In particular, these cross linked silicone polymers of Formula I with SUD VI cross link units include examples such as the branched multi-block carboxy-silicone polymer (may also be known under the tradename Belsil® P1101) (INCI name: Crotonic Acid/Vinyl C8-12 Isoalkyl Esters/VA/Bis-Vinyldimethicone Crosspolymer, also known by the technical name of Crotonic Acid/Vinyl C8-12 Isoalkyl Esters/VA/divinyldimethicone Crosspolymer) from Wacker Chemie AG. Additional suitable carboxysilicone polymers are described, for example, in patent applications WO 95/23579 and EP-A-0,219,830, which are hereby incorporated by reference in their entirety.

Highly acidic silicone polymers of Formula I having SUD I with B1 methyl as the termini and SUD III as the internal silicone units are sold, for example, under the name HUILE M 642 by the company Wacker, under the names SLM 23 000/1 and SLM 23 000/2 by the company Wacker, under the name 176-12057 by the company General Electric, under the name FZ 3703 by the company OSI and under the name BY 16 880 by the company Toray Silicone.

Suitable silicone carboxylates may be chosen from water soluble silicone compounds comprising at least two carboxylic acid groups, oil soluble silicone compounds comprising at least two carboxylic acid groups, water-dispersible silicone compounds comprising at least two carboxylic acid groups, and silicone compounds comprising at least two carboxylic acid groups which are soluble in organic solvents. In one embodiment, the silicone carboxylate further comprises at least one alkoxylated organic chain, wherein the at least one alkoxy group may be chosen from terminal alkoxy groups, pendant alkoxy groups, and alkoxy groups which are intercalated in the skeleton of the at least one silicone compound. Non-limiting examples of at least one alkoxy group include ethylene oxide groups and propylene oxide groups.

The carboxylic acid groups of the silicone polymers may be chosen from carboxylic acid groups in free acid form, i.e., —COOH, and carboxylic acid groups in salt form, i.e., —COOM, wherein M may be chosen from inorganic cations, such as, for example, potassium cations and sodium cations, and organic cations.

In another embodiment, the acid bearing organo-silicone block polymer of Formula II may have SUD and OUD units arranged so that SUD II and VI provide the internal silicone units and OUD VII provides the termini. In this embodiment, the organic group (org) bonded to the carboxylic acid group A1 may be a polyolefin, polyester, polyether, polyamide, polyurethane, polyurea moiety at each end of the polysilicone chain. Each of the terminal organic polymer moieties is terminated by a carboxylic acid group which may include carboxylic acid alone or a carboxylic acid with an organic connecting group as described above. Another similar embodiment in which the polymer backbone is all silicone comprises Formula I in which SUD I with B1 as methyl terminates the silicone polymer and SUD II and SUD III provide the internal silicone units. A1 of SUD III comprises a polyolefin, polyester, polyether, polyamide, polyurethane, polyurea moiety terminated by a carboxylic acid group. Non-limiting examples of silicone carboxylates include those commercially available from Noveon under the name Ultrasil® CA-1 Silicone (Dimethicone PEG-7 Phthalate) and Ultrasil® CA-2 Silicone (Dimethicone PEG-7 Succinate). Non-limiting examples of silicone carboxylates include those described in U.S. Pat. Nos. 5,248,783 and 5,739,371, the disclosures of which are incorporated herein by reference.

Optional Reactive Termini for the First Component

The organic and/or silicone polymer of the first component may optionally have reactive termini designed to self-combine or to combine with the fourth component. The reactive termini option for the first component includes groups other than the CDI link groups that combine with carbodiimide. In this optional form, the reactive termini for the first component are capable of self-reacting to chain extend the organic and/or silicone polymer molecules or may react with a co-reactant (the fourth component) to couple the organic and/or silicone polymer molecules together, thus also chain extending these polymer molecules.

The optional reactive terminus for the organic and/or silicone polymer of the first component may be a reactive silyl group or a reactive organic group. The reactive silyl group may be a silyl group that self combines by aqueous catalyzed condensation, or a pair of silyl groups that combine by catalytic hydrosilylation or a pair of silyl groups substituted by organic moieties that combine by reactive organic group addition. Embodiments of silyl groups that combine by condensation include Si—OH, Si—OR, and derivatives such as Si—R—OH combined with Si—OH or Si—OR wherein R in these instances is a mono or divalent small saturated organic group. Embodiments of a pair of silyl groups that combine by hydrosilylation include silylhydride (Si—H) and any double bonded carbon group such as vinyl, acetylenyl, aldehydyl, norbornenyl, cyclopentadienyl and similar groups. Embodiments of a pair of silyl groups that combine by organic addition include organic groups bound to silyl that will undergo Michael addition, epoxide addition, anhydride addition or Schiff base formation.

The reactive silyl group bound to the organic and/or silicone polymer of the first component can be prepared by techniques known in the art. For example, the organic or silicone polymer having terminal vinyl groups can be trans hydrosilylated with alkoxysilyl hydride to form terminal alkoxysilyl groups on the organic or silicone polymer. Similarly, the organic or silicone polymer having terminal hydroxyl groups can be condensed with a silanol compound bearing a vinyl group to prepare a silyl vinyl terminal groups.

The reactive organic group may be any group that will undergo a Michael addition, an anhydride addition, a Schiff base formation or an epoxide addition. The Michael addition involves a pair of organic groups comprising a vinylacyloxy group and a nucleophile such as an amine or thiol or hydroxyl. The anhydride addition involves a pair of organic groups comprising a carboxyl anhydride and a nucleophile such as an amine, thiol or hydroxyl. The Schiff base formation involves an aldehyde and an amine nucleophile. The epoxide addition involves an alkyl epoxide and a nucleophile such as an amine, thiol or hydroxyl group.

The reactive organic group bound to the organic or silicone polymer can be prepared by techniques known in the art. For example, a typical synthesis follows the outline give above for the reactive silyl group. The reactive organic group a vinylcarbonyloxy group, an anhydridoalkyl group, an aldehydoalkyl group or an epoxyalkyl group. These groups can be attached to the termini of organic polymers through amide, urethane or ester formation or by polymerization termination with the reactive group coupled with a polymerizable vinyl group. The resulting organic and/or silicone polymer will have the reactive organic groups as its termini.

The optional reactive termini for the organic and/or silicone polymers of the first component are of the same class of reactive groups given below for the polycarbodiimide with reactive termini. The selections of reactive termini for the first component and the second component are independent. When reactive termini are present on both of the first and second components, the resulting starting organic and/or silicone polymer and polycarbodiimide compounds may have weight average molecular weights ranging from low to high. Starting with a low weight average molecular weight for the first and second components having reactive termini delivers flexibility in the development of the polymer network forming the coating on the treatable material. Moreover, molecular entanglement is promoted so that development of a remanent coating is rapid even when a class or type of in situ couplings may progress at a slow rate.

Tables I through IV given below in the polycarbodiimide section provide exemplary embodiments of the combinations of configurations for the reactive silyl groups and the reactive organic groups which may be applied to chain extend the organic and/or silicone polymer of the first component. The preferred reactive termini for the organic and/or silicone polymer of the first component is the self reactive silyl group such as but not limited to trimethoxy silyl or methoxy dimethyl silyl or a similar alkoxysilyl group.

B. Second Component: Polycarbodiimide

The second component of the multicomponent composition comprises a polycarbodiimide alone or in compatible medium. The polycarbodiimide has at least two carbodiimide groups, preferable from about two to about one thousand carbodiimide groups per molecule, more preferably from about two to about five hundred carbodiimide groups per molecule and most preferably up to about 200 carbodiimide groups per molecule. The carbodiimide groups of the polymer may be arranged as a linear chain or as pendant groups attached to an organic polymer chain. The polycarbodiimide is capable of reaction with all forms of the CDI groups mentioned above and preferably, the polycarbodiimide may be combined with the acid bearing compound (acid bearing organic or silicone or organosilicone polymer or small molecule) having carboxylic acid groups. In the subsequent passages, the preferred carboxylic acid-polycarbodiimide combination is discussed with the understanding that the other CDI link groups may also function in this capacity. With this preference in mind, the combination of the acid bearing compound of the first component and the polycarbodiimide provides a polymeric network connected by N-acyl urea bonds.

More specifically, the polycarbodiimide embodiments of the second component have Formula V. These embodiments may be maintained in neet condition or in compatible, inert solvent as a separate second component of the multicomponent composition until the multicomponent composition is to be applied to keratin material.

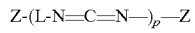   Formula V

In Formula V, Z is a terminal group of the polycarbodiimide and may be reactive or inert and preferably is reactive. L is an organic linker group derived from the formation of Formula V by catalytic conversion of diisocyanates of the formula OCN-L-NCO. The designator p is an integer of at least 2 so that the polycarbodiimide of Formula V contains at least 2 carbodiimide groups. The organic linker group L may be an aromatic, alkaromatic or saturated linear, branched or cyclic aliphatic divalent radical of 2 to 30 carbons optionally with one or more non-pendant heteroatoms including nitrogen, oxygen, sulfur or any combination thereof in the aliphatic chain or the aromatic group, such as but not limited to groups such as polyurethane or polyether as in polyethylene glycol. In its reactive form Z may react with itself to chain extend polycarbodiimide molecules or Z may react with a co-reactant (the fourth component) to couple polycarbodiimide molecules together, thus also chain extending the polycarbodiimide molecules.

Embodiments of Z include radicals of the formula Y—X wherein Y is an organic moiety and X is a reactive terminus or an inert terminus. As a reactive terminus, X may be configured as a reactive silyl group or as a reactive organic group. As an inert terminus, X may be configured as a linear, branched or cyclic saturated aliphatic group of 1 to 50 carbons or an aromatic group of 6 to 18 carbons, the aliphatic and aromatic groups optionally including from one to 10 heteroatoms selected from nitrogen, oxygen, sulfur or any combination thereof and the aliphatic or aromatic group may be partially or fully fluorinated. The group X includes a connecting group CG which bonds X to Y. The group CG may be a single covalent bond, a saturated C—C link, an unsaturated covalent C—C link, an amide group, an ester group, a carbonate group, a thioester group, an ether group, a urethane group a thiourethane group or a urea group. Y may be a divalent organic radical selected from a saturated aliphatic group of 1 to 36 carbons or an aromatic group or alkaromatic of 6 to 24 carbons, and the aliphatic or aromatic group may optionally include one or more non-pendant heteroatoms such as nitrogen, oxygen, sulfur or any combination thereof such as but not limited to ether links, ester links, amide links, urethane links, carbonate links, urethane links. Y is bonded to L through a connecting group CG. The CG connecting X to Y and the CG connecting Y to L may be the same or may differ and each is independent of the other. Polycarbodiimides with alkoxysilyl or hydroxysilyl groups at their termini are disclosed in U.S. Pat. No. 5,258,481, the disclosure of which is incorporated herein by reference. Polycarbodiimides with non-carbodiimide silyl and organic groups at their termini that are capable of self-reacting and/or capable of reacting with another difunctional compound to chain extend the polycarbodiimide are disclosed in U.S. Pat. No. 9,546,301, the disclosure of which is incorporated herein by reference.

Preferred embodiments of the polycarbodiimides have Formula VI in which L, X and Y are the same as defined above for Formula V; and Y is connected to L through the CG group NHCOA in which A is oxygen, nitrogen or sulfur to provide a urethane group, a thiourethane group, or a urea group. The designators m and m' of Formula VI may be zero or an integer of at least 1 and preferably from 1 to about 1000. The designator n of Formula VI may be zero or an integer of at least 1, preferably 1 to 1000. The sum of m+(m' times n) must be at least 2 so that at least two carbodiimide groups are present per molecule.

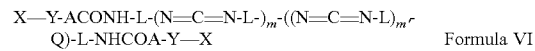   Formula VI

The group Q of Formula VI is an organopolymeric or organo-oligomeric moiety of repeating units of linear, branched or cyclic saturated aliphatic groups or aromatic groups or alkylaromatic groups coupled by repeating carbonate, ester, ether, amide, urethane or urea links or any combination thereof. Q may contain from about 2 to about 1000 repeating units. Each saturated aliphatic group of a repeating unit may have from 1 to 50 carbons and optionally may have heteroatoms in the aliphatic chain, the heteroatoms being one or more of nitrogen, oxygen, sulfur or any combination thereof. Each aromatic group of a repeating unit may have from 5 to 24 carbons and optionally may have heteroatoms in the aromatic group, the heteroatoms being one or more of nitrogen, oxygen, sulfur or any combination thereof. Each alkylaromatic group of a repeating unit may have from 5 to 18 carbons in the aromatic group and from 1 to 6 carbons in the alkyl group. The alkylaromatic group may also be two aromatic groups bonded to a divalent alkyl group. The aromatic group may optionally have one or more heteroatoms including nitrogen, oxygen, sulfur or any combination thereof. The group Q is present only when the designator n is other than zero. Because designators m and n may be zero, three arrangements of the innerconnected carbodiimide groups are possible. The innerconnection of these arrangements is the connection between individual carbodiimide groups. It is not the end portion connection with the Y—X terminus. In all three arrangements, the end portion connection of the innerconnected carbodiimides to Y—X is accomplished through the organic linker, CG described above as NHCOA. The first innerconnection is one in which the carbodiimide groups are inner connected only by the organic linker group L. The second is one in which the carbodiimide groups are inner connected only by the organopolymeric or organo-oligomeric moiety Q. The third is one in which the carbodiimide groups are innerconnected by both of Q and L. Polycarbodiimides having embodiments of the Q moiety but without reactive termini that are not carbodiimide are disclosed in U.S. Pat. Nos. 6,492,484, and 10,011,677, the disclosures of which are incorporated herein by reference. These polycarbodiimides may be converted to polycarbodiimides with reactive termini according to the methods described in U.S. Pat. Nos. 5,258,481 and 9,546,301, the disclosures of which for the purpose of such conversion are incorporated herein by reference.

For Formula V and Formula VI, the reactive terminus X may be a reactive silyl group or a reactive organic group as mentioned above. The reactive silyl group may be a silyl group that self combines by aqueous catalyzed condensation, or a pair of silyl groups that combine by catalytic hydrosilylation or a pair of silyl groups substituted by organic moieties that combine by reactive organic group addition. Embodiments of silyl groups that combine by condensation include Si—OH, Si—OR, and derivatives such as Si—R—OH combined with Si—OH or Si—OR wherein R in these instances is a mono or divalent small saturated organic group. Embodiments of a pair of silyl groups that combine by hydrosilylation include silylhydride (Si—H) and any double bonded carbon group such as vinyl, acetylenyl, aldehydyl, norbornenyl, cyclopentadienyl and similar groups. Embodiments of a pair of silyl groups that combine by organic addition include organic groups bound to silyl that will undergo Michael addition, anhydride addition epoxide addition or Schiff base formation.

The reactive silyl group bound to the polycarbodiimide can be prepared by techniques known in the art. For example, a polycarbodiimide intermediate can be prepared by catalyzing diimide formation from a diisocyanate having an L or Q group or a combination thereof as the organic moiety terminated by the isocyanate groups. The intermediate polycarbodiimide has isocyanate groups at its termini. An T-Y—X compound in which T is an alcohol, amine or thiol terminating one end of Y and the reactive silyl group X terminating the other end is combined with the intermediate polycarbodiimide to form the polycarbodiimide with reactive silyl termini. The coupling of the T-Y—X compound and the intermediate polycarbodiimide forms urethane, urea or thiourethane groups as the coupling group between Y and L or Q of the intermediate polycarbodiimide. The T-Y—X compound is prepared by hydrosilylation of a corresponding T-Y-vinyl compound and the corresponding silyl hydride.

The reactive organic group may be any group that will undergo a Michael addition, an anhydride addition, a Schiff base formation or an epoxide addition. The Michael addition involves a pair of organic groups comprising a vinylcarbonyloxy group and a nucleophile such as an amine or thiol or hydroxyl. The anhydride addition involves a pair of organic groups comprising a carboxyl anhydride and a nucleophile such as an amine, thiol or hydroxyl. The Schiff base formation involves an aldehyde and an amine nucleophile. The epoxide addition involves an alkyl epoxide and a nucleophile such as an amine, thiol or hydroxyl group.

The reactive organic group bound to the polycarbodiimide can be prepared by techniques known in the art. For example, a typical synthesis follows the outline give above for the reactive silyl group. For the reactive organic group, X is a vinylcarbonyloxy group, an anhydridoalkyl group, an aldehydoalkyl group or an epoxyalkyl group and in these instances the acyloxy or alkyl group binds the reactive center to L. The T-Y—X compound combines with the terminal isocyanate groups of the intermediate polycarbodiimide to form the polycarbodiimide with reactive organic groups as its termini.

Tables I through IV provide exemplary embodiments of the combinations of configurations for the reactive silyl groups and the reactive organic groups which may be applied to chain extend the polycarbodiimide.

TABLE I

| Condensation | | | |
|---|---|---|---|
| 1$^{st}$ Reactive silyl group | 2$^{nd}$ Reactive silyl group | Variation | Product* |
| —Me$_2$SiOR, R = alkyl of 1 to 6 carbons, alkoxy silyl | —Me$_2$SiOR, R = alkyl of 1 to 6 carbons, alkoxy silyl | Each Si bonded to 1, 2 or 3 RO groups | —Me$_2$Si—O—SiMe$_2$— variation produces 1, 2 or 3 silyloxysilyl bonds |
| —Me$_2$SiOH | —Me$_2$SiOH | Each Si bonded to 1, 2 or 3 OH groups | —Me$_2$Si—O—SiMe$_2$— |
| —Me$_2$SiOH | —Me$_2$SiOR, R = alkyl of 1 to 6 carbons, alkoxy silyl | Si—OH bonded to 1, 2 or 3 HO groups, SiOR bonded to 1, 2 or 3 OR groups | —Me$_2$Si—O—SiMe$_2$—, or —Me(RO)Si—O—SiMe$_2$—, and similar arrangements |
| —Me$_2$SiO—C=OCH$_3$ | —Me$_2$SiO—C=OCH$_3$ or —Me$_2$SiOH or —Me$_2$SiOR | Acyl group may be larger than acetoxy | —Me$_2$Si—O—SiMe$_2$—, or —Me(RO)Si—O—SiMe$_2$—, and similar arrangements |
| —Me$_2$Si—R—OH | —Me$_2$SiO—C=OCH$_3$ or —Me$_2$SiOH or —Me$_2$SiOR | R is alkyl, not sterically hindered | —Me$_2$Si—R—O—SiMe$_2$— and similar arrangements |

*The number of hydroxyls and/or alkoxys and/or acyloxys present on the two silicon atoms determines the number of silicon-oxygen-silicon bonds formed. The valence of —Me$_2$Si indicates the silyloxy group bond with the remainder of the coupled polycarbodiimide molecule.

TABLE II

Hydrosilylation

| 1st Reactive silyl group* | 2nd Reactive silyl group | Variation | Product** |
|---|---|---|---|
| —Me$_2$Si—CH=CHR | —Me$_2$Si—H | —Me$_2$Si—R'—CH=CHR, R' can be alkyl, not sterically hindered | —Me$_2$Si—CH$_2$CHR—SiMe$_2$— |
| —Me$_2$Si—CH=O | —Me$_2$Si—H | —Me$_2$Si—R'—CH=O, R' can be alkyl, not sterically hindered | —Me$_2$Si—CH$_2$—O—SiMe$_2$— |

*The silyl olefin may be silyl-norbornene, a silyl cyclopentadiene, a silyl maleimide and/or similar olefinic groups bound directly or through a carbon chain to a silyl group.
**The silicon hydride will add across any olefin that is not significantly sterically hindered. A transition metal complex catalyst is needed. The valence of —Me$_2$Si indicates the silylalkyl group bond with the remainder of the coupled polycarbodiimide molecule

TABLE III

Organic addition with silyl group

| 1st Reactive silyl group* | 2nd Reactive group* | Variation | Product |
|---|---|---|---|
| —Me$_2$Si—OC(=O)CR=CHR, e.g., (meth)acrylate, crotonate, alkenoyloxy, | X—R'-silicone-R'—X; or X—R'—X, X = NH$_2$, OH, SH as a difunctional amine, alcohol, thiol, aminoalcohol or aminothiol | R can be H or alkyl of 1 to 3 carbons, R' can be alkyl 1-6 carbons, phenyl | —Me$_2$Si—OC(=O)CRH—CHR—X—R'-silicone-R'X—CHR—CHRC(=O)—SiMe$_2$—; or —Me$_2$Si—OC(=O)CRH—CHR—X—R'—X—CHR—HRC(=O)—SiMe$_2$—; each X independently is NH, S or O |
| —Me$_2$Si—R'—CH—△—R with triangle as epoxide | X—R'-silicone-R'—X; or X—R'—X, X = NH$_2$, OH, SH as a difunctional amine, alcohol, thiol, aminoalcohol or aminothiol | R can be H or alkyl of 1 to 3 carbons, R' can be alkyl 1-6 carbons, phenyl | —Me$_2$Si—R'—CHOH—CHR—X-R'silicone-R'X—CHR—CHOH—R'—SiMe$_2$—; or —Me$_2$Si—R'—CHOH—CHR—X—R'—X—CHR—CHOH—R'—SiMe$_2$—; each X independently is NH, S or O |
| —Me$_2$Si—R'—C(=O)OC(=O)—CH$_2$R, e.g. anhydride | X—R'-silicone-R'—X; or X—R'—X, X = NH$_2$, OH, SH as a difunctional amine, alcohol, thiol, aminoalcohol or aminothiol | R can be H or alkyl of 1 to 3 carbons, R' can be alkyl 1-6 carbons, phenyl | —Me$_2$Si—R'—C(=O)—X—R'-silicone-R'—X—C(=O)—R'—SiMe$_2$—; or —Me$_2$Si—R'—C(=O)—X—R'—X—C(=O)—R'—SiMe$_2$—; each X independently is NH, S or O, product is diamide, diester or dithioester |

*Addition to an oxyacylvinyl group as a Michael addition, addition to an alkylepoxide such as propylepoxide, addition to an anhydride, the 1st reactive silyl groups form the reactive polycarbodiimide termini. The triangle indicates an epoxy group, i.e., an oxiranyl group. The R group is bound to the CH of the oxiranyl group.
**The 2nd reactive group is a fourth component, separately added. It may be an organosilicone compound with its termini having the functional groups or it may be a difunctional organic small molecule.
***The valence of —Me$_2$Si indicates the silylalkyl group bond with the remainder of the coupled polycarbodiimide molecule.

TABLE IV

Organic Addition, no silyl

| 1st Reactive organic group* | 2nd organic coupler | Variation | Product** |
|---|---|---|---|
| —Y—OC(=O)CR=CHR, e.g., (meth)acrylate, crotonate, alkenoyloxy, Y is as defined above | X—R'—X, X = NH$_2$, OH, SH, as a difunctional amine, alcohol, thiol, aminoalcohol or aminothiol | R can be H or alkyl of 1 to 3 carbons, R' can be alkyl 1-6 carbons, phenyl | —Y—OC(=O)CRH—CHR—X—R'—X—CHR—CHR—C(=O)—O—Y—, each X independently is NH, S or O |
| —Y—R'—CH—△—R with triangle as epoxide, Y is as defined above | X—R'—X, X = NH$_2$, OH, SH, as a difunctional amine, alcohol, thiol, aminoalcohol or aminothiol | R can be H or alkyl of 1 to 3 carbons, R' can be alkyl 1-6 carbons, phenyl | —Y—R'—CHOH—CHR—X—R'—X—CHR—CHOH—R'—Y, each X independently is NH, S or O |

TABLE IV-continued

Organic Addition, no silyl

| 1st Reactive organic group* | 2nd organic coupler | Variation | Product** |
|---|---|---|---|
| —Y—R'—C(=O)OC(=O)—CH$_2$R, e.g. anhydride, Y is as defined above | X—R'—X, X = NH$_2$ OH, SH, as a difunctional amine, alcohol, thiol, aminoalcohol or aminothiol | R can be H or alkyl of 1 to 3 carbons, R' can be alkyl 1-6 carbons, phenyl | —Y—R'—C(=O)—X—R'—X—C(=O)—R'—Y—, X is NH, S or O, product is amide, ester or thioester, each X independently is NH, S or O |

*The triangle indicates an epoxy group, i.e., an oxiranyl group. The R group is bound to the CH of the oxiranyl group.
**The organic coupler is the fourth component and is a difunctional small molecule. It combines with two polycarbodiimides to form a chain extension bridge. The valence of —Y indicates the Y group bond with the remainder of the coupled polycarbodiimide molecule.

Additional Embodiments of Polycarbodiimides with Reactive Termini

Additional embodiments of the polycarbodiimide with reactive termini may be prepared from a combination of diisocyanates and a monoisocyanate carrying the group that will become the reactive terminus. These embodiments are prepared by combining the diisocyanate and monoisocyanate in proportions and in a sequence that forms the polycarbodiimide moiety from the diisocyanates and terminates the chain growth with the monoisocyanate. There are several options for the composition of the mono and/or diisocyanate which may be used in the process. The mono-isocyanate may be an isocyanate containing a linear or branched alkyl, alkylene, alkyl-aryl or alkylene-aryl group with 6-25 carbon atoms. For example, it may be an alkyl-, cycloalkyl, alkyl-aryl, or arylalkyl functional isocyanate, such as hexylisocyanate, octylisocyanate, undecylisocyanate, dodecylisocyanate, hexadecylisocyanate, octadecylisocyanate, cyclohexylisocyanate, phenylisocyanate, tolylisocyanate, 2-heptyl-3,4-bis(9-isocyanatononyl)-1-pentylcyclohexane.

A further option is that the mono-isocyanate and/or polyisocyanate is the adduct of a polyisocyanate and a hydroxyl- or amine functional compound with a linear or branched alkyl, alkylene, alkyl-aryl or alkylene-aryl group with 4-25 carbon atoms.

A further option is that the mono-isocyanate is an isocyanate containing an alkyl, an alkylene, an alkyl-aryl or an alkylene-aryl group which contains 1-50 fluorine atoms. Examples of these are fluorophenylisocyanate, fluorotolyliso-cyanate and 3-(trifluoromethyl)phenylisocyanate.

A further option is that the mono-isocyanate and/or polyisocyanate is the adduct of a polyisocyanate and a hydroxyl- or amine functional compound with an alkyl, an alkylene, an alkyl-aryl or an alkylene-aryl group containing 1-50 fluorine atoms.

A further option is that the mono-isocyanate and/or polyisocyanate is the adduct of a polyisocyanate and a hydroxyl functional silicon or amine functional silicon, a hydroxyl alkyl functional silicon or an amino-alkyl functional silicon.

The polyisocyanate which is used for the preparation of the polycarbodiimide is toluene-2,4-diisocyanate, toluene-2,6-diisocyanate and mixtures thereof, is diphenylmethane-4,4-diisocyanate, 1,4-phenylenediisocyanate, dicyclohexylmethane-4,4'-diisocyanate, 3-isocyanatomethyl-3,5,5-trimethylcyclo-hexylisocyanate, 1,6-hexyldiisocyanate, 1,4-cyclohexyldiiso-cyanate, norbonyldiisocyanate, or a mixture thereof. The polyisocyanates that are preferably used are di-cyclohexylmethaan-4,4'-diisocyanate or 3-isocyanatomethyl-3,5,5-trimethylcyclo-hexylisocyanate.

The mono-isocyanate that contains one or multiple additional reactive functional groups and that contributes to the formation of an isocyanate functional polycarbodiimide is an isocyanate compound with one or multiple reactive groups which is not a carbodiimide, with a reactivity towards functional groups of a fourth difunctional compound or with a capability for self-condensation or self-addition, directly or after hydrolysis. The reactive functional group can be a halogen; alkenyl; ary-1-alkene; alkynyl; arylalkynyl; alkadiene; aldehyde; dialkyl-acetal; dithioacetal; ketone; unsaturated aldehyde; ketone or carboxylic ester; nitrile; imine; alkylalkoxy silane; alkoxy-silane; anhydride; mixed anhydride; oxime-protected diisocyanate; diketone; ketoester; thioketoester; ketothioester; thioketothioester; or a mixture of one or multiple of such reactive groups.

The reactive functional group can also be a reactive ring system or contain such a system. The reactive ring system can be any ring system that can open upon an electrophilic or nucleophilic attack by a fourth component. The reactive ring system can by any three, four, five, six, seven or eight membered ring that contains one or multiple nitrogen and/or oxygen and/or sulfur and/or keto and/or keto-enol functions.

Examples of such reactive ring systems are aziridine, epoxide, thiirane, azirine, oxirene, thiirene, azetidine, oxetane, thietane, beta-lactam, beta-lactone, thiethanon, fu-ran, pyrroline, dihydrofuran, dihydrothiophene, pyrrolidine, tetrahydrofuran, tetrahydrothiophene, oxazolidine, dioxolane, oxathiolane, thiazolidine, imidazoline, dithiolane, pyra-zolidine, pyrazoline, oxazoline, thiazoline, imidazoline, dioxole, oxazolon, pyrrolidone, butyrolactone, thiobutyrolactone, butyrothiolactone, thiobutyrothiolactone, oxazolidone, dioxolane-2-on, thiazolidinone, dihydropyridine, tetrahydro-pyridine, pyran, dihydropyran, tetrahydropyran, succinic acid anhydride, succinimide, thiopyran, dihydrothiopyran, tetrahy-drothiopyran, dihydropyrimidine, tetrahydropyrimidine, hexa-hydropyrimidine, dioxane, morpholine, thiamorpholine, dithiane and triazine.

The mono-isocyanate that contains one or multiple additional reactive functional groups and that contributes to the formation of the isocyanate functional polycarbodiimide is preferably an isocyanate compound that contains a trimethoxysilane, dimethoxymethylsilane or a tri-ethoxysilane group because these alkoxysilane groups contribute effectively to the crosslinking reaction by self-condensation, directly or after hydrolysis.

The mono-isocyanate or poly-isocyanate that contains an additional reactive group is preferably (3-isocyanato-propyl)trimethoxysilane, (3-isocyanatopropyl)tri-ethoxysilane, or (3-isocyanatopropyl)methyldimethoxysilane.

The carbodiimide catalyst which is used in the process may be any conventional carbodiimide catalyst, but preferably 1-methylphospholene-oxide is used.

Exemplary nucleophilic compounds containing at least diamine and/or hydroxyl functions include but are not limited to alkylene diamines and diols having from 2 to 20 linear or branched carbons as well as oligomer and polymer diamines and diols. Examples of such oligomers and polymers include a polyethoxy mono- or diol with a molecular weight between 100 and 3000 Dalton, a polyethoxy/polypropoxy mono- or diol with a molecular weight between 100 and 3000-Dalton and an ethoxy/propoxy ratio between 100/0 and 25/75, a polyethoxy mono- or diamine with a molecular weight between 100 and 3000, a polyeth-oxy/polypropoxy mono- or diamine with a molecular weight between 100 and 3000 Dalton and an ethoxy/propoxy ratio between 100/0 and 25/75, a diol or diamine containing a pendant polyalkoxy chain, an hydroxyl- or amine alkylsulphonate, or a dialkylamino-alkyl-alcohol or amine, or a mixture thereof. When incorporated as the fourth component to chain extend the reactive carbodiimide, the oligomers and polymers may contribute conditioning qualities to the keratin coloration composition.

The compounds that contains a reactive proton can be a ring system if this ring system contains a reactive proton such as in 2-methylaziridine, 4-dimethyloxazolidine, thiazolidine and the like. The reactive proton can be present in a hydroxyl compound or an amine compound. These are connected to the additional functional group or reactive ring system directly or by an optional alkyl, cycloalkyl or aryl group, such as in 1-(2-hydroxyethyl)-ethyleneimine, glycidol, N-cyclo-hexyl-3-hydroxy-azetidine, 2-ethyl-3-hydroxyethyl-2-methyl-oxazolidine, 4-ethyl-4-hydroxy-oxazoline, allyl alcohol, methylethylketone oxime, 1-amino-3-(triethoxysilyl)-propane, 1-amino-3-(trimethoxysilyl)-propane. A further option is that the reactive proton is present in a hydroxyl compound or amine compound and that these are connected to an additional functional group directly or by an optional alkyl, cycloalkyl or aryl group on one or multiple additional functional groups. An example is di-(3-trimethoxy-silylpropyl)-amine. Also compounds with two or more reactive protons can be used, such as for example N-(3-trimethoxysilylpropyl)-1,2-diaminoethane.

Accordingly, embodiments of the polycarbodiimide of Formulas V and VI according to the invention include but are not limited to the exemplary and descriptive polycarbodiimide compounds characterized by the foregoing passages. All of these embodiments are capable of self-reacting to chain extend, such as but not limited to the self-reacting alkoxysilyl group, or are capable of chain extending through combination of a reactive terminus group and a fourth component that is a difunctional compound of appropriate nucleophilic or electrophilic character, such as but not limited to nucleophiles such as diamines, dialcohols, dithiols, aminoalcohols, aminothiols, dithioalcohols; and electrophiles such as hydronium from a mineral or organic acid (proton in water or alcohol), Lewis acid such as boronic compounds.

Additional embodiments of the polycarbodiimides include those having pendant or branched carbodiimide groups such as those depicted below. For the pendant arrangement, the carbodiimide is attached through a saturated aliphatic or aromatic group to a monomeric unit that can be polymerized into an organic polymer chain. Such groups as vinyl and other similar olefinic groups are examples of monomeric units. For the branched arrangement, the branches may be established though use of branched saturated aliphatic groups bearing multiple isocyanate groups. The isocyanate groups may be catalytically converted to the carbodiimide groups as described above.

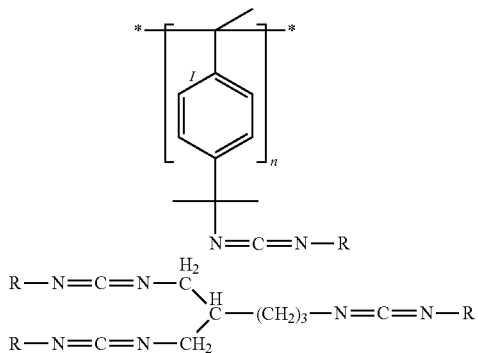

Examples of polycarbodiimides with non-reactive termini include those such as the CARBODILITE series, V-02, V02-L2, SV-02, E-02, V-10, SW-12G, E-03A, commercially sold by Nisshinbo.

Examples of polycarbodiimides with reactive termini include those such as RelcaLink 10 and Permutex XR commercially sold by Stahl B.V.

C: Third Component: Base Compound, Amine Polymer

Embodiments of the third component may combine with embodiments of the first and second components of the multicomponent composition to meld together (e.g., blend, combine, unite together as one) these components into a colored coating on treatable material that displays significant remanence. Embodiments of the substantive feature of the third component are the base compound. Embodiments of the base compound incorporate amine groups into and onto an organic or silicone core or chain. The base compound preferably has a weight average molecular weight of about 150 Da to about 1 MDa. When the base compound is a polymer, preferably about 400 Da to about 500 KDa, more preferably about 400 Da to about 250KDa, most preferably about 2 KDa to about 100 KDa.

Embodiments of the base compound as an organic core with amine groups may be one or more amine polymer(s). The amine polymer(s) may comprise one or more amino functional group(s) per polymer chain, wherein the amino functional group(s) are selected from the group consisting of primary, secondary and/or tertiary amino functional groups and mixtures thereof, preferably from the group consisting of secondary and tertiary amino functional groups and mixtures thereof.

Embodiments of the base compound may be selected from the group consisting of polyethyleneimine, polyallylamine hydrochloride, polydiallyldimethylammonium chloride, polyvinylamine, aminopolysaccharide, aminosilicones, copolymers thereof and mixtures thereof. The polymer(s) may preferably be selected from the group consisting of polyethyleneimine, aminosilicone, polydiallyldimethylammonium chloride, copolymers thereof and mixtures thereof. Additional examples include triethoxysilylamine, 1,1,1-triethoxy, 2,2-dimethyl-2-aminodisiloxane and aminoalkylmonoethoxydimethylsilane, aminoalkyldiethoxymethylsilane and aminoalkyltriethoxysilane with 1 to 6 carbons in the alkyl group, preferably 2 or 3 carbons.

Preferred base compounds are those carrying amine functionality. These embodiments of the base compound may be linear or branched and/or may be random or block copolymers.

As amine polymer(s) such as the embodiments of the base compound described above, exemplary selections include:
a) Linear polyethyleneimine of the formula:

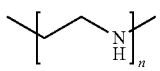

in which n is an integer representing the degree of polymerization, wherein n ranges from 5 to 25,000, alternatively from 11 to 2,500;
b) Branched polyethyleneimine consisting of primary, secondary and tertiary amine groups of the formula:

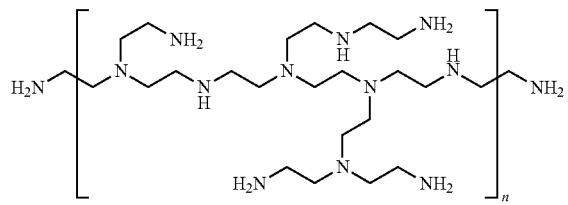

in which n is an integer representing the degree of polymerization, wherein n ranges from 2 to 4,000, alternatively from 5 to 500;
c) Polyallylamine hydrochloride of the formula:

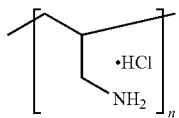

in which n is an integer representing the degree of polymerization, wherein n ranges from 50 to 20,000, alternatively from 5 to 1250;
d) Polydiallyldimethylammonium chloride of the formula:

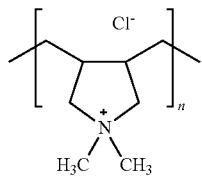

in which n is an integer representing the degree of polymerization, wherein n ranges from 10 to 20,000, alternatively from 150 to 4,000; copolymers thereof and mixtures thereof.

These embodiments of the base compound, e.g., the amino polymer(s), may have a charge density when fully protonated of at least 0.3, preferably at least 0.6, more preferably at least 0.8, even more preferably at least 1.0 positive charges per monomer unit.

Embodiments of the base compound may also be amino silicone compounds. Embodiments of the amino silicone polymer base compound may comprise any silicone polymer chain that incorporates amine functional groups into the silicone polymer. The amino silicone compounds may also be aminosiloxane compounds or oligomers and aminosilane compounds.

A preferred silicone polymer is one having amine functional groups (hereinafter an aminosilicone polymer). The molar ratio of siloxane monomeric units with at least one pendant organic amine group (hereinafter SiA moieties) to siloxane monomeric units having silicon bonded to a substituent selected from the group consisting of alkyl (C1 to C6) (hereinafter SiC moieties) is in the range of from about 1:1000 to 1:10 (ratio of SiA units to SiC units), preferably 1:1000 to 1:25, more preferably 1:600 to 1:50, most preferably 1:400 to 1:75 or 1:300 to 1:200. An SiA moiety may contain more than one amine group in which case it counts as just one SiA moiety. An SiC moiety may contain any number of other pendant groups as long as a primary, secondary, tertiary or quaternary amine group is not present. The aminosilicone polymer may have a weight average molecular weight ranged from about 10 kDa to about 150 kDa, preferably about 18 kDa to about 130 kDa, more preferably about 22 kDa to about 120 kDa.

The amine functional groups of the aminosilicone polymer may be primary, secondary, tertiary amine groups or quaternary ammonium groups or any combination thereof. The secondary, tertiary or quaternary amine groups may be substituted by alkyl groups of 1 to 6 carbons, such as methyl, ethyl, propyl, butyl, pentyl or hexyl or any combination thereof. The amine functional groups may be organic pendant groups wherein the amine group terminates the end of the organic group. The pendant organic amine group is bonded to the silicone backbone by a carbon to silicon bond between the organic group and a siloxane monomeric unit as —O—Si(R')$_2$—O— wherein each R' is independently selected from a pendant organic amine group and an alkyl group of 1 to 6 carbons and at least one R' group is a pendant organic amine group. The organic amine group may be a linear alkyl group of 1 to 16 carbons or a branched or cyclic alkyl group of 3 to 16 carbons. The alkyl group may contain one or more heteroatoms and/or hetero-groups in the chain including such groups as —NH—, —O—, —S—, —CONH— or —NHCO—, —SO$_2$NH— or —NHSO$_2$—. Typical pendant amine groups include such arrangements as:
—(CH$_2$)$_3$—NH—(CH$_2$)$_3$NH$_2$, —CH$_2$—CH(CH$_3$)—CH$_2$—NH—(CH$_2$)$_3$NH$_2$
—(CH$_2$)$_3$—CONH—(CH$_2$)$_3$NH$_2$, —(CH$_2$)$_3$—NHCO—(CH$_2$)$_3$NH$_2$ and
single amine groups such as —(CH$_2$)$_n$—NH$_2$ wherein n is 2 to 6, preferably 3 or 4 or branched chain versions thereof such as —CH$_2$—CH$_2$—CH$_2$—NH$_2$, —CH$_2$—CH(CH$_3$)—CH$_2$—NH$_2$.

The amine group or groups may be pendant to the silicone chain at uniform or random locations along and within the silicone chain. The amine functional group may also terminate the ends of the silicone chain but an aminosilcone polymer having terminal amine groups preferably will also have pendant amine groups along the silicone chain. If the aminosilicone polymer contains only terminal amine groups, its weight average molecular weight preferably will be low so that its SiA:SiC ratio will conform to the foregoing values.

The silicone chain of the aminosilicone polymer may be linear, branched or crosslinked. In addition to the SiA and SiC moieties, aminosilicone may also include any one or more of MDTQ groups of the formulas A, B, C and D wherein R is a methyl group:
A) —O(R)$_2$Si—O— (known as a D siloxane unit)
B) —O(R)SI(—O—)$_2$ or —O—Si(—O—)$_2$—O— (known as T siloxane unit and Q sesquisilicate unit respectively)
C) (R)$_3$SI—O— (known as M siloxane unit).

For this embodiment of the aminosilicone polymer component of the base compound the A), B), C) and D) groups constitute together the SiC moieties defined above. The A) group provides a linear silicone chain link, the B) group provides a branched or crosslinked silicone chain link, the C and D groups provide a silicone chain termination. The distribution of the SiA moiety and the A), B), C), and D) groups of the SiC moiety follows ordered or random arrangement and the SiA to SiC ratios and weight average molecular weight ranges given above.

D. Fourth Component

The fourth component is a functional compound that is adapted to combine with the polycarbodiimide with reactive termini that do not self-react. Embodiments of the fourth component include nucleophilic compounds having at least two nucleophilic functional groups. These embodiments include but are not limited to diamines, dialcohols, dithiols, aminoalcohols, aminothiols and thiol-alcohols as well as the amine polymers of the third component. The nucleophilic functional compounds form stable links with the reactive termini that are not self-reacting.

E. Medium

The medium of the multicomponent composition embodiments of the invention may be an organic compound that is capable of being intimately mixed or preferably forming a solution with up to 20 percent by weight water. The preferred medium comprises embodiments of alcoholic solvents such as an alkyl alcohol of 1 to 6 carbons with no intentionally added water or with intentionally added water up to about 10 weight percent, preferably up to about 5 weight percent, more preferably up to about 2 or 3 weight percent relative to the total weight of the medium. It is recognized that alcohol solvents absorb water from the atmosphere so that an alcoholic solvent with no intentionally added water may contain a slight amount of water. The polarity and protonic character of the medium are important for control of the several reactions that occur when the components of the multicomponent composition are combined. These reactions include the carboxylic acid-carbodiimide reaction and the reactive termini reaction such as the alkoxysilyl condensation to form silyloxysilyl linkages. Preferably, the medium for the first and second components is an alkyl alcohol with no intentionally added water. Preferably the medium for the third component is water so that when the three components are applied to the treatable material to provide an inchoate coating, the alcoholic medium combined with water is present.

As shown by the experimental examples, it has been discovered that the identity of the medium plays a role in obtaining a substantially complete, uniform, appropriately sized coating of the applied multicomponent composition on the treatable material, especially keratin material and specifically hair. The examples show that when the medium for application is water, the multicomponent composition reaction rate is increased to an extent that development of a substantially uniform, appropriately sized coating is difficult to obtain. The examples also show that when the medium for application is a non-polar, aprotic, lipophilic solvent such as dodecane, the multicomponent composition reaction rate is so slow that development of the combined product occurs over a period of multiple hours if not days. The experimental examples provide an understanding that a balance of hydrophilic and lipophilic character and a small degree of protonic character provide an appropriate reaction rate. This balance is achieved through use of a linear monoalcohol of 1 to 6 carbons, preferably methanol, ethanol or propanol, more preferably ethanol as the medium. These alcohol solvents are not naturally anhydrous in that they absorb water from the atmosphere. Consequently, they may serve as the multicomponent medium without intentional addition of water. Nevertheless, a minor amount of water up to a maximum of about 10% preferably up to about 5%, more preferably up to about 2% by weight relative to the total weight of the medium, may be added to manage the hydrophilic/lipophilic character and ionic/protonic balance of the medium. The water addition is desirable when the polycarbodiimide and optionally the first component have reactive termini that are self-reacting, such as alkoxy silyl and/or hydroxysilyl groups.

According to at least one embodiment of the present disclosure, the organic solvent is chosen from ethanol, isopropanol, butanol or pentanol.

The medium with or without one or more volatile organic solvent may be present in the composition according to the present disclosure in an amount ranging from about 0.1% to about 95% by weight, such as from about 1% to about 70% by weight, for example ranging from 5% to 90% by weight relative to the total weight of the composition.

Viscosity, Composition Concentrations

The viscosity of the composition functions to hold the composition with pigment microparticles in place on the treatable material while the in situ linked coating is formed. The viscosity substantially avoids free translational flow of the composition. Free translation flow would cause the composition to rapidly run and drip off the surfaces of the hair strands. Nevertheless, the viscosity is not so high that it will not undergo self-leveling to substantially uniformly coat the treatable material. Appropriate viscosity of the composition is the result of the interaction of the organic polymer, the in situ material, the base compound, their concentrations, the pigment microparticles, and as appropriate, an optional viscosity control agent, an optional suspending agent and an optional thickening agent. Generally, the viscosity of the composition may range from about 0.001 to about 2000 Pa s−1. Viscosity measurements are carried out on a controlled stress rheometer e.g. Using an AR2000 type manufactured by TA Instruments, or equivalent instrument. A 6 cm flat acrylic cross hatched parallel plate geometry (TA item 518600.901) and a stainless steel cross hatched base plate (TA item 570011.001) are used. The rheometer is prepared for flow measurements as per standard manufacturer procedure. The parallel plate geometry gap is set to 1000 microns. The flow procedure is programmed to the rheometer with the following conditions: continuous stress ramp 0.1-300 Pa over 2 minutes at 25° C., including 250 measurement points in linear mode. The product is loaded into the geometry as per standard procedure and the measurement commences at 5 min after the mixture preparation. Shear stress value at 10 sec-1 shear rate is obtained from the shear stress vs. shear rate curve, and the corresponding viscosity is calculated by dividing the obtained shear stress by 10.

The concentration of the CDI link compound and preferably the acid bearing compound in the composition may range from about 0.1% to about 90%, preferably about 1% to about 40%, more preferably about 2% to about 30%, most preferably about 2% to about 15% of CDI link compound by weight relative to the total weight of the composition. Specific concentrations of acid bearing compound include about 0.1%, about 0.5%, about 1%, about 2%, about 4%, about 6%, about 8%, about 10%, about 12%, about 14%, about 16%, about 18%, about 20%, about 22% about 24%, about 26%, about 28% or about 30% by weight relative to the total weight of the composition. The concentration of the in situ linking material (the polycarbodiimide) may range from about 0.1% to about 50% and is approximately about half of the concentration by weight of the acid bearing compound. Preferably the preferred ranges and specific concentrations of the in situ linking material are approximately half of those for the acid bearing compound. These concentration ranges preferably apply when the acid bearing compound is other than an acid bearing small molecule. The concentration range of the third component is given above in the third component section. The concentration range of the fourth compound, when present, will be determined by the concentration of the in situ linking material and may be approximately from about half of, to about the same as the molar concentration of the in situ linking material. The determination of the concentration for embodiments of the Acid bearing compound and in situ linking material and third component will depend in part upon the resulting viscosity, the saturation point of the acid bearing compound and in situ linking material and base compound in the medium. As discussed above, the viscosity is managed so that the composition will not run off the surfaces of strands of hair yet will level and flow to substantially coat those surfaces. Development of appropriate viscosity in part by management of the concentration of the acid bearing compound and in situ linking material can be experimentally determined by routine methods such as formulation of several samples of differing concentrations of polymer in the composition, coating those samples on a hair tress and observing the flow, spread and leveling of the composition on the hair strands.

The multicomponent composition can be applied simultaneously, sequentially or in pre-combined form to a treatable material such as a hair tress using the coloring procedure described herein afterwards. The top of the hair strand, where it is glued together is clamped in a stand such that the hair is aligned vertically downwards. After a 5 minute dwell time it is observed if any and how much product has dripped from the hair tress. The results obtained from the several samples can be plotted against flow time and leveling time to determine an appropriate concentration or range of concentrations of the organic polymer in the composition. A preferred concentration of the combination of CDI link compound and in situ linking material in the composition ranges from about 1% to about 60%, more preferably about 2% to about 40% and most preferably about 3% to about 30% by weight relative to the total weight of the composition. The weight amounts of CDI link compound and in situ linking material may be determined by calculation of amounts needed to substantially or essentially, or completely react the carboxylic acid groups with the carbodiimide groups, also taking into account the optional interaction between the carboxylic acid groups and the amine groups of the third component. The calculation of amounts will depend upon the molecular weights or weight average molecular weights of the CDI link compound, the in situ linking material and the third component and their relative numbers of functional/reactive groups.

The extent of in situ linking between the first, second and third functional groups may be controlled by manipulation of ratios, amounts present and concentrations as well as by physical means as described above so that the mechanical and chemical properties of the coating as described herein are preserved. In connection with hair, these properties include ability to adhere to hair strands, ability to maintain flexibility and free flowing character of the hair, ability to provide remanence, avoidance of stickiness and avoidance of clumping.

The glass transition temperatures of the organic polymer and the in situ linking material and the base compound in part contribute to the flexibility, strength, hardness and similar qualities of the coating on the treatable material surfaces. The glass transition temperature of these embodiments are given with each section described above. This glass transition temperature or Tg determines the solid-solid transition of the polymer from a hard glassy material to a soft rubbery material. If the Tg of the polymer is too high, the coating on the treatable material will be stiff and inflexible. This is an undesirable result. The coating should be soft, flexible and unnoticeable to touch and sight yet should not flake, break-up or otherwise release from the keratin fiber, and especially from human hair, when stroked by a hand or brushed with a brush. The Tg of a polymer can be measured using ASTM D7426-08 (2008).

F. Plasticizer

If the glass transition temperature of the multicomponent composition and or the substantive ingredients of the first, second and/or third components are too high for the desired use yet the other properties of the polymer are appropriate, such as but not limited to color and remanence, one or more plasticizers can be combined with the multicomponent composition embodiments so as to lower the Tg of the organic polymer and provide the appropriate feel and visual properties to the coating. The plasticizer can be incorporated directly in the coloring composition or can be applied to the hair before or after the coloring composition. The plasticizer can be chosen from the plasticizers usually used in the field of application. Appropriate selection includes choice of a plasticizer that does not interfere with or compete with the carbodiimide-CDI link group reaction or with the reactive termini combination.

The plasticizer or plasticizers can have a molecular mass of less than or equal to 5,000 g/mol, such as less than or equal to 2,000 g/mol, for example less than or equal to 1,000 g/mol, such as less than or equal to 900 g/mol. In at least one embodiment, the plasticizer, for example, has a molecular mass of greater than or equal to 40 g/mol.

Thus, the multicomponent composition can also comprise at least one plasticizer. For example, non-limiting mention can be made, alone or as a mixture, of common plasticizers such as: glycols and derivatives thereof, silicones, silicone polyethers, polyesterpolyols; adipic acid esters (such as diisodecyladipate), trimellitic acid esters, sebacic acid esters, azalaeic acid esters; nonlimiting examples of glycol derivatives are diethylene glycol ethyl ether, diethylene glycol methyl ether, diethylene glycol butyl ether or diethylene glycol hexyl ether, ethylene glycol ethyl ether, ethylene glycol butyl ether, or ethylene glycol hexyl ether; polyethylene glycols, polypropylene glycols, polyethylene glycol-polypropylene glycol copolymers, and mixtures thereof, such as high molecular weight polypropylene glycols, for example having a molecular mass ranging from 500 to 15,000, for instance glycol esters; propylene glycol derivatives such as propylene glycol phenyl ether, propylene glycol diacetate, dipropylene glycol ethyl ether, tripropylene glycol methyl ether, diethylene glycol methyl ether, and dipropylene glycol butyl ether. Such compounds are sold by Dow Chemical under the names DOWANOL PPH and DOWANOL DPnB; acid esters, for example esters of carboxylic acids, such as triacids, citrates, phthalates, adipates, carbonates, tartrates, phosphates, and sebacates; esters derived from the reaction of a monocarboxylic acid of formula R11COOH with a diol of formula HOR12OH in which R11 and R12, which can be identical or different, are chosen from a linear, branched or cyclic, saturated, or unsaturated hydrocarbon-based chain containing, for example, from 3 to 15 carbon atoms for example the monoesters resulting from the reaction of isobutyric acid and octanediol such as 2,2,4-trimethyl-1,3-pentanediol, such as the product sold under the reference TEXANOL ESTER ALCOHOL by the company Eastman Chemical; oxyethylenated derivatives, such as oxyethylenated oils, such as plant oils, such as castor oil; mixtures thereof.

Among the esters of tricarboxylic acids mention can be made of the esters of triacids wherein the triacid corresponds to formula

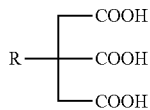

wherein R is a group —H, —OH or —OCOR' wherein R' is an alkyl group containing from 1 to 6 carbon atoms. For example, R can be a group —OCOCH3. The esterifying alcohol for such tricarboxylic acids may be those described above for the monocarboxylic acid esters.

The plasticizer can be present in the composition of the present disclosure in an amount from about 0.01% to 20%.

G. Pigments

The color composition embodiments of the present invention make it possible to obtain colored and remnant coatings, without substantially altering the keratin fibers. As used herein, the term "pigment" generally refers to any particle colorant having or containing pigment material that gives hair fibers color including black and white, such as titanium dioxide that give only white to hair fibers. The pigments are substantially water-insoluble. The pigments, to distinguish from dyes presented in molecular from, are also referred to as pigment microparticles or pigment particles. The terms pigment microparticles and pigment particles are synonymous and are used herein interchangeably. The pigments can be organic, inorganic, or a combination of both. The pigments may be in pure form or coated, for example with a polymer or a dispersant.

Selections, multiple kinds and varying forms of the pigment microparticles as described in the following passages can be incorporated in any of the first, second and third components of the multicomponent composition, or can be incorporated in any two of these components or in all three. Preferably, pigment microparticles can be incorporated in either or both of the first and second components. More preferably, pigment particles can be incorporated in the first component.

The at least one pigment that can be used can be chosen from the organic and/or mineral pigments known in the art, such as those described in Kirk-Othmer's Encyclopedia of Chemical Technology and in Ullmann's Encyclopedia of Industrial Chemistry. The pigments comprised in the microparticles comprising at least one pigment will not substantially diffuse or dissolve into keratin fibers. Instead, the pigment comprised in the microparticles comprising at least one pigment will substantially remain separate from but attached to the keratin fibers.

The at least one pigment can be in the form of powder or of pigmentary paste. It can be coated or uncoated. The at least one pigment can be chosen, for example, from mineral pigments, organic pigments, elemental metal and their oxides, and other metal modifications, lakes, pigments with special effects such as nacres or glitter flakes, and mixtures thereof.

Pigment Shape

The pigment microparticles can have any suitable shape, including substantially spherical. But the pigment microparticles can also be oval, elliptical, tubular, irregular, etc., or even combinations of various shapes. In addition, the pigment microparticles can have two dimensions, length and width/diameter, of similar magnitude. In addition, the pigment microparticles can be micro platelets, i.e. having a thickness that is substantially smaller than the planar dimension. For example, five, ten or even 20 times smaller in thickness than in the planer dimension. In one embodiment with any of the reactive components of the instant invention, the pigments may be surface treatable, surface coated or encapsulated.

In a particular aspect, the pigment microparticles can have a shape approximating that of a sphere, in which case the microparticles are referred to as being microspheres. Pigment microparticles which can be described as microspheres are understood as particles having an aspect ratio, defined as a function of the largest diameter, or largest dimension, dmax and the smallest diameter, or smallest dimension, dmin, which can be orthogonal to each other: AR=dmax/dmin which is from about 1:1 to 10:1, preferably from 1:1 to 5:1, more preferably from 1:1 to 4:1, such as from 1:1 to 3:1. More particularly, the expression "spherical-type" means that the pigment microparticles have a shape approximating that of a sphere. In other words, the pigment microparticles can be nearly orbicular in shape and can have a cross-sectional geometry that is essentially circular. Although not excluded, this does not necessarily mean that the pigment microparticles have the shape of a perfect sphere or ball. More likely, the shape of the pigment microparticles can exhibit a certain deviation from a sphere as long as the skilled person considers the shape as being similar to a sphere or as an approximation of a sphere.

In addition, the pigment microparticles can have a rather two-dimensional shape, with the smallest dimension substantially smaller than the two other dimensions, in which case the microparticles are referred to as being 2-dimensional microparticles. For example, the thickness of the microparticles can be significantly less than their length and width. The length and width can be of similar magnitude. Examples includes pigment microparticles having a shape of platelets, i.e. with a thickness that is substantially smaller than the planar dimension. For example, the aspect ratio AR=dmax/dmin, as defined above, of microparticles having a substantially two-dimensional shape, can be from about 10:1 to about 1000:1, preferably from about 10:1 to about 800:1, preferably from about 20:1 to about 800:1, preferably from about 10:1 to about 600:1, preferably from about 20:1 to about 600:1. Typically, the 2D-microparticles have a largest and a smallest dimension in their planer dimension, which both are significantly larger than the smallest dimension of the 2D-microparticles extending perpendicular to the planer dimension.

According to an embodiment, the pigments can include pigment microparticles of different shape. For example, microparticles of different size can be used to provide different reflecting and absorbing properties. Microparticles having different shape can also be formed of different pigment material. Furthermore, microparticles having different shape can also formed of different pigment material to provide different color.

Pigment Size

The pigments can be present in the composition in undissolved form. Depending on the shape, the pigments can have a D50[vol] particle diameter of from 0.001 micron to 1 micron.

For example, pigments that can be described as being microspheres can have a D50[vol] particle diameter of from 0.01 micron to 1 micron, preferably of from 0.015 micron to 0.75 micron, more preferably of from 0.02 micron to 0.50 micron. The microspheres can also have a D50[vol] particle diameter of from 0.6 micron to 0.9 micron, preferably of from 0.08 micron to 0.9 micron, and more preferably between of from 0.08 micron to 0.9 micron, such as from 0.08 micron to 0.8 micron, or such as of from 0.8 micron to 0.6 micron. According to an embodiment, the microspheres can also have a D50[vol] particle diameter of from 0.1 micron to 1 micron, preferably of from 0.12 micron to 1 micron, and more preferably between of from 0.16 micron to 1 micron, such as of from 0.2 micron to 1 micron, or such as of from 0.08 micron to 0.4 micron. The terms "micron" and "microns" describe the size in micrometers [μm].

In further embodiments, which can be combined with other embodiments described herein, the pigments, which can be described as microspheres, can have a D90[vol] particle diameter of from 0.1 micron to 1 micron, preferably of from 0.2 micron to 1 micron, and more preferably between of from 0.3 micron to 1 micron, such as of from 0.3 micron to 0.9 micron, or such as of from 0.4 micron to 0.8 micron, or such as of from 0.5 micron to 0.9 micron.

In some embodiments described herein, the pigments, which can be described as microspheres, can have a D10[vol] particle diameter of from 0.02 micron to 0.3 micron, preferably of from 0.06 micron to 0.3 micron, more preferably of from 0.08 micron to 0.3 micron, such as of from 0.08 micron to 0.2 micron, or such as of from 0.1 micron to 0.2 micron, or such as 0.12 micron to 0.3 micron.

In embodiments described herein, the D10[vol] particle diameter can be of from 0.02 micron to 0.3 micron and the D90[vol] can be of from 0.3 micron to 1 micron. In further embodiments, the D10[vol] particle diameter can be of from 0.06 micron to 0.2 micron and the D90[vol] can be of from 0.4 micron to 1 micron.

The particle diameter is represented by D10, D50 and/or by D90, which is the median diameter by volume. D10, D50 and D90 is measured with a Malvern Mastersizer 2000, which is a laser diffraction particle sizer and it is measured according to ISO 13320:2009(en) with Hydro 2000 G or Hydro 2000S where the dispersant is water or ethanol. Detection range is from 0.01 micron to 2000 micron. D50 is expressed as x50 in ISO 13320:2009(en).

The term "D10," as used herein refers, to the 10th percentile number- or volume-based median particle diameter, which is the diameter below which 10% by number or volume of the particle population is found. The term "D50," as used herein refers, to the 50th percentile number- or volume-based median particle diameter, which is the diameter below which 50% by number or volume of the particle population is found. The term "D90," as used herein refers, to the 90th percentile number- or volume-based median particle diameter, which is the diameter below which 90% by number or volume of the particle population is found. The number or volume measurement is indicated by [num] for number or [vol] for volume. If not indicated otherwise, the particle size is given as D10[vol], D50[vol], and D90[vol], respectively.

Laser diffraction measures particle size distributions by measuring the angular variation in intensity of light scattered as a laser beam passes through a dispersed particulate sample analyzer and the particle size is reported as a volume equivalent sphere diameter. A discussion of calculating D50 is provided in Barber et al, Pharmaceutical Development and Technology, 3(2), 153-161 (1998), which is incorporated herein by reference. Pigment microparticles having a D50[vol] particle diameter of less than 20 nm may enter the cuticles and are therefore difficult to remove. For scattering purposes, Pigment(s) having a D10[vol] particle diameter of at least 60 nm, or at least 80 nm can be used. Pigment(s) having a D50[vol] particle diameter of more than 1 micron typically do not sufficiently adhere onto hair fibers.

According to an embodiment, the particle size distribution, either relative to the number or volume of the particles, of the pigment microparticles can be at least bi-modal. A bi-modal particle size distribution has two distinct peaks which are spaced relative from, while tri-modal particle size distribution has three distinct peaks. The term "peak" means a local maximum of the distribution curve. The "distance" between two peaks, expressed relative to the particle size, can be at least 0.05 micron, preferably at least 0.1 micron, such as at least 0.2 micron. Providing an at least bi-modal particle size distribution allows to tailor the optical appearance of the colored hair. For example, the scattering properties varies with the particle size so that particles of different size scatter the light into different directions.

The at least bi-modal particle size distribution can be relative to pigment microparticles formed by the same pigment material. In addition to that or alternatively, the at least bi-model particle size distribution can be provided by pigment microparticles of different pigment material.

The size of pigment microparticles which can be described to have a 2-dimensional shape, and which are referred to as 2-dimensional microparticles can be determined by SEM. The size of 2-dimensional microparticles can also be determined by laser diffraction measurements. The particle size determined by laser diffraction is a mean size of the different dimensions of the 2-dimensional particles. The apparent D50[vol] particle diameter of 2-dimensional microparticles, as measured by SEM, can be from 0.5 micron to 50 microns, more preferably from 0.8 micron to 20 microns, more preferably from 1 micron to 15 microns, more preferably from 1.5 micron to 10 microns.

According to an embodiment, pigment particles are referred to as being microspheres can be used light-scattering and/or light absorbing purposes. Those particles, due to their pigment material, impart the hair with a specific color.

According to an embodiment, pigment particles are referred to as being 2-dimensional microparticles can be mainly used for light-reflecting and/or light absorbing purposes. Those particles, due to their pigment material, mainly reflect the light without significantly alter the color of the light.

The pigment microparticles can be light absorbing, but which for wavelengths of visible light provide negligible to low or no scattering. While not wishing to bound by any specific theory, it is believed that such pigments can provide more chromatic colors. Such pigment microparticles can have a D50[vol] value between about 0.001 micron and about 0.15 micron, between about 0.005 micron and about 0.1 micron or between about 0.010 micron and about 0.075 micron.

The pigment microparticles can be predominantly light scattering for wavelengths of visible light and provide low light absorption. While not wishing to bound by any specific theory, it is believed that such pigments can provide the visual effect of lightening the hair. Such pigment microparticles, which can be microspheres, can have a D50[vol] value between about 0.05 micron to about 1 micron, between 0.08 micron to about 0.9 micron, between about 0.05 micron and about 0.75 micron, between about 0.1 micron and about 0.5 micron or about 0.15 micron and about 0.4 micron. Such materials can have a refractive index above 1.5, above 1.7 or above 2.0.

Pigments made from metal and metal like materials which can conduct electricity, and which can absorb light and re-emit the light out of the metal to give the appearance of strong reflectance. While not wishing to be bound by any specific theory, it is believed that the absorbed light will induce alternating electric currents on the metal surface, and that this currents immediately re-emit light out of the metal. Such pigment microparticles can be platelets, e.g., having a thickness that is substantially smaller than the planar dimension. For example about five, about 10 or even about 400 times smaller in thickness than in the planer. Such platelets can have a thickness less than about 30 nm, but with a planar dimension less than about 10 micron wide. Platelets larger in size, such as 50 microns are even available in this thickness of 10 microns.

The pigment microparticles can be a composite formed by two different types of pigment microparticles. Examples include a composite of a 2-dimensional microparticle and at least one micro spherical particle (microsphere), a composite of different micro spherical particles, and a composite of different 2-dimensional particles. Composite particles formed by 2-dimensional microparticles to which micro spherical particles adhere provide an attractive alternative to a pure mixture of 2-dimensional microparticles and micro spherical particles. For example, a metallic 2-dimensional microparticle can carry one or more micro spherical particle such as one or more organic micro spherical particle. The micro spherical particles attached or bonded to the 2-dimensional microparticle can be formed of the same pigment material or can be formed of different pigment material. Composite microparticles formed of 2-dimensional microparticles and micro spherical particles can provide multiple functionality in one particle such as (metallic) reflectance and dielectric scattering, reflectance and absorption.

Pigment microparticles may be materials which are composite comprising a core of pigments made from metal and metal like materials which can conduct electricity, and which can absorb light and re-emit the light out of the metal to give the appearance of strong reflectance. While not wishing to be bound by any specific theory, it is believed that the absorbed light will induce alternating electric currents on the metal surface, and that this currents immediately re-emit light out of the metal. Upon this pigment light absorbing microparticles is immobilized. Such pigment microparticles can be platelets, e.g., having a thickness that is substantially smaller than the planar dimension. For example, five, ten or even 20 times smaller in thickness than in the planer. Such platelets can have a planer dimension less than 15 microns, but with a thickness less than 1 microns, more preferably with a planer dimension less than 12 microns but with a thickness less than 750 nm, even more preferably with a plan dimension less than 10 microns and a thickness less than 0.5 micron. The light absorbing microparticles can have D50 [vol] value between 0.001 micron and 0.15 micron, more preferably between 0.002 micron and 0.1 micron and even more preferable between 0.005 micron and 0.075 micron.

The light absorbing microparticles may also include dyes, pigments, or materials with color centers in the crystal structure, or photonic structures resulting in destructive or constructive interference, diffraction or other structures and materials mentioned in the book "The Physics and Chemistry of Color: the Fifteen Causes of Color", 2nd Edition by K. I. Nassau (ISBN 978-0-471-39106-7).

The pigment microparticles can be both light scattering and absorbing for wavelengths of visible light. While not wishing to bound by any specific theory, it is believed that such pigments can provide both some visual effect of lightening the hair. Such pigment microparticles can have a D50[num] value between about 50 nm and about 750 nm, between about 100 nm and about 500 nm or between about 150 nm and about 400 nm. Such materials have a refractive index above about 1.5, above about 1.7 or above about 2.0.

According to an embodiment, different pigment microparticles are combined to provide reflective, transmitting and refractive properties of the hair colored with the color composition described herein. A microparticle combination can be a material composite using at least two different pigment materials to form the pigment microparticles. In addition to, or alternating to, the microparticle combination, a mixture of separate pigment microparticles of different type can be used to bring about the desired reflective, transmitting and refractive properties.

The composite pigments, combination of pigments, and mixtures of pigment microparticles eliminate, or at least significantly reduce, hair penetration and scattering by light and thus eliminate the perception of pigment of natural hair color change.

Pigment Concentration

The color composition for coloring hair fibers according to the present disclosure comprises microparticles comprising at least one pigment. The color composition comprises from about 0.01% to about 40%, about 0.05% to about 35%, about 0.1 to about 25%, or about 0.15% and about 20% pigment(s), by weight of the color composition.

Pigment Material

The material of the pigment microparticles can be inorganic or organic. Inorganic-organic mixed pigments are also possible.

According to an embodiment, inorganic pigment(s) are used. The advantage of inorganic pigment(s) is their excellent resistance to light, weather, and temperature. The inorganic pigment(s) can be of natural origin, and are, for example, derived from material selected from the group consisting of chalk, ochre, umber, green earth, burnt sienna, and graphite. The pigment(s) can preferably be white pigments, such as, for example, titanium dioxide or zinc oxide. The pigment(s) can also be colored pigments, such as, for example, ultramarine or iron oxide red, luster pigments, metal effect pigments, pearlescent pigments, and fluorescent or phosphorescent pigments. The pigment(s) can be selected from the group consisting of metal oxides, hydroxides and oxide hydrates, mixed phase pigments, sulfur-containing silicates, metal sulfides, complex metal cyanides, metal sulfates, chromates and molybdates, alloys, and the metals themselves. The pigment(s) can be selected from the group consisting of titanium dioxide (CI 77891), black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), Prussian blue (ferric ferrocyanide, CI 77510), carmine (cochineal), zinc sulfide, barium sulfate, zinc oxide, siliconised titanium dioxide, siliconised zinc sulfide, siliconised zinc oxide, and mixtures thereof. The pigment(s) can be selected from the group consisting of iron oxide, titanium dioxide, mica, borosilicate, and combinations thereof. The pigment(s) can comprise an iron oxide (Fe2O3) pigment. The pigment(s) can comprise a combination of mica and titanium dioxide.

The pigment(s) can be pearlescent and colored pigment(s), and can preferably be based on mica which are coated with a metal oxide or a metal oxychloride, such as titanium dioxide or bismuth oxychloride, and optionally further color-imparting substances, such as iron oxides, Prussian blue, ultramarine, and carmine. The color exhibited by a pigment can be adjusted by varying the layer thickness. Such pigments are sold, for example, under the trade names Rona®, Colorona®, Dichrona®, RonaFlair®, Ronastar®, Xirona® and Timiron® all of which are available from Merck, Darmstadt, Germany. For example, Xirona® is a brand for color travel pigments that display color shifting effects depending on the viewing angle and are based on either natural mica, $SiO_2$ or calcium aluminum borosilicate flakes, coated with varying layers of TiO2. Pigment(s) from the line KTZ® from Kobo Products, Inc., 3474 So. Clinton Ave., So. Plainfield, USA, are also useful herein, in particular the Surface Treatable KTZ® Pearlescent Pigments from Kobo. Particularly useful are KTZ® FINE WHITE (mica and TiO2) having a D50 particle diameter of 5 to 25 micron and also KTZ® CELESTIAL LUSTER (mica and TiO2, 10 to 60 micron) as well as KTZ® CLASSIC WHITE (mica and TiO2, 10 to 60 micron). Also useful are SynCrystal Sapphire from Eckart Effect Pigments, which is a blue powder comprising platelets of synthetic fluorphlogopite coated with titanium dioxide, ferric ferrocyanide and small amounts of tin oxide. Also useful is SYNCRYSTAL Almond also from Eckart, which is a beige powder with a copper reflection color and is composed of platelets of synthetic fluorphlogopite and coated with titanium dioxide and iron oxides. Also useful is Duocrome® RV 524C from BASF, which provides a two color look via a lustrous red powder with a violet reflection powder due to its composition of mica, titanium dioxide and carmine. The colored pigment(s) can be lightly bright colored pigment(s) and can particularly be white color variations.

The pigment(s) can be organic pigments. The at least one pigment can be an organic pigment. As used herein, the term "organic pigment" means any pigment that satisfies the definition in Ullmann's encyclopedia in the chapter on organic pigments. For instance, the at least one organic pigment can be chosen from nitroso, nitro, azo, xanthene, quinoline, anthraquinone, phthalocyanin, copper phthalocyanin, copper hexadecachlorophthalocyanine, 2-[(2-Methoxy-4-nitrophenyl)azo]-N-(2-methoxyphenyl)-3-oxobutyramide, metal-complex, isoindolinone, isoindoline, quinacridone, perinone, perylene, diketopyrrolopyrrole, thioindigo, dioxazine, triphenylmethane, dimethylquinacridone and quinophthalone compounds, Azo-dyes, Nonionic azo dyes, Anionic Azo dyes, Cationic azo dyes, Complex forming azo dye, aza annulene dyes, aza analogue of diarylmethane dyes, aza annulene dyes, Nitro-dyes and their pigments, Carbonyl dyes and their pigments (for example, Anthrachinon dyes, indigo), Sulfur dyes, Florescence dyes, Anthracene or Insoluble alkali or earth metal acid dyes.

Or the pigment can be at least one of uncolored and UV absorbing.

The organic pigment(s) can be selected from the group consisting of natural pigments sepia, gamboge, bone charcoal, Cassel brown, indigo, chlorophyll and other plant pigments. The synthetic organic pigments can be selected from the group consisting of azo pigments, anthraquinoids, indigoids, dioxazine, quinacridone, phthalocyanine, isoindolinone, perylene and perinone, metal complex, alkali blue, diketopyrrolopyrrole pigments, and combinations thereof. A particularly preferred pigment is 7-Bis(1,3-dichloropropan-2-yl)benzo[lmn][3,8]phenanthrolin-1,3,6,8(2H,7H)-tetraon.

According to an embodiment, the pigment(s) can be selected from the pigment group consisting of, including any combination thereof (with CI meaning color index and CAS meaning Chemical Abstract Service Number):

Pigment Black 10 [C.I. 77265, (CAS: 7782-42-5)], Pigment Black 11 [C.I. 77499, (CAS: 12227-89-3)], Pigment Black 12 [C.I. 77543, (CAS: 68187-02-0)], Pigment Black 13 [C.I. 77322, (CAS: 1307-96-6)], Pigment Black 14 [C.I. 77728, (CAS: 83512-98-5)], Pigment Black 15 [C.I. 77403, (CAS: 1317-38-0)], Pigment Black 17 [C.I. 77975, (CAS: 1314-98-3)], Pigment Black 18 [C.I. 77011, (CAS: 12001-98-8)], Pigment Black 23 [C.I. 77865, (CAS: 68187-54-2)], Pigment Black 24 [C.I. 77898, (CAS: 68187-00-8)], Pigment Black 25 [C.I. 77332, (CAS: 68186-89-0)], Pigment Black 26 [C.I. 77494, (CAS: 68186-94-7)], Pigment Black 27 [C.I. 77502, (CAS: 68186-97-0)], Pigment Black 28 [C.I. 77428, (CAS: 68186-91-4)], Pigment Black 29 [C.I. 77498, (CAS: 68187-50-8)], Pigment Black 30 [C.I. 77504, (CAS: 71631-15-7)], Pigment Black 31 [C.I. 71132, (CAS: 67075-37-0)], Pigment Black 32 [C.I. 71133, (CAS: 83524-75-8)], Pigment Black 33 [C.I. 77537, (CAS: 188735-18-4)], Pigment Black 34 [C.I. 77770, (CAS: 1317-33-5)], Pigment Black 6 [C.I. 77266, (CAS: 1333-86-4)], Pigment Black 7 [C.I. 77266, (CAS: 1333-86-4)], Pigment Black 8 [C.I. 77268, (CAS: 1339-82-8)], Pigment Black 9 [C.I. 77267, (CAS: 8021-99-6)], Pigment Blue 10 [C.I. 44040, (CAS: 1325-93-5)], Pigment Blue 15 [C.I. 74160, (CAS: 147-14-8)], Pigment Blue 16 [C.I. 74100, (CAS: 574-93-6)], Pigment Blue 18 [C.I. 42770, (CAS: 1324-77-2)], Pigment Blue 21 [C.I. 69835, (CAS: 1324-26-1)], Pigment Blue 22 [C.I. 69810, (CAS: 1324-27-2)], Pigment Blue 25 [C.I. 21180, (CAS: 10127-03-4)], Pigment Blue 26 [C.I. 21185, (CAS: 5437-88-7)], Pigment Blue 28 [C.I. 77346, (CAS: 1345-16-0)], Pigment Blue 29 [C.I. 77007, (CAS: 57455-37-5)], Pigment Blue 30 [C.I. 77420, (CAS: 1339-83-9)], Pigment Blue 32 [C.I. 77365, (CAS: 69458-70-4)], Pigment Blue 33 [C.I. 77112, (CAS: 8046-59-1)], Pigment Blue 34 [C.I. 77450, (CAS: 1317-40-4)], Pigment Blue 35 [C.I. 77368, (CAS: 83712-59-8)], Pigment Blue 36 [C.I. 77343, (CAS: 68187-11-1)], Pigment Blue 56 [C.I. 42800, (CAS: 6417-46-5)], Pigment Blue 57 [C.I. 42795, (CAS: 5905-38-4)], Pigment Blue 60 [C.I. 69800, (CAS: 81-77-6)], Pigment Blue 61 [C.I. 42765, (CAS: 1324-76-1)], Pigment Blue 62 [C.I. 42595, (CAS: 82338-76-9)], Pigment Blue 63 [C.I. 73015, (CAS: 16521-38-3)], Pigment Blue 64 [C.I. 69825, (CAS: 130-20-1)], Pigment Blue 65 [C.I. 59800, (CAS: 116-71-2)], Pigment Blue 66 [C.I. 73000, (CAS: 482-89-3)], Pigment Blue 71 [C.I. 77998, (CAS: 68186-95-8)], Pigment Blue 72 [C.I. 77347, (CAS: 68186-87-8)], Pigment Blue 73 [C.I. 77364, (CAS: 68187-40-6)], Pigment Blue 74 [C.I. 77366, (CAS: 68412-74-8)], Pigment Blue 75 [C.I. 74160, (CAS: 3317-67-7)], Pigment Blue 76 [C.I. 742520, (CAS: 176365-61-0)], Pigment Blue 78 [C.I. 42090, (CAS: 68921-42-6)], Pigment Blue 79 [C.I. 741300, (CAS: 14154-42-8)], Pigment Blue 9 [C.I. 42025B, (CAS: 596-42-9)], Pigment Brown 1 [C.I. 12480, (CAS: 6410-40-8)], Pigment Brown 10 [C.I. 77227, (CAS: 12013-69-3)], Pigment Brown 11 [C.I. 77495, (CAS: 64294-89-9)], Pigment Brown 2 [C.I. 12071, (CAS: 10279-43-3)], Pigment Brown 22 [C.I. 10407, (CAS: 29398-96-7)], Pigment Brown 23 [C.I. 20060, (CAS: 35869-64-8)], Pigment Brown 24 [C.I. 77310, (CAS: 68186-90-3)], Pigment Brown 26 [C.I. 71129, (CAS: 81-33-4)], Pigment Brown 27 [C.I. 73410, (CAS: 3989-75-1)], Pigment Brown 28 [C.I. 69015, (CAS: 131-92-0)], Pigment Brown 33 [C.I. 77503, (CAS: 68186-88-9)], Pigment Brown 34 [C.I. 77497, (CAS: 68187-10-0)], Pigment Brown 35 [C.I. 77501, (CAS: 68187-09-7)], Pigment Brown 37 [C.I. 77890, (CAS: 70248-09-8)], Pigment Brown 38 [C.I. 561660, (CAS: 126338-72-5)], Pigment Brown 39 [C.I. 77312, (CAS: 71750-83-9)], Pigment Brown 6 [C.I. 77491, 77492 and 77499, (CAS: 52357-70-7)], Pigment Brown 9 [C.I. 77430, (CAS: 8014-85-5)], Pigment Green 10 [C.I. 12775, (CAS: 61725-51-7)], Pigment Green 12 [C.I. 10020, (CAS: 84682-41-7)], Pigment Green 15 [C.I. 77600, (CAS: 12224-92-9)], Pigment Green 17 [C.I. 77288, (CAS: 1308-38-9)], Pigment Green 18 [C.I. 77289, (CAS: 12001-99-9)], Pigment Green 19 [C.I. 77335, (CAS: 8011-87-8)], Pigment Green 20 [C.I. 77408, (CAS: 8007-61-2)], Pigment Green 21 [C.I. 77410, (CAS: 12002-03-8)], Pigment Green 22 [C.I. 77412, (CAS: 1345-20-6)], Pigment Green 23 [C.I. 77009, (CAS: 1344-98-5)], Pigment Green 24 [C.I. 77013, (CAS: 1345-00-2)], Pigment Green 26 [C.I. 77344, (CAS: 68187-49-5)], Pigment Green 27 [C.I. 77520, (CAS: 15418-51-6)], Pigment Green 36 [C.I. 74265, (CAS: 14302-13-7)], Pigment Green 37 [C.I. 74255, (CAS: 1330-37-6)], Pigment Green 38 [C.I. 74265, (CAS: 14302-13-7)], Pigment Green 42 [C.I. 74260, (CAS: 1328-53-6)], Pigment Green 47 [C.I. 59825, (CAS: 128-58-5)], Pigment Green 50 [C.I. 77377, (CAS: 68186-85-6)], Pigment Green 51 [C.I. 77300, (CAS: 68553-01-5)], Pigment Green 54 [C.I. 59830, (CAS: 25704-81-8)], Pigment Green 58 [C.I. 742655, (CAS: 1143572-73-9)], Pigment Green 8 [C.I. 10006, (CAS: 16143-80-9)], Pigment Green 9 [C.I. 49415, (CAS: 1326-13-2)], Pigment Orange 1 [C.I. 11725, (CAS: 6371-96-6)], Pigment Orange 13 [C.I. 21110, (CAS: 3520-72-7)], Pigment Orange 14 [C.I. 21165, (CAS: 6837-37-2)], Pigment Orange 15 [C.I. 21130, (CAS: 6358-88-9)], Pigment Orange 16 [C.I. 21160, (CAS: 6505-28-8)], Pigment Orange 17 [C.I. 15510, (CAS: 15782-04-4)], Pigment Orange 17 [C.I. 15510, (CAS: 15876-51-4)], Pigment Orange 18 [C.I. 15970, (CAS: 1325-14-0)], Pigment Orange 19 [C.I. 15990, (CAS: 5858-88-8)], Pigment Orange 20 [C.I. 77202, (CAS: 12656-57-4)], Pigment Orange 21 [C.I. 77601, (CAS: 1344-38-3)], Pigment Orange 22 [C.I. 12470, (CAS: 6358-48-1)], Pigment Orange 23 [C.I. 77201, (CAS: 1345-09-1)], Pigment Orange 24 [C.I. 12305, (CAS: 6410-27-1)], Pigment Orange 3 [C.I. 12105, (CAS: 6410-15-7)], Pigment Orange 31 [C.I. 20050, (CAS: 5280-74-0)], Pigment Orange 34 [C.I. 21115, (CAS: 15793-73-4)], Pigment Orange 39 [C.I. 45370, (CAS: 15876-57-0)], Pigment Orange 4 [C.I. 12459, (CAS: 21889-27-0)], Pigment Orange 40 [C.I. 59700, (CAS: 128-70-1)], Pigment Orange 43 [C.I. 71105, (CAS: 4424-06-0)], Pigment Orange 44 [C.I. 21162, (CAS: 17453-73-5)], Pigment Orange 45 [C.I. 77601, (CAS: 59519-55-0)], Pigment Orange 46 [C.I. 15602, (CAS: 63467-26-5)], Pigment Orange 5 [C.I. 12075, (CAS: 3468-63-1)], Pigment Orange 6 [C.I. 12730, (CAS: 6407-77-8)], Pigment Orange 61 [C.I. 11265, (CAS: 40716-47-0)], Pigment Orange 64 [C.I. 12760, (CAS: 72102-84-2)], Pigment Orange 65 [C.I. 48053, (CAS: 20437-10-9)], Pigment Orange 66 [C.I. 48210, (CAS: 68808-69-5)], Pigment Orange 67 [C.I. 12915, (CAS: 74336-59-7)], Pigment Orange 68 [C.I. 486150, (CAS: 42844-93-9)], Pigment Orange 69 [C.I. 56292, (CAS: 85959-60-0)], Pigment Orange 7 [C.I. 15530, (CAS: 5850-81-7)], Pigment Orange 71 [C.I. 561200, (CAS: 84632-50-8)], Pigment Orange 72 [C.I. 211095, (CAS: 384329-80-0)], Pigment Orange 73 [C.I. 561170, (CAS: 84632-59-7)], Pigment Orange 75 [C.I. 772830, (CAS: 12014-93-6)], Pigment Orange 77 [C.I. 59105, (CAS: 1324-11-4)], Pigment Red 10 [C.I. 12440, (CAS: 6410-35-1)], Pigment Red 100 [C.I. 13058, (CAS: 6371-55-7)], Pigment Red 101 [C.I. 77491, (CAS: 1309-37-1)], Pigment Red 101 [C.I. 77015, (CAS: 529484-30-8)], Pigment Red 103 [C.I. 77601, (CAS: 59519-56-1)], Pigment Red 104 [C.I. 77605, (CAS: 12656-85-8)], Pigment Red 105 [C.I. 77578, (CAS: 1314-41-6)], Pigment Red 106 [C.I. 77766, (CAS: 1344-48-5)], Pigment Red 107 [C.I. 77060, (CAS: 1345-04-6)], Pigment Red 108 [C.I. 77202, (CAS: 58339-34-7)], Pigment Red 109 [C.I. 77482, (CAS: 1345-24-0)], Pigment Red 11 [C.I. 12430, (CAS: 6535-48-4)], Pigment Red 112 [C.I. 12370, (CAS: 6535-46-2)], Pigment Red 113 [C.I. 77201, (CAS: 1345-09-1)], Pigment Red 114 [C.I. 12351, (CAS: 6358-47-0)], Pigment Red 115 [C.I. 15851, (CAS: 6358-40-3)], Pigment Red 117 [C.I. 15603, (CAS: 10142-77-5)], Pigment Red 119 [C.I. 12469, (CAS: 72066-77-4)], Pigment Red 12 [C.I. 12385, (CAS: 6410-32-8)], Pigment Red 121 [C.I. 77302, (CAS: 12125-42-7)], Pigment Red 122 [C.I. 73915, (CAS: 980-26-7)], Pigment Red 13 [C.I. 12395, (CAS: 6535-47-3)], Pigment Red 133 [C.I. 15920, (CAS: 5280-67-1)], Pigment Red 14 [C.I. 12380, (CAS: 6471-50-7)], Pigment Red 141 [C.I. 20044, (CAS: 3864-06-0)], Pigment Red 144 [C.I. 20735, (CAS: 5280-78-4)], Pigment Red 146 [C.I. 12485, (CAS: 5280-68-2)], Pigment Red 147 [C.I. 12433, (CAS: 68227-78-1)], Pigment Red 148 [C.I. 12369, (CAS: 94276-08-1)], Pigment Red 149 [C.I. 71137, (CAS: 4948-15-6)], Pigment Red 15 [C.I. 12465, (CAS: 6410-39-5)], Pigment Red 150 [C.I. 12290, (CAS: 56396-10-2)], Pigment Red 151 [C.I. 15892, (CAS: 61013-97-6)], Pigment Red 157 [C.I. 12355, (CAS: 6471-49-4)], Pigment Red 16 [C.I. 12500, (CAS: 6407-71-2)], Pigment Red 162 [C.I. 12431, (CAS: 6358-59-4)], Pigment Red 163 [C.I. 12455, (CAS: 6410-37-3)], Pigment Red 164 [C.I. 212855, (CAS: 72659-69-9)], Pigment Red 166 [C.I. 20730, (CAS: 3905-19-9)], Pigment Red 168 [C.I. 59300, (CAS: 4378-61-4)], Pigment Red 169 [C.I. 45160, (CAS: 12237-63-7)], Pigment Red 17 [C.I. 12390, (CAS: 6655-84-1)], Pigment Red 170 [C.I. 12475, (CAS: 2786-76-7)], Pigment Red 170 [C.I. 12474, (CAS: 36968-27-1)], Pigment Red 171 [C.I. 12512, (CAS: 6985-95-1)], Pigment Red 172 [C.I. 45430, (CAS: 12227-78-0)], Pigment Red 173 [C.I. 45170, (CAS: 12227-77-9)], Pigment Red 174 [C.I. 45410, (CAS: 15876-58-1)], Pigment Red 175 [C.I. 12513, (CAS: 6985-92-8)], Pigment Red 177 [C.I. 65300, (CAS: 4051-63-2)], Pigment Red 179 [C.I. 71130, (CAS: 5521-31-3)], Pigment Red 18 [C.I. 12350, (CAS: 3564-22-5)], Pigment Red 181 [C.I. 73360, (CAS: 2379-74-0)], Pigment Red 184 [C.I. 12487, (CAS: 99402-80-9)], Pigment Red 185 [C.I. 12516, (CAS: 51920-12-8)], Pigment Red 187 [C.I. 12486, (CAS: 59487-23-9)], Pigment Red 188 [C.I. 12467, (CAS: 61847-48-1)], Pigment Red 189 [C.I. 71135, (CAS: 2379-77-3)], Pigment Red 19 [C.I. 12400, (CAS: 6410-33-9)], Pigment Red 190 [C.I. 71140, (CAS: 6424-77-7)], Pigment Red 192 [C.I. 739155, (CAS: 61968-81-8)], Pigment Red 193 [C.I. 16185, (CAS: 12227-62-2)], Pigment Red 195 [C.I. 70320, (CAS: 4203-77-4)], Pigment Red 196 [C.I. 67000, (CAS: 2379-79-5)], Pigment Red 198 [C.I. 73390, (CAS: 6371-31-9)], Pigment Red 2 [C.I. 12310, (CAS: 6041-94-7)], Pigment Red 200 [C.I. 15867, (CAS: 58067-05-3)], Pigment Red 200 [C.I. 15867, (CAS: 32041-58-0)], Pigment Red 202 [C.I. 73907, (CAS: 3089-17-6)], Pigment Red 208 [C.I. 12514, (CAS: 31778-10-6)], Pigment Red 21 [C.I. 12300, (CAS: 6410-26-0)], Pigment Red 210 [C.I. 12477, (CAS: 61932-63-6)], Pigment Red 211 [C.I. 15910, (CAS: 85702-54-1)], Pigment Red 212 [C.I. 12360, (CAS: 6448-96-0)], Pigment Red 214 [C.I. 200660, (CAS: 40618-31-3)], Pigment Red 216 [C.I. 59710, (CAS: 1324-33-0)], Pigment Red 22 [C.I. 12315, (CAS: 6448-95-9)], Pigment Red 220 [C.I. 20055, (CAS: 68259-05-2)], Pigment Red 221 [C.I. 20065, (CAS: 71566-54-6)], Pigment Red 222 [C.I. 123665, (CAS: 20981-12-8)], Pigment Red 224 [C.I. 71127, (CAS: 128-69-8)], Pigment Red 226 [C.I. 597200, (CAS: 72828-01-4)], Pigment Red 229 [C.I. 77006, (CAS: 85536-78-3)], Pigment Red 230 [C.I. 77003, (CAS: 68187-27-9)], Pigment Red 231 [C.I. 77005, (CAS: 68186-99-2)], Pigment Red 232 [C.I. 77996, (CAS: 68412-79-3)], Pigment Red 233 [C.I. 77301, (CAS: 68187-12-2)], Pigment Red 235 [C.I. 77290, (CAS: 68201-65-0)], Pigment Red 236 [C.I. 77863, (CAS: 68187-53-1)], Pigment Red 242 [C.I. 20067, (CAS: 52238-92-3)], Pigment Red 243 [C.I. 15910, (CAS: 50326-33-5)], Pigment Red 243 [C.I. 15910, (CAS: 431991-58-1)], Pigment Red 247 [C.I. 15915, (CAS: 43035-18-3)], Pigment Red 248 [C.I. 200552, (CAS: 80648-58-4)], Pigment Red 251 [C.I. 12925, (CAS: 74336-60-0)], Pigment Red 253 [C.I. 12375, (CAS: 85776-13-2)], Pigment Red 254 [C.I. 56110, (CAS: 84632-65-5)], Pigment Red 255 [C.I. 561050, (CAS: 54660-00-3)], Pigment Red 256 [C.I. 124635, (CAS: 79102-65-1)], Pigment Red 257 [C.I. 562700, (CAS: 70833-37-3)], Pigment Red 258 [C.I. 12318, (CAS: 57301-22-1)], Pigment Red 259 [C.I. 77007, (CAS: 113956-14-2)], Pigment Red 260 [C.I. 56295, (CAS: 71552-60-8)], Pigment Red 261 [C.I. 12468, (CAS: 16195-23-6)], Pigment Red 264 [C.I. 561300, (CAS: 88949-33-1)], Pigment Red 265 [C.I. 772830, (CAS: 12014-93-6)], Pigment Red 267 [C.I. 12396, (CAS: 68016-06-8)], Pigment Red 268 [C.I. 12316, (CAS: 16403-84-2)], Pigment Red 269 [C.I. 12466, (CAS: 67990-05-0)], Pigment Red 271 [C.I. 487100, (CAS: 85958-80-1)], Pigment Red 273 [C.I. 16035, (CAS: 68583-95-9)], Pigment Red 274 [C.I. 16255, (CAS: 12227-64-4)], Pigment Red 3 [C.I. 12120, (CAS: 2425-85-6)], Pigment Red 30 [C.I. 12330, (CAS: 6471-48-3)], Pigment Red 32 [C.I. 12320, (CAS: 6410-29-3)], Pigment Red 37 [C.I. 21205, (CAS: 6883-91-6)], Pigment Red 38 [C.I. 21120, (CAS: 6358-87-8)], Pigment Red 39 [C.I. 21080, (CAS: 6492-54-2)], Pigment Red 4 [C.I. 12085, (CAS: 2814-77-9)], Pigment Red 40 [C.I. 12170, (CAS: 2653-64-7)], Pigment Red 41 [C.I. 21200, (CAS: 6505-29-9)], Pigment Red 42 [C.I. 21210, (CAS: 6358-90-3)], Pigment Red 48 [C.I. 15865, (CAS: 3564-21-4)], Pigment Red 48 [C.I. 15865, (CAS: 1325-12-8)], Pigment Red 48 [C.I. 15865, (CAS: 7585-41-3)], Pigment Red 48 [C.I. 15865, (CAS: 7023-61-2)], Pigment Red 48 [C.I. 15865, (CAS: 15782-05-5)], Pigment Red 48 [C.I. 15865, (CAS: 5280-66-0)], Pigment Red 48 [C.I. 15865, (CAS: 71832-83-2)], Pigment Red 48 [C.I. 15865, (CAS: 68966-97-2)], Pigment Red 49 [C.I. 15630, (CAS: 1248-18-6)], Pigment Red 49 [C.I. 15630, (CAS: 1325-06-0)], Pigment Red 49 [C.I. 15630, (CAS: 1103-38-4)], Pigment Red 49 [C.I. 15630, (CAS: 1103-39-5)], Pigment Red 49 [C.I. 15630, (CAS: 6371-67-1)], Pigment Red 5 [C.I. 12490, (CAS: 6410-41-9)], Pigment Red 50 [C.I. 15500, (CAS: 5850-76-0)], Pigment Red 50 [C.I. 15500, (CAS: 6372-81-2)], Pigment Red 51 [C.I. 15580, (CAS: 5850-87-3)], Pigment Red 52 [C.I. 15860, (CAS: 5858-82-2)], Pigment Red 52 [C.I. 15860, (CAS: 1325-11-7)], Pigment Red 52 [C.I. 15860, (CAS: 17852-99-2)], Pigment Red 52 [C.I. 15860, (CAS: 17814-20-9)], Pigment Red 52 [C.I. 15860, (CAS: 12238-31-2)], Pigment Red 53 [C.I. 15585, (CAS: 2092-56-0)], Pigment Red 53 [C.I. 15585, (CAS: 1325-04-8)], Pigment Red 53 [C.I. 15585, (CAS: 67990-35-6)], Pigment Red 53 [C.I. 15585, (CAS: 73263-40-8)], Pigment Red 54 [C.I. 14830, (CAS: 6373-10-0)], Pigment Red 55 [C.I. 15820, (CAS: 141052-43-9)], Pigment Red 57 [C.I. 15850, (CAS: 5858-81-1)], Pigment Red 57 [C.I. 15850, (CAS: 17852-98-1)], Pigment Red 57 [C.I. 15850, (CAS: 55491-44-6)], Pigment Red 58 [C.I. 15825, (CAS: 1325-09-3)], Pigment Red 58 [C.I. 15825, (CAS: 7538-59-2)], Pigment Red 58 [C.I. 15825, (CAS: 15782-03-3)], Pigment Red 58 [C.I. 15825, (CAS: 76613-71-3)], Pigment Red 58 [C.I. 15825, (CAS: 64552-28-9)], Pigment Red 6 [C.I. 12090, (CAS: 6410-13-5)], Pigment Red 60 [C.I. 16105, (CAS: 15782-06-6)], Pigment Red 60 [C.I. 16105, (CAS: 1325-16-2)], Pigment Red 61 [C.I. 24830, (CAS: 1325-29-7)], Pigment Red 62 [C.I. 23295, (CAS: 109823-18-9)], Pigment Red 63 [C.I. 15880, (CAS: 21416-46-6)], Pigment Red 63 [C.I. 15880, (CAS: 6417-83-0)], Pigment Red 63 [C.I. 15880, (CAS: 15792-20-8)], Pigment Red 63 [C.I. 15880, (CAS: 35355-77-2)], Pigment Red 64 [C.I. 15800, (CAS: 16508-79-5)], Pigment Red 64 [C.I. 15800, (CAS: 6371-76-2)], Pigment Red 65 [C.I. 18020, (CAS: 1325-21-9)], Pigment Red 66 [C.I. 18000, (CAS: 1325-19-5)], Pigment Red 67 [C.I. 18025, (CAS: 1325-22-0)], Pigment Red 68 [C.I. 15525, (CAS: 5850-80-6)], Pigment Red 69 [C.I. 15595, (CAS: 5850-90-8)], Pigment Red 7 [C.I. 12420, (CAS: 6471-51-8)], Pigment Red 70 [C.I. 15590, (CAS: 5850-89-5)], Pigment Red 77 [C.I. 15826, (CAS: 6358-39-0)], Pigment Red 8 [C.I. 12335, (CAS: 6410-30-6)], Pigment Red 83 [C.I. 58000, (CAS: 104074-25-1)], Pigment Red 84 [C.I. 58210, (CAS: 1328-07-0)], Pigment Red 85 [C.I. 63350, (CAS: 6370-96-3)], Pigment Red 86 [C.I. 73375, (CAS: 6371-26-2)], Pigment Red 89 [C.I. 60745, (CAS: 6409-74-1)], Pigment Red 9 [C.I. 12460, (CAS: 6410-38-4)], Pigment Red 90 [C.I. 45380, (CAS: 15876-39-8)], Pigment Red 93 [C.I. 12152, (CAS: 6548-36-3)], Pigment Red 95 [C.I. 15897, (CAS: 72639-39-5)], Pigment Red 99 [C.I. 15570, (CAS: 5850-85-1)], Pigment Violet 10

[C.I. 42535, (CAS: 1325-82-2)], Pigment Violet 12 [C.I. 58050 (CAS: 1328-03-6)], Pigment Violet 13 [C.I. 125085, (CAS: 83399-83-1)], Pigment Violet 14 [C.I. 77360, (CAS: 10101-56-1)], Pigment Violet 15 [C.I. 77007, (CAS: 12769-96-9)], Pigment Violet 16 [C.I. 77742, (CAS: 10101-66-3)], Pigment Violet 19 [C.I. 46500, (CAS: 1047-16-1)], Pigment Violet 20 [C.I. 58225, (CAS: 6486-92-6)], Pigment Violet 23 [C.I. 51319, (CAS: 215247-95-3)], Pigment Violet 25 [C.I. 12321, (CAS: 6358-46-9)], Pigment Violet 27 [C.I. 42535, (CAS: 12237-62-6)], Pigment Violet 29 [C.I. 71129, (CAS: 81-33-4)], Pigment Violet 3 [C.I. 42535, (CAS: 68647-35-8)], Pigment Violet 3 [C.I. 42535, (CAS: 68308-41-8)], Pigment Violet 3 [C.I. 42535, (CAS: 67989-22-4)], Pigment Violet 31 [C.I. 60010, (CAS: 1324-55-6)], Pigment Violet 33 [C.I. 60005, (CAS: 1324-17-0)], Pigment Violet 36 [C.I. 73385, (CAS: 5462-29-3)], Pigment Violet 37 [C.I. 51345, (CAS: 17741-63-8)], Pigment Violet 38 [C.I. 73395, (CAS: 2379-75-1)], Pigment Violet 47 [C.I. 77363, (CAS: 68610-13-9)], Pigment Violet 48 [C.I. 77352, (CAS: 68608-93-5)], Pigment Violet 49 [C.I. 77362, (CAS: 16827-96-6)], Pigment Violet 5 [C.I. 58055, (CAS: 1328-04-7)], Pigment Violet 6 [C.I. 58060, (CAS: 6483-85-8)], Pigment Violet 6 [C.I. 58060, (CAS: 1328-05-8)], Pigment Violet 7 [C.I. 58065, (CAS: 1328-06-9)], Pigment Violet 8 [C.I. 18005, (CAS: 1325-20-8)], Pigment Yellow 1 [C.I. 11680, (CAS: 2512-29-0)], Pigment Yellow 10 [C.I. 12710, (CAS: 6407-75-6)], Pigment Yellow 100 [C.I. 19140, (CAS: 12225-21-7)], Pigment Yellow 104 [C.I. 15985, (CAS: 15790-07-5)], Pigment Yellow 105 [C.I. 11743, (CAS: 12236-75-8)], Pigment Yellow 109 [C.I. 56284, (CAS: 5045-40-9)], Pigment Yellow 11 [C.I. 10325, (CAS: 2955-16-0)], Pigment Yellow 110 [C.I. 56280, (CAS: 5590-18-1)], Pigment Yellow 111 [C.I. 11745, (CAS: 15993-42-7)], Pigment Yellow 112 [C.I. 70600, (CAS: 475-71-8)], Pigment Yellow 114 [C.I. 21092, (CAS: 68610-87-7)], Pigment Yellow 115 [C.I. 47005, (CAS: 68814-04-0)], Pigment Yellow 116 [C.I. 11790, (CAS: 61968-84-1)], Pigment Yellow 117 [C.I. 48043, (CAS: 21405-81-2)], Pigment Yellow 118 [C.I. 77894, (CAS: 61512-65-0)], Pigment Yellow 119 [C.I. 77496, (CAS: 68187-51-9)], Pigment Yellow 12 [C.I. 21090, (CAS: 6358-85-6)], Pigment Yellow 123 [C.I. 65049, (CAS: 4028-94-8)], Pigment Yellow 124 [C.I. 21107, (CAS: 67828-22-2)], Pigment Yellow 126 [C.I. 21101, (CAS: 90268-23-8)], Pigment Yellow 127 [C.I. 21102, (CAS: 68610-86-6)], Pigment Yellow 128 [C.I. 20037, (CAS: 79953-85-8)], Pigment Yellow 129 [C.I. 48042, (CAS: 15680-42-9)], Pigment Yellow 13 [C.I. 21100, (CAS: 5102-83-0)], Pigment Yellow 130 [C.I. 117699, (CAS: 23739-66-4)], Pigment Yellow 133 [C.I. 139395, (CAS: 85702-53-0)], Pigment Yellow 134 [C.I. 21111, (CAS: 31775-20-9)], Pigment Yellow 138 [C.I. 56300, (CAS: 30125-47-4)], Pigment Yellow 139 [C.I. 56298, (CAS: 36888-99-0)], Pigment Yellow 14 [C.I. 21095, (CAS: 5468-75-7)], Pigment Yellow 147 [C.I. 60645, (CAS: 4118-16-5)], Pigment Yellow 148 [C.I. 50600, (CAS: 20572-37-6)], Pigment Yellow 15 [C.I. 21220, (CAS: 6528-35-4)], Pigment Yellow 150 [C.I. 12764, (CAS: 872613-79-1)], Pigment Yellow 153 [C.I. 48545, (CAS: 29204-84-0)], Pigment Yellow 155 [C.I. 200310, (CAS: 68516-73-4)], Pigment Yellow 157 [C.I. 77900, (CAS: 68610-24-2)], Pigment Yellow 158 [C.I. 77862, (CAS: 68186-93-6)], Pigment Yellow 159 [C.I. 77997, (CAS: 68187-15-5)], Pigment Yellow 16 [C.I. 20040, (CAS: 5979-28-2)], Pigment Yellow 160 [C.I. 77991, (CAS: 68187-01-9)], Pigment Yellow 161 [C.I. 77895, (CAS: 68611-43-8)], Pigment Yellow 162 [C.I. 77896, (CAS: 68611-42-7)], Pigment Yellow 163 [C.I. 77897, (CAS: 68186-92-5)], Pigment Yellow 164 [C.I. 77899, (CAS: 68412-38-4)], Pigment Yellow 167 [C.I. 11737, (CAS: 38489-24-6)], Pigment Yellow 168 [C.I. 13960, (CAS: 71832-85-4)], Pigment Yellow 169 [C.I. 13955, (CAS: 73385-03-2)], Pigment Yellow 17 [C.I. 21105, (CAS: 4531-49-1)], Pigment Yellow 173 [C.I. 561600, (CAS: 51016-63-8)], Pigment Yellow 174 [C.I. 21098, (CAS: 78952-72-4)], Pigment Yellow 176 [C.I. 21103, (CAS: 90268-24-9)], Pigment Yellow 177 [C.I. 48120, (CAS: 60109-88-8)], Pigment Yellow 179 [C.I. 48125, (CAS: 63287-28-5)], Pigment Yellow 180 [C.I. 21290, (CAS: 77804-81-0)], Pigment Yellow 181 [C.I. 11777, (CAS: 74441-05-7)], Pigment Yellow 182 [C.I. 128300, (CAS: 67906-31-4)], Pigment Yellow 183 [C.I. 18792, (CAS: 65212-77-3)], Pigment Yellow 184 [C.I. 771740, (CAS: 14059-33-7)], Pigment Yellow 185 [C.I. 56290, (CAS: 76199-85-4)], Pigment Yellow 188 [C.I. 21094, (CAS: 23792-68-9)], Pigment Yellow 190 [C.I. 189785, (CAS: 94612-75-6)], Pigment Yellow 191 [C.I. 18795, (CAS: 129423-54-7)], Pigment Yellow 191 [C.I. 18795, (CAS: 154946-66-4)], Pigment Yellow 192 [C.I. 507300, (CAS: 56279-27-7)], Pigment Yellow 193 [C.I. 65412, (CAS: 70321-14-1)], Pigment Yellow 194 [C.I. 11785, (CAS: 82199-12-0)], Pigment Yellow 199 [C.I. 653200, (CAS: 136897-58-0)], Pigment Yellow 2 [C.I. 11730, (CAS: 6486-26-6)], Pigment Yellow 202 [C.I. 65410, (CAS: 3627-47-2)], Pigment Yellow 203 [C.I. 117390, (CAS: 150959-17-4)], Pigment Yellow 213 [C.I. 117875, (CAS: 220198-21-0)], Pigment Yellow 218 [C.I. 561805, (CAS: 910868-14-3)], Pigment Yellow 220 [C.I. 561806, (CAS: 17352-39-5)], Pigment Yellow 227 [C.I. 777895, (CAS: 1374645-21-2)], Pigment Yellow 3 [C.I. 11710, (CAS: 6486-23-3)], Pigment Yellow 30 [C.I. 77592, (CAS: 1345-30-8)], Pigment Yellow 31 [C.I. 77103, (CAS: 10294-40-3)], Pigment Yellow 33 [C.I. 77223, (CAS: 8012-75-7)], Pigment Yellow 34 [C.I. 77603, (CAS: 1344-37-2)], Pigment Yellow 35 [C.I. 77205, (CAS: 90604-89-0)], Pigment Yellow 36 [C.I. 77956, (CAS: 49663-84-5)], Pigment Yellow 37 [C.I. 77199, (CAS: 90604-90-3)], Pigment Yellow 38 [C.I. 77878, (CAS: 1315-01-1)], Pigment Yellow 39 [C.I. 77086, (CAS: 1303-33-9)], Pigment Yellow 4 [C.I. 11665, (CAS: 1657-16-5)], Pigment Yellow 41 [C.I. 77588, (CAS: 8012-00-8)], Pigment Yellow 42 [C.I. 77492, (CAS: 51274-00-1)], Pigment Yellow 43 [C.I. 77492, (CAS: 64294-91-3)], Pigment Yellow 44 [C.I. 77188, (CAS: 1345-08-0)], Pigment Yellow 45 [C.I. 77505, (CAS: 1328-64-9)], Pigment Yellow 46 [C.I. 77577, (CAS: 1317-36-8)], Pigment Yellow 48 [C.I. 77610, (CAS: 592-05-2)], Pigment Yellow 5 [C.I. 11660, (CAS: 4106-67-6)], Pigment Yellow 53 [C.I. 77788, (CAS: 8007-18-9)], Pigment Yellow 55 [C.I. 21096, (CAS: 6358-37-8)], Pigment Yellow 6 [C.I. 11670, (CAS: 4106-76-7)], Pigment Yellow 60 [C.I. 12705, (CAS: 6407-74-5)], Pigment Yellow 61 [C.I. 13880, (CAS: 5280-69-3)], Pigment Yellow 62 [C.I. 13940, (CAS: 12286-66-7)], Pigment Yellow 62 [C.I. 13940, (CAS: 5280-70-6)], Pigment Yellow 65 [C.I. 11740, (CAS: 6528-34-3)], Pigment Yellow 7 [C.I. 12780, (CAS: 6407-81-6)], Pigment Yellow 73 [C.I. 11738, (CAS: 13515-40-7)], Pigment Yellow 74 [C.I. 11741, (CAS: 6358-31-2)], Pigment Yellow 75 [C.I. 11770, (CAS: 52320-66-8)], Pigment Yellow 77 [C.I. 20045, (CAS: 5905-17-9)], Pigment Yellow 81 [C.I. 21127, (CAS: 22094-93-5)], Pigment Yellow 83 [C.I. 21108, (CAS: 5567-15-7)], Pigment Yellow 83 [C.I. 21107, (CAS: 15110-84-6)], Pigment Yellow 9 [C.I. 11720, (CAS: 6486-24-4)], Pigment Yellow 93 [C.I. 20710, (CAS: 5580-57-4)], Pigment Yellow 94 [C.I. 20038, (CAS: 5580-58-5)], Pigment Yellow 95 [C.I. 20034, (CAS: 5280-80-8)], Pigment Yellow 98 [C.I. 11727, (CAS: 32432-45-4)], Prussian blue [C.I. 77510, (CAS: 12240-15-2)], Pigment Blue 1 [(CAS: 1325-87-7)], Pigment Blue 1 [(CAS: 69980-72-9)], Pigment Blue 1 [(CAS: 68409-66-5)], Pigment Blue 10 [(CAS: 84057-86-3)], Pigment Blue 12 [(CAS: 1325-77-5)], Pigment Blue 14 [(CAS: 1325-88-8)], Pigment Blue 2 [(CAS: 1325-94-6)], Pigment Blue 3 [(CAS: 1325-79-7)], Pigment Blue 9 [(CAS: 1325-74-2)], Pigment Green 1 [(CAS: 1325-75-3)], Pigment Green 3 [(CAS: 68845-37-4)], Pigment Green 4 [(CAS: 61725-50-6)], Pigment Red 80 [(CAS: 12224-98-5)], Pigment Red 81 [(CAS: 80083-40-5)], Pigment Red 81 [(CAS: 75627-12-2)], Pigment Red 81 [(CAS: 68310-07-6)], Pigment Red 81 [(CAS: 85959-61-1)], Pigment Red 81 [(CAS: 63022-06-0)], Pigment Red 81 [(CAS: 63022-07-1)], Pigment Violet 1 [(CAS: 1326-03-0)], Pigment Violet 2 [(CAS: 1326-04-1)], Pigment Violet 2 [(CAS: 103443-41-0)], Pigment Violet 4 [(CAS: 1325-80-0)], Pigment Black 1 [(CAS: 73104-73-1)], Pigment Black 1 [(CAS: 9064-44-2)], Pigment Black 11 [(CAS: 120899-48-1)], Pigment Black 11 [(CAS: 128666-38-6)], Pigment Black 11 [(CAS: 128666-37-5)], Pigment Black 11 [(CAS: 128666-36-4)], Pigment Black 11 [(CAS: 147858-25-1)], Pigment Black 16 [(CAS: 7440-66-6)], Pigment Black 19 [(CAS: 874954-47-9)], Pigment Black 2 [(CAS: 12236-57-6)], Pigment Black 20 [(CAS: 12216-93-2)], Pigment Black 21 [(CAS: 12216-94-3)], Pigment Black 22 [(CAS: 55353-02-1)], Pigment Black 3 [(CAS: 945563-42-8)], Pigment Black 35 [(CAS: 945563-51-9)], Pigment Black 5 [(CAS: 945563-45-1)], Pigment Blue 1 [(CAS: 68647-33-6)], Pigment Blue 10 [(CAS: 308086-15-9)], Pigment Blue 11 [(CAS: 71798-70-4)], Pigment Blue 13 [(CAS: 945558-73-6)], Pigment Blue 15-Pigment Green 7 mixt. [(CAS: 1026025-11-5)], Pigment Blue 15-Pigment Red 122-Pigment Yellow 74 mixt. [(CAS: 1357447-02-9)], Pigment Blue 151 [(CAS: 685529-31-1)], Pigment Blue 16 [(CAS: 424827-05-4)], Pigment Blue 17 [(CAS: 153640-87-0)], Pigment Blue 17 [(CAS: 71799-04-7)], Pigment Blue 19 [(CAS: 58569-23-6)], Pigment Blue 2 [(CAS: 1126074-38-1)], Pigment Blue 20 [(CAS: 945558-74-7)], Pigment Blue 209 [(CAS: 215590-82-2)], Pigment Blue 23 [(CAS: 57486-30-3)], Pigment Blue 24 [(CAS: 1042940-03-3)], Pigment Blue 28 [(CAS: 151732-17-1)], Pigment Blue 29 [(CAS: 151732-19-3)], Pigment Blue 31 [(CAS: 945558-75-8)], Pigment Blue 4 [(CAS: 945558-70-3)], Pigment Blue 5 [(CAS: 945558-72-5)], Pigment Blue 52 [(CAS: 945558-90-7)], Pigment Blue 53 [(CAS: 945558-91-8)], Pigment Blue 53 [(CAS: 190454-42-3)], Pigment Blue 56 [(CAS: 64427-27-6)], Pigment Blue 58 [(CAS: 12236-58-7)], Pigment Blue 59 [(CAS: 12236-59-8)], Pigment Blue 6 [(CAS: 371759-37-4)], Pigment Blue 61 [(CAS: 1126075-97-5)], Pigment Blue 63 [(CAS: 815586-00-6)], Pigment Blue 67 [(CAS: 945558-93-0)], Pigment Blue 68 [(CAS: 129406-28-6)], Pigment Blue 69 [(CAS: 945558-94-1)], Pigment Blue 7 [(CAS: 71838-91-0)], Pigment Blue 7 [(CAS: 120177-75-5)], Pigment Blue 70 [(CAS: 72827-99-7)], Pigment Blue 77 [(CAS: 945558-95-2)], Pigment Blue 8 [(CAS: 12224-90-7)], Pigment Blue 80 [(CAS: 391663-82-4)], Pigment Blue 81 [(CAS: 945558-98-5)], Pigment Blue 83 [(CAS: 1126076-49-0)], Pigment Blue 84 [(CAS: 2095508-48-6)], Pigment Brown 126 [(CAS: 128664-60-8)], Pigment Brown 29 [(CAS: 109414-04-2)], Pigment Brown 3 [(CAS: 1325-24-2)], Pigment Brown 30 [(CAS: 135668-57-4)], Pigment Brown 31 [(CAS: 126338-71-4)], Pigment Brown 32 [(CAS: 72828-00-3)], Pigment Brown 36 [(CAS: 945563-08-6)], Pigment Brown 4 [(CAS: 109944-91-4)], Pigment Brown 40 [(CAS: 945563-13-3)], Pigment Brown 41 [(CAS: 211502-16-8)], Pigment Brown 42 [(CAS: 211502-17-9)], Pigment Brown 43 [(CAS: 75864-23-2)], Pigment Brown 44 [(CAS: 945563-18-8)], Pigment Brown 45 [(CAS: 945563-37-1)], Pigment Brown 46 [(CAS: 945563-38-2)], Pigment Brown 47 [(CAS: 945563-39-3)], Pigment Brown 48 [(CAS: 2170864-80-7)], Pigment Brown 5 [(CAS: 16521-34-9)], Pigment Brown 6 [(CAS: 1275574-14-5)], Pigment Green 1 [(CAS: 68814-00-6)], Pigment Green 1 [(CAS: 68123-12-6)], Pigment Green 13 [(CAS: 148092-61-9)], Pigment Green 14 [(CAS: 114013-40-0)], Pigment Green 16 [(CAS: 65505-26-2)], Pigment Green 2 [(CAS: 12213-69-3)], Pigment Green 2 [(CAS: 76963-33-2)], Pigment Green 25 [(CAS: 945560-75-8)], Pigment Green 45 [(CAS: 945561-39-7)], Pigment Green 46 [(CAS: 945561-40-0)], Pigment Green 48 [(CAS: 945561-55-7)], Pigment Green 49 [(CAS: 945561-56-8)], Pigment Green 52 [(CAS: 945562-08-3)], Pigment Green 55 [(CAS: 945563-02-0)], Pigment Green 56 [(CAS: 945563-05-3)], Pigment Green 59 [(CAS: 2170445-83-5)], Pigment Green 6 [(CAS: 945559-56-8)], Pigment Green 62 [(CAS: 2108056-55-7)], Pigment Green 63 [(CAS: 2108056-56-8)], Pigment Green 7 [(CAS: 68022-83-3)], Pigment Green 77 [(CAS: 12715-62-7)], Pigment Green 7-Pigment Yellow 93 mixt. [(CAS: 1046461-83-9)], Pigment Orange 12 [(CAS: 945426-49-3)], Pigment Orange 20 [(CAS: 957128-28-8)], Pigment Orange 25 [(CAS: 12224-97-4)], Pigment Orange 32 [(CAS: 945426-51-7)], Pigment Orange 36 [(CAS: 12236-62-3)], Pigment Orange 38 [(CAS: 12236-64-5)], Pigment Orange 42 [(CAS: 12768-99-9)], Pigment Orange 43-Pigment Orange 64 mixt. [(CAS: 1046461-84-0)], Pigment Orange 47 [(CAS: 71819-73-3)], Pigment Orange 48 [(CAS: 71819-74-4)], Pigment Orange 49 [(CAS: 71819-75-5)], Pigment Orange 50 [(CAS: 76780-89-7)], Pigment Orange 51 [(CAS: 61512-61-6)], Pigment Orange 52 [(CAS: 61512-62-7)], Pigment Orange 53 [(CAS: 945426-52-8)], Pigment Orange 54 [(CAS: 945426-53-9)], Pigment Orange 55 [(CAS: 304891-88-1)], Pigment Orange 56 [(CAS: 74433-73-1)], Pigment Orange 57 [(CAS: 945426-54-0)], Pigment Orange 58 [(CAS: 945426-55-1)], Pigment Orange 59 [(CAS: 304891-93-8)], Pigment Orange 60 [(CAS: 68399-99-5)], Pigment Orange 62 [(CAS: 52846-56-7)], Pigment Orange 63 [(CAS: 76233-79-9)], Pigment Orange 70 [(CAS: 914936-31-5)], Pigment Orange 74 [(CAS: 516493-26-8)], Pigment Orange 76 [(CAS: 945426-61-9)], Pigment Orange 79 [(CAS: 945426-62-0)], Pigment Orange 8 [(CAS: 945426-48-2)], Pigment Orange 80 [(CAS: 945426-63-1)], Pigment Orange 81 [(CAS: 656223-72-2)], Pigment Orange 82 [(CAS: 2170864-77-2)], Pigment Orange 86 [(CAS: 1883421-38-2)], Pigment Orange 9 [(CAS: 71799-05-8)], Pigment Red 1 [(CAS: 39781-24-3)], Pigment Red 102 [(CAS: 1332-25-8)], Pigment Red 108 [(CAS: 918496-78-3)], Pigment Red 110 [(CAS: 854102-21-9)], Pigment Red 111 [(CAS: 12224-99-6)], Pigment Red 118 [(CAS: 945428-13-7)], Pigment Red 120 [(CAS: 57485-96-8)], Pigment Red 123 [(CAS: 24108-89-2)], Pigment Red 134 [(CAS: 12286-59-8)], Pigment Red 135 [(CAS: 945428-14-8)], Pigment Red 136 [(CAS: 945428-21-7)], Pigment Red 137 [(CAS: 71799-07-0)], Pigment Red 139 [(CAS: 12262-44-1)], Pigment Red 140 [(CAS: 383890-12-8)], Pigment Red 142 [(CAS: 109944-97-0)], Pigment Red 143 [(CAS: 12286-63-4)], Pigment Red 152 [(CAS: 405113-25-9)], Pigment Red 154 [(CAS: 109944-98-1)], Pigment Red 155 [(CAS: 109944-99-2)], Pigment Red 156 [(CAS: 109945-00-8)], Pigment Red 158 [(CAS: 945552-90-9)], Pigment Red 159 [(CAS: 109945-01-9)], Pigment Red 160 [(CAS: 854524-60-0)], Pigment Red 161 [(CAS: 945552-91-0)], Pigment Red 165 [(CAS: 12225-03-5)], Pigment Red 167 [(CAS: 12236-66-7)], Pigment Red 176 [(CAS: 12225-06-8)], Pigment Red 178 [(CAS: 3049-71-6)], Pigment Red 17-Pigment Red 150-Pigment White 18 mixt. [(CAS: 2247196-29-6)], Pigment Red 180 [(CAS: 12769-00-5)], Pigment Red 182 [(CAS: 61036-51-9)], Pigment Red 183 [(CAS: 51920-11-7)], Pigment Red 191 [(CAS: 85068-75-3)], Pigment Red 199 [(CAS: 61901-78-8)], Pigment Red 20 [(CAS: 945426-74-4)], Pigment Red 200 [(CAS: 67801-10-9)], Pigment Red 201 [(CAS: 68258-66-2)], Pigment Red 202-Pigment Violet 19 mixt. [(CAS: 1122063-75-5)], Pigment Red 203 [(CAS: 945553-87-7)], Pigment Red 204 [(CAS: 438231-79-9)], Pigment Red 205 [(CAS: 741692-71-7)], Pigment Red 206 [(CAS: 71819-76-6)], Pigment Red 207 [(CAS: 71819-77-7)], Pigment Red 215 [(CAS: 304892-29-3)], Pigment Red 217 [(CAS: 155421-17-3)], Pigment Red 218 [(CAS: 383891-32-5)], Pigment Red 219 [(CAS: 909006-21-9)], Pigment Red 223 [(CAS: 26789-26-4)], Pigment Red 225 [(CAS: 125270-32-8)], Pigment Red 227 [(CAS: 71872-64-5)], Pigment Red 228 [(CAS: 304898-64-4)], Pigment Red 234 [(CAS: 945554-26-7)], Pigment Red 237 [(CAS: 220424-27-1)], Pigment Red 238 [(CAS: 140114-63-2)], Pigment Red 239 [(CAS: 220424-28-2)], Pigment Red 240 [(CAS: 141489-67-0)], Pigment Red 241 [(CAS: 945554-27-8)], Pigment Red 244 [(CAS: 882858-66-4)], Pigment Red 245 [(CAS: 68016-05-7)], Pigment Red 246 [(CAS: 431991-59-2)], Pigment Red 249 [(CAS: 97955-62-9)], Pigment Red 25 [(CAS: 945426-75-5)], Pigment Red 250 [(CAS: 146358-78-3)], Pigment Red 252 [(CAS: 945554-31-4)], Pigment Red 26 [(CAS: 109944-92-5)], Pigment Red 262 [(CAS: 211502-19-1)], Pigment Red 263 [(CAS: 278792-06-6)], Pigment Red 270 [(CAS: 251086-13-2)], Pigment Red 272 [(CAS: 350249-32-0)], Pigment Red 276 [(CAS: 945554-32-5)], Pigment Red 277 [(CAS: 945554-33-6)], Pigment Red 278 [(CAS: 945554-34-7)], Pigment Red 279 [(CAS: 832743-59-6)], Pigment Red 280 [(CAS: 945554-58-5)], Pigment Red 281 [(CAS: 945554-64-3)], Pigment Red 282 [(CAS: 938065-79-3)], Pigment Red 283 [(CAS: 945554-67-6)], Pigment Red 284 [(CAS: 1089180-60-8)], Pigment Red 285 [(CAS: 1248412-35-2)], Pigment Red 29 [(CAS: 109944-93-6)], Pigment Red 34 [(CAS: 71872-60-1)], Pigment Red 35 [(CAS: 104491-86-3)], Pigment Red 46 [(CAS: 945427-33-8)], Pigment Red 47 [(CAS: 945427-55-4)], Pigment Red 48 [(CAS: 16013-44-8)], Pigment Red 48 [(CAS: 17797-35-2)], Pigment Red 48-Pigment Red 122 mixt. [(CAS: 1046461-81-7)], Pigment Red 48 [(CAS: 218138-44-4)], Pigment Red 48 [(CAS: 218138-41-1)], Pigment Red 48 [(CAS: 68023-17-6)], Pigment Red 51 [(CAS: 25705-30-0)], Pigment Red 51 [(CAS: 446242-29-1)], Pigment Red 52 [(CAS: 27757-95-5)], Pigment Red 52 [(CAS: 67828-72-2)], Pigment Red 52 [(CAS: 218138-27-3)], Pigment Red 53 [(CAS: 15958-19-7)], Pigment Red 56 [(CAS: 25310-96-7)], Pigment Red 57 [(CAS: 88593-07-1)], Pigment Red 58 [(CAS: 25310-97-8)], Pigment Red 59 [(CAS: 945427-99-6)], Pigment Red 60 [(CAS: 446245-60-9)], Pigment Red 63 [(CAS: 5858-84-4)], Pigment Red 63 [(CAS: 16510-21-7)], Pigment Red 63 [(CAS: 1325-13-9)], Pigment Red 64 [(CAS: 5858-77-5)], Pigment Red 68 [(CAS: 25311-19-7)], Pigment Red 71 [(CAS: 384329-78-6)], Pigment Red 72 [(CAS: 945428-03-5)], Pigment Red 73 [(CAS: 109944-94-7)], Pigment Red 74 [(CAS: 109944-95-8)], Pigment Red 75 [(CAS: 109944-96-9)], Pigment Red 78 [(CAS: 71799-06-9)], Pigment Red 81-Pigment White 21 mixt. [(CAS: 192390-71-9)], Pigment Red 82 [(CAS: 110927-51-0)], Pigment Red 88 [(CAS: 14295-43-3)], Pigment Red 90 [(CAS: 51868-24-7)], Pigment Red 92 [(CAS: 909006-04-8)], Pigment Red 94 [(CAS: 12213-62-6)], Pigment Red 96 [(CAS: 945428-04-6)], Pigment Red 97 [(CAS: 239795-92-7)], Pigment Red 98 [(CAS: 945428-07-9)], Pigment Violet 1 [(CAS: 63022-09-3)], Pigment Violet 1 [(CAS: 62973-79-9)], Pigment Violet 11 [(CAS: 875014-31-6)], Pigment Violet 11 [(CAS: 765310-46-1)], Pigment Violet 122 [(CAS: 104491-87-4)], Pigment Violet 123 [(CAS: 80619-33-6)], Pigment Violet 17 [(CAS: 945554-69-8)], Pigment Violet 18 [(CAS: 945554-81-4)], Pigment Violet 21 [(CAS: 945555-53-3)], Pigment Violet 26 [(CAS: 945556-80-9)], Pigment Violet 28 [(CAS: 12236-70-3)], Pigment Violet 30 [(CAS: 12225-07-9)], Pigment Violet 32 [(CAS: 12225-08-0)], Pigment Violet 34 [(CAS: 12612-32-7)], Pigment Violet 35 [(CAS: 55177-94-1)], Pigment Violet 39 [(CAS: 64070-98-0)], Pigment Violet 39 [(CAS: 68477-21-4)], Pigment Violet 4 [(CAS: 68310-88-3)], Pigment Violet 40 [(CAS: 61968-83-0)], Pigment Violet 41 [(CAS: 945557-07-3)], Pigment Violet 42 [(CAS: 71819-79-9)], Pigment Violet 43 [(CAS: 79665-29-5)], Pigment Violet 44 [(CAS: 87209-55-0)], Pigment Violet 45 [(CAS: 945557-40-4)], Pigment Violet 46 [(CAS: 945557-42-6)], Pigment Violet 5 [(CAS: 22297-70-7)], Pigment Violet 50 [(CAS: 76233-81-3)], Pigment Violet 51 [(CAS: 945557-43-7)], Pigment Violet 52 [(CAS: 945557-99-3)], Pigment Violet 53 [(CAS: 945558-15-6)], Pigment Violet 54 [(CAS: 1126076-80-9)], Pigment Violet 55 [(CAS: 1126076-86-5)], Pigment Violet 56 [(CAS: 1126076-93-4)], Pigment Violet 7 [(CAS: 16035-60-2)], Pigment Violet 9 [(CAS: 945554-68-7)], Pigment Yellow 1 [(CAS: 12240-03-8)], Pigment Yellow 102 [(CAS: 12236-74-7)], Pigment Yellow 103 [(CAS: 12225-22-8)], Pigment Yellow 106 [(CAS: 12225-23-9)], Pigment Yellow 107 [(CAS: 12270-64-3)], Pigment Yellow 113 [(CAS: 14359-20-7)], Pigment Yellow 120 [(CAS: 29920-31-8)], Pigment Yellow 121 [(CAS: 14569-54-1)], Pigment Yellow 122 [(CAS: 852620-87-2)], Pigment Yellow 125 [(CAS: 304891-45-0)], Pigment Yellow 131 [(CAS: 945423-41-6)], Pigment Yellow 132 [(CAS: 945424-04-4)], Pigment Yellow 135

[(CAS: 945424-77-1)], Pigment Yellow 136 [(CAS: 181285-33-6)], Pigment Yellow 140 [(CAS: 945425-58-1)], Pigment Yellow 141 [(CAS: 945425-59-2)], Pigment Yellow 142 [(CAS: 177020-91-6)], Pigment Yellow 143 [(CAS: 945425-60-5)], Pigment Yellow 144 [(CAS: 945425-61-6)], Pigment Yellow 145 [(CAS: 115742-72-8)], Pigment Yellow 146 [(CAS: 945425-66-1)], Pigment Yellow 149 [(CAS: 945425-67-2)], Pigment Yellow 150 [(CAS: 939382-97-5)], Pigment Yellow 151 [(CAS: 31837-42-0)], Pigment Yellow 154 [(CAS: 68134-22-5)], Pigment Yellow 156 [(CAS: 63661-26-7)], Pigment Yellow 165 [(CAS: 865763-85-5)], Pigment Yellow 166 [(CAS: 76233-82-4)], Pigment Yellow 170 [(CAS: 31775-16-3)], Pigment Yellow 171 [(CAS: 53815-04-6)], Pigment Yellow 172 [(CAS: 76233-80-2)], Pigment Yellow 175 [(CAS: 35636-63-6)], Pigment Yellow 178 [(CAS: 945425-73-0)], Pigment Yellow 17 [(CAS: 221358-38-9)], Pigment Yellow 18 [(CAS: 1326-11-0)], Pigment Yellow 18 [(CAS: 68310-89-4)], Pigment Yellow 186 [(CAS: 945425-92-3)], Pigment Yellow 187 [(CAS: 131439-24-2)], Pigment Yellow 189 [(CAS: 69011-05-8)], Pigment Yellow 191 [(CAS: 1051932-58-1)], Pigment Yellow 195 [(CAS: 135668-58-5)], Pigment Yellow 196 [(CAS: 945425-96-7)], Pigment Yellow 197 [(CAS: 945425-97-8)], Pigment Yellow 198 [(CAS: 516493-10-0)], Pigment Yellow 20 [(CAS: 61512-63-8)], Pigment Yellow 200 [(CAS: 945425-98-9)], Pigment Yellow 201 [(CAS: 945425-99-0)], Pigment Yellow 204 [(CAS: 945426-05-1)], Pigment Yellow 205 [(CAS: 945426-18-6)], Pigment Yellow 206 [(CAS: 945426-19-7)], Pigment Yellow 207 [(CAS: 945426-23-3)], Pigment Yellow 208 [(CAS: 945426-25-5)], Pigment Yellow 209 [(CAS: 945426-27-7)], Pigment Yellow 21 [(CAS: 945421-49-8)], Pigment Yellow 210 [(CAS: 945426-35-7)], Pigment Yellow 211 [(CAS: 945426-36-8)], Pigment Yellow 212 [(CAS: 945426-37-9)], Pigment Yellow 214 [(CAS: 577980-23-5)], Pigment Yellow 215 [(CAS: 913621-26-8)], Pigment Yellow 216 [(CAS: 817181-98-9)], Pigment Yellow 217 [(CAS: 945426-39-1)], Pigment Yellow 219 [(CAS: 874963-72-1)], Pigment Yellow 221 [(CAS: 945426-41-5)], Pigment Yellow 223 [(CAS: 2095507-47-2)], Pigment Yellow 224 [(CAS: 1207669-05-3)], Pigment Yellow 23 [(CAS: 4981-43-5)], Pigment Yellow 231 [(CAS: 2148300-50-7)], Pigment Yellow 25 [(CAS: 945421-63-6)], Pigment Yellow 26 [(CAS: 945421-64-7)], Pigment Yellow 27 [(CAS: 945421-65-8)], Pigment Yellow 28 [(CAS: 945421-66-9)], Pigment Yellow 29 [(CAS: 945421-67-0)], Pigment Yellow 34 [(CAS: 147858-25-1)], Pigment Yellow 36 [(CAS: 37300-23-5)], Pigment Yellow 37 [(CAS: 68859-25-6)], Pigment Yellow 40 [(CAS: 13782-01-9)], Pigment Yellow 47 [(CAS: 12060-00-3)], Pigment Yellow 50 [(CAS: 945421-71-6)], Pigment Yellow 51 [(CAS: 945421-76-1)], Pigment Yellow 56 [(CAS: 12225-09-1)], Pigment Yellow 58 [(CAS: 12225-11-5)], Pigment Yellow 61 [(CAS: 12286-65-6)], Pigment Yellow 72 [(CAS: 945421-81-8)], Pigment Yellow 79 [(CAS: 331414-25-6)], Pigment Yellow 8 [(CAS: 71872-65-6)], Pigment Yellow 80 [(CAS: 945421-85-2)], Pigment Yellow 82 [(CAS: 12225-14-8)], Pigment Yellow 84 [(CAS: 945421-87-4)], Pigment Yellow 85 [(CAS: 12286-67-8)], Pigment Yellow 86 [(CAS: 12286-68-9)], Pigment Yellow 86 [(CAS: 5280-65-9)], Pigment Yellow 88 [(CAS: 945422-67-3)], Pigment Yellow 89 [(CAS: 945422-85-5)], Pigment Yellow 90 [(CAS: 713104-87-1)], Pigment Yellow 91 [(CAS: 945423-18-7)], Pigment Yellow 96 [(CAS: 12213-63-7)], Pigment Yellow 97 [(CAS: 12225-18-2)], Pigment Yellow 99 [(CAS: 12225-20-6)]

The pigment(s) used in the color composition can include at least two different pigments selected from the above pigment group, or can include at least three different pigments selected from the above pigment group. According to an embodiment, the pigment(s) used in the color composition can include at least one yellow pigment selected from the yellow pigment group consisting of a Pigment Yellow 83 (CI 21108), CAS #5567-15-7, Pigment Yellow 155 (C.I. 200310), (CAS: 68516-73-4), Pigment Yellow 180 (C.I. 21290), (CAS: 77804-81-0).

In addition to the at least one yellow pigment, or alternatively, the pigments(s) used in the color composition can include at least one red pigment selected from the red pigment group consisting of Pigment Red 5 (CI 12490), (CAS #6410-41-9), Pigment Red 112 (CI 12370), (CAS #6535-46-2), Pigment Red 122 (CI 73915), (CAS #980-26-7).

In addition to the at least one yellow pigment and/or the at least one red pigment, or alternatively, the pigments(s) used in the color composition can include at least one green pigment selected from the green pigment group consisting of Pigment Green 36, (C.I. 74265), (CAS: 14302-13-7).

In addition to the at least one yellow pigment and/or the at least one red pigment and or the at least one green pigment, or alternatively, the pigments(s) used in the color composition can include at least one blue pigment selected from the blue pigment group consisting of Pigment Blue 16, (CAS: 424827-05-4), Pigment Blue 60 (C.I. 69800), (CAS: 81-77-6), Pigment Blue 66, (C.I. 73000), (CAS: 482-89-3)

In addition to the at least one yellow pigment and/or the at least one red pigment and/or the at least one green pigment, and/or the at least one blue pigment or alternatively, the pigments(s) used in the color composition can include at least one black pigment selected from the black pigment group consisting of Pigment Black 6 (C.I. 77266), (CAS 1333-86-4), Pigment Black 7 (C.I. 77266), (CAS 1333-86-4). An additional combination can include aluminium flake with a red, blue, green, yellow or any combination thereof.

The pigment(s) can optionally have a surface zeta potential of $\geq \pm 15$ mV, preferably $\geq \pm 20$ mV, more preferably $\geq +25$ mV. The surface zeta potential can be measured with a zetasizer, for example, a Zetasizer 3000 HS. Surface zeta potential measurements are conducted, for example, according to ISO 13099.

For example, the white or colored organic pigments can be chosen from carmine, carbon black, aniline black, melanin, azo yellow, quinacridone, phthalocyanin blue, sorghum red, the blue pigments codified in the Color Index under the references CI 42090, 69800, 69825, 73000, 74100, and 74160, the yellow pigments codified in the Color Index under the references CI 11680, 11710, 15985, 19140, 20040, 21090, 21100, 21108, 47000, 47005 and 77492.

The green pigments codified in the Color Index under the references CI 61565, 61570, 74265, and 74260, the orange pigments codified in the Color Index under the references CI 11725, 12075, 15510, 45370, and 71105, the red pigments codified in the Color Index under the references CI 12085, 12120, 12370, 12420, 12490, 14700, 15525, 15580, 15585, 15620, 15630, 15800, 15850, 15865, 15880, 17200, 26100, 45380, 45410, 45430, 58000, 73360, 73915, 75470, and 77491 and the pigments obtained by oxidative polymerization of indole or phenolic derivatives.

Non-limiting examples that can also be mentioned include pigmentary pastes of organic pigments, such as the products sold by the company Hoechst under the names: JAUNE COSMENYL IOG: Pigment Yellow 3 (CI 11710); JAUNE COSMENYL G: Pigment Yellow 1 (CI 11680); ORANGE COSMENYL GR: Pigment Orange 43 (CI 71105); ROUGE COSMENYL R: Pigment Red 4 (CI 12085); CARMINE COSMENYL FB: Pigment Red 5 (CI 12490); VIOLET COSMENYL RL: Pigment Violet 23 (CI 51319); BLEU COSMENYL A2R: Pigment Blue 15.1 (CI 74160); VERT COSMENYL GG: Pigment Green 7 (CI 74260); and NOIR COSMENYL R: Pigment Black 7 (CI 77266).

The at least one pigment in accordance with the present disclosure can also be in the form of at least one composite pigment as described in European Patent Publication No. EP 1 184 426 A2. These composite pigments can be, for example, compounds of particles comprising a mineral core, at least one binder for ensuring the binding of the organic pigments to the core, and at least one organic pigment at least partially covering the core.

The at least one pigment in accordance with the present disclosure can be in the form of small undissolved microparticles, which do not diffuse into the hair color, but deposit on the outer wall of the keratin fiber. Suitable color pigments can be of organic and/or inorganic origin. But the pigments can also be inorganic color pigments, given the excellent light, weather and/or temperature resistance thereof.

Inorganic pigments, whether natural or synthetic in origin, include those produced from chalk, red ocher, umbra, green earth, burnt sienna or graphite, for example. Furthermore, it is possible to use black pigments, such as iron oxide black, color pigments such as ultramarine or iron oxide red, and fluorescent or phosphorescent pigments as inorganic color pigments.

Colored metal oxides, metal hydroxides and metal oxide hydrates, mixed phase pigments, sulfurous silicates, silicates, metal sulfides, complex metal cyanides, metal sulfates, metal chromates and/or metal molybdates are particularly suitable. In particular, preferred color pigments are black iron oxide (CI 77499), yellow iron oxide (CI 77492), red and brown iron oxide (CI 77491), manganese violet (CI 77742), ultramarine (sodium aluminum sulfosilicates, CI 77007, Pigment Blue 29), chromium oxide hydrate (CI 77289), iron blue (ferric ferrocyanide, CI 77510) and/or carmine (cochineal).

The at least one pigment can also be colored pearlescent pigments. These are usually mica-based and can be coated with one or more metal oxides from the group consisting of titanium dioxide (CI 77891), black iron oxide (CI 77499), yellow iron oxide (CI 77492), red and brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Mica forms part of the phyllosilicates, including muscovite, phlogopite, paragonite, biotite, lepidolite, and margarite. To produce the pearlescent pigments in combination with metal oxides, the mica, primarily muscovite or phlogopite, is coated with a metal oxide.

As an alternative to natural mica, it is also optionally possible to use synthetic mica coated with one or more metal oxides as the pearlescent pigment. Such suitable pearlescent pigments based on natural micas are described in, e.g., WO 2005/065632. The at least one pigment can also be pearlescent pigments based on natural or synthetic mica and are coated with one or more of the aforementioned metal oxides.

The color of the respective pigments can be varied by varying the layer thickness of the metal oxide or metal oxides.

The at least one pigment can also be at least one inorganic color pigment selected from the group consisting of colored metal oxides, metal hydroxides, metal oxide hydrates, silicates, metal sulfides, complex metal cyanides, metal sulfates, bronze pigments and/or colored pigments based on mica, which are coated with at least one metal oxide and/or a metal oxychloride.

The at least one pigment can also be at least one mica-based colored pigment, which is coated with one or more metal oxides from the group consisting of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

The at least one pigment can also be color pigments commercially available, for example, under the trade names Rona®, Colorona®, Dichrona® and Timiron® from Merck, Ariabel® and Unipure® from Sensient, Prestige® from Eckart Cosmetic Colors, and Sunshine® from Sunstar.

The at least one pigment can also be color pigments bearing the trade name Colorona® are, for example: Colorona Copper, Merck, MICA, CI 77491 (IRON OXIDES); Colorona Passion Orange, Merck, Mica, CI 77491 (Iron Oxides), Alumina; Colorona Patina Silver, Merck, MICA, CI 77499 (IRON OXIDES), CI 77891 (TITANIUM DIOXIDE); Colorona RY, Merck, CI 77891 (TITANIUM DIOXIDE), MICA, CI 75470 (CARMINE); Colorona Oriental Beige, Merck, MICA, CI 77891 (TITANIUM DIOXIDE), CI 77491 (IRON OXIDES); Colorona Dark Blue, Merck, MICA, TITANIUM DIOXIDE, FERRIC FERROCYANIDE; Colorona Chameleon, Merck, CI 77491 (IRON OXIDES), MICA; Colorona Aborigine Amber, Merck, MICA, CI 77499 (IRON OXIDES), CI 77891 (TITANIUM DIOXIDE); Colorona Blackstar Blue, Merck, CI 77499 (IRON OXIDES), MICA; Colorona Patagonian Purple, Merck, MICA, CI 77491 (IRON OXIDES), CI 77891 (TITANIUM DIOXIDE), CI 77510 (FERRIC FERROCYANIDE); Colorona Red Brown, Merck, MICA, C1 77491 (IRON OXIDES), CI 77891 (TITANIUM DIOXIDE); Colorona Russet, Merck, CI 77491 (TITANIUM DIOXIDE), MICA, CI 77891 (IRON OXIDES); Colorona Imperial Red, Merck, MICA, TITANIUM DIOXIDE (CI 77891), D&C RED NO. 30 (CI 73360); Colorona Majestic Green, Merck, CI 77891 (TITANIUM DIOXIDE), MICA, CI 77288 (CHROMIUM OXIDE GREENS); Colorona Light Blue, Merck, MICA, TITANIUM DIOXIDE (CI 77891), FERRIC FERROCYANIDE (CI 77510); Colorona Red Gold, Merck, MICA, CI 77891 (TITANIUM DIOXIDE), CI 77491 (IRON); Colorona Gold Plus MP 25, Merck, MICA, TITANIUM DIOXIDE (CI 77891), IRON OXIDES (CI 77491); Colorona Carmine Red, Merck, MICA, TITANIUM DIOXIDE, CARMINE Colorona Blackstar Green, Merck, MICA, CI 77499 (IRON OXIDES); Colorona Bordeaux, Merck, MICA, CI 77491 (IRON OXIDES); Colorona Bronze, Merck, MICA, CI 77491 (IRON OXIDES); Colorona Bronze Fine, Merck, MICA, CI 77491 (IRON OXIDES); Colorona Fine Gold MP 20, Merck, MICA, CI 77891 (TITANIUM DIOXIDE), CI 77491 (IRON OXIDES); Colorona Sienna Fine, Merck, MICA, CI 77491 (IRON OXIDES), MICA Colorona Sienna, Merck, MICA, CI 77491 (IRON OXIDES); Colorona Precious Gold, Merck, Mica, CI 77891 (Titanium dioxide), Silica, CI 77491 (Iron oxides), Tin oxide; Colorona Sun Gold Sparkle MP 29, Merck, MICA, TITANIUM DIOXIDE, IRON OXIDES, MICA, CI 77891, CI 77491 (EU); Colorona Mica Black, Merck, CI 77499 (Iron oxides), Mica, CI 77891 (Titanium dioxide) Colorona Bright Gold, Merck, Mica, CI 77891 (Titanium dioxide), CI 77491 (Iron oxides); Colorona Blackstar Gold, Merck, MICA, CI 77499 (IRON OXIDES); color pigments bearing the trade name Unipure® are, for example: Unipure Red LC 381 EM, Sensient CI 77491 (Iron Oxides), Silica; Unipure Black LC 989 EM, Sensient, CI 77499 (Iron Oxides), Silica; Unipure Yellow LC 182 EM, Sensient, CI 77492 (Iron Oxides), Silica.

Depending on the degree of the change in color that is desired on the keratin fiber, the at least one pigment can also be can be used in varying amounts. The more color pigment that is used, the higher is the extent of the change in color in general. Starting at a certain usage amount, however, the adherence of the pigments to the keratin fiber approaches a limiting value, beyond which it is no longer possible to increase the extent of the change in color by further increasing the pigment amount used. While not wishing to be bound by any specific theory, it is believed that when a certain thickness is achieved, an insignificant amount of the incident lights passes through the pigment layer to make a difference to the observed color due to the hair itself. The rest of the light is either scattered back towards the surface or absorbed.

The at least one pigment can be partially (Scheme 1, (b), where the dark oval represents a pigment, even though the pigment can be white or colorless) or completely enveloped in a matrix (e.g., a polymer matrix or an inorganic matrix; (Scheme 1, (a)). Or the pigment can be adhered to the surface of a matrix that can be colored or colorless (Scheme 1 (c)).

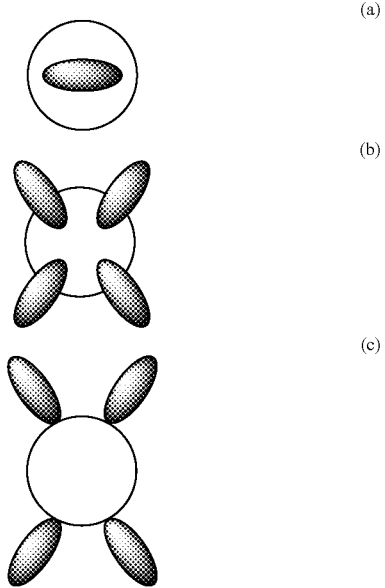

Scheme 1

(a)

(b)

(c)

The matrix can be, e.g., CaCO3, MnCO3. Or the matrix can be a melamine formaldehyde matrix.

In another example, the at least one pigment can be encapsulated in silica, as described in Published U.S. Appl. No. 2007/0134180. Other examples of encapsulated pigments include encapsulated Carmine, Iron Oxides, Titanium dioxide, and Chrome Oxide/Hydroxide, the colorants D&C Red 21 Aluminum Lake, D&C Red 7 Calcium Lake, D&C Green 6 Liposoluble, and Aluminium Blue #1 (Indigo Carmine Lake). The encapsulated pigment can be titanium dioxide (used to lighten other pigments and to lend opacity to formulations) in any one of its mineral forms anatase, brookite or rutile, or mixtures thereof. Or the pigment can be at least one iron oxide in any of the 3 basic colors—red, black and yellow iron oxides, or mixtures thereof. From these 3 oxides and the addition of titanium dioxide, any shade of brown (skin tones) can be achieved.

The organic pigment can also be a lake. As used herein, the term "lake" means at least one dye adsorbed onto insoluble particles, the assembly thus obtained remaining insoluble during use. The inorganic substrates onto which the dyes are adsorbed can be, for example, alumina, silica, calcium sodium borosilicate, calcium aluminum borosilicate, calcium carbonate, manganese carbonate, aluminum, nitro-dyes, triarylmethin dyes, Azo-dyes, Anthrazen, Acid dyes, polymethine dyes, triarylmethin dyes, aza annulene dyes and polymethine dyes.

Among the dyes, non-limiting mention can be made of cochineal carmine. Non-limiting mention can also be made of the dyes known under the following names: D&C Red 21 (CI 45 380), D&C Orange 5 (CI 45 370), D&C Red 27 (CI 45 410), D&C Orange 10 (CI 45 425), D&C Red 3 (CI 45 430), D&C Red 4 (CI 15 510), D&C Red 33 (CI 17 200), D&C Yellow 5 (CI 19 140), D&C Yellow 6 (CI 15 985), D&C Green (CI 61 570), D&C Yellow 1 0 (CI 77 002), D&C Green 3 (CI 42 053), and D&C Blue 1 (CI 42 090). A non-limiting example of a lake that can be mentioned is the product known under the following name: D&C Red 7 (CI 15 850:1).

The at least one pigment can also be a pigment with special effects. As used herein, the term "pigments with special effects" means pigments that generally create a non-uniform colored appearance (characterized by a certain shade, a certain vivacity, and a certain lightness) that changes as a function of the conditions of observation (light, temperature, observation angles, etc.). They thus contrast with white or colored pigments that afford a standard uniform opaque, semi-transparent, or transparent shade.

Several types of pigments with special effects exist, including those with a low refractive index, such as fluorescent, photochromic, or thermochromic pigments, and those with a high refractive index, such as nacres or glitter flakes. Examples of pigments with special effects of which non-limiting mention can be made include nacreous pigments such as mica coated with titanium or with bismuth oxychloride, colored nacreous pigments such as titanium mica with iron oxides, titanium mica for example with ferric blue or with chromium oxide, titanium mica with an organic pigment of the abovementioned type, and also nacreous pigments based on bismuth oxychloride. Nacreous pigments of which non-limiting mention can be made include the CELLINI nacres sold by Engelhard (mica-TiO2-lake), PRESTIGE sold by Eckart (mica-TiO2), PRESTIGE BRONZE sold by Eckart (mica-Fe2O3), and COLORONA sold by Merck (mica-TiO2-Fe2O3).

In addition to nacres on a mica support, multilayer pigments based on synthetic substrates such as alumina, silica, sodium calcium borosilicate, calcium aluminum borosilicate, and aluminum, can be envisaged.

Non-limiting mention can also be made of pigments with an interference effect that are not fixed onto a substrate, for instance liquid crystals (HELICONES HC from Wacker) and holographic interference flakes (GEOMETRIC PIGMENTS or SPECTRA F/X from Spectratek). Pigments with special effects also comprise fluorescent pigments, whether these are substances that are fluorescent in daylight or that produce an ultraviolet fluorescence, phosphorescent pigments, photochromic pigments, thermochromic pigments, and quantum dots, sold, for example, by the company Quantum Dots Corporation.

Quantum dots are luminescent semiconductive nanoparticles capable of emitting, under light excitation, irradiation with a wavelength ranging from 400 nm to 700 nm. These nanoparticles are known from the literature. They can be manufactured, for example, according to the processes described, for example, in U.S. Pat. No. 6,225,198 or 5,990,479, in the publications cited therein, and also in the following publications: Dabboussi B. O. et al. "(CdSe)ZnS core-shell quantum dots: synthesis and characterization of a size series of highly luminescent nanocrystallites" Journal of Physical Chemistry B, vol. 101, 1997 pp. 9463-9475 and Peng, Xiaogang et al. "Epitaxial growth of highly luminescent CdSe/CdS core/shell nanocrystals with photostability and electronic accessibility", Journal of the American Chemical Society, vol. 119, No. 30, pp. 7019-7029, all of the foregoing publications are incorporated herein by reference.

The variety of pigments that can be used in the present disclosure makes it possible to obtain a wide range of colors, and also optical effects such as metallic effects or interference effects.

The pigments that can be used in the present disclosure can transmit light of various wavelengths, including visible light (e.g., light having a wavelength of above 350 nm). The pigment(s) can also transmit light of certain wavelengths, but also reflect light of certain wavelengths. And the pigment(s) can also be 100% reflective. For examples, reflective pigments provide a high specular reflection of visible light. Reflective pigments include those that are partially or completely coated with a non-matt and non-scattering surface layer of a metal or metal oxide. The substrate can be chosen from glasses, ceramics, graphite, metal oxides, aluminas, silicas, silicates, especially aluminosilicates and borosilicates and synthetic mica (e.g., fluorophlogopite), to name a few. The metal or metal oxide can be, without limitation, titanium oxides, iron oxides, tin oxide, chromium oxide, barium sulfate, MgF2, CeF3, ZnS, ZnSe, SiO2, Al2O3, MgO, Y2O3, SeO3, SiO, HfO2, ZrO2, CeO2, Nb2O5, Ta2O5 and MoS2, and mixtures thereof. Reflective pigments can have a spectral reflectance in the visible spectrum of at least 70%.

Other reflective pigments include those having non-goniochromatic layered structure of two or more polymeric and/or metallic layers of different refractive indices. For example, reflective particles comprising layers of 2,6-polyethylene naphthalate (PEN) and of polymethyl (meth)acrylate are sold by 3M under the name Mirror Glitter™. Other effect pigments are available under the trade name Metasomes Standard/Glitter in various colors (yellow, red, green, blue) from Flora Tech.

Color Gamut for Pigment Blends

CIE L*a*b* (CIELAB) is a color space specified by the International Commission on Illumination. It describes all the colors visible to the human eye and serves as a device-independent model to be used as a reference.

The three coordinates of CIELAB represent the lightness of the color (L*=0 yields black and L*=100 indicates diffuse white; specular white may be higher), its position between red/magenta and green (a*, negative values indicate green while positive values indicate magenta) and its position between yellow and blue (b*, negative values indicate blue and positive values indicate yellow).

Since the L*a*b* model is a three-dimensional model, it can be represented properly only in a three-dimensional space. Two-dimensional depictions include chromaticity diagrams: sections of the color solid with a fixed lightness.

Because the red-green and yellow-blue opponent channels are computed as differences of lightness transformations of (putative) cone responses, CIELAB is a chromatic value color space.

In the present invention, the color gamut is determined by adding each pigment to be tested in the hair coloring composition, and then individually tested at a level such that when applied to hair, the resulting CIELAB lightness or L* value of the colored hair is 60±2. The level of pigment needed will depend on the pigment being tested. Two hair tresses (Kerling, Natural White special quality) have the hair coloring composition applied as described in the present invention. A Minolta spectrophotometer CM-2600d is used to measure the color of the dried hair tresses, five points on both the front and back sides, and the values averaged. The D65 L*a*b values are calculated. When at least three pigments have each been measured such that their resulting color reside within the target L* values of 60 2 the color gamut can be calculated. First the lengths of each side of the resulting triangle of each combination of three pigments in the a*b plane are computed using the following expressions. To calculate the distance between pigments 1 and pigment 2 the following equation is used:

$$\text{Side Length } SL_{12}=((a_{pigment\ 1}-a_{pigment\ 2})^2+(b_{pigment\ 1}-b_{pigment\ 2})^2)^{0.5}.$$

This is computed for each pair of pigments. Then for a series of three pigments.

The resulting color gamut is calculated using the expression:

$$\text{Color Gamut}=(S(S-SL_{12})(S-SL_{13})(S-SL_{23}))^{0.5}$$

wherein $SL_{12}$, $SL_{13}$, and $SL_{23}$ are the three lengths of the sides of the triangle within the a*b plane, and $S=(SL_{12}+SL_{13}+SL_{23})/2$. Where more than three pigments are used, this calculation can be performed for each combination of the three pigment from the more than three pigments used, and the largest Color Gamut is selected.

The hair coloring composition embodiments of the present invention can also have a color gamut of greater than 250, greater than 500, greater than 750, greater than 800, greater than 900, greater than 1100 or even greater than 1250.

Experiments Performed for Color Gamut

Using the above expression, for each combination of three pigments possible from Color Gamut Tables 1, as illustrated below, the color gamut at a nominal L value of 60 was calculated.

Color Gamut Table 1

| Pigment | Name | Supplier | wt % level | L | a | b |
|---|---|---|---|---|---|---|
| Blue 15 | PV Fast Blue BG-NIP | Clariant | 0.155 | 59.3 | −18.7 | −2.1 |
| Blue 16 | Phthalocyanine | Carbosynth | 0.280 | 59.4 | −17.3 | 1.5 |
| Blue 66 | Indigo 229296 | Aldrich | 0.105 | 60.0 | −3.1 | 6.8 |
| Blue 60 | Paliogen Blau L 6482 | BASF | 0.260 | 60.7 | −3.9 | 5.9 |
| Black 7 | Midnight Black | Geotech | 0.045 | 59.8 | 0.0 | 12.3 |
| Green 36 | Heliogen Green K 9362 | BASF | 0.509 | 60.1 | −32.8 | 20.2 |
| Red 112 | Permanent Red FGR 250 | Clariant | 0.150 | 60.1 | 29.8 | 18.8 |
| Red 122 | Hostaperm Pink E02-EDW VP4034 | Clariant | 0.140 | 59.5 | 24.9 | 6.1 |
| Violet 19 | Ink Jet Magenta E5B 02 M250 | Clariant | 0.200 | 60.6 | 28.1 | 10.1 |
| Red 5 | Permanent Carmine FB01 | Clariant | 0.140 | 59.7 | 30.1 | 14.4 |
| Yellow 155 | Ink Jet Yellow 4GC | Clariant | 16.92 | 61.8 | 9.6 | 74.4 |
| Yellow 83 | Novoperm Yellow HR 70 | Clariant | 1.059 | 60.0 | 12.5 | 61.8 |
| Yellow 180 | Toner Yellow HG | Clariant | 9.16 | 61.4 | 11.2 | 72.8 |

These were formulated within an example formulation described later using an appropriate level of first, second and third compositions.

A few examples are exemplified of combinations of pigments and their resulting color gamut. One skilled in the art would be able to perform this for all of the possible permutations of pigments that are assessed according the description above.

FIGS. 1 to 6 show plots of color gamut triangles created for a series of three pigment selections.

FIG. 1 shows that a combination of Pigment Green 36, Pigment Yellow 83 and Pigment Red 122 a large triangle is plotted in the a*b* color plane with an area of 1520.

Figure 2:
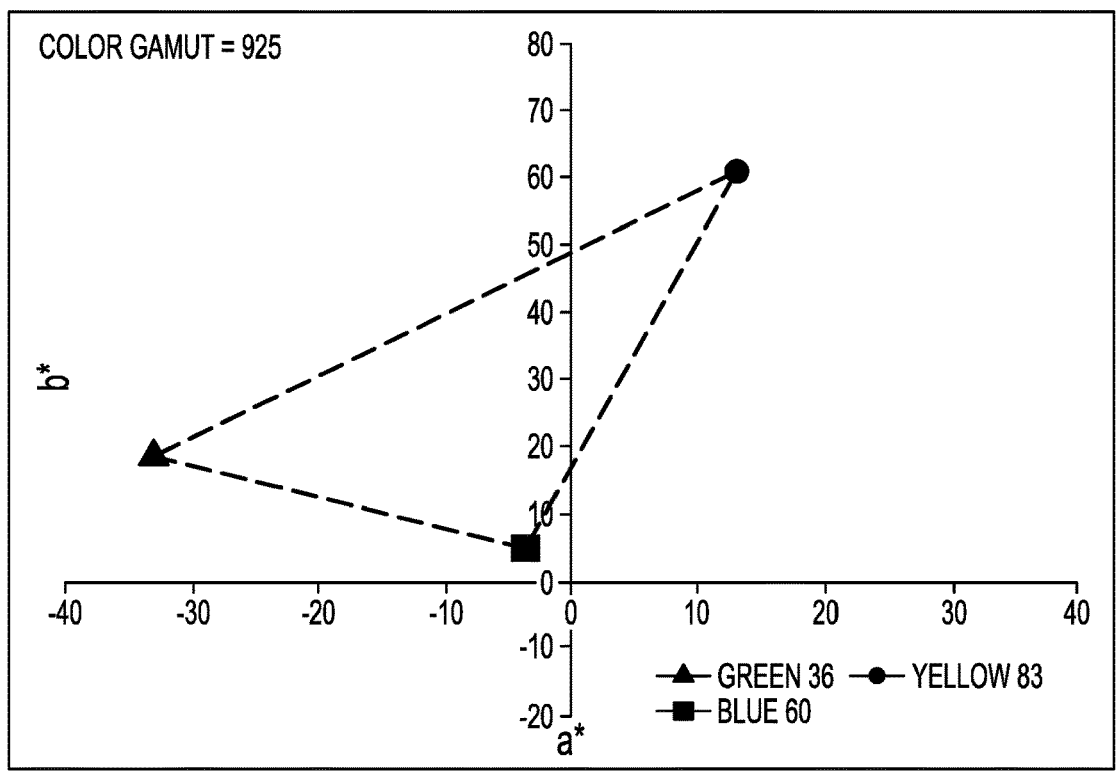
FIG. 2 depicts a Gamut plot of green, yellow and blue pigments.

FIG. 2 shows that the combination of Pigment Green 36, Pigment Yellow 83 and Pigment Blue 60 gives a smaller triangle win an area of 925.

Figure 3:
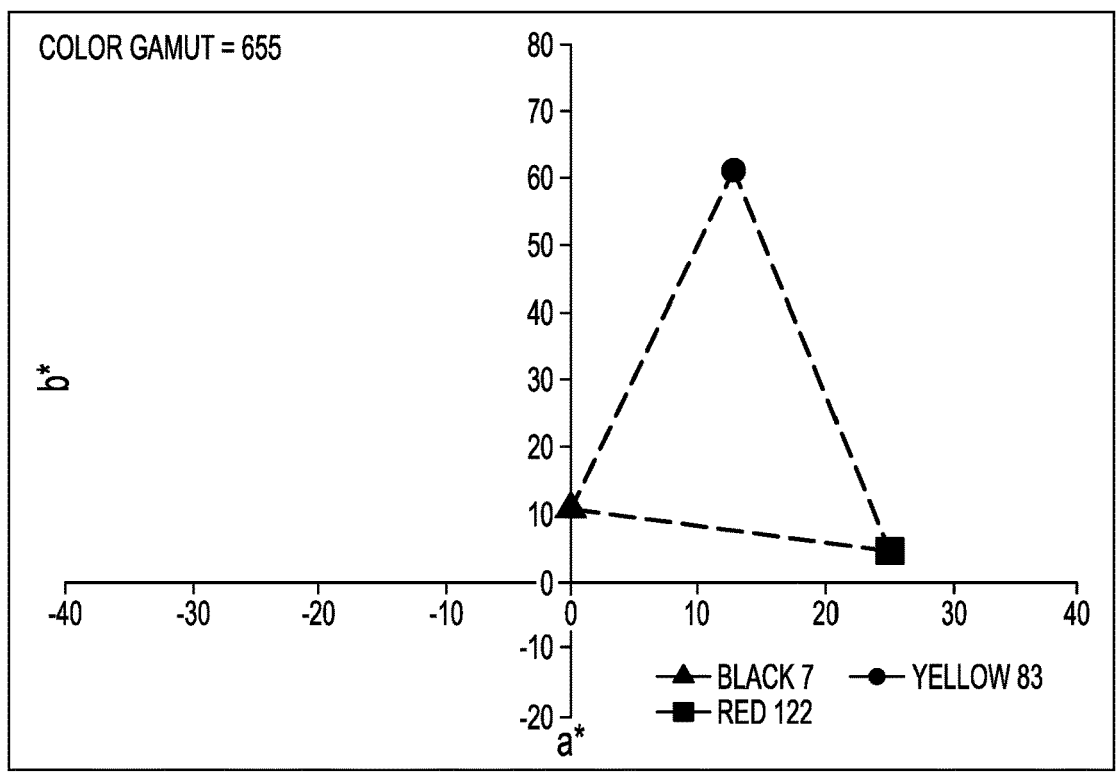
FIG. 3 depicts a Gamut plot of black, yellow and red pigments.

FIG. 3 shows the combination of Pigment Black 7, Pigment Yellow 83 and Pigment Red 122 gives a smaller triangle win an area of 655.

Figure 4:
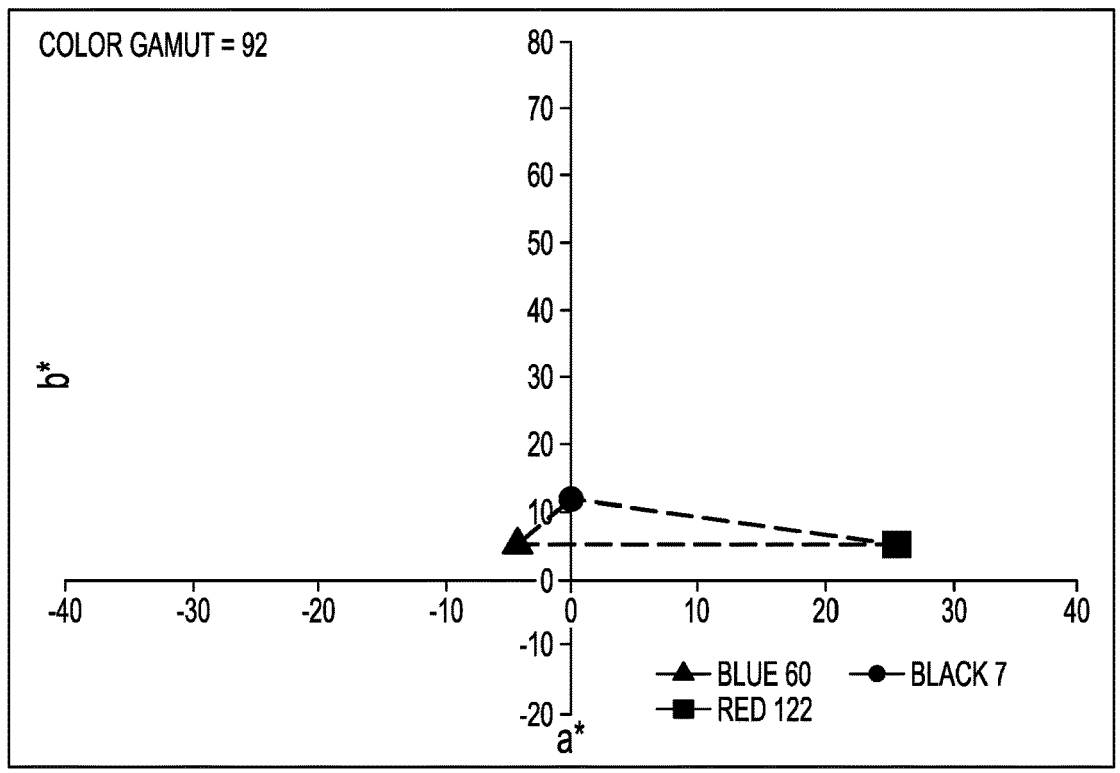
FIG. 4 depicts a Gamut plot of black blue and red pigments.

FIG. 4 shows the combination of Pigment Black 7, Pigment Blue 60 and Pigment Red 122 gives a smaller triangle win an area of 92.

A second series of example are made for how to assess more than three pigments and their resulting color gamut. When plotted a series of triangles can be plotted as shown and for each the areas is assessed. For such a system the color gamut is defined as the largest of the triangles formed.

Figure 5:
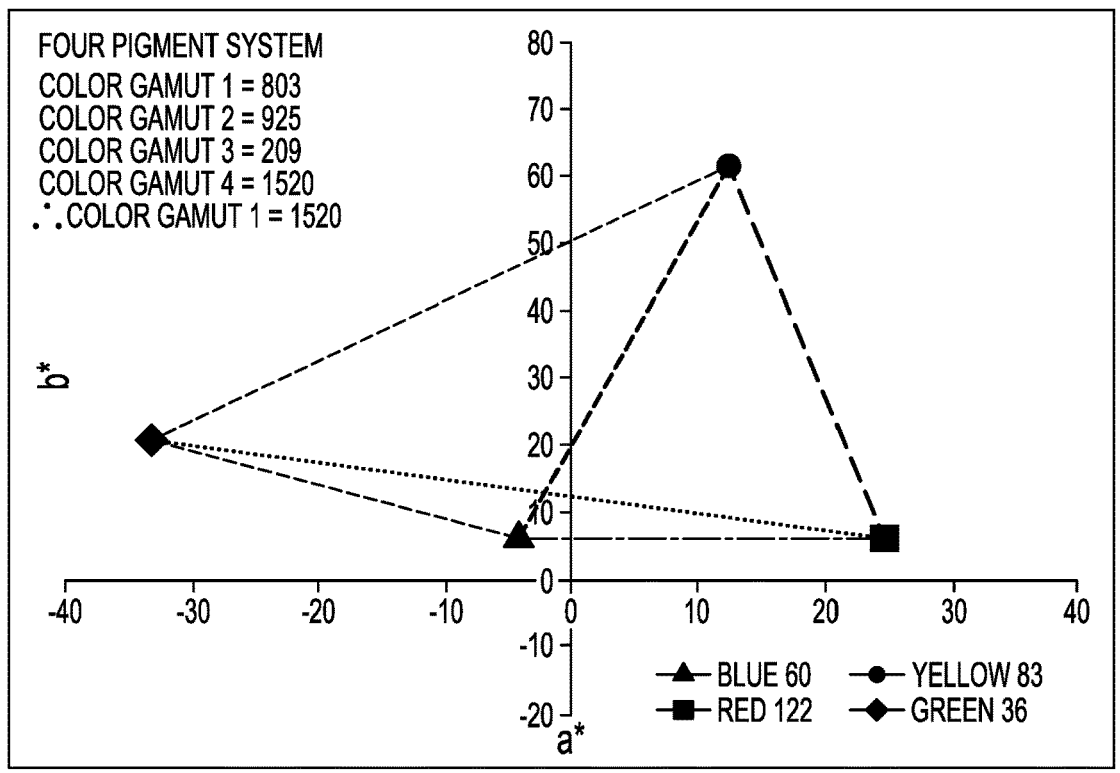
FIG. 5 depicts a Gamut plot of green, yellow, blue and red pigments.

FIG. 5 shows a combination of Pigment Green 36, Pigment Yellow 83, Pigment Blue 60 and Pigment Red 122 a series of triangles are plotted with areas of 803, 925, 209 and 1520. The color gamut of this pigment system is 1520. [Alterative calculation of total area would yield, 1728]

Figure 6:
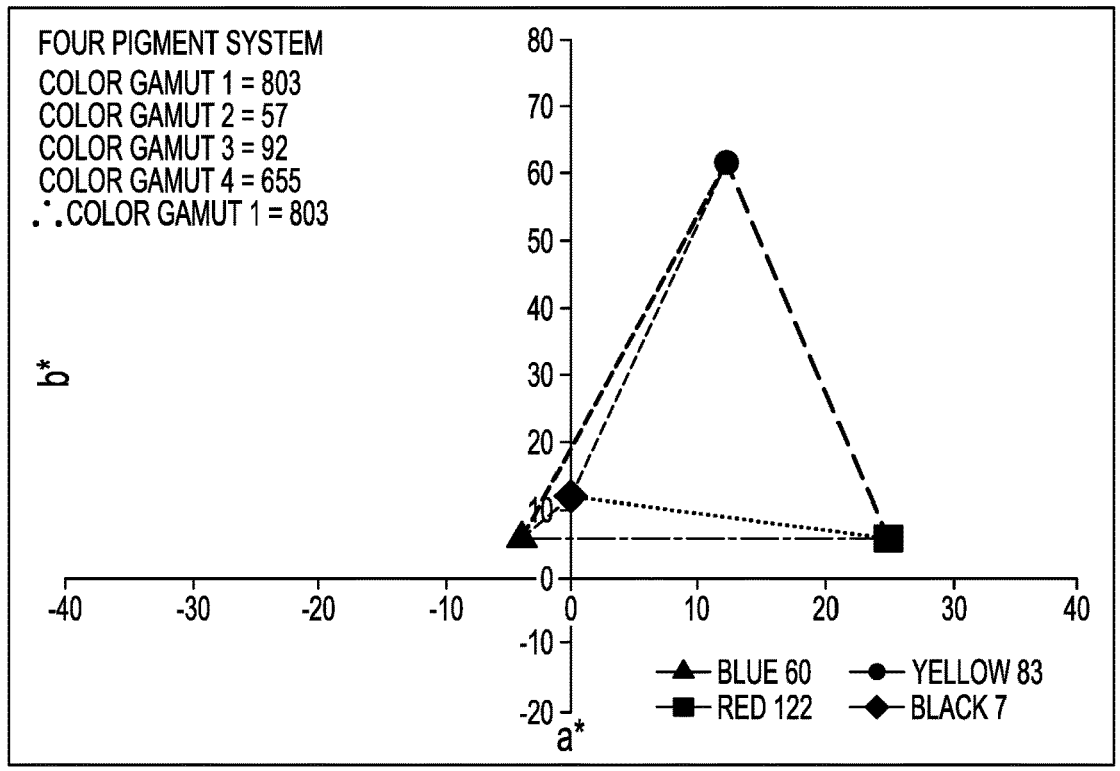
FIG. 6 depicts a Gamut plot of black, yellow and blue and red pigments.

FIG. 6 shows a combination of Pigment Black 7, Pigment Yellow 83, Pigment Blue 60 and Pigment Red 122 a series of triangles are plotted with areas of 803, 57, 92 and 655. The color gamut of the pigment system is 803 [alternative approach would be the same]

In an embodiment more than one multicomponent coloring composition can be applied to the hair in a sequential manner. For example it may be that a first multicomponent is applied to the hair which contains pigment microparticles that substantially scatter and/or reflect light such that it produces the visual effect of making the hair look lighter in color, after which a second multicomponent composition is applied which contains pigment microparticles that substantially absorbs light and provides color to the hair and wherein the combination of the sequential addition of a first and second multicomponent colorant compositions provides the final hair color. For example a first multicomponent colorant composition may comprise metallic flakes and the second multicomponent colorant composition may contain organic pigment microparticles. It may also be that more than a first a second multicomponent colorants are applied to the hair to achieve the desired color result, that three or more multicomponent colorant compositions are applied.

H. THE pH

The multicomponent composition embodiments in accordance with the present disclosure can have a pH ranging from about 4 to about 10, preferably about 5 to about 9. The pH is also dynamically managed to control the rate of reaction of the CDI link compound and the polycarbodiimide and if present, the reactive termini. Maintaining a slightly to moderately basic pH during the mixing and preapplication stages involving the first and second components controls the CDI link compound reaction with carbodiimide when the CDI link compound is a preferred acid compound. The basic pH shunts the acid-carbodiimide mechanism toward the starting compounds because protons from the acid are required as part of this mechanism. Use of a volatile organic base such as ethanolamine or another volatile amine compound accomplishes this aspect. Once mixed and applied to the treatable material, the volatile base may be volatilized and the pH of the mixture reverts to acidic. The reversion initiates the acid-carbodiimide reaction mechanism. In other embodiments, an inorganic base such as sodium hydroxide may also be employed to maintain a basic pH. Use of a dilute acid initiating medium can be employed to move the pH to an appropriate acidic value and initiate the acid-carbodiimide reaction. Because the primary solvent for the first and second components is alcohol but under ordinary conditions, one or more of the substances of the first and second components is premixed with water, at least some amount of water may be present. As a result, the pH of the first, second, third and fourth components maintained separately will be established by the primary material in the component when placed in an alcohol medium. For the first component, the pH will be controlled by the acid groups of the CDI link compound when placed in an alcohol medium. As explained above, preferably the form of the CDI link compound is controlled by a volatile base so that it is in a partially to substantially neutralized form when mixed with the second component. The in situ linking is then initiated by reversion of the pH to an acidic condition. Generally, depending upon the intrinsic reactivity of the CDI link compound and the polycarbodiimide, management of the pH is a minor or null factor for reaction rate. Accordingly, a general procedure regarding pH follows the intrinsic acid or base nature of the first, second and third components.

I. Dispersants

It will be apparent to one skilled in the art that careful and selective choice of dispersant can help to maximize performance in terms of maximizing the amount of color produced from an immobilized film, maximizing the remanence or wash fastness, and enabling removal of the color.

For example, in the case where the binder polymer is anionic in nature, dispersants which are anionic or nonionic are preferably chosen, rather than cationic, as this avoids undesired precipitation in the formula prior to it forming a colored film on the keratin—i.e. utilizing the principle of avoiding opposing charges. The electrostatic, ionic and functional character of the dispersant also is chosen to be compatible with and to not interfere with the in situ combination of the CDI compound and polycarbodiimide and with the reactive termini of the first and/or second components. More preferably, the dispersant is chosen to be compatible with and miscible with the first and second components with and without medium and is simultaneously chosen not to be compatible with and preferably is also substantially immiscible with the third component with and without its medium, if any. When these preferences are present, the dispersant migrates to the first and second component layer of the coating and does not substantially mix with the third component layer when it is applied as a pretreatment. This arrangement can operate as a helpful adjunct during the removal step, the "off" step described below.

Likewise, the principle of choosing chemically similar dispersant and first component, e.g., binder (for example, a silicone first component paired with a silicone dispersant), can be followed to ensure maximum compatibility.

As well as compatibility as noted above, the other critical criterion in selecting dispersant(s) is their ability to enable pigment to be dispersed down to the primary particle size, preferably with the minimum amount of input mechanical energy. It will be recognized by someone skilled in the art that the concentration of dispersing agent is also a critical factor. In general, it is usually required that there is a minimum amount for dispersing activity and that below this, the system is either not fully dispersed or, worse, that the dispersant acts as a flocculant.

These two considerations together are used to define preferred materials and their respective concentrations.

It may also be the case, depending on the type of binder polymer used, that the binder itself is also a dispersant (see below for discussion of classes of dispersant). In such cases it is possible that no further dispersing additive may be needed.

Combination of the dispersed polymer mixture with the first, second and/or third components can be made in any manner; however, it is preferred to combine the dispersed polymer mixture with the first and/or second components and apply the first and/or second components as described below and to have performed the pretreatment with the third component. This order of combination of the dispersed polymer mixture with the first and/or second components delivers the dispersed pigment mixture with the first and second component coating layer and on top of the third component pretreatment layer. While the layers intermix to a slight to moderate to essentially full extent, at least a portion of the dispersed pigment mixture resides over the pretreatment layer. This arrangement of the coating at least in part enables removal of the coating when the "off" techniques described below are practiced.

J. Dispersants, Kinds, Properties and Chemistry

Dispersants are amphiphilic or amphiphathic meaning that they are chemical compounds possessing both hydrophilic (water-loving, polar) and lipophilic (fat-loving) properties. Dispersants are surface-active polymers that allow the homogeneous distribution and stabilization of solids, e.g. pigments in a liquid medium (like a binder), by lowering the interfacial tension between the two components. As a result, agglomerates are broken up into primary particles and protected by a protecting dispersant envelope of a re-agglomeration.

The dispersants can be subdivided on the basis of the stabilization mechanism in
 1. dispersants for electrostatic stabilization
  a. Anionic dispersing additives
   i. Polyacrylates
   ii. Polyphosphates
  b. Neutral dispersing additives
  c. Cationic dispersing additives
 2. Dispersants for steric stabilization
Electrostatic Stabilization The pigment surface is occupied by an additive carrying an ionic charge. All pigment particles are charged the same. The mutual repulsion by the charge is greater than the attractions of the pigment particles. The electrostatic stabilization has its relevance mostly in water-based paint systems.

Polyanionic dispersing additives: polycarboxylates (mostly salts of polyacrylic acids), polyphosphates divided into linear polyphosphates and cyclic metaphosphates, polyacrylates
  salts of polyacrylic acid, as cations, sodium and ammonium are preferred, these polyacrylates are water-soluble, technical products have molecular weights in the range of 2000 to 20,000 g/mol, optimum is about 8000 g/mol
  Sodium and ammonium salts of the homo- or copolymers of acrylic acid, methacrylic acid or maleic acid
Steric Stabilization The attractive forces between the pigment particles are effective only over relatively small distances of the particles from each other. The approach of two particles to each other can be prevented by molecules that are firmly anchored to the pigment surface and carry groups that extend from the surface and may reduce the potential for the pigments to contact one another. By sufficiently long chain lengths, agglomeration can be prevented. Also, the substances added to avoid agglomeration and other undesirable pigment particle interactions preferably are chosen to minimize or avoid interaction with the CDI link compound-polycarbodiimide combination and reaction.
  Water-soluble polymers
  Block or graft copolymers, so-called AB block copolymers
  Example: AB block polymer of 2-vinylpyridine and methacrylic acid ester Example: AB block copolymer of polyester (based caprolactam) and triethylenetetramine Typical functional groups for the A segment are carboxyl, amine, sulfate and phosphate for inogenous bonds or polyether and polyamide for hydrogen bonds. B represents the solvated side chain, molecular weights 1000 to 15000 g/mol, e.g. modified polyacrylates or polyhydroxystearates; however interference with the acid-carbodiimide reaction is to be minimized or preferably avoided.

Hydrophilic moieties (e.g., polyethers) and pigment affinic groups (e.g. Groups) containing oligomers or polymers.

The following types are distinguished according to the number of monomer types used in the production:

Homopolymers: only one kind of monomer
Copolymers: two monomers
Terpolymers: three monomers
Classification according to distribution of the monomers in the polymer:

Statistical polymers: A and B segments are distributed arbitrarily
Block polymers: the monomers are grouped into blocks
Graft polymers: these consist of a linear homopolymer backbone on which side chains of other monomer blocks are grafted Some examples of dispersants for solvent-based systems are:
oligomeric titanates and silanes for inorganic pigments with OH or carboxy groups.
Oligomeric polymeric carboxylic acids for inorganic pigments (cationic).
Polyamines for inorganic pigments, e.g., cationic polymers.
Salts of long-chain polyamines and polycarboxylic acids for inorganic and organic pigments (electroneutral).
Amine/amide-functional polyesters/polyacrylates for the stabilization of organic pigments.

Some examples of dispersants for aqueous systems are:
Inorganic dispersants such as fine-grained CaCO3, Ca3(PO4)2, polyphosphates, polyphosphoric acids.
Nonionic surfactants such as ethoxlyated fatty alcohol (e.g. Neodol 25-9), ethoxylated oils (e.g. ethxylated castor oil under the tradename Cremophore RH410)
Block and graft copolymers of the type having distinct hydrophilic and hydrophobic blocks (e.g. ethylene oxide-propylene oxide polymers under the tradename Poloxamer)
Anionic surfactants consisting of the unethoxylated or ethoxylated salts of acids (e.g. sodium ceteth-10-phosphate under the tradename Crodafos).

Examples and classes of nonionic surfactants that can function as dispersants include oligomers (e.g., example, oligomers have up to 20 monomeric units, polymers have at least 20 monomeric units), polymers, and/or a mixture of several thereof, bearing at least one functional group with strong affinity for the surface of the pigment microparticles. For example, they can physically or chemically attach to the surface of the pigment microparticles. These dispersants also contain at least one functional group that is compatible with or soluble in the continuous medium. For example, 12-hydroxystearic acid esters and C8 to C20 fatty acid esters of polyols such as glycerol or diglycerol are used, such as poly(12-hydroxystearic acid) stearate with a molecular weight of about 750 g/mol, such as the product sold under the name SOLSPERSE 21,000 by the company Avecia, polyglyceryl-2 dipolyhydroxystearate (CTFA name) sold under the reference DEHYMYLS PGPH by the company Henkel, or polyhydroxystearic acid such as the product sold under the reference ARLACEL P100 by the company Uniqema, and mixtures thereof. Similar dispersants will function to disperse the polar functional silicone polymers that are not readily dispersible and/or are not at least partially soluble in aqueous media.

The foregoing dispersant category involving cationic polymers includes polymers such as quaternary ammonium polymers. Examples of quaternary ammonium derivatives of polycondensed fatty acids include, such as for instance, SOLSPERSE 17,000 sold by the company Avecia, and polydimethylsiloxane/oxypropylene mixtures such as those sold by the company Dow Corning under the references DC2-5185 and DC2-5225 C.

The dispersant can be a polyolefin polymer. These dispersants include but are not limited to an olefinic polymer having a molecular weight of about 100 g/mol to about 5,000,000 g/mol, such as about 1,000 g/mol to about 1,000,000 g/mol. Examples of polymers, include, but are not limited to poly(ethylene), poly(propylene), poly(butylene), poly(isobutylene), poly(isoprene), poly(acetal), poly(ethylene glycol), poly(propylene glycol), poly(butylene glycol), poly(methylmethacrylate), poly(dimethylsiloxane), poly(vinylalcohol), poly(styrene), poly(maleic anhydride), poly(ethylmethacrylate), poly(isobutylmethacrylate), poly(methacrylate), poly(butylmethacrylate), poly(n-butylmethacrylate), poly(vinyl butyrate), poly(vinyl chloride), polysiloxane, and mixtures thereof. The polymers can be random, block, or alternating copolymers. In some embodiments, the polymer is a co-polymer that is made from two or more different monomers, such as the monomers that make the polymers described above. Examples of co-polymers include, but are not limited to polyethers, polyesters, polyamides, acrylics, and polystyrenes. The co-polymer can be alternating monomers, random, or block. Examples include a polyether of alternating or block PEO, PPO groups.

Representative dispersants are also available from a variety of suppliers, and include various nonionic (e.g., ethoxylated) and anionic (e.g., non-ethoxylated salt) forms including agents from Air Products and Chemicals, Inc. (e.g., SURFYNOL™ PSA336); Archer Daniels Midland Co. (e.g., ULTRALEC™ F deoiled lecithin); Ashland Inc. (e.g., NEKAL™ WS-25-I, which is a sodium bis(2,6-dimethyl 4heptyl)sulfosuccinate); BASF (e.g., DISPEX™ AA 4144, DISPEX ULTRA FA 4425 which is a fatty acid-modified emulsifier having a viscosity of 40,000 cps, DISPEX ULTRA FA 4420 which is a fatty acid-modified emulsifier and a dark brown liquid of unspecified viscosity, DISPEX ULTRA FA 4431 which is an aliphatic polyether with acidic groups having a viscosity of 350 cps, DISPEX ULTRA PA 4501 which is a fatty acid modified polymer having a viscosity of 10,000 cps, DISPEX ULTRA PA 4510, EFKA™ PU 4010, EFKA PU 4047 which is a modified polyurethane, EFKA PX 4300, EFKA ULTRA PA 4510 and EFKA ULTRA PA 4530 which are modified polyacrylates, EFKA FA 4620 which is an acidic polyether having a viscosity of 1,400 cps, EFKA FA 4642 which is an unsaturated polyamide and acid ester salt having a viscosity of 2,000 cps, HYDROPALAT™ WE 3135, HYDROPALAT WE 3136 and HYDROPALAT WE 3317 which are difunctional block copolymer surfactants terminating in primary hydroxyl groups and having respective viscosities of 375, 450 and 600 cps, and TETRONIC™ 901 and TERTRONIC 904 which are tetrafunctional block copolymers terminating in primary hydroxyl groups and having respective viscosities of 700 and 320 cps); Borchers (e.g., BORCHI™ Gen 0451 which is a polyurethane oligomer having a viscosity of about 30,000 cps, BORCHI Gen 0652 which is an amine neutralized acrylic acid copolymer having a viscosity of about 75-300 cps, and BORCHI Gen 1252 and BORCHI Gen 1253 which are acrylic ester copolymers having respective viscosities of about 1,500-3,500 and 50-300 cps); Byk-Chemie (e.g., BYK™ 156 which is a solution of an ammonium salt of an acrylate copolymer, DISPERBYK™ which is a solution of an alkyl ammonium salt of a low-molecular-weight polycarboxylic acid polymer, DISPERBYK-102 which is an acidic copolymer, DISPERBYK™-145 which is a phosphoric ester salt of a high molecular copolymer with pigment affinic groups and a liquid of unspecified viscosity, DISPERBYK-190 which is a solution of a high molecular weight block copolymer with pigment affinic groups, DISPERBYK-2013 which is a structured copolymer with pigment affinic groups having a viscosity of 8,600 cps, DISPERBYK-2055 which is a copolymer with pigment affinic groups and a liquid of unspecified viscosity, DISPERBYK-2060 which is a solution of a copolymer with pigment affinic groups having a viscosity of 3,600 cps, DISPERBYK-2061 which is a solution of a copolymer with pigment affinic groups having a viscosity of 491 cps, DISPERBYK-2091, DISPERBYK-2200 which is a high molecular weight copolymer with pigment affinic groups sold in solid form as pastilles and BYKJET™-9152 which is a copolymer with pigment affinic groups having a viscosity of 21,600 cps); Clariant (e.g., DISPERSOGEN™ 1728 which is an aqueous solution of a novolac derivative having a viscosity of 4,000 cps, DISPEROGEN 2774 which is a novolac alkoxylate having a viscosity of 4,000 cps, GENAPOL™ X 1003 and GENAPOL X 1005 which are fatty alcohol ethoxylates having respective viscosities of about 400 cps and 1,300 cps, HOSTAPAL BV concentrate which is a sulfate ester having a viscosity of about 2,700 cps); Cray Valley (e.g., SMA1440H which is an ammonia salt of a styrene maleic anhydride copolymer solution); Dow Chemical Co. (e.g., the TAMOL™ family of dispersants including TAMOL 165A and TAMOL 731A); Elementis (e.g., NUOSPERSE™ FA196 which has a viscosity of 1,200 cps); Lubrizol (e.g., SOLSPERSE™ 27000, SOLSPERSE 28000, SOLSPERSE 32000, SOLSPERSE 39000, SOLSPERSE 64000, SOLSPERSE 65000, SOLSPERSE 66000, SOLSPERSE 71000, SOLSPERSE M387, SOLPLUS™ R700 and SOLPLUS K500); Ethox Chemicals, LLC (e.g., the E-SPERSE™ family of dispersants and ETHOX™ 4658); Evonik (e.g., TEGO™ DISPERS 656, TEGO DISPERS 685, TEGO DISPERS 750W and TEGO DISPERS 757W); Rhodia Solvay Group (e.g., ABEX 2514 and ABEX 2525 which are nonionic surfactants, RHODACAL™ IPAM which is isopropyl amine dodecylbenzene sulfonate having a viscosity of 10,000 cps, RHODAFAC™ RS-710 which is a polyoxyethylene tridecyl phosphate ester, and the RHODOLINE™ family of dispersants including RHODOLINE 4170 and RHODOLINE 4188); Sasol Wax GmbH (e.g., ADSPERSE™ 100, ADSPERSE 500 and ADSPERSE 868) and Stepan Company (e.g., G-3300 which is an isopropyl amine salt of an alkyl aryl sulfonate having a viscosity of about 6000 cps, POLYSTEP™ A-15 which is a sodium dodecylbenzene sulfonate having a viscosity of about 85 cps, POLYSTEP B-11 and POLYSTEP B-23 which are ethoxylated ammonium lauryl ether sulfates respectively containing 4 or 12 moles of ethylene oxide and having respective viscosities of 66 and 42 cps, and POLYSTEP B-24 which is sodium lauryl sulfate having a viscosity of 100 cps).

Commercial dispersant compositions and systems of the synthetic kind described above are sold by several companies who manufacture polymer systems. These include:

BASF

Water-Based System—
 Dispex® Ultra FA, Dispex® AA, Dispex® CX, Dispex® Ultra PX, Dispex® Ultra PA Solvent based system
 Efka® FA, Dispex® Ultra FA, Efka® FA, Efka® PU, Efka® PA, Efka® PX Clariant
 Dispersogen® 1728, Dispersogen® 2774, Dispersogen® 3169, Dispersogen® AN 100, Dispersogen® AN 200, Dispersogen® ECS, Dispersogen® ECO, Dispersogen® LFS 6, Dispersogen® PCE, Dispersogen® PL 30, Dispersogen® PL 40, Dispersogen® PTS, Dispersogen®, Emulsogen® LCN 217, Emulsogen® TS 200, Dispersogen®, Dispersogen® FN, Dispersogen® FSE, Dispersogen® MT 200, Dispersogen® LFH, Dispersogen® 145, Dispersogen® 4387, Hostapal® BV, Dispersogen® LEC, Dispersogen® PSM, Polyglykol 200 LVC, Polyglykol G500, Polyglykol 300, Polyglykol 400

Lubrizol
 Solsperse™ 3000, Solsperse™, Solsperse™ 8000, Solsperse™, Solsperse™ 12000S, Solsperse™ 13300, Solsperse™ 13400, Solsperse™ 13500, Solsperse™ 13650, Solsperse™ 13940, Solsperse™ 16000, Solsperse™ 17000, Solsperse™ 17940 Solsperse™ 17000, Solsperse™ 18000, Solsperse™ 19000, Solsperse™ 20000 Solsperse™ 21000 Solsperse™ 22000 Solsperse™ 24000SC, Solsperse™ 26000, Solsperse™ 27000, Solsperse™ 28000 Solsperse™ 32000 Solsperse™ 32500 Solsperse™ 32600 Solsperse™ 33000 Solsperse™ 35000, Solsperse™ 35100 Solsperse™ 35000, Solsperse™ 36000 Solsperse™ 36600, Solsperse™ 37500 Solsperse™ 38500, Solsperse™ 39000, solsperse W100.

Byk
 DISPERBYK-102, DISPERBYK-103, DISPERBYK-106, DISPERBYK-107, DISPERBYK-108, DISPERBYK-109, DISPERBYK-110, DISPERBYK-111, DISPERBYK-115, DISPERBYK-118, DISPERBYK-130, DISPERBYK-140, DISPERBYK-142, DISPERBYK-145, DISPERBYK-161, DISPERBYK-162, DISPERBYK-163, DISPERBYK-164, DISPERBYK-166, DISPERBYK-167, DISPERBYK-168, DISPERBYK-170, DISPERBYK-171, DISPERBYK-174, DISPERBYK-180, DISPERBYK-181, DISPERBYK-182, DISPERBYK-184, DISPERBYK-185, DISPERBYK-187, DISPERBYK-190, DISPERBYK-191, DISPERBYK-192, DISPERBYK-193, DISPERBYK-194 N, DISPERBYK-199, DISPERBYK-2000, DISPERBYK-2001, DISPERBYK-2008, DISPERBYK-2009, DISPERBYK-2010, DISPERBYK-2012, DISPERBYK-2013, DISPERBYK-2015, DISPERBYK-2022, DISPERBYK-2023, DISPERBYK-2025, DISPERBYK-2026, DISPERBYK-2050, DISPERBYK-2055, DISPERBYK-2060, DISPERBYK-2061, DISPERBYK-2062, DISPERBYK-2070, DISPERBYK-2080, DISPERBYK-2081, DISPERBYK-2096, DISPERBYK-2117, DISPERBYK-2118, DISPERBYK-2150, DISPERBYK-2151, DISPERBYK-2152, DISPERBYK-2155, DISPERBYK-2157, DISPERBYK-2158, DISPERBYK-2159, DISPERBYK-2163, DISPERBYK-2164, DISPERBYK-2200, DISPERBYK-2205

DOW
　　TAMOL™ 1124; TAMOL™ 1254; TAMOL™ 165A; TAMOL™ 2002; TAMOL™ 2011; TAMOL™ 681; TAMOL™ 731A; TAMOL™ 851; TAMOL™ 901; TAMOL™ 945; TAMOL™ 960; TAMOL™ 963; TAMOL™ 983

Following the foregoing principles and guidelines, the pigment microparticles can be dispersed in the composition with the addition of at least one of a dispersant and a wetting agent. While not wishing to be bound by any specific theory, it is believed that only when the pigments are de-aggregated into their primary particles do they deliver the optimum optical performance. For examples, pigments with a primary particle size of 0.02 micron which provide brilliant bright colors, when present as aggregates of around 0.3 micron provide duller colors.

The dispersant serves to protect the pigment microparticles against agglomeration or flocculation either in the dry state or in the solvent. Dispersants also serve as wetting agents. In this capacity, dispersants as wetting agents can be low or higher molecular weight monomeric surfactants (for example, anionic, cationic or amphoteric surfactants). Dispersants as wetting agents can be higher molecular weight surface-active or pigment particle affinic polymers (for example, polyelectrolyte dispersants such as maleic acid copolymers, and polyurethanes or polyacrylates containing carboxylic acid, amine or isocyanate pigment affinic anchor groups or polyethylene imines) or other type of polyelectrolytes.

Representative wetting agents include those available from a variety of suppliers including Air Products and Chemicals (e.g., CARBOWET™ GA-210 surfactant which has a viscosity of 80 cps, CARBOWET GA-221 surfactant which has a viscosity of 100 cps, DYNOL™ 607 superwetter which has a viscosity of 205 cps and DYNOL 800 superwetter which has a viscosity of 230 cps); Dow Chemical Co. (e.g., CAPSTONE™ fluorosurfactants FS 31, FS 34, FS 35, FS 61 and FS 64); and Stepan Company (e.g., STEPWET™ DOS-70 surfactant which contains 70% active ingredients and has a viscosity of 200 cps, and STEPWET DOS-70EA surfactant which contains 70% active ingredients and has a viscosity of 220 cps).

K. Incorporation of Pigment in Disperant

The pigments described herein can be chosen and/or modified to be similar enough such that a single dispersant can be used. In other instances, where the pigments are different, but compatible, two or more different dispersants can be used. Because of the extreme small size of the pigment microparticles and their affinity, combination of the pigment microparticles and dispersant to form a substantially homogeneous dispersion that can subsequently be modified and/or diluted as desired is to be accomplished before combination with any or all of the first, second and third components of the multicomponent composition and preferably with only the first and/or second components.

The pigment microparticles can be dispersed and stabilized in the medium by one or more dispersants the properties and kinds of which are described above. The dispersant can either be added to the medium, or to a precursor medium or can form a coating on the microparticles to facilitate dispersion. It is also possible to provide the microparticles with a coating of a dispersant material and additionally provide a further dispersant to the medium, or to a precursor medium, which is used to form the final medium.

The dispersant, either added to the medium or provided as coating, facilitates wetting of the microparticles, dispersing of the microparticles in the medium, and stabilizing of the microparticles in the medium.

The wetting includes replacing of materials, such as air, adsorbed on the surface of the pigment microparticles and inside of agglomerates of the microparticles by the medium. Typically, a complete wetting of the individual microparticles is desired to singularize the particles and to break off agglomerates formed by microparticles adhering to each other.

After wetting, the microparticles can be subjected to de-aggregate and de-agglomerate step, generally referred to as dispersing step. The dispersing step typically includes the impact of mechanical forces such as shear to singularize the microparticles. In addition to shearing to singularize, the microparticles can be broken into even smaller microparticles using, for example, roller mills, high speed mixers, and bead mills. Usual practice involves substantially homogeneous dispersion of the pigments in dispersant through the use of high shear mixing; for example, through use to the appropriate ball mill, ultra high-pressure homogenizer or other system known by those skilled in the art of pigment dispersion.

During wetting and dispersing, the exposed total surface area of the microparticles increases which is wetted by the dispersant. The amount of the dispersant may be gradually increased during dispersing to account for the increased surface area.

The dispersant also functions as de-flocculation agent keeping the dispersed microparticles in a dispersed state and prevent that they flocculate to form loose aggregates. This stabilization is also needed for long term storage purposes. Different type of stabilization such as electrostatic stabilization and steric stabilization are possible, and the type of dispersant is selected in view of the medium and the material of the microparticles.

The dispersant may be added to a dry powder of the pigment particles when the particles are milled to a desired size. During milling, or any other suitable technique to singularize the pigment particles or to break them into smaller part, the dispersant comes in contact with and adheres to the surface of the microparticles. Freshly generated microparticle surface during milling will be coated by the dispersant so that, after milling, the microparticles with a coating formed by the dispersant are provided.

The coating with the dispersant can also be carried out in a liquid carrier medium to which the dispersant is added. The microparticles can also be milled in the liquid carrier.

L. Optional Components

Optional components of the composition include suspending agents, leveling agents and viscosity control agents. The suspending agents help maintain the pigment particles in dispersed condition and minimize or negate their agglomeration. Suspending agents include fatty acid esters of polyols such as polyethylene glycol and polypropylene glycol. These are similar to plasticizers and function in similar fashion to allow pigment particles to "slip" by each other without retarding or binding interaction. They act as grease in this fashion. Additionally, suspending agents in part participate in promoting the stable dispersion of the pigment particles and avoid settling. The CDI link compound such as a carboxylic acid polymer also participates through its solubilization or interaction with the pigment particles and with the medium. The suspending agents provide another factor for maintaining the stable dispersion. They not only provide the "grease" to facilitate Brownian movement but also in part stabilize through interaction as emulsifiers of the pigment particles in the medium. Optional components also are to be chosen so that they do not interfere or only minimally interfere with the CDI link compound-polycarbodiimide coupling reaction.

The multicomponent composition embodiments in accordance with the present invention can also optionally contain at least one adjuvant, chosen, for example, from reducing agents, fatty substances, softeners, antifoams, moisturizers, UV-screening agents, mineral colloids, peptizers, solubilizers, fragrances, anionic, cationic, nonionic, or amphoteric surfactants, proteins, vitamins, propellants, oxyethylenated or non-oxyethylenated waxes, paraffins, C10-C30 fatty acids such as stearic acid or lauric acid, and C10-C30 fatty amides such as lauric diethanolamide.

The multicomponent composition embodiments in accordance with the present invention can further optionally contain one or more additives, including, but not limited to, antioxidants (e.g., phenolics, secondary amines, phosphites, thioesters, and combinations thereof), crosslinking agents, reactive diluents (e.g., low molecular weight mono- or di-functional, non-aromatic, (meth)acrylate monomers such as 1,6-hexanediol di(meth)acrylate, tripropylene glycol di(meth)acrylate, isobornyl(meth)acrylate, 2(2-ethoxyethoxy)ethyl(meth)acrylate, n-vinyl formamide, tetrahydrofurfuryl(meth)acrylate, polyethylene glycol di(meth)acrylate, tripropylene glycol di(meth)acrylate, neopentyl glycol dialkoxy di(meth)acrylate, polyethyleneglycol di(meth)acrylate, and mixtures thereof), non-reactive diluents (e.g., ethylene glycol, di(ethylene glycol), tetra(ethylene glycol), glycerol, 1,5-pentanediol, ethylene glycol monomethyl ether, ethylene glycol dimethyl ether, triethylene glycol monomethyl ether, 2-ethoxyethanol, solketal, benzonitrile, hexamethylphosphoramide, 2-N-methylpyrrolidinone and N,N-dimethylformamide); dyes, fillers (e.g., silica; carbon black; clay; titanium dioxide; silicates of aluminum, magnesium, calcium, sodium, potassium and mixtures thereof; carbonates of calcium, magnesium and mixtures thereof; oxides of silicon, calcium, zinc, iron, titanium, and aluminum; sulfates of calcium, barium, and lead; alumina trihydrate; magnesium hydroxide and mixtures thereof), plasticizers (e.g., petroleum oils such as ASTM D2226 aromatic oils; paraffinic and naphthenic oils; polyalkylbenzene oils; organic acid monoesters such as alkyl and alkoxyalkyl oleates and stearates; organic acid diesters such as dialkyl, dialkoxyalkyl, and alkyl aryl phthalates, terephthalates, sebacates, adipates, and glutarates; glycol diesters such as tri-, tetra-, and polyethylene glycol dialkanoates; trialkyl trimellitates; trialkyl, trialkoxyalkyl, alkyl diaryl, and triaryl phosphates; chlorinated paraffin oils; coumarone-indene resins; pine tars; vegetable oils such as castor, tall, rapeseed, and soybean oils and esters and epoxidized derivatives thereof; esters of dibasic acids (or their anhydrides) with monohydric alcohols such as o-phthalates, adipates and benzoates; and the like and combinations thereof), processing aids, ultraviolet stabilizers (e.g., a hindered amine, an o-hydroxy-phenylbenzotriazole, a 2-hydroxy-4-alkoxybenzophenone, a salicylate, a cyanoacrylate, a nickel chelate, a benzylidene malonate, oxalanilide, and combinations thereof), and combinations thereof.

An additional additive may be a tactile hair modification agent. These may include, but are not limited to, a softening and/or lubricating and/or anti-static and/or hair alignment and/or anti-frizz benefit and/or impact on the keratin fibres.

M. Solids Content

Embodiments of the multicomponent composition include solids and liquids. The solids comprise any substance or material of the multicomponent composition that in a form uncombined with any other material, solvent, liquid or substance is has a solid physical form at ambient conditions. Included at least are the organic polymer, the in situ linking material and the pigment microparticles of the multicomponent composition. The medium, in contrast is a liquid and functions as a solvent and/or a liquid in which solid particles are dispersed. The optional components as well as the plasticizer, dispersing agent, surface treatment agent, cross linking agent and other materials added to the medium, if any, are included in the solids content as long as they remain with the organic polymer, in situ linking material and pigment microparticles following application and setting of the multicomponent composition as a coating on strands of human hair. This includes substances that ordinarily would be regarded as liquids because they would remain in the coating on strands of hair. The solids content of the multicomponent composition may range from about 1 wt % to about 90 wt % relative to the total weight of the composition. A preferred solids content ranges from about 2 wt % to about 60 wt % and another preferred solids content ranges from about 4 wt % to about 40 wt % relative to the total weight of the composition. An especially preferred solids content range is about 4 wt % to about 20 wt % with contents of about 2 wt %, about 4 wt %, about 5 wt %, about 6 wt %, about 7 wt %, about 8 wt %, about 9 wt % and about 10 wt % being more especially preferred.

Testing the Flexibility of a Coating of the Multicomponent Composition

With the film prepared above, it can also be tested for optical density to check that the polymer film does not itself alter the hair appearance of the hair too significantly.

Further the polymer preferably can have a glass transition point (Tg) as described above so that it is possible to prevent the colored coating from being damaged or cracked and to secure washing and friction remanence.

The composition coating can have a surface energy between about 20 and about 50 mN m−1. The composition coating preferably has high transmission, to ensure that it does not interfere with the optics of the hair color. The polymer preferably has a refractive index between 1.4 and 1.6.

Application of First, Second, Third and/or Fourth Components of the Multicomponent Composition to Treatable Material The first, second, third and fourth components of the multicomponent composition may be maintained in separate storage compartments or in separate kit form when the first, second and third functional groups of these components will react if together. Additionally, the substantive constituent of the fourth component is maintained separately if it will catalyze or otherwise cause reaction of such functional groups. A convenient storage means can be utilized such as plastic squeeze tubes, plastic bottles, glass containers, sachets, multi-compartment containers, tooles, spottles syringes and plunger operated dispensing devices. Unit amounts for combination can be formulated so that the entire contents of a unit of the first component can be combined with the entire contents of the second component for application to the treatable material. Alternatively, metered or calibrated dispensing containers for providing measured amounts of the components as directed by printed instructions can be provided. With some embodiments, multiple components can be pre-combined for storage and handling as long as a substantive constituent that would cause in situ linking is maintained in a separate compartment.

Use of the foregoing delivery means enables preparation of an embodiment for practice of the method of the present invention. This embodiment may comprise sequential, simultaneous or premixed application of the first and second components to treatable material or textiles. Pigment microparticles may be incorporated in either or both of the first and second components. This aspect of application provides a layer of combined first and second components on the treatable material or textiles that will undergo transformation to a coating in which the first and second functional groups of these components in situ interact to covalently, electrostatically, coordinately, ionically, dipolar-wise, or entanglement-wise connect as the completed coating. Preferably the pairs of first and second functional groups are chemically reactive so that covalent and/or coordinate bonds are formed between the organic polymer and the in situ linking material. More preferably, these pairs are chemically reactive to form covalent bonds between the organic polymer and the in situ linking material. With this aspect alone, the resulting coating on treatable material, such as but not limited to hair, provides good remanence against repeated shampooing, rinsing and contact with mild detergents, soap and similar wash substances.

Pretreatment with Third Component

Another embodiment of the method according to the present invention may comprise application of the third component to the treatable material as a pretreatment before application of the first and second components as described above. According to this embodiment of the method, the third component containing the base compound with or without pigment, and preferably without pigment, is applied on or to at least a portion of the treatable material such as hair, and preferably throughout the treatable material. While it is not a limitation of the invention, it is believed that the pretreatment addition of the third component enables enhancement of adhesion between the hair, pigments and first and second components. It is believed that the amine groups of the third component interact with complementary chemical groups on the treatable material, especially keratin material, and most favorably with hair. It is also believed that the amine groups of the third component interact with the acid groups of the CDI link compound to promote tight electrostatic and other entanglements. Although it is not a limitation of the invention, it is further believed that the combination of the first and second components also interacts with complementary groups of the treatable material. It is believed that these chemical interactions, which may be covalent, coordinate, electrostatic, ionic, dipolar and/or entanglement in nature function as melding between and among the treatable material, the pigment microparticles, the CDI link compound, the in situ linking material and the base compound.

Pretreatment with the third component may be carried out prior to application of the first and second components. Pretreatment may be carried out immediately prior to application of the first and second components, or at least 1 hour prior to application of the first and second components, or at least 24 hours prior to application of the first and second components, or at least 10 days prior to application of the first and second components, or at least one month prior to application of the first and second components. Preferably, pretreatment may be carried out immediately prior to or within a few minutes up to an hour before application of the first and second components. Typically, the third component is at least partially dried with optional heating to at least substantially remove or otherwise eliminate the medium of the third component. For example, excess medium may be removed by contacting with an abosrbant fabric or surface or the hair may by heated with a hair drier. Preferably, removal of third component medium is accomplished before application of the first and second components.

Core and Shell Alternative

According to an embodiment in which pigment microparticles are incorporated into the third component, at least some of categories of the base compound can be employed to provide a "core-shell structure" (core-shell morphology) for the pigment microparticles. In the case that the base compound and pigment(s) have a "core-shell structure", the "core" corresponds to the "naked" pigment which features the same properties as defined hereinbefore with reference to the "pigment(s)". The "shell" corresponds to a coating layer of base compound surrounding the "core". The pigments having a core-shell structure may have a $D_{50}$(Vol) particle diameter of from 20 nm to 1 micron, typically 60 nm to 900 nm, more typically 100 nm to 600 nm. As such, embodiments of the present invention also relate to a treatable material treatment composition comprising a core-shell pigment microparticle arrangement, wherein the core comprises an inorganic and/or organic pigment microparticle material, and the shell comprises at least one base compound, the at least one core-shell construct having a $D_{50}$(Vol) particle diameter of 20 nm to 1 µm. The shell surrounding the core may comprise one or more polymeric shell layers. Typically, the shell may comprise a base compound wherein the base compound is a polymeric shell layer.

A further embodiment involving the core and shell alternative may be accomplished by pretreatment of a prepared dispersion of pigment microparticles with a portion of base compound in appropriate medium to provide a dispersion of pigment microparticles as the core and shell construct ready to be combined with any of the first, second and third components. The combination of the microparticle core and shell dispersion with any of the first, second and third components as desired can provide the core and shell microparticles dispersed in any of the first, second and third components, in any two or in all three components.

Application of First and Second Components Following Pretreatment

As described above, first and second components may be applied to the treatable material in combination with the foregoing pretreatment with the third component or may be applied without such pretreatment. In either arrangement, embodiments of the first and second components are maintained separately when the first and second functional groups constitute reactive pairs as described above. Application of the first and second components to pretreated treatable material or to treatable material that has not been pretreated may be accomplished by sequential application of the first and second components or simultaneous application of these components to the hair. Typically for sequential application, either of the first and second components may be applied first, preferably the first component is applied first, especially for embodiments including pretreatment with the third component. Alternatively, the first and second components may be mixed together to form a premix immediately before application to the treatable material. Typically, the rate of reaction of the carboxylic acid and the carbodiimide is pre-adjusted through medium control, pH adjustment if needed, concentration, steric interaction, temperature, and similar factors controlling reaction rate so that a premix preferably will not substantially interact before the premix is applied to the treatable material. The practice of this step with the pre-treatment embodiment initially introduces combined first and second components on top of the pretreatment layer of base compound on the treatable material. Because the first and second components are in a medium, penetration, combination, mixing and/or melding of the first and second components into the pretreatment layer is believed to be accomplished. The penetration is believed to enable the linking among the CDI link compound, the in situ linking material, the base compound and the treatable material.

Application of the first and second components to pre-treated treatable material is preferably carried out after pretreatment. This sequence may be carried out immediately after pretreatment, or at least 1 hour after pretreatment, or at least 24 hours after pretreatment, or at least 10 days after pretreatment, or at least one month after pretreatment.

The sequential, simultaneous or premix application of the first and second components may be applied to at least a portion of the treatable material or may be applied all over the treatable material. The portions of first and second components may be applied sequentially, simultaneously or as a premix in a single application over all the treatable material or may be applied step-by-step to the treatable material. The first and second components may be applied step-by-step, for example, in case the treatable material is damaged. Applying the first and second components in a step-by-step manner as described above, may help to ensure that the treatable portions of the treatable material are saturated with the combined first and second components and may therefore provide a better coverage of the treatable material.

The multicomponent composition can be applied to treatable material using the coloring procedure described herein afterwards.

Manipulative Techniques for Application

After the pretreatment of the third component has been accomplished, and the pretreated treatable material, e.g. pretreated keratin fibers, optionally rinsed, the pretreated treatable material can be dried. The treatable material can be dried using an elevated temperature. The temperature of the treatable material can be increased to elevated temperatures above room temperature such as 40° C. or higher, for example using a hair drier. While the treatable material is being dried, some form of interdigitated implement can be used to help separate portions of the treatable material, and especially separate hair strands from one another. Examples of interdigitated devices include a comb or a brush. The treatable material can be dried with a hair drier while simultaneously being combed or brushed until it is dry to the touch. Alternatively, other means can be employed to dry and separate the treatable material such as hair simultaneously. For example, using a combination of air movement and vibrations will accomplish distribution of the multicomponent composition throughout the strands of hair.

Operational Method for Coating Treatable Material Such as Hair

The performance of operational method aspects of the present invention can be applied to keratin fibers to form a coating of the multicomponent composition. This aspect of the invention concerns a method for coloring treatable material and comprises applying embodiments of one or more multicomponent compositions for a time sufficient to deposit an effective colored coating on the treatable material such as each keratin fiber or hair strand. A somewhat to substantially overall distribution of the coating on the length and circumference of each fiber is produced.

To accomplish this aspect, embodiments of the first, second and third components of multicomponent composition are applied to the treatable material according to the sequences described above by brushing, painting, spraying, atomizing, squeezing, printing, rubbing massaging or in some manner coating the treatable material such as hair strands with the embodiments. Following application of a compositional embodiment to the treatable material such as hair strands, the composition is set, cured, linked, coordinated and/or otherwise melded together preferably by warming with blown warm air from a hair dryer or similarly treatable to remove the medium, initiate in situ linking of the organic polymer, the in situ linking material, the base compound, the treatable material and if present, remove the volatile base. The setting leaves a substantial to essentially complete overall linked coating of the organic polymer, in situ linking material and base compound containing dispersed pigment microparticles and optional additional components.

The in situ linking of the substantive constituents of first, second and third components during application provides a linked coating that enables it to resist its removal by washing with dilute mixtures of soap and water or shampoo and water. Color remanence is developed so that washing with dilute aqueous soap solution or dilute aqueous shampoo will not substantially remove the coating, but the coating can be facilely removed by use of a transformation trigger. The properties of the coating include remanence, flexibility, adhesion, abrasion resistance and remanence which are due at least in part to the linked character of the composition constituents including at least the organic polymer, the in situ linking material and the base compound and their intermolecular entwining, ionic and electrostatic intermolecular interaction, covalent and/or non-covalent linking, dipole interaction and lipophilic interaction of neutral moieties of these compositional constituents.

Selection of the substantive constituents of the multicomponent composition can be made on the basis of properties such as a solid lattice formation and interaction with the pigment microparticles. Such properties include the flexibility, the hardness, the adhesion, the remanence, the resistance to water or to other chemical compounds, and the abrasion resistance. It is also possible to take advantage of the more versatile properties of block polymers (polymers comprising at least two distinct polymer segments), grafted polymers (polymers containing a polymeric side chain grafted onto the homopolymer or copolymer backbone), or random copolymers (polymers comprising at least two different monomers). In the block copolymers, for example, the amount of hard and soft blocks has a significant impact on the properties of the polymer.

The multicomponent compositions in accordance with the present disclosure can have a viscosity that can be controlled to enable the product to be applied to the hair using either a brush and bowl or a bottle, but with sufficient rheology such that it does not drip and run from the hair onto the face or body.

Alternatively, low viscosity formulations may be applied to the hair via a suitable application device such that it does not drip and run form the hair onto the face and body.

The multicomponent compositions can be utilized in concentrated form or in serial dilutions, to provide for a consistent color results substantially along the entire length of the keratin fibers.

The aspect of coloring mammalian or synthetic keratin fibers with a multicomponent composition as described above includes a method for this coloring. The method comprises:
(i) applying the above-described multicomponent composition to keratin fibers to obtain an effective, deposited coloring amount of the combined composition including pigment microparticles and optional additional components;
(ii) setting the multicomponent composition by removing or otherwise eliminating the medium (e.g., by drying the composition); and.
(iii) setting the interaction among the first, second and third components and optional fourth component of the multicomponent composition by initiating the in situ linking among these groups.

During the setting/drying step, color distribution can be facilitated by concurrently moving and/or stroking the hair with an interdigitating device. Interdigitating devices include a comb or brush. The interdigitating device needs to be pulled substantially along the hair strands from root to tip. It can be pulled through at a rate of 0.1 cm s−1 to 50 cm s−1 or at a rate between 0.5 cm s−1 to 20 cm s−1

The multicomponent composition is applied to the mammalian or synthetic keratin fibers in any suitable way including spraying the multicomponent composition, massaging the keratin fibers by hand, after applying the multicomponent composition to the hand or by combing, brushing or otherwise applying the multicomponent composition throughout the mammalian or synthetic keratin fibers.

Unlike current hair coloring approaches that use dyes, the color with the multicomponent compositions described herein occurs on the surface of the hair strands. Current dye based approaches do provide the head of hair with some color variation, as the strands are not identical, and some of these differences are preserved after coloring. There are also differences root to tip which also helps to provide some variation. Using a pigment based surface coloring system such as that of the present invention, the variation of the underlying hair can be substantially removed, leading to a more homogeneous color result. This color result can be a more homogenous application of color. To obtain a somewhat non-homogeneous application of color that tends toward a more natural look, the user can apply the inventive multicomponent composition by any of several techniques.

The methods by which the multicomponent compositions described herein are applied can be modified, such that the user applies the product in one region of the hair, and then can apply a diluted version in another region of the hair. The dilution formula is specially chosen to be compatible with the colorant formulation and reduces the coloring strength, while maintaining the longevity of the color result. This can effectively be a "blank" formulation, which contains broadly the same materials as the coloring formulation, but with lower or no pigments present. When diluted the ratio of the diluent to colorant can be between about 10:1 and about 1:10, about 8:1 and about 1:2 or about 5:1 and about 1:1.

Alternatively, the amount of multicomponent composition applied can be altered in different regions of the hair, for example half the product is applied in the lengths of the hair, leading to a less colorful result. The difference in amounts applied in one region of the hair versus another can be between about 4:1 and about 1:4 or about 2:1 and about 1:2.

Alternatively, a combination of this approaches may be used to deliver the target color variation.

When the foregoing techniques are not possible to be applied, rather than apply a single hair color, it may be possible to apply two or more hair colors to different regions of the hair. When this is done, the different hair colors preferably provide complimentary colors so as to develop an attractive result. The difference in colors that can be used, based on the end result on hair tresses (as described later—natural white hair non-pre-bleached) are as follows. As described within the CIELCh system:

Color 1 ($LCh$) versus Color 2 ($LCh$)

Color 1 $L$-15<Color 2 $L$<Color 1 $L$+15

0 or Color 1 $C$-10<Color 2 $C$<Color 1 $C$+10

Color 1 $h$-45<Color 2 $h$<Color 1 $h$+45

Those skilled in the art of color measurements will know how to interpret difference in hue angles, h, when they extend from low positive values to those near to 360 degrees due to the periodic circular nature of the hue angle.

The method for use of the multicomponent composition in accordance with the present invention can occur during any suitable period. The period of application can be from about 0 to 30 minutes, but in any event a period that is sufficiently long to permit the coating of pigment microparticles to coat and adhere or bind to each separate keratin fiber, substantially along the entire length of each keratin fiber. The resultant is keratin fibers having a color and permanence that is at least equivalent to the color resulting from oxidative hair color, except under much milder conditions.

The multicomponent compositions described herein can be prepared by the manufacturer as a full shade, e.g., one that is ready to apply to the hair, and then shipped as a discrete unit to the user. The user may need to re-blend the multicomponent composition prior to application to ensure that the multicomponent composition delivers the optimum performance. Such re-blending can require shaking the multicomponent composition for about 1 to about 120 seconds or from about 3 to about 60 seconds. Reblending may also be performed by stirring the multicomponent composition prior to use. This may occur for about 1 to about 120 seconds or from about 3 to about 60 seconds. Although the multicomponent compositions according to the present invention are designed to provide stable suspensions of the pigment particles, the re-blending to agitate the microparticles and resuspend them in a substantially uniform distribution is desirable.

Multiple compositions comprising different pigments can be blended together prior to application to the keratin fibers. Such blending can be done in a manner so as to apply a plurality of complementary surface colors to the keratin fibers.

The multicomponent compositions can include multiple layers, involving multiple applications of at least the first and second components following the first application of the three components. It may be beneficial also to periodically reapply the third component. The techniques for applying multiple layers follow the techniques described above for application of a single multicomponent composition.

The coating of pigment microparticles comprising at least one pigment in a coating of the substantive constituents of the multicomponent composition can be adhered to the treatable material such as hair utilizing a coating having a total thickness at any given point along the hair fiber of less than about 5 m, preferably less than about 2 m as measured using a scanning electron microscope (SEM). To make such measurements, a coated hair sample can be embedded in a suitable resin, and then sectioned root to tip using techniques known to those skilled in the art of scanning electron microscopy. The thickness of the layer on the surface can then be assessed along the line of cuticles over a length of at least 100 m. The thickness of layer is determined by averaging 10 points evenly spaced over the section of interest.

As described above, application of the multicomponent composition to sections of treatable material such as sections of hair strands can be varied. In addition to varying the concentration of the pigment microparticles and optional coloring agent, different shades and/or colors of multicomponent composition can be applied to different sections of a strand of hair or a group of strands of hair. For example, the hair roots, mid sections and tips sometimes or often have different shades of color in their natural condition. This variation can be mimicked, altered or covered through use of differing shades or colors of the multicomponent composition. Roots, for example can be covered with a lighter shade and the tips can be covered with a darker shade to produce a two tone variation of the hair. Application to the hair of a first portion of multicomponent composition followed by stripping the composition from the hair mid sections and ends followed by setting the remaining composition on the hair roots will provide a first hair color coating on the roots. The mid-sections and tips can be dipped or brush applied with a second portion of multicomponent composition to complete the two color or two tone treatment. The use of multiple multicomponent compositions to produce multiple coatings on the hair can provide overlapping, sequential or coterminous coatings on the hair according to typical and routine techniques for applying multiple versions of hair color practiced by professional hair salons.

Post Treatment

An optional post treatment composition can be applied after treating the treatable material such as hair with the multicomponent compositions described herein. This can be applied either directly after completion of coloring with the multicomponent composition. The post treatment can be either single application or multiple application across time. The post treatment can be used to improve one or more of: feel, resistance to shampoo/conditioner/water washing treatments, and shine of the hair. Nonlimiting examples of materials used to improve the feel are those which impart lubricity to the treatable material such as hair strands and/or help the hair strands separate during the drying steps. These materials include, for example silicone conditioners, silicone polyethers, silicone polyglucose, polyisobutene, copolymers of ethylene and propylene oxide, and commonly used cosmetic oils and waxes. Nonlimiting examples of materials used to improve shampoo wash resistance are materials which act as a 'sacrificial layer' for example polymeric silicones and their copolymers, silicone resins, cosmetics oils and waxes. Nonlimiting examples of materials used to improve the shine of hair (meaning a decrease of the full width at half maximum parameter of the specular reflection curve as measured by a goniophotometer) are those materials which form a smooth film above the previously applied pigment polymer composite on the hair. In general, any cosmetically known film forming material can be used, but preferred are materials such as polymeric silicones and polycationic materials.

Removal of Color Coating

Hair colorants made from the multicomponent composition are very resistant to everyday hair treatments (such as washing with shampoo, conditioner etc) can be removed via use of specifically designed "removal formulations." These are specific chemical mixtures, described herein, and are designed to work by one or both of two broad mechanisms: cleavage of linking groups in one or both of the combined first and second components and solvation of components of the colored coating.

First, the mixture can be made to be a solvent for the pigment itself. In this case, the mechanism of removal involves first dissolution of the pigment from the binding matrix, followed by removal from the hair by rinsing with water or some other carrier. In this case it is believed, whilst not being bound by theory, that the chemical nature of the pigment, even when in dissolved form, is such that there is minimal attraction/solubility in the hair matrix itself, thus allowing removal of the color.

Second, the "removal formulation" can be made such that it dissolves, weakens or chemically breaks down the polymer coating holding the pigment on the hair. In this case it is believed, whilst not being bound by theory, that the pigments embedded in the binder matrix are released due to weakening or dissolution of the coating itself and, because the coloring material is a pigment, it has minimal attraction for the hair surface and is too big to penetrate the hair, and in consequence this facilitates removal of the color.

The combination of the above mechanisms will also provide the desired result of removal of the color.

Attacking the N-acylurea bonds of the polymer network of the coating on the treatable material such as hair can have a dramatic impact on the properties of the coating which is adhered to the surface. An agent that cleaves those bonds can act as a trigger agent to divide the polymeric network and enable surfactant and solvent to readily disperse the cleaved coating. Such agents include basic amino alcohols such as dimethylaminoethanol (dimethylethanolamine, DMEA), dimethylaminopropanol, and similar amino alkanol agents such as monoethanolamine, diethanolamine and triethanolamine. These amino alcohols can be formulated in aqueous medium to enable coating removal. Additionally, or alternatively, fatty organic acids such as dodecylbenzene sulfonic acid or oleic acid may be combined with non-aqueous medium such as a volatile, harmless hydrocarbon including but not limited to dodecane to trigger removal. These organic acids function as surfactants to lift the coating from the treatable material surfaces and to break the N-acylurea bonds which cleaves the polymeric network of the coating. The concentration of the trigger agent in alcoholic medium such as methanol, ethanol or aqueous medium or in non-aqueous medium may range from about 0.1% to about 15% by weight, preferably about 0.5% to about 10% by weight, more preferably about 1% to about 7.5% by weight relative to the total weight of the removal solution.

The N-acylurea-organic or silicone polymer coating will contain a group L, the linker group and L will typically contains a cleavable linkage, such as an ester, imide, amide and the like. This linkage is susceptible to hydrolysis and can be cleaved using basic or acid lysis. The cleavage will include a counter-nucleophile which can be water or a small molecular weight monofunctional amine or thiol.

The N-acylurea-organic or silicone polymer having chain extensions with siloxane condensation, a strong acid such as dodecyl benzene sulfonic acid (DBSA) or a source of fluoride anion tetrabutylammonium fluoride (TBAF) in appropriate solvent as described in combination with Hansen solubility parameters including δd+δp+δh wherein δd is from 13 to 25, preferably 15-19 and δp is from 0 to 15, preferably 0 to 5 and δh is from 0 to 25, preferably 0 to 8.

Additionally, the formed N-acylurea (carbodiimide reactive product) can be cleaved through use of a small molecular weight monofunctional amine or thiol to end-cap the N-acyl urea group and reverse the crosslinking.

Also, if silicone polymeric bridges are present in the silicone polymer or in the organic polymer, an organic acid (such as DBSA) may be used to de-polymerize the chain. It is also advantageous in all "off" techniques to employ an off reagent also has some surfactant quality.

When the multicomponent composition is applied to the hair, the multi-application process physically distributes the components to cover all of the hair. The spraying, massaging, combing and/or hand manipulating the pretreatment and the first and second components produces the full coverage and at the same time leaves thin spots in the otherwise substantially uniform coating. This activity also will aid in the removal process.

Remanence and Treatable Material Inspection

Damage caused to the hair by application of the multicomponent composition and removal of the resulting coating can be assessed by FT-IR (Fourier Transform Infrared) method, which has been established to be suitable for studying the effects of keratin surface damage. Strassburger, J., J. Soc. Cosmet Chem., 36, 61-74 (1985); Joy, M. & Lewis, D. M., Int. J. Cosmet. Sci., 13, 249-261 (1991); Signori, V. and Lewis, D. M., Int. J. Cosmet. Sci., 19, 1-13 (1997)). In particular, these authors have shown that the method is suitable for quantifying the amount of cysteic acid. In general, the oxidation of cystine is thought to be a suitable marker by which to monitor the overall oxidation of the keratinous part of the fiber. Net, the measurement of cysteic acid units by FT-IR is commonly used.

Signori and Lewis (D. M., Int. J. Cosmet. Sci., 19, 1-13 (1997)) have shown that FT-IR using a diamond Attenuated Total Internal Reflection (ATR) cell is a sensitive and reproducible way of measuring the cysteic acid content of single fibers and bundles. Hence, the method that we have employed to measure the cysteic acid content of multiple fiber bundles and full hair switches, is based upon the FTIR diamond cell ATR method employed by Signori and Lewis (1997). The detailed description of the method used for testing the different damage inhibitors follows thereafter:

A Perkin Elmer Spectrum® 1 Fourier Transform Infrared (FTIR) system equipped with a diamond Attenuated Total Internal Reflection (ATR) cell was used to measure the cysteic acid concentration in mammalian or synthetic hair. In this method, hairswitches of various sizes and colors can be used. The switches were platted (-1 plait per cm) in order to minimize variations in surface area of contact between readings. The Oxidative hair Treatment Protocol described above was repeated for 5 cycles to mimic the behavior of hair after repeated bleaching cycles. Following this treatment, four readings per switch were taken (⅓ and ⅔s down the switch on both sides), and an average calculated. Backgrounds were collected every 4 readings, and an ATR cell pressure of 1 N/m was employed. The cell was cleaned with ethanol between each reading, and a contamination check performed using the monitor ratio mode of the instrument. As prescribed by Signori & Lewis in 1997, a normalized double derivative analysis routine was used. The original spectra were initially converted to absorbance, before being normalized to the 1450 cm$^{-1}$ band (the characteristic and invariant protein $CH_2$ stretch). This normalized absorbance was then twice derivatised using a 13 point averaging. The value of the 1450 cm$^{-1}$ normalized 2nd derivative of the absorbance at 1040 cm$^{-1}$ was taken as the relative concentration of cysteic acid. This figure was multiplied by $-1\times10^{-4}$ to recast it into suitable units. It was found that virgin mammalian or synthetic hair produced a value of around 20 cysteic acid units, and heavily oxidized hair produced values of around 170. The following instrumental conditions were employed:

Spectral Resolution—4 cm$^{-1}$
Data Interval—0.7 cm$^{-1}$
Mirror Scan Speed—0.2 cm s$^{-1}$
Number of Background Scans—20
Number of Sample Scans—20
Scan Range—4000 cm$^{-1}$ to 600 cm$^{-1}$ When the compositions of the current invention can be applied to the hair and then removed there can be a non-significant change to the level of damage to the hair, whereas with conventional oxidative colorants there can be a large increase in the measured damage.

The instant disclosure is not limited in scope by the specific compositions and methods described herein, since these embodiments are intended as illustration of several aspects of the disclosure. Any equivalents are intended to be within the scope of this disclosure. Indeed, various modifications in addition to those shown and described herein can be within the grasp of those with ordinary skill in the art. Such modifications are also intended to fall within the scope of the appended claims.

Color Selection

Also contemplated herein are multicomponent compositions having a given color area (gamut principle described above) defined by color coordinates (a*, b*) in the color space represented by the L*a*b* color system, which can be divided into a plurality of color areas. Each of the plurality of colors obtained from the area surrounding a given set of hair fibers is judged to belong to which color area of the colored area of a certain color. The number of colors judged for each color area is counted, and the color of the color area with the largest number of colors is selected as a representative color of the area surrounding a given set of hair fibers. The compositions are capable of delivering colors on hair (test method herein for fade) such that the results colors lie within the range of about 18<L<about 81, about −2<a<about 45, and about −13<b<about 70.

Also contemplated herein are multicomponent compositions that do not change the hair color, but instead change some other feature of the hair including shine (e.g., making it shinier or matte), the thickness of the hair and/or the feel of the hair.

When the color is removed from the treatable material such as hair, the waste water/composition can be treatable to remove the pigments from the waste water effluent system. This can be achieved by filtration, or through cyclone technology, where the density differences are used to force the pigments to the settle, and the water to pass through.

Examples

Application of Color Composition to Hair Tress
Hair Preparation

Two types of hair were used: un-damaged and damaged. The hair is supposed to simulate real world hair conditions where the hair is weathered over time and damaged. This damage results in a difference in surface charge and surface structure and can affect the coating quality.

Un-damaged hair: Natural white undamaged human hair was purchased from Kerling International Haarfabrik GmbH, Backnang, Germany company in the form of 10 cm long and 1 cm wide strands. This hair was used as received.

Natural dark brown, Level 4 hair was purchased from Kerling International Haarfabrik GmbH, Backnang, Germany company in the form of 10 cm long, 1 cm wide strands. This hair was used as received.

Damaged hair which was produced following this procedure: Natural white undamaged human hair was purchased from Kerling International Haarfabrik GmbH, Backnang, Germany company in the form of 10 cm long and 1 cm wide strands and was bleached. The strand was treatable with a mixture of Blondor Multi-Blonde bleach powder available from Wella Professionals mixed 1 part with 1.5 parts of 12% Welloxon Perfect available from Wella Professionals. About 4 g of this mixture was applied to each gram of hair. The tresses were then incubated in an oven at 45 C for 30 minutes after which they are rinsed in water, 37+−2 C with a flow rate of 4 L/min for 2 minutes and the hair is then dried with a standard Hair dryer from Wella.

Hair Pre-Treatment

Hair preparation as described above was treatable with the pre-treatment composition described below in Table 3, one gram of composition per one gram of hair. The composition was left on the hair for 5 min. The hair was then dried using a blow dryer to result in dry hair. Alternatively, the hair could be left wet, the excess of the composition was removed with an absorbent material, for example a towel.

Third Component Mixture Preparation Procedure

The Third Component hair pre-treatment compositions were prepared by mixing the single raw materials as listed in Table 3 and mixing in a beaker with a magnetic stirrer for a minimum 10 min. The mixtures appeared homogeneous and transparent after mixing. The components of pre-treatment composition can in some cases be added to the Multicomponent Coloring Composition instead of being used a separate hair-pre treatment step.

Pigment Premix Mixture Preparation Procedure

The Pigment Premixes listed in Table 1 were prepared according to the following procedure:

Medium (water and 2-butoxyethanol or isododecane) and dispersant are placed in an appropriate mixing vessel and homogenized with either a dissolver (e.g. DISPERMAT of the LC or CV series of VMA Getzmann GmbH) or a rotor stator mixer (e.g. Ultra Turrax T18 of company IKA). The dry pigment powder is slowly added under constant dispersing, and, after the addition is completed, the mixture is pre-dispersed for approx. five minutes.

Afterwards, the pigment slurry is transferred to a bead mill (e.g. Dyno Mill Research Lab of company WAB), remainings in the mixing vessel are washed with remaining medium and added to the material on the mill. The slurry is circulated for 15 minutes at a rate of 3500 rpm with material temperature not exceeding 30° C.

Fineness of dispersion is controlled by means of a grindometer; the presence of pigment agglomerates indicates that dispersion time has to be prolonged in order to grind down the pigment material to primary particle size.

After adequate fineness is achieved, the pigment paste is collected from the mill and can be used for further experiments.

Pastes of different pigments can be mixed in order to achieve the desired color shade. Typical batch size ranges from 100 g of pigment pre-mix and higher.

Multicomponent Coloring Composition Making Procedure

The Multicomponent Coloring Compositions in Table 2 were prepared by weighing the materials listed for First Component in Table 2, including the Pigment Paste as identified in Table I. The pH was adjusted using the pH adjustors as described in Table 2. This mixture was then mixed at least 10 min using a magnetic stirrer to give the First Component. The second component was added to the First component no longer than 1 hour before treating the hair. Once the First and Second Component were added together, they were mixed for 5 min using a rotor stator mixer (e.g. Ultra Turrax T18 of company IKA) to afford a colored Multicomponent Coloring Composition. This composition is colored and intransparent due to the presence of pigment. No agglomerates or precipitate is present in this composition while applied to the hair.

General Coloring Procedure:

To the pre-treatable hair tress described above is added a freshly prepared multi-component color composition as described above, 1 gram per 1 gram of hair. The application is accomplished by a slow distribution and spreading on the hair tress, for example, with fingers, brush, comb or other manipulation instrument. The slow distribution can be accomplished by application with a syringe or a pipette serially to portions of the hair tress. The excess is removed with absorbent tissue material and the resulting colored hair tress is blow dried with combing using a hair dryer to achieve better hair individualization. The treatable hair tress may be kept at rest for a time period as much as a day at room temperature or at least above 17° C.

Standard Wash Procedure

The standard wash procedure is used to determine the remanence of the colored hair tresses.

Rinse the hair tress for approximately 10 seconds with water (4 L min−1) at approximately 37+/−2 C.

Apply 0.1 g "Wella Professional Brilliance Shampoo for fine and normal hair" without dilution to the individual colored hair tress described above.

Shampoo is worked into the colored hair tress in the absence of water dilution for 30 sec with fingers by using stroking motion into the hair.

The shampooed colored hair tress is rinsed with water for approximately 30 seconds.

The rinsed colored hair tress is then dried using a hot blow dryer while mechanically separating the fibers in the keratin material until uniformly dry.

Steps 1-5 described above represent one cycle of the standard wash procedure.

Repeat of standard wash cycle for multiple cycles and comparison of the multiply washed hair tress to an unwashed colored hair tress which indicates the degree of color remanence using the Color Remanence Scoring Values described below.

Following the application procedure and technique described above, the following combinations of organic polymer, in situ linking material, base compound, pigment and medium can be applied to human hair. The different component details are presented in Tables 1 to 5.

Color Remanence Assessment

Remanence was assessed visually by comparing the washed samples versus a retained tress which had been colored but not washed. They were graded on a 5 point scale according to the following criteria. 1 no color left, 2 faint color, 3 washed-out color, 4 intense color with some color loss, 5 color unchanged versus reference.

The table below indicates the weight percentage of base compound(s) in the pre-treatment composition.

|  |  |  | Pigment Premix Compositions | | | | | |
|---|---|---|---|---|---|---|---|---|
| Material | Name | Supplier | A | B | C | D | E | F |
| Pigment Red 112 | Permanent Red FGR 70 | Clariant |  |  |  |  | 4.2 |  |
| Pigment Red 122 | Hostaperm Pink E | Clariant |  |  |  | 20 |  |  |
| Pigment Yellow 83 | Novoperm Yellow HR 70 | Clariant |  |  |  |  | 13.6 |  |
| Pigment Green 36 | Heliogen Green K 9362 | BASF | 20 | 20 | 20 |  |  |  |
| Pigment Black 7 | Midnight Black | Geotech |  |  |  |  | 2.2 |  |
| Aluminium Flakes | EMRS D710 * | Toyal |  |  |  |  |  | 10 |
| Dispersant | Solsperse W100 | Lubrizol | 10 |  |  | 10 | 10 |  |
| Dispersant | 2-Ethylhexanoic Acid | Sigma-Aldrich |  | 20 |  |  |  |  |
| Diluent | 2-butoxyethanol | Sigma-Aldrich | 10 |  |  | 10 | 10 |  |
| Diluent | Di-water | Lab sourced | 60 |  |  | 60 | 60 |  |
| Diluent | Isododecane | Sigma-Aldrich |  | 60 |  |  |  |  |
| Diluent | Propyleneglycol Monomethyl Ether | Toyal |  |  |  |  |  | 90 |
| Diluent | Ethanol |  |  |  | 80 |  |  |  |

* The EMRS-D710 raw material from Toyal contains 10% aluminum flakes in Propyleneglycol Monomethyl Ether

TABLE 2

Multicomponent Coloring Composition
The table below indicates the weight perentage of base compound(s) in the pre-treatment composition.

|  | 1 | 2 | 3 | 4 | 5 | 6 | 7 | 8 | 9 | 10 | 11 | 12 |
|---|---|---|---|---|---|---|---|---|---|---|---|---|
| First Component Pigment Premix | | | | | | | | | | | | |
| A |  |  | 5.0 | 5.0 |  |  | 5.0 |  |  |  |  |  |
| B | 5.0 | 5.0 |  |  |  | 5.0 |  |  |  | 5.0 | 5.0 | 5.0 |
| C |  |  |  |  |  |  |  | 5.0 |  |  |  |  |
| D |  |  |  |  |  |  |  |  |  |  |  |  |
| E |  |  |  |  |  |  |  |  |  |  |  |  |
| F |  |  |  |  |  |  |  |  |  |  |  |  |
| Organic Polymer | | | | | | | | | | | | |
| Carbopol Ultrez 10 |  |  |  |  |  |  |  |  |  |  |  |  |
| Belsil P1101* | 10 | 10 | 10 | 10 |  | 10 | 10 | 10 | 10 | 10 | 10 | 10 |
| PERMUTHANE EX-RU-73-982 |  |  |  |  | 3.0 |  |  |  |  |  |  |  |
| Epomin P-1050 (MW 70.000) |  |  |  |  |  |  |  |  |  |  |  |  |
| Medium | | | | | | | | | | | | |
| Isododecane | Qs 100 |  |  |  |  |  |  |  |  |  |  |  |
| Isopropanol |  | Qs 100 |  |  |  | Qs 100 |  |  |  | Qs 100 | Qs 100 | Qs 100 |
| Ethanol |  |  | Qs 100 | Qs 100 |  |  | Qs 100 | Qs 100 | Qs 100 |  |  |  |
| Deionized Water pH = 7 |  |  |  | 50 | Qs 100 |  |  |  |  | 50 | 50 | 50 |
| pH Adjuster | | | | | | | | | | | | |
| Ammonia |  |  |  |  |  |  |  |  |  |  |  | pH = 10-11 |
| Sodium Hydrochloric acid |  |  |  |  |  |  |  |  |  |  |  |  |
| 36% Hydrochloric acid |  |  |  |  |  |  |  |  |  | pH = 2 to 3 | pH = 5-6 |  |

TABLE 2-continued

| Second Component | | | | | | | | | | | | |
|---|---|---|---|---|---|---|---|---|---|---|---|---|
| PERMUTEX XR-13-554 | 2.0 | 2.0 | 2.0 | 2.0 | | | | | 2.0 | 2.0 | 2.0 | |
| PERMUTEX XR-5577 | | | | | | | | | | | | |
| PERMUTEX XR-13-621 | | | | | 2.4 | | | | | | | |

Multicomponent Coloring Composition
The table below indicates the weight perentage of base compound(s) in the pre-treatment composition.

| | 13 | 14 | 15 | 16 | 17 | 18 | 19 | 20 | 21 | 22 | 23 | 24 | 25 |
|---|---|---|---|---|---|---|---|---|---|---|---|---|---|
| First Component Pigment Premix | | | | | | | | | | | | | |
| A | 5.0 | 5.0 | 5.0 | 5.0 | | | | 5.0 | 5.0 | | 5.0 | | |
| B | | | | | | | | | | | | | |
| C | | | | | | | | | | | | | |
| D | | | | | 5.0 | 5.0 | 5.0 | | | 5.0 | | | |
| E | | | | | | | | | | | | 5.0 | |
| F | | | | | | | | | | | | | 30 |
| Organic Polymer | | | | | | | | | | | | | |
| Carbopol Ultrez 10 | | | | | | | | | | | | | |
| Belsil P1101* | 10 | 10 | 10 | 10 | 10 | 10 | 10 | 10 | 10 | 10 | 10 | 10 | 10 |
| PERMUTHANE EX-RU-73-982 | | | | | | | | | | | | | |
| Epomin P-1050 (MW 70.000) | | | | | 1.0 | 1.0 | 1.0 | | | | | | |
| Medium | | | | | | | | | | | | | |
| Isododecane | | | | | | | | | | | | | |
| Isopropanol | | | | | | | | Qs 100 | Qs 100 | | | | |
| Ethanol | Qs 100 | Qs 100 | Qs 100 | Qs 100 | Qs 100 | Qs 100 | Qs 100 | | | Qs 100 | Qs 100 | Qs 100 | Qs 100 |
| Deionized Water pH = 7 | 50 | 50 | 50 | 50 | | | | | | | | | |
| pH Adjuster | | | | | | | | | | | | | |
| Ammonia | | | pH = 10-11 | | pH = 10-11 | pH = 10-11 | pH = 10-11 | pH = 10-11 | pH = 10-11 | pH = 10-11 | pH = 10-11 | pH = 10-11 | pH = 10-11 |
| Sodium Hydrochloric acid | | | | pH = 10-11 | | | | | | | | | |
| 36% Hydrochloric acid | pH = 2 to 3 | pH = 7 | | | | | | | | | | | |
| Second Component | | | | | | | | | | | | | |
| PERMUTEX XR-13-554 | 2.0 | 2.0 | 2.0 | 2.0 | | 2.0 | | | | 2.0 | 2.0 | 2.0 | 2.0 |
| PERMUTEX XR-5577 | | | | | | | 5.0 | 5.0 | | | | | |
| PERMUTEX XR-13-621 | | | | | | | | | | | | | |

*Belsil P1101 contains 50% ethanol

TABLE 3

Third Components containing a base compound(s)
The table below indicates the weight percentage of base compound(s) in the pre-treatment composition.

| | | | Third Components | |
|---|---|---|---|---|
| Material | Name | Supplier | P1 | P2 |
| PEI | Epomin P-1050 (MW 70.000) | Nippon Shukobai | 1 | |
| APTES | (3-Aminopropyl)-triethoxysilane | Shin-Etsu | | 1 |
| Medium | DI water | Lab sourced | Qs 100 | Qs 100 |

PEI stands for Polyethylenimine

TABLE 4

Color Removal Compositions

| | | | Color Removal Compositions | | |
|---|---|---|---|---|---|
| Material | Name | Supplier | R1 | R2 | R3 |
| MEA | Monoethanolamine | | 10 | | |
| DBSA | Dodecylbenzenesulfonic acid | | | 4 | 1 |
| OLA | Oleic acid | | | | 10 |
| Medium | DI water | Lab sourced | Qs 100 | | |
| Medium | isododecane | | | Qs 100 | Qs 100 |

TABLE 5

Experiments with different Coloring Compositions, Hair pre-treatments and Removal Compositions

| Experiment | Third component Pre-treatment from Table 5 | Multi-component Coloring Composition from Table 2 | Water w/w % | Post-treatement | Color remanence at 15 washes on un-damaged hair | Color remanence at 15 washes on damaged hair | Color remanence after treatment with Removal Composition R1 on un-damaged hair | Color remanence after treatment with Removal Composition R1 on damaged hair | Color remanence after treatment with Removal Composition R2 on un-damaged hair | Color remanence after treatment with Removal Composition R2 on damaged hair |
|---|---|---|---|---|---|---|---|---|---|---|
| EXP 1 | none | 1 | 0 | 1 day r.T. | 2 | 2 | 1 | 1 | 1 | 1 |
| EXP 2 | none | 2 | 0 | 1 day r.T. | 5 | 3 | 1 | 2 | 1 | 1 |
| EXP 3 | none | 3 | 3 | 1 day r.T. | 5 | 3 | 2 | 2 | 2 | 2 |
| EXP 4 | none | 4 | 53 | 1 day r.T. | 4 | 3 | 2 | 2 | 2 | 2 |
| EXP 5 | none | 5 | 94.6 | 1 day r.T. | 1* | 1* | N/A | N/A | N/A | N/A |
| EXP 6 | none | 5 | 94.6 | 5 days r.T. | 3* | 2* | N/A | N/A | N/A | N/A |
| EXP 7 | P1 | 5 | 94.6 | 1 day r.T. | 2* | 2* | N/A | N/A | N/A | N/A |
| EXP 8 | P1 | 5 | 94.6 | 5 days r.T. | 5 | 4 | N/A | N/A | N/A | N/A |
| EXP 9 | none | 6 | 0 | 1 day r.T. | 1 | 1 | 1 | 1 | 1 | 1 |
| EXP 10 | none | 7 | 3 | 1 day r.T. | 1 | 1 | 1 | 1 | 1 | 1 |
| EXP 11 | none | 8 | 3 | 1 day r.T. | 1 | 1 | 1 | 1 | 1 | 1 |
| EXP 12 | none | 10 | 50 | 1 day r.T. | 5 | 5 | 1 | 2 | 1 | 2 |
| EXP 13 | none | 11 | 50 | 1 day r.T. | 3 | 3 | 2 | 2 | 2 | 2 |
| EXP 14 | none | 12 | 50 | 1 day r.T. | 3 | 3 | 1 | 1 | 1 | 2 |
| EXP 15 | none | 13 | 53 | 1 day r.T. | 4 | 4 | 2 | 2 | 3 | 3 |
| EXP 16 | none | 14 | 53 | 1 day r.T. | 4 | 3 | 2 | 3 | 3 | 3 |
| EXP 17 | None | 15 | 53 | 1 day r.T. | 5 | 4 | 3 | 3 | 2 | 2 |
| EXP 18 | None | 16 | 53 | 1 day r.T. | 4 | 3 | 2 | 2 | 2 | 2 |
| EXP 19 | P1 | 2 | 0 | 1 day r.T. | 5 | 5 | 3 | 4 | 3 | 4 |
| EXP 20 | P2 | 2 | 0 | 1 day r.T. | 5 | 5 | 3 | 4 | 2 | 3 |
| EXP 21 | none | 17 | 3.5 | 1 day r.T. | 1 | 1 | 1 | 1 | 1 | 1 |
| EXP 22 | none | 18 | 3.5 | 1 day r.T. | 5 | 5 | 2 | 4 | 5 | 5 |
| EXP 23 | none | 19 | 6.5 | 1 day r.T. | 1 | 1 | 1 | 1 | 1 | 1 |
| EXP 24 | none | 20 | 6 | 1 day r.T. | 2 | 3 | 1 | 1 | 1 | 1 |
| EXP 25 | none | 21 | 3 | 1 day r.T. | 5 | 4 | 3 | 4 | 1 | 2 |
| EXP 26 | P1 | 2 | 6 | 1 day r.T. | 4 | 3 | 1 | 1 | 1 | 1 |
| EXP 27 | P1 | 21 | 3 | 1 day r.T. | 5 | 5 | 5 | 4 | 3 | 3 |
| EXP 28 | none | 22 | 3 | 1 day r.T | 5 | 5 | 4 | 4 | 3 | 3 |
| EXP 29 | P1 | 22 | 3 | 1 day r.T | 5 | 5 | 5 | 5 | 4 | 4 |
| EXP 30 | none | 23 | 3 | 1 day r.T | 5 | 3 | 3 | 3 | 2 | 3 |
| EXP 31 | P1 | 23 | 3 | 1 day r.T | 5 | 5 | 5 | 5 | 5 | 5 |
| EXP 32 | none | 24 | 0 | 1 day r.T | 5 | 3 | 3 | 3 | 2 | 2 |
| EXP 33 | P1 | 24 | 0 | 1 day r.T | 5 | 5 | 5 | 5 | 4 | 4 |
| EXP 34 | none | 25 | 0 | 1 day r.T | 5 | 5 | 5 | 5 | 5 | 5 |
| EXP 35 | none | 25 | 0 | 1 day r.T | 4** | N/A | 2** | N/A | 2** | N/A |
| EXP 36 | P1 | 25 | 0 | 1 day r.T | 5 | 5 | 5 | 5 | 5 | 5 |
| EXP 37 | P1 | 25 | 0 | 1 day r.T | 4** | N/A | 3** | N/A | 3** | N/A |

*Assessment after 5 washes
**Assessment on dark hair

Discussion

Table 5 provides an overview of the experiments performed on hair. After the column describing the experiment number, the next column (Column 2) describes the hair pre-treatment that was used referring to Table 3. In the third column, the Multicomponent Coloring composition from Table 2 is being referred. In the fourth column the total water content is given as the water is coming also from some raw materials or pigment premixes from Table 1. In the fifth column any post-treatments of the colored hair are described, such as different curing times, temperatures etc. The remaining columns contain the results on damaged and undamaged hair after washing and removal with removal compositions from Table 4.

The crosslinking reaction rate should influence the film-formation process. Polymer crosslinking is known to enable pigment encapsulation. EXP 1 through EXP 4 examine the influence of medium polarity. The lowest polarity medium being isododecane in Composition 1, followed by isopropanol of composition 2, then ethanol in Composition 3 and finally the most polar medium is water/ethanol mixture of composition 4. The color remanence results after 15 washes show that the coating formed in EXP 1 is not very robust, while the coating formed in EXP 2 is already very robust with only some color loss on damaged hair. The coating formed in EXP 3 is very robust with no color loss on damaged or undamaged hair. The coating of EXP 4 is not robust, because the reaction proceeded too quickly and the reagents reacted already during the application, resulting in very spotty initial color. This spotty initial color washed away a bit 15 washes, resulting in washed-out color appearance, especially on damaged hair. We can see that increasing the medium polarity from EXP 1 to EXP 4 increases the rate of the reaction. The ideal reaction rate for good remanence is in the isopropanol and ethanol range. The higher polarity medium of water results in a crosslinking reaction that is too fast with a corresponding non-uniform coating. This non-uniform coating is more susceptible to being washed out. If the medium polarity is too low (EXP 1), the crosslinking reaction is not complete and the color remanence is low.

The coating in EXP 1 could be removed with either alkaline removal formula R1 or acidic removal formula R2. The coating achieved in EXP 2 could not be completely removed by alkaline removal composition R1, but could be completely removed with acidic removal composition R2. For the coating achieved in EXP 3, some color was still left over after treatment with the color removal composition R1. However, it was completely removed with acidic composition R2. In EXP 4 the alkali MEA based removal composition R1 could not completely remove the coating and removal composition R2 still left some color on the hair. We can see that the solvent polarity affects the removal ease. The more polar the solvent, the more difficult the coating is to remove.

EXP 5 through EXP 8 show the use of a carboxylate polyurethane dispersion (PERMUTHANE EX-RU-73-982) in combination with a carbodiimide crosslinker (Composition 5) and the influence of pre-treatment P1 and post-application curing time. The pH of the mixture was 8.5 upon mixing. When the coating was cured for 1 day at room temperature after application and without pre-treatment P1 (EXP 5), the color was completely removed even after 5 shampoo washes. Without pre-treatment and with longer curing time, 5 days at room temperature, more color is left (EXP 6). When the pre-treatment P1 is used, some color is left after 5 shampoo washes and 1 day of room temperature curing (EXP 7). However, if the same composition 5 with pretreatment P1 is left to cure for 5 days at room temperature (EXP 80, the coating has very good shampoo resistance, with the color displaying perfect remanence on damaged hair and very slight washout on undamaged hair.

EXP 9 through EXP 11 are control experiments to show the influence of using the polymer alone without a crosslinker and also the influence of dispersant. In EXP 9 we are testing a non-aqueous formula in isopropanol and using 2-ethylhexanoic acid as a dispersant (Composition 6). This composition is analogous to the one used in EXP 2, except there is no carbodiimide crosslinker present. The color remanence is virtually non-existent, with all color washed out after 15 washes. The initial color in EXP 9 could also be very effectively removed with either alkaline (R1) or acidic removal composition (R2). In EXP 10 the composition used (Composition 7) is analogous to the Composition 3 used in EXP 3, except that the carbodiimide crosslinker is absent. Again, there is no color remanence after 15 washes and the color is easily removed with an alkaline or acidic removal compositions. In EXP 11 the influence of dispersant was checked against EXP 10. The dispersant was removed and only pigment and solvent were used, with some sonication enabling the pigment dispersal. Again, there was no color remanence and the color was easily removed with compositions R1 and R2. The conclusion from EXP 9 through EXP 11 is that the presence of the carbodiimide crosslinker is essential to achieve good color remanence, even when the other variables (solvent polarity, dispersant) are varied to attempt to optimize the coating. The choice of dispersant does not seem to influence the removal or enhance the color remanence inherently.

EXP 12 to EXP 14 the pH influence was tested. The compositions used are mixtures of water and isopropanol and differ only in the pH of the composition applied to the hair. EXP 12 uses a low pH composition and the resulting color is very intense and macroscopically uniform. Under a microscope one can observe that the color is composed of microscopic spots. The color remanence is very good with the color staying very strong after 15 washes on damaged and undamaged hair.

In EXP 12 works in alkaline (composition R1) or acidic (composition R@), but there is a little of color still left on the hair after the color removal treatment in both cases. EXP 13 is done at slightly acidic pH 5-6 and the resulting coating is macroscopically spotty and the color remanence after 15 washes is not very good. The color removal is similar to EXP 12, with basic (R1) and acidic (R2) removal compositions removing most of the color, but not completely. EXP 14 is done at high pH, which is achieved by addition of a volatile base (Ammonia). The initial color appearance is macroscopically uniform and the tresses appear more shiny than the tresses made by EXP 12 and EXP 13. The color remanence is not so good, with the color washing out substantially after 15 washes on damaged and undamaged hair. The color removal is easy, with basic composition R1 and the acidic composition R2 as well, although there is a little color left on the damaged tips after treatment with acidic composition R2. The conclusion is that we need high pH to get a uniform coating which is wash resistant, but we need a low pH and high solvent polarity (from EXP 1-4) to get a fast reaction rate and good crosslinking.

EXP 15 through EXP 18 are an effort of optimization where the solvent polarity is increased vs. EXP 13-EXP 14. The isopropanol in EXP 12-EXP 14 is changed to ethanol in EXP 15 through EXP 18. The pH is varied again and the influence on coating quality examined. EXP 15 was performed at low pH and the initial color is macroscopically patchy. The polymer was apparently crosslinked already in the pot and particulate matter was deposited on hair. The resulting patchy coating is quite wash resistant, with good color remanence. If we compare this to EXP 12, where the solvent was isopropanol and the pH was low, we see that EXP 15 has much better color remanence. The color is not so easy to remove, with alkaline removal R1 removing more color than acidic removal R2. EXP 16 was performed at neutral pH=7 and the initial color looks macroscopically uniform, with patchy dots visible at closer inspection. After 15 washes the color on the damaged hair washes out a bit more than the color on undamaged hair. The alkaline removal composition R1 removed some color, giving the tress a washed-out appearance which was slightly less intense than after 15 washes. EXP 17 was done at high pH where the alkali used to adjust the pH was a volatile amine (Ammonia). The coating appears uniform to the eye and shinier than the neutral pH coating from EXP 16 or the low pH coating from EXP 15. The color remanence after 15 washes is excellent on damaged and undamaged hair. Removal of the color with alkaline composition R1 results in washed-out tress appearance. Removal of the color in EXP 17 with acidic removal composition R2 results in less color remaining on the hair, but it is not completely gone. Since we learned that the crosslinking reaction proceeds faster at low pH (EXP 12 and EXP 15), while the film uniformity is better at high pH (EXP 14 and EXP 17). However, the alkali used in EXP 17 is volatile, so we wanted to check in EXP 18 if the alkali volatility can influence the film formation. We used a non-volatile alkali (sodium hydroxide) to adjust the pH in Composition 16 and produced the coated hair strands in EXP 18. The initial color appeared uniform and shiny. The color remanence however was not as good as in EXP 17, where a volatile alkalizer (ammonia) was used. The color appeared a bit more washed out after 15 washes, especially on damaged hair. The color in EXP 18 was also a bit more removeable in comparison to EXP 17. From the experiments EXP 15 through EXP 18 we see that the starting pH needs to be high to achieve a uniform coating, but a volatile alkalizer needs to be used to drop the pH during film formation in order to achieve a lasting coating.

For the next set of experiments we are showing the influence of the hair pre-treatment. Since our goal was to develop a hair color coating with high remanence, yet removable, we decided to use a lower solvent polarity (isopropanol) and introduced two hair pre-treatments to attempt to increase the color remanence. EXP 19 through EXP 22 are showing the result of using isopropanol as the solvent and polyethyleneimine and (3-Aminopropyl)triethoxysilane as a pre-treatment. The reference experiment without any hair pre-treatment is EXP 2, where the same solvent and pigment/sdispersant was used at high pH. In EXP 19 we introduce a polyethyleneimine hair pre-treatment by soaking the hair in a pre-treatment composition P1 for 5 min, then blow drying until it is dry. The coloring composition 2 is added subsequently. Compared to EXP 2 the color remanence in EXP 19 is better, with no color loss on undamaged or damaged hair after 15 washes. However, the color removal becomes more difficult when compared to EXP 2 with some color removed, but a washed out color remaining on undamaged and intense color remaining on damaged hair with either the alkaline (R1) or acidic (R2) removal compositions. The EXP 20 introduces a (3-Aminopropyl)triethoxysilane hair pre-treatment. The hair was soaked for 5 min in freshly made pre-treatment composition P2, then blow dried and the coloring composition 2 was applied subsequently. The results are similar to EXP 19, with excellent color remanence after 15 washes. The color removal in EXP 20 with alkaline removal composition R1 still leaves a lot of color on the tress, same as in EXP 19. The removal with acidic composition R2 improves upon EXP 19 a bit, but there is still a lot of color left on undamaged and damaged hair. The conclusion of EXP 19 and EXP 20 is that a pre-treatment by polyethyleneimine or a (3-Aminopropyl)triethoxysilane can improve the color remanence. The color removal is also affected, with these hair pre-treatments making the color removal more difficult.

In EXP 21 through EXP 23 we have investigated the role of polyethyleneimine by adding it into the coloring composition instead of as a pre-treatment. We also checked a different polycarbodiimide crosslinker without any siloxane groups (XR-5577). In EXP 21 the polyethyleneimine was added directly to the organic polymer and pigment mixture as described in Composition 17. The carbodiimide crosslinker was left out to check if the polyethyleneimine and the carboxylic acid containing polymer P1101 are ionically interconnected and crosslinked to provide color remanence. The results show that this acid-base ionic interaction is not strong enough to provide color remanence—all the color is gone after 15 washes from undamaged and damaged hair. In EXP 22 we then added the same crosslinker XR-13-554 to the polyethyleneimine, pigment and solvent composition (Composition 18). The results show that the color remanence is excellent, however the removal with alkaline composition R1 did not improve and the removal with acidic composition R2 does not seem to have much effect at all. The conclusion from EXP 22 is that the polyethyleneimine can also be used as part of the formula instead of as a pre-treatment to enhance color remanence. In EXP 23 Composition 19 was used, where the polyethyleneimine was added in the composition and the polycarbodiimide crosslinker used was a water dispersion XR-5577, which has 40% active ingredient content, bringing the total polycarbodiimide to the same level as in EXP 22. The results are very different with this material, with no color remanence after 15 washes and the removal being quite easily achievable. The conclusion from EXP 23 is that the choice of polycarbodiimide crosslinker is important for achieving better color remanence. The more crosslinker XR-5577 which does not contain additional siloxane crosslinking groups provides no color remanence if polyethyleneimine is added directly into the formula. In contrast, when XR-13-554 crosslinker with siloxane groups is used as in EXP 22, the composition provides excellent color remanence.

To further examine the effect of polycarbodiimide choice and the effect of the polyethyleneimine pre-treatment, we have conducted the experiments EXP 24 through EXP 32. In EXP 24 we compare the performance of the XR-5577 crosslinker in isopropanol vs the XR-13-554 without any hair pre-treatment (EXP 25). In EXP 24 we use the green pigment with W100 dispersant and in isopropanol. The color remanence after 15 washes is low, with most color removed on undamaged hair and some washed-out looking color remaining on the damaged hair. The color could be removed with either R1 or R2 removal compositions. In EXP 25 we used the siloxane containing polycarbodiimide XR-13-554 with all the other components of the composition the same as in EXP 24. The color remanence is significantly better after 15 washes, although a small amount of color does wash off on the damaged hair, with the color still looking intense. The removal with alkaline composition R1 is not very successful with a lot of color remaining especially on damaged hair. The removal with acidic composition R2 is very good, with only a hint of color remaining on damaged hair. In the experiments EXP 26 and EXP 27 we checked the influence of polyethyleneimine pre-treatment with both polycarbodiimide crosslinkers. In EXP 26 we used the XR-5577 in conjunction with a polyethyleneimine pre-treatment. The color remanence improved versus EXP 24 where we did not use the pre-treatment P1. The color removal was possible and complete with both removal compositions R1 and R2. In EXP 27 we used the siloxane containing polycarbodiimide XR-13-554 in conjunction with P1 pre-treatment. The color remanence was excellent with no color getting washed out. However, the color removal was also difficult. Alkaline removal R1 did not remove any color and acidic removal R2 removed some color. If we compare the performance of the two polycarbodiimides we can see that the siloxane-containing carbodiimide crosslinker XR-13-554 always performs better in color remanence, whether it is without P1 pre-treatment (EXP 25 vs EXP 24) or with the P1 pre-treatment (EXP 27 vs. EXP 26). Therefore the presence of siloxane groups on the polycarbodiimide crosslinker is beneficial for color remanence.

In the experiments EXP 28 through EXP 38 we checked the performance of the color coating with differently colored pigments. The solvent chosen was ethanol, because it provided the best compromise between coating uniformity and color remanence. EXP 28 and EXP 29 examine the performance with Pigment Red 122. In EXP 28 the performance was tested without the hair pre-treatment. Color remanence after 15 washes was excellent. Color removal was not possible with either alkaline R1 or acidic removal composition R2. The color remaining was still very intense with some slight change observable vs. initial color. Once the P1 pre-treatment is added in EXP 29, the color remanence is again excellent and removal is even more difficult with the coating showing excellent stability versus alkaline composition R1 and acidic composition R2. EXP 30 and 31 were repeated with the green Pigment Green 36. EXP 32 and EXP 33 illustrate the performance with a mixture of pigments that gave a brown color. In EXP 30 and EXP 32 with green and brown color and without pre-treatment P1 we see similar behavior with some color washing out of the damaged hair after 15 washes. The color removal is performing also similarly for both these colors, with the alkaline removal R2 removing just a small amount and the acidic removal R2 removing more color, with some still remaining. Once the pre-treatment P1 is introduced in EXP 31 and EXP 33 the color remanence improves with no color washing out on either damaged or undamaged hair. The removal also becomes more difficult with alkaline removal R1 basically ineffective and acidic removal R1 being less effective than in EXP 30 and EXP 32 where the pre-treatment P1 was not used. In EXP 34 through EXP 37 we show the performance of the color coating with aluminum flakes EMRS-D710. In EXP 34 we use Composition 25 which contains 30% of raw material pigment dispersion EMRS-D710. On white tresses which had damaged tips there is excellent color remanence after 15 washes on damaged and undamaged hair. However, when we do the experiment (EXP 35) on undamaged dark tresses where the underlying color can be more easily seen, we can see that there is slight color loss. The coating appears very resistant to alkali composition R1 and acidic composition R1 when done on white damage and undamaged hair. However, when the experiment was done on dark undamaged hair (EXP 35), some more color is removed with speckled silvery flecks staying on the hair after treatment with both, the alkaline R1 and acidic composition R2. In EXP 36 we added the pre-treatment P1 to the hair before applying the aluminum flake-containing composition 25. The color remanence on damaged and undamaged hair was excellent with no color loss. In EXP 37 we repeated EXP 36 on dark undamaged hair and saw some color loss after 15 washes. After removal with alkaline composition R1 or R2 in EXP 36 no color loss was observed. However, in EXP 37 on dark undamaged hair, we could see that some color did get lost during alkaline (R1) and acidic removal (R2) with the color appearing metallic grey with some dark spots showing of the underlying hair color.

Embodiment Statements

1. A multicomponent in situ linkable composition for coloring treatable material, comprising:
   a first component comprising a CDI link compound having at least two groups capable of covalent in situ linkage with a carbodiimide group and having inert or reactive termini;
   a second component comprising an in situ linking material having at least two carbodiimide groups and having inert or reactive termini,
   the reactive termini of the CDI link compound and the in situ linking material being selected independently, being self-reactive or reactive with a reaction partner and the reactive termini being different from the carbodiimide group;
   pigment microparticles in one or both of the first and second components or as a separate component.
2. A multicomponent composition of statement 1 further comprising a third component comprising a base compound having amine groups; the third component being separate from the first and second components; and the first, second and third components being capable of covalent, ionic, entanglement, electrostatic or coordination in situ linkage or a combination thereof among each other.
3. A multicomponent composition of any of the preceding statements further comprising a medium in any one or more of the first, second and third components.
4. A multicomponent composition of any of the preceding statements wherein the CDI link compound comprises a small organic molecule or a polymer comprising a linear, branched, cyclic, dendritic, graft, block, star or fullerene organic compound; or a polymer comprising a linear, branched cyclic, cage, graft, block or dendritic silicone compound; or a graft, block or pendant polymeric combination of a linear, branched, cyclic, dendritic, star or fullerene organic polymeric moiety and a linear, branched, cyclic, cage or dendritic silicone polymeric moiety, the groups of the CDI link compound that are capable of in situ covalent linkage with the polycarbodiimide are selected from carboxylic acid, sulfonic acid, phosphoric acid, amine, thiol or any combination thereof and the CDI link compound has inert or reactive termini, the reactive termini being different from carbodiimide.
5. A multicomponent composition of claim 4 wherein the CDI link compound groups are carboxylic acid groups.
6. A multicomponent composition of any of the preceding statements further comprising a fourth component comprising the reaction partner comprising a nucleophilic molecule having at least two functional groups capable of forming linkages with the termini of the in situ linking material and/or CDI link compound when the in situ linking material and/or CDI link compound have reactive termini that are reactive with the reaction partner, the nucleophilic molecule being a saturated linear, branched or cyclic aliphatic compound of 2 to 24 carbons or an aromatic or alkylaromatic compound of 6 to 21 carbons and the functional group being a diamine, a diol, a dithiol, an aminoalcohol, an aminothiol, an alcohol thiol or any combination thereof.
7. A multicomponent composition according any of the preceding statements wherein
   the CDI link compound comprises the organic polymer with at least two carboxylic acid groups and with inert or reactive termini and
   the organic polymer comprises a polyolefin, a polyester, a polycarbonate, a polyallyl alcohol, a ketone resin, a polyether, a polyimine, a polyurethane, a polyurea, a polyglycol, a polyamide, a polypeptide, a carbohydrate compound, a cellulose, a cellulose derivative, a cellulose ester, a hydroxylated cellulose, a carboxyl cellulose, a hydroxyl cellulose ester, a hydroxy cellulose carboxylic acid, an alginate, a gum, a polysaccharide, an amino acid polymer, a gelatin, an oligopeptide, a polypeptide, a protein, a carbohydrate-amino acid such as a glycosylated peptide, a carbohydrate-purine/pyrimidine base, a polynucleoside, a biopolymer, a (meth) acrylic copolymer, a crotonic copolymer, a polyurethane-polyglycol copolymer, a polycarbonate diol, a styrene-allyl alcohol copolymer, a polyol, a natural gum, polyvinyl acetate, polyvinylpyrrolidone, polynipam, a polymer based on one or more olefin monomers, a polymer based on ester units of diacids/diol monomers, a co-polymer based on polyolefin, polyacrylate and silicone, a polymer based on ester units of hydroxy acid monomers, a polymer based on ether monomeric units, a polymer based on thioether monomeric units, a polymer based on polyol monomeric units, a polymer based on alkylene oxide monomeric units, a polymer based on of alkylene imine monomeric units, a polymer based on urethane monomeric units, a polymer based on urea monomeric units, a polymer based on amide units of diacid/diamine monomers, a polymer based on amide units of amino acid monomeric units or a polymer having repeating residues based on carbon or carbon in combination with other atoms comprising oxygen and/or nitrogen and/or sulfur, and any combination thereof;

the carboxylic acid group is covalently linked to the organic polymer through a carbon connection unit comprising a linear, branched or cyclic C1-C24 alkyl or alkoxy unit, a C2-C24 alkanoyl unit, a C6-C24 aromatic unit, a C5-C24 heteroaromatic unit having one or two heteroatoms selected from nitrogen, oxygen and sulfur, a $(C_z—O—C_z)_n$ polyether unit wherein z is an integer of 1 to 6 and n is an integer of 2 to 6, a $(C_y—NH—C_y)_m$ polyimino unit wherein y is an integer of 1 to 6 and m is an integer of 2 to 6; or the carboxylic acid group is covalently linked to the organic polymer through a silicon connection unit comprising a Si1-Si48 organosiloxane unit having methyl as the organo group with silicon of the connection unit bonded to the carboxylic acid group through an alkylenyl group of one to three carbons or through an oxyalkylenyl group of one to three carbons;

the in situ linking material comprises a polycarbodiimide with inert or reactive termini.

8. A multicomponent composition of any of the preceding statements 1-6 wherein the CDI link compound comprises a silicone polymer with carboxylic acid groups and inert or reactive termini and the silicone polymer comprises D type dialkylsiloxane units and/or substituted diorganosiloxane units, M type mono-alkylsiloxane units and/or M-type mono-alkoxysiloxane units and D type carboxylic acid substituted diorganosiloxane units and/or M type carboxylic acid substituted mono-organosiloxane units, wherein the alkyl group of the D and M units is alkyl of 1 to 6 carbons, the alkoxy group of the M units is alkoxy of 1 to 6 carbons, the organo group of the M and D units is alkyl of 1 to 6 carbons, aromatic group of 6 to 10 carbons and the alkyl and/or aromatic group is optionally substituted by amide, sulfonamide, alkoxy of 1 to 3 carbons, and the carboxylic acid substituted organo group is an alkyl of 1 to 6 carbons bearing a carboxylic acid group or phenyl bearing a carboxylic acid group, the M and D units other than those with carboxylic acid groups being SiC units and the M and D units with carboxylic acid groups being SiA units; the ratio of SiA to SiC being in a range of about 1:1000 to about 1:10.

9. A multicomponent composition of statement 8 wherein the silicone polymer further comprises T type alkylsiloxane units and Q type siloxane units, the number of T and/or Q units of the silicone polymer being in the range of 1 to 6, preferably 1 to 3 and the T and Q units being included in the SiC units.

10. A multicomponent composition of any of the preceding statements wherein the CDI link compound is a silicone or organic polymer with carboxylic acid groups having a modest to significant acid value ranging up to about 700, preferably about 10 to about 600, more preferably 10 to 400, most preferably 10-300 with typical acid numbers ranging approximately 10-150; and a weight average molecular weight in the range of about 2 KDa to about 5 MDa, preferably about 2 KDa to about 100 KDa, more preferably about 2 KDa to about 50-80 KDa.

11. A multicomponent composition of any of the preceding statements wherein the in situ linking material is a polycarbodiimide of Formula V $$Z\text{-}(L\text{-}N\!\!=\!\!C\!\!=\!\!N\text{—})_p\text{—}Z \qquad \text{Formula V}$$

wherein Z is an inert or reactive terminal group of the polycarbodiimide and is other than a carbodiimide; L is an organic linker group; and p is an integer of at least 2.

12. A multicomponent composition of claim 11 wherein L is a saturated aliphatic divalent radical, an aromatic divalent radical, an alkylaromatic divalent radical or a polymer or oligomeric divalent radical with repeating olefinic, carbonate, ester, ether, amide, urethane or urea linkages, and p is an integer of 2 to 1000.

13. A multicomponent composition of claim 12 wherein L is a saturated aliphatic divalent radical selected from linear or branched or cyclic alkylenyl of 2 to 20 carbons, an aromatic divalent radical selected from benzene or diphenyl or an alkylaromatic divalent radical selected from p-dimethylenylphenyl or methylenyldiphenyl.

14. A multicomponent composition of any of the preceding statements wherein CDI link compound has reactive termini and/or the in situ linking material is a polycarbodiimide with reactive termini and the reactive termini are self-reacting alkoxysilyl groups or hydroxysilyl groups or a combination thereof.

15. A multicomponent composition of any of the preceding statements wherein the CDI link compound has reactive termini and/or the in situ linking material is a polycarbodiimide with reactive termini and the reactive termini are reactive with a reaction partner, and the reaction partner is a fourth component comprising a nucleophilic compound with at least two functional groups and the functional groups are amine, hydroxyl, thiol or a combination thereof and/or the fourth component comprises the third component.

16. A multicomponent composition of statement 15 wherein the reactive termini are silyl groups bonded to alkylenyloxycarbonylvinyl having 1 to 6 carbons in the alkylenyl group, alkylenyl epoxide having 3 to 6 carbons in the alkylenyl group or alkylenylaldehyde having 1 to 6 carbons in the alkylenyl group.

17. A multicomponent composition of statement 15 wherein the reactive termini are organic groups selected from alkylenyloxycarbonylvinyl having 1 to 6 carbons in the alkylenyl group, alkylenyl epoxide having 3 to 6 carbons in the alkylenyl group, alkylenylcarbonyloxycarbonylmethyl having 2 to 6 carbons in the alkylenyl group, or alkylenylaldehyde having 1 to 6 carbons in the alkylenyl group.

18 A multicomponent composition of any of statements 15-17 wherein the in situ linking material has reactive termini and the CDI link compound does not have reactive termini.

19. A multicomponent composition of any of statements 15-17 wherein the in situ linking material and the CDI link compound both have reactive termini.

20. A multicomponent composition of any of statements 2-14 wherein the third component is present and in situ linking material is a polycarbodiimide with inert termini and the inert termini are linear or branched alkyl of 1 to 6 carbons, or cyclic alkyl of 3 to 6 carbons, alkyl amide, alkylester, phenyl, alkyl phenyl with 1 to 3 carbons in the alkyl group or partially or fully fluorinated versions thereof, and the CDI link compound is an organic polymer or silicone polymer with inert termini or with reactive termini.

21. A multicomponent composition according to any of the preceding statements wherein the organic polymer comprises at least olefinic carboxylic acid monomeric units comprising (meth)acrylic acid, crotonic acid, pentenoic acid, hexenoic acid, maleic acid, fumaric acid, glutaconic acid, itaconic acid, citraconic acid, mesaconic acid or any combination thereof.

22. A multicomponent composition according to any of the preceding statements wherein the organic polymer comprises at least olefinic carboxylic acid monomeric units comprising (meth)acrylic acid, crotonic acid, maleic acid, fumaric acid, itaconic acid or a combination thereof.

23. A multicomponent composition according to statement 21 or 22 wherein the organic polymer further comprises olefinically polymerized backbones and silicone cross linking bridges wherein the silicone bridges comprise M type mono-alkylsiloxane units and D type dialkylsiloxane units wherein the M and D siloxane units form a divalent silicone oligomer or polymer terminated by vinyl groups and the vinyl groups are polymerized into the olefinic backbone of the organic polymer so as to provide the silicone cross linking bridges.

24. A multicomponent composition of any of the preceding statements including the third component wherein the base compound of the third component has a weight average molecular weight of about 150 Da to about 1 MDa and the base compound is selected from aminosilane, aminoalkyl mono, di or trialkoxy silane, aminosiloxane, aminosilicone or a linear or branched polymer comprising linear polyethyleneimine, linear or branched polyethylene imine, aminopolysaccharide, a copolymer of aminoethyl (meth)acrylate and ethyl (meth)acrylate, polyallylamine hydrochloride, polydiallyldimethyl ammonium chloride, polyvinylamine, (vinylamine-styrene) copolymer, poly(omega-aminoalkyl (meth)acrylate), polyvinylpyrrolidone poly (2-oxazoline) and random or block copolymers thereof and mixtures thereof.

25. A multicomponent composition of any of the preceding statements wherein the organic or silicone or organosilicone polymer comprises a random distribution of monomer residues or a block arrangement of monomeric residues.

26. A multicomponent composition according to any of the preceding statements comprising a CDI link compound as an organic polymer as a block copolymer with acid containing monomer and the block copolymer further comprises optional blocks of a silicone polymer or an organosilicone polymer.

27. A multicomponent composition according to any of the preceding statements wherein the organic polymer comprises at least an acid monomer as (meth)acrylic acid and/or crotonic acid at about 0.3% to about 75% by weight, a hydroxyethyl or hydroxypropyl (meth)acrylate and/or crotonate at about 0% to about 20% by weight, a hydrophobic monomer as methyl or ethyl (meth)acrylate and/or crotonate at about 5% to about 20% by weight, and an olefin monomer at zero percent up to about 10% by weight, wherein all weights are relative to the total weight of the polymer.

28. A multicomponent composition according to any of the preceding statements wherein the organic polymer comprises at least monomeric units of alkyl (meth)acrylate and/or crotonate, and (meth)acrylic acid and/or crotonic acid; and the acid number of the polymer is from about 50 to about 600 preferably about 100 to about 400.

29. A multicomponent composition of any of the preceding statements further comprising the third component, the base compound being an amino polymer.

30. A multicomponent composition of statement 29 wherein the aminopolymer is polyethyleneimine.

31. A multicomponent composition comprising:
a first component comprising a CDI link compound comprising an organic polymer or a silicone polymer with at least two carboxylic acid groups and with inert or reactive termini;

a second component comprising an in situ linking material comprising a polycarbodiimide with reactive or inert termini;
a third component comprising polyethyleneimine;
the first, second and third components being separate,
pigment particles in the first or second component or in both of the first and second components; wherein,
the organic polymer comprises a copolymer of an acidic olefinic monomer selected from (meth)acrylic acid, crotonic acid, maleic acid, fumaric acid, itaconic acid or any combination thereof, and one or more optional vinyl ester, vinyl alkyl or vinyl aromatic monomers and terminated with alkylalkoxysilyl groups or inert alkyl groups;
the silicone polymer comprises D type dialkylsiloxane units and/or substituted diorganosiloxane units, M type mono-alkylsiloxane units and/or M-type mono-alkoxysiloxane units and D type carboxylic acid substituted diorganosiloxane units and/or M type carboxylic acid substituted mono-organosiloxane units;
the polycarbodiimide has Formula V

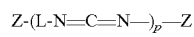

Z-(L-N=C=N—)$_p$—Z    Formula V wherein Z is a terminal group of the polycarbodiimide and is reactive or inert; the designator p is an integer of at least 2 so that the polycarbodiimide of Formula V contains at least 2 carbodiimide groups; L comprises an organic linker group comprising an aromatic, alkaromatic or saturated linear, branched or cyclic aliphatic divalent radical of 2 to 30 carbons optionally with one or more non-pendant heteroatoms including nitrogen, oxygen, sulfur or any combination thereof in the aliphatic chain or the aromatic group.

32. A multicomponent composition of any of the preceding statements wherein the polycarbodiimide has Formula VI

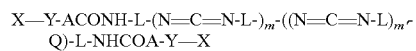

X—Y-ACONH-L-(N=C=N-L-)$_m$-((N=C=N-L)$_m$-Q)-L-NHCOA-Y—X    Formula VI wherein the organic linker group L comprises an aromatic, alkaromatic or saturated linear, branched or cyclic aliphatic divalent radical of 2 to 30 carbons optionally with one or more non-pendant heteroatoms including nitrogen, oxygen, sulfur or any combination thereof in the aliphatic chain or the aromatic group, such as but not limited to groups such as polyurethane or polyether as in polyethylene glycol; A is NH, S or O; Y is a divalent organic radical selected from a saturated aliphatic group of 1 to 36 carbons or an aromatic group or alkaromatic of 6 to 24 carbons, and the aliphatic or aromatic group may optionally include one or more non-pendant heteroatoms such as nitrogen, oxygen, sulfur or any combination thereof such as but not limited to ether links, ester links, amide links, urethane links, carbonate links, urethane links; X is configured as a reactive silyl group or as a reactive organic group or as an inert terminus; as an inert terminus, X may be configured as a linear, branched or cyclic saturated aliphatic group of 1 to 50 carbons or an aromatic group of 6 to 18 carbons, the aliphatic and aromatic groups optionally including from one to 10 heteroatoms selected from nitrogen, oxygen, sulfur or any combination thereof and the aliphatic or aromatic group may be partially or fully fluorinated; X includes a connecting group CG which bonds X to Y; the group CG may be a single covalent bond, a saturated C—C link, an unsaturated covalent C—C link, an amide group, an ester group, a carbonate group, a thioester group, an ether group, a urethane group a thiourethane group or a urea group; Q comprises an organopolymeric or organo-oligomeric moiety of repeating units of linear, branched or cyclic saturated aliphatic groups or aromatic groups or alkylaromatic groups coupled by repeating carbonate, ester, ether, amide, urethane or urea links or any combination thereof, the designators m and m' are zero or an integer of at least 1 and preferably from 1 to about 1000; the designator n is zero or an integer of at least 1, preferably 1 to 1000; and the sum of m+(m' times n) equals at least 2.

33. A multicomponent composition of statement 31 or 32 wherein the in situ linking material has reactive termini and the CDI link compound does not have reactive termini.

34. A multicomponent composition of statement 31 or 32 wherein the in situ linking material and the CDI link compound both have reactive termini.

35. A multicomponent composition of statement 34 wherein the CDI link compound is an organic polymer with at least two carboxylic acid groups.

36. A multicomponent composition of statement 34 wherein the CDI link compound is a silicone polymer with at least two carboxylic acid groups.

37. A multicomponent composition of statement 34 wherein the CDI link compound is a graft copolymer of an organic polymer and silicone segments, the silicone segments being graft bridges cross linking the organic polymer molecules.

38. A multicomponent composition of any of statements 31-37 wherein the reactive termini are alkyl mono, di or tri silyl groups having at least one terminal alkoxy substituent.

39. A multicomponent composition of any of the preceding statements comprising a third component of a base compound and a medium, wherein the base compound is polyethyleneimine at a concentration of 0.1-5% in medium relative to the total weight of the combination of the base compound and the medium.

40. A multicomponent composition of any of the preceding statements wherein the weight percentages of the CDI link compound and the in situ linking material are in a ratio of about 100:1 to 1:1, preferably about 50:1 to 1.5:1, more preferably about 10:1 to 2:1, most preferably about 8:1 to 2:1. and the weight percentage of CDI link compound is between 1-60 wt. %, preferably about 1-30 wt %, more preferably 2-15 wt %, most preferably about 2 to about 10 wt % and especially at about 4-6 wt %, and the CDI link compound is an organic polymer with at least two carboxylic acid groups or a silicone polymer with at least two carboxylic acid groups.

41. The multicomponent composition of the preceding statements, wherein at least one portion of the pigment microparticles is an organic pigment.

42. The multicomponent composition of the preceding statements, wherein the composition has a pigment solids content of about 0.1 wt % to about 30 wt % preferably about 0.2 wt % to about 10 wt % relative to the total weight of the composition.

43. The multicomponent composition of the preceding statements, wherein the pigment selected has a hair color gamut of greater than about 250.

44. The multicomponent composition of the preceding statements, wherein the pigment microparticles have a D50 [vol] particle diameter between 0.001 microns and 0.5 microns, preferably between 0.01 microns and 0.5 microns.

45. The multicomponent composition of the preceding statements, wherein the composition comprises at least one pigment microparticle that has a flake morphology.

46. The multicomponent composition of the preceding statements and any combination thereof further comprising metallic microplatelets or microparticles which impart reflection to the colored human hair strands.

47. A multicomponent composition of the preceding statements wherein the flake factor is greater than 10.

48. A multicomponent composition of any of the preceding statements any combination thereof further comprising one or more of a plasticizer, a wetting agent, anti-agglomeration agent, preservative, fragrance, an organic dye compound, a feel modification agent or a thickening agent; the dispersant, anti-agglomeration agent capable of providing dispersion of the pigment particles, the plasticizer and thickener capable of providing viscosity parameters to enable flow and hold of the composition on the keratin fibers.

49. A multicomponent composition of the preceding statements wherein the pigment microparticles comprise organic pigment microparticles, which imparts color to the hair, having a given D50[vol], and pigment microparticles, for providing light scattering properties to the colored hair, having a D50[vol] which is larger than the D50[vol] value of the organic pigment microparticles.

50. A multicomponent composition of any of the preceding statements and any combination thereof, wherein the composition has a viscosity of from about 0.001 to about 2000 Pa s$^{-1}$.

51. A multicomponent composition of any of the preceding statements wherein the pigment microparticles are combined with dispersant.

52. A multicomponent composition of statement 51 wherein the dispersant is at least in part compatible with the first and second components and is at least in part incompatible with the third component.

53. A multicomponent composition of any of the preceding statements wherein the pigment microparticles and dispersant are combined with either or both of the first and second components before application to the treatable material and the dispersant is at least in part compatible with the first or second component or both.

54. A multicomponent composition of the preceding statements wherein the composition has the physical character of a foam or a gel.

55. A multicomponent composition the preceding composition statements wherein the medium comprises a organic medium that is partially miscible with water.

56. A multicomponent composition of any of the preceding statements wherein the medium is ethanol or isopropanol.

57. A multicomponent composition of preceding statements wherein the second component is free of a medium.

58. A multicomponent composition of the preceding statements wherein the concentration relation of combined polymers to pigment on a weight to weight comparison of polymer to pigment provides more polymer by weight than pigment by weight.

59. A multicomponent composition according to the preceding statements, further comprising an excipient selected from a preservative, a fragrance, a surfactant, a feel modification agent and a thickening agent or a combination thereof.

60. A multicomponent composition of the preceding statements wherein the pigment particles are combined with at least a dispersing agent and the concentration of the dispersing agent is in an amount able to generate a positive or negative zeta potential in the composition.

61. A multicomponent composition of statement 60 wherein the dispersing agent is a nonionic surfactant selected from ethoxylated aliphatic alcohol, polyoxyethylene glycol, esters of fatty acids and glycerol, polyethylene glycol esters of fatty acids, anhydrosorbitol esters, polyethoxylated sorbitol esters, polysorbates, poloxamer, nonoxynol, fatty alcohol, tritan, tween, alkoxylated, hydrogenated castor oil.

62. A multicomponent composition of any of the preceding statements wherein the excipient includes at least a thickening agent and the concentration of the thickening agent is sufficient to maintain a suspension of metallic flakes or pigments in the composition.

63. A method for preparing the multicomponent composition the preceding statements comprising dispersing dry pigment microparticles in a portion of a medium to form a slurry, adding additional medium to the slurry and applying a high energy dispersing procedure to prepare a premix of the pigment particles in the medium.

64. A method of statement 63 wherein the medium comprises at least a dispersant.

65. A method of statement 63 further comprising combining the first or second component or the first and second components with portions of the premix to form a substantially uniform dispersion of the pigment particles in the first or second component or in both of the first and second components.

66. A method of statement 65 wherein the pigment particles are dispersed in one or both of the first and second components.

67. A method of statement 54 wherein the pigment particles are in both components and pigment with the first component differ from the pigment particles with the second component.

68. A method of any of preceding statements wherein the high energy dispersing technique includes ultra-high speed, high energy mixing.

69. A kit comprising a multicompartment container, each container comprising one of the first, second and third components of the multicomponent composition of any of the preceding statements.

70. A composition according to any of the preceding statements comprising a pre-application formulation of a mixture of the first and second components.

71. A composition according to the preceding composition statements including the third component wherein the first component is maintained in a first compartment, the second component is maintained in a second compartment and the third component is maintained in a third compartment.

72. A composition according to the preceding composition statements not including the third component wherein the first component is maintained in a first compartment, the second component is maintained in a second compartment.

73. A composition according to statement 71 or 72 comprising a preapplication formulation of a mixture of the first and second components.

74. A method for coloring keratin material comprising applying first to the keratin material the third component of statement 71 to form pretreated treatable material, especially keratin material.

75. A method of statement 74 further comprising optionally or at least partially drying the third component on the treatable material, especially keratin material.

76. A method of statement 74 further comprising combining the first and second components of statement 71 to form to form an in situ coloring mixture, applying the in situ coloring mixture to the pretreated treatable material, especially keratin material, and causing the in situ coloring mixture to form a colored coating on the treatable material, especially keratin material.

77. A method of statement 76 further comprising drying the colored coating on the treatable material, especially keratin material.

78. A method for coloring treatable material, especially keratin material comprising combining the first and second components of statement 72 to form a color formulation and applying the color formulation to the treatable material, especially keratin material to form a coated treatable material, especially a coated keratin material and causing the coated treatable material, especially the coated keratin material to become a colored coating on the treatable material, especially the keratin material.

79. A colored coating for hair strands produced according to the method of statement 76 or 78.

80. A colored coating for hair strands according to statement 79 wherein the composition forms a solid, flexible elastic film on each individualized hair fibre in which are embedded the pigment particles.

81. A colored coating for hair strands according to statement 80 wherein the film has the microscopic appearance of a semicontinuous or continuous coating 82. A colored coating for hair strands according to statements 79-81 which are resistant to color fading by repeated washings according to a standard wash procedure.

83. A colored coating for hair strands according to statement 82 wherein the repeated washings number 5 to 15.

84. A colored coating for hair strands according to statement 83 wherein the repeated washing number 15 or more.

85. A color removal composition for applying to color coated hair strands comprising applying one or more of a surfactant, a solvent, a strong acid, a strong base, a polyelectrolyte, an ionic compound to remove the color coating.

86. A method for removing color from a colored coating of any of statements 79-84 comprising applying a color removal composition comprising one or more of a surfactant, a solvent, a strong acid, a strong base, a polyelectrolyte, and/or an ionic compound to remove the color coating.

87. A method according to statement 86 comprising combining the colored hair strands with an aqueous-organic mixture of a fatty organic sulfonic acid or an aminoalcohol or a combination thereof applied simultaneously or sequentially, agitating the mixture on the hair and washing with a basic aqueous solution of detergent with optional brushing.

88. A method according to statement 86 comprising combining the colored hair strands with an aqueous-organic mixture of a tetrabutylammonium fluoride or an aminoalcohol or a combination thereof applied simultaneously or sequentially, agitating the mixture on the hair and washing with a basic aqueous solution of detergent with optional brushing.

89. A method according to any of statements 86-88 comprising adding one or more of heat, electromagnetism, mechanical energy, or cooling.

90. A method of removal of a colored coating according to claim 86 wherein the removal composition is selected according to its ability to chemically break down covalent bonds in the in situ cross linked multicomponent composition.

91. A method according to statement 86 wherein the acid is dodecylbenzene sulfonic acid and the ionic compound is tetrabutylammonium fluoride.

92. A method for color removal according to any of statements 86-91 comprising use of a removal composition with a Hansen solubility parameter of δd+δp+δh wherein δd is from 13 to 25, preferably 15-19 and δp is from 0 to 15, preferably 0 to 5 and δh is from 0 to 25, preferably 0 to 8.

93. A multicomponent composition of statement 20 wherein the CDI link compound has inert termini.

94. A multicomponent composition of statement 20 wherein the CDI link compound has reactive termini.

95. Use of a multicomponent composition of any of the statements 1 to 62 to form a color coating or a colored coating on keratin material.

96. Use of a removal composition according to statement 85 or 92 to remove a color coating or a colored coating from keratin material.

97. Use of a removal composition according to statement 85 or 92 to remove a color coating or a colored coating from keratin material, which color coating or colored coating has been formed by the use of a multicomponent composition of any of the statements 1 to 62.

SUMMARY STATEMENTS

The inventions, examples and results described and claimed herein may have attributes and embodiments include, but not limited to, those set forth or described or referenced in this application.

All patents, publications, scientific articles, web sites and other documents and ministerial references or mentioned herein are indicative of the levels of skill of those skilled in the art to which the invention pertains, and each such referenced document and material is hereby incorporated by reference to the same extent as if it had been incorporated verbatim and set forth in its entirety herein. The right is reserved to physically incorporate into this specification any and all materials and information from any such patent, publication, scientific article, web site, electronically available information, text book or other referenced material or document.

The written description of this patent application includes all claims. All claims including all original claims are hereby incorporated by reference in their entirety into the written description portion of the specification and the right is reserved to physically incorporated into the written description or any other portion of the application any and all such claims. Thus, for example, under no circumstances may the patent be interpreted as allegedly not providing a written description for a claim on the assertion that the precise wording of the claim is not set forth in haec verba in written description portion of the patent.

While the invention has been described in conjunction with the detailed description thereof, the foregoing description is intended to illustrate and not limit the scope of the invention, which is defined by the scope of the appended claims. Thus, from the foregoing, it will be appreciated that, although specific nonlimiting embodiments of the invention have been described herein for the purpose of illustration, various modifications may be made without deviating from the scope of the invention. Other aspects, advantages, and modifications are within the scope of the following claims and the present invention is not limited except as by the appended claims.

What is claimed is:

1. A multicomponent in situ linkable composition for coloring keratin material, comprising:
   a first component comprising a CDI link compound having at least two groups capable of covalent in situ linkage with a carbodiimide group, the groups being carboxylic acid groups, sulfonic acid groups, phosphoric acid groups or any combination thereof and the CDI link compound having inert or first reactive termini, the first reactive termini being self-reactive alkoxysilyl groups or hydroxysilyl groups or a combination thereof;
   a second component comprising an in situ linking material having at least two carbodiimide groups and having second reactive termini, the second reactive termini being self-reactive alkoxysilyl groups or hydroxysilyl groups or a combination thereof;
   the second reactive termini of the in situ linking material and the first reactive termini CDI link compound being independently selected; and,
   pigment microparticles in one or both of the first and second components; or as a separate component; and,
   wherein the first and second components are present in separate container units; and
   wherein the first and second components are combinable to form a mixture of first and second components for coloring keratin material.

2. A multicomponent composition of claim 1 wherein the groups of the CDI link compound are carboxylic acid groups.

3. A multicomponent composition of claim 1 wherein the first and second components are combined as a mixture prior to coloring the keratin material.

4. A multicomponent composition of claim 1 further comprising a third component comprising a base compound having amine groups; wherein the base compound is selected from the group consisting of polyethylene imine, polyallylamine, polydiallyldimethylammonium chloride, polyvinyl amine, aminopolysaccharide, amino silicone, copolymers thereof, and triethoxysilyl amine, 1,1,1-triethoxy, 2,2-dimethyl-2-aminodisolxane, aminoalkylmonoethoxydimethylsilane, aminoalkyl diethoxymethyl silane and aminoC1-C6 alkyltriethoxysilane, and wherein the third component is present in a container unit separate from the first and second components.

5. A multicomponent composition of claim 3, further comprising a third component comprising a base compound having amine groups; wherein the base compound is selected from the group consisting of polyethylene imine, polyallylamine, polydiallyldimethylammonium chloride, polyvinyl amine, aminopolysaccharide, amino silicone, copolymers thereof, and triethoxysilyl amine, 1,1,1-triethoxy, 2,2-dimethyl-2-aminodisolxane, aminoalkylmonoethoxydimethylsilane, aminoalkyl diethoxymethyl silane and aminoC1-C6 alkyltriethoxysilane, and wherein the third component is present in a container unit separate from the first and second components and the third component is a pretreatment for the keratin material prior to coloring the keratin material with the mixture of the first and second components.

6. A multicomponent composition of claim 1 wherein the CDI link compound comprises a small organic molecule with carboxylic acid groups or a polymer with carboxylic acid groups; and the polymer comprises a linear, branched, or block organic polymer; a linear, branched cyclic, or block silicone polymer; or a block or pendant combination polymer of a linear, or branched, organic polymer moiety and a linear, or branched silicone polymer moiety; and the termini of the organic polymer, the silicone polymer or the combination polymer are inert or are first reactive termini; and when the CDI link compound comprises an organic or silicone or combination polymer; the organic or silicone or combination polymer has an acid value ranging up to about 700 and a weight average molecular weight in the range of about 2 KDa to about 5 MDa.

7. A multicomponent composition of claim 6 wherein the acid value ranges from about 250 to about 600, preferably 100 to 400, more preferably from 50 to about 300 and the weight average molecular weight is in a preferable range of about 2 KDa to about 100 KDa, more preferably about 2 KDa to about 50-80 KDa.

8. A multicomponent composition of claim 1 wherein the in situ linking material is a polycarbodiimide of Formula V

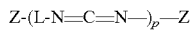

Z-(L-N=C=N—)$_p$—Z      Formula V wherein Z is a group terminating the polycarbodiimide and is terminated by the second reactive termini; p is an integer of at least 2, preferably an integer of 2 to about 1000; L is an organic linker group comprising a saturated aliphatic divalent radical, an aromatic divalent radical, an alkyl aromatic divalent radical or a polymeric or an oligomeric divalent radical with repeating olefinic, carbonate, ester, ether, amid, urethan or ureal linkages.

9. A multicomponent composition of claim 1 wherein the CDI link compound is a polymer with first reactive termini.

10. A multicomponent composition of claim 1 wherein the CDI link compound is a polymer with inert termini.

11. A multicomponent composition according to claim 6 wherein the CDI link compound comprises an organic or combination polymer comprising at least olefinic carboxylic acid monomeric units comprising (meth)acrylic acid, crotonic acid, pentenoic acid, hexenoic acid, maleic acid, fumaric acid, glutaconic acid, itaconic acid, citraconic acid, mesaconic acid or any combination thereof.

12. A multicomponent composition according to claim 11 wherein the combination polymer comprises olefinically polymerized backbones and silicon cross linking bridges wherein the silicone bridges comprises M type mono-alkyl siloxane units and D type dialkysiloxane units wherein the M and D siloxane units form a divalent silicone oligomer or polymer terminated by vinyl groups and the vinyl groups are polymerized into the olefinic backbone of the organic polymer so as to provide the silicon cross linking bridges.

13. A composition according to claim 11 wherein the organic or combination polymer comprises monomeric units of alkyl (meth)acrylate and/or crotonate, and (meth)acrylic acid and/or crotonic acid; and the acid number of the polymer is from about 50 to about 600 preferably about 100 to about 400.

14. A multicomponent in situ linkable composition for coloring keratin material, comprising:
a first component comprising an organic or silicone polymer with at least two carboxylic acid groups and inert termini or first reactive termini, the first reactive termini being self-reactive;
a second component comprising an in situ linking material comprising a polycarbodiimide with second reactive termini, the second reactive termini being self-reactive;
the second and first reactive termini respectively of the in situ linking material and the organic or silicone polymer with at least two carboxyl groups being independently selected and both being different from the carbodiimide group;
a third component selected from the group consisting of polyethylene imine, polyallylamine, polydiallyldimethylammonium chloride, polyvinyl amine, aminopolysaccharide, amino silicone, copolymers thereof, and triethoxysilyl amine, 1,1,1-triethoxy, 2,2-dimethyl-2-aminodisolxane, aminoalkylmonoethoxydimethylsilane, aminoalkyl diethoxymethyl silane and aminoC1-C6 alkyltriethoxysilane;
pigment particles in the first or second component or in both of the first and second components;
the first, second and third components being present in separate container units until their the combination of the first and second components as a keratin material coloring composition, and the third component as a separate pretreatment of the keratin material prior to treatment of the keratin material with the keratin material coloring composition;
wherein,
the organic polymer comprises a copolymer comprising an acidic olefinic monomers selected from (meth) acrylic acid, crotonic acid, maleic acid, fumaric acid, itaconic acid or any combination thereof, and non-acidic olefinic monomers, and the organic polymer having inert termini or having self-reactive first termini comprising alkyl alkoxysilyl groups or hydroxysilyl groups or a combination thereof;
the silicone polymer comprises M trialkylsiloxane units, D dialkylsiloxane units, and optional T alkysiloxane units, and at least two of the D units have pendant alkylcarboxylic acid groups, the silicone polymer having inert termini or self-reactive first termini comprising alkoxysilyl groups or hydroxysilyl groups or a combination thereof;
the polycarbodiimide has Formula V

Z-(L-N=C=N—)$_p$—Z wherein Z is a terminal group of the polycarbodiimide and has reactive second termini comprising alkoxysilyl groups or hydroxysilyl groups or a combination thereof, the designator p is an integer of at least 2 so that the polycarbodiimide of Formula V contains at least 2 carbodiimide groups; L is an organic linker group comprising an aromatic, alkaromatic or saturated linear, branched or cyclic aliphatic divalent radical of 2 to 30 carbons optionally with one or more non-pendant heteroatoms including nitrogen, oxygen sulfur or any combination thereof in the aliphatic or the aromatic group; and wherein,
the organic copolymer optionally further comprises olefinically polymerized backbones and silicone cross linking bridges wherein the silicone bridges comprise M type mono-alkylsiloxane units and D type dialkylsiloxane units and the M and D siloxane units comprise a divalent silicone oligomer or polymer which polymer or polymer is terminated by vinyl groups and the vinyl groups are polymerized into the olefinic backbone of the organic polymer so as to provide the silicone cross linking bridges.

15. A multicomponent composition of claim 14 wherein the polycarbodiimide of Formula V is Formula VI

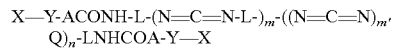

X—Y-ACONH-L-(N=C=N-L-)$_m$-((N=C=N)$_{m'}$
Q)$_n$-LNHCOA-Y—X      Formula VI wherein the organic linker group L comprises an aromatic, alkaromatic or saturated linear, branched or cyclic aliphatic divalent radical of 2 to 30 carbons optionally with one or more non-pendant heteroatoms including nitrogen, oxygen, sulfur or any combination thereof in the aliphatic chain or the aromatic group; A is NH, S or O; Y is a divalent organic radical selected from a saturated aliphatic group of 1 to 36 carbons or an aromatic group or alkaromatic group of 6 to 24 carbons, and the aliphatic or aromatic group may optionally include one or more non-pendant heteroatoms selected from nitrogen, oxygen, sulfur or any combination thereof; X is configured as the reactive second termini; Q comprising an organopolymer or organo-oligomer moiety of repeating units of linear, branched or cyclic saturated aliphatic groups or aromatic groups or alkaromatic groups coupled by repeating carbonate, ester, ether, amid, urethan or urea links or any combination thereof; the designators m and m' are zero or an integer of at least 1 and preferably from 1 to about 1000; the designator n is zero or an integer of at least 1, preferably 1 to 1000; and the sum of m+(m' times n) equals at least 1; and wherein the first component has reactive first termini and the first and second reactive termini respectively of the first component and the polycarbodiimide are independently selected from alkoxysilyl or hydroxysilyl or any combination thereof.

16. A method for coloring keratin material comprising applying to keratin material a mixture of the first and second components of the multicomponent in situ linkable composition of claim 1 for a time sufficient to deposit an effective colored coating on the keratin material.

17. A method for coloring keratin material according to claim 16 further comprising applying the third component of claim 5 to the keratin material before applying the mixture of the first and second components to the keratin material.

\* \* \* \* \*